US011224680B2

(12) United States Patent
Kang et al.

(10) Patent No.: US 11,224,680 B2
(45) Date of Patent: Jan. 18, 2022

(54) COMPOSITIONS FOR CELL-BASED THREE DIMENSIONAL PRINTING

(71) Applicant: REVOTEK CO., LTD, Sichuan (CN)

(72) Inventors: Yujian James Kang, Chengdu (CN); Xiao Zuo, Chengdu (CN)

(73) Assignee: REVOTEK CO., LTD, Chengdu (CN)

( * ) Notice: Subject to any disclaimer, the term of this patent is extended or adjusted under 35 U.S.C. 154(b) by 0 days.

(21) Appl. No.: 15/488,336

(22) Filed: Apr. 14, 2017

(65) Prior Publication Data

US 2017/0216498 A1  Aug. 3, 2017

Related U.S. Application Data

(63) Continuation of application No. PCT/CN2016/078678, filed on Apr. 7, 2016.

(30) Foreign Application Priority Data

| Apr. 7, 2015 | (CN) | 201510160942.0 |
| Oct. 22, 2015 | (CN) | 201510689089.1 |
| Oct. 22, 2015 | (CN) | 201510690578.9 |
| Oct. 22, 2015 | (CN) | 201510698379.2 |

(51) Int. Cl.
| *A61L 31/16* | (2006.01) |
| *A61L 31/04* | (2006.01) |
| *B33Y 10/00* | (2015.01) |
| *B33Y 30/00* | (2015.01) |
| *C09D 11/03* | (2014.01) |
| *C09D 11/04* | (2006.01) |
| *A61L 27/44* | (2006.01) |
| *A61L 27/20* | (2006.01) |
| *A61L 27/22* | (2006.01) |
| *A61L 27/38* | (2006.01) |
| *A61L 27/48* | (2006.01) |
| *A61L 27/50* | (2006.01) |
| *B28B 1/00* | (2006.01) |
| *B33Y 70/00* | (2020.01) |
| *A61B 17/00* | (2006.01) |

(52) U.S. Cl.
CPC ......... *A61L 31/16* (2013.01); *A61L 27/20* (2013.01); *A61L 27/222* (2013.01); *A61L 27/38* (2013.01); *A61L 27/3808* (2013.01); *A61L 27/3826* (2013.01); *A61L 27/3834* (2013.01); *A61L 27/44* (2013.01); *A61L 27/48* (2013.01); *A61L 27/50* (2013.01); *A61L 31/047* (2013.01); *B28B 1/001* (2013.01); *B33Y 10/00* (2014.12); *B33Y 30/00* (2014.12); *C09D 11/03* (2013.01); *C09D 11/04* (2013.01); *A61B 2017/00004* (2013.01); *A61B 2017/00526* (2013.01); *A61B 2017/00893* (2013.01); *A61F 2240/001* (2013.01); *A61F 2250/0067* (2013.01); *A61L 2400/06* (2013.01); *B33Y 70/00* (2014.12)

(58) Field of Classification Search
None
See application file for complete search history.

(56) References Cited

U.S. PATENT DOCUMENTS

| 6,783,964 B2 | 8/2004 | Opara |
| 8,697,057 B2 | 4/2014 | Van Epps |
| 9,441,194 B2 | 9/2016 | Nakayama et al. |
| 9,442,105 B2 | 9/2016 | Shepherd et al. |
| 2006/0198865 A1* | 9/2006 | Freyman ............ A61L 27/3804 424/423 |
| 2013/0164339 A1 | 6/2013 | Murphy et al. |
| 2014/0120192 A1 | 5/2014 | Nakayama et al. |
| 2014/0127290 A1 | 5/2014 | He et al. |
| 2014/0274802 A1 | 9/2014 | Shepherd et al. |
| 2015/0037445 A1* | 2/2015 | Murphy ............. B29C 67/0088 425/131.1 |
| 2019/0216988 A1 | 7/2019 | Kang |

FOREIGN PATENT DOCUMENTS

| CN | 101721390 A | 6/2010 |
| CN | 101829361 A | 9/2010 |
| CN | 102070895 A1 | 5/2011 |
| CN | 102091056 A | 6/2011 |
| CN | 102218161 A | 10/2011 |
| CN | 103756955 A | 4/2014 |
| CN | 103930066 A | 7/2014 |
| CN | 104068945 A | 10/2014 |

(Continued)

OTHER PUBLICATIONS

US 4,487,758 A, 12/1984, Goosen et al. (withdrawn)
Gomez (Oxidation of sodium alginate and characterization of the oxidized derivatives, 2007).*
Kim (Generation of core-shell microcapsules with three-dimensional focusing device for efficient formation of cell spheroid, 2011).*
Boland, Thomas. Application of Inkjet Printing to Tissue Engineering. Biotechnol. J. 2006, 1 910-917. (Year: 2006).*
Augst, A.D. et al. (2006). "Alginate Hydrogels as Biomaterials," *Macromol. Biosci.* 6(8):623-633.
Boeuf, S. et al. (2010). "Chondrogenesis of Mesenchymal Stem Cells: Role of Tissue Source and Inducing Factors," *Stem Cell Research & Therapy* 1(4):31-40.

(Continued)

*Primary Examiner* — Nghi V Nguyen
(74) *Attorney, Agent, or Firm* — Morrison & Foerster LLP

(57) ABSTRACT

A bio-ink composition comprises a plurality of bio-block, in which the bio-blocks can serve as basic building blocks in cell-based bioprinting. The bio-blocks, pharmaceutical compositions comprising the bio-blocks, methods of preparing artificial tissues, tissue progenitors, or multi-dimensional constructs, and methods of preparing the bio-blocks are also provided. The bio-blocks, and the multi-dimensional constructs, artificial tissues, and tissue progenitors comprising the bio-blocks or prepared by the methods described herein are useful for tissue engineering, in vitro research, stem cell differentiation, in vivo research, drug screening, drug discovery, tissue regeneration, and regenerative medicine.

25 Claims, 24 Drawing Sheets

(56) References Cited

FOREIGN PATENT DOCUMENTS

| CN | 104146793 A | | 11/2014 |
|---|---|---|---|
| JP | 2009-519042 A | | 5/2009 |
| JP | 2012120696 A | | 6/2012 |
| KR | 101472045 B1 | * | 12/2014 |
| WO | WO-2007/070660 A2 | | 6/2007 |
| WO | WO-2007/070660 A3 | | 6/2007 |
| WO | WO-2007/078922 A2 | | 7/2007 |
| WO | WO-2009/102484 A2 | | 8/2009 |
| WO | WO-2012/122105 A1 | | 9/2012 |
| WO | WO-2013/040078 A2 | | 3/2013 |
| WO | WO-2013/040087 A2 | | 3/2013 |
| WO | WO-2014/039427 A1 | | 3/2014 |
| WO | WO-2014/151921 A1 | | 9/2014 |
| WO | WO-2015/017579 A1 | | 2/2015 |
| WO | WO-2015/123183 A1 | | 8/2015 |
| WO | WO-2016/161941 A1 | | 10/2016 |
| WO | WO-2016/161944 A1 | | 10/2016 |

OTHER PUBLICATIONS

Doyle, A. et al. (1998). *Cell and Tissue Culture: Laboratory Procedures in Biotechnology*, New York: Wiley, 354 pages.

Fakhry, M. et al. (2013). "Molecular Mechanisms of Mesenchymal Stem Cell Differentiation Towards Osteoblasts," *World J. Stem Cells* 5(4):136-148.

International Search Report and Written Opinion dated Jan. 4, 2016, for PCT/CN2015/075967 filed on Apr. 7, 2015, 6 pages.

International Search Report dated Jul. 13, 2016 for PCT/CN2016/078638 filed on Apr. 7, 2016, 4 pages.

International Search Report dated Jul. 14, 2016 for PCT/CN2016/078678 filed on Apr. 7, 2017, 4 pages.

Khalil, S. et al. (2007). "Biopolymer Deposition for Freeform Fabrication of Hydrogel Tissue Constructs," *Mater. Sci. Eng. C* 27(3):469-478.

Kolesky, D.B. et al. (2014). "3D Bioprinting of Vascularized, Heterogeneous Cell-Laden Tissue Constructs," *Advanced Materials* 26(19):3124-3130.

Malda J. et al. (2013). "$25^{th}$ Anniversary Article: Engineering Hydrogels for Biofabrication," *Advanced Materials* 25(36):5011-5028.

Murphy, S.V. et al. (2014). "3D Bioprinting of Tissues and Organs," *Nature Biotechnology* 32(8):773-785.

Othon, C.M. et al. (2008). "Single-Cell Printing to Form Three-Dimensional Lines of Olfactory Ensheathing Cells," *Biomedical Materials* 3(3):034101, 6 Pages.

Perez, R.A. et al. (2014). "Utilizing Core-Shell Fibrous Collagen-Alginate Hydrogel Cell Delivery system for Bone Tissue Engineering," *Tissue Engineering: Part A* 20(1&2):103-115.

Written Opinion of the International Searching Authority dated Jul. 13, 2016 for PCT/CN2016/078638 filed on Apr. 7, 2016, 5 pages.

Written Opinion of the International Searching Authority dated Jul. 14, 2016 for PCT/CN2016/078678 filed on Apr. 7, 2016, 5 pages.

Jakab, K. et al. (Jun. 2010; e-pub. Jun. 2, 2010). "Tissue Engineering by Self-Assembly and Bio-Printing of Living Cells," *Biofabrication* 2(2):1-14, 34 pages.

Mironov, V. et al. (Apr. 1, 2009; e-pub. Jan. 26, 2009). "Organ Printing: Tissue Spheroids as Building Blocks," *Biomaterials* 30(12):2164-2174, 22 pages.

Velasco, D. et al. (Jun. 11, 2012; e-pub. Mar. 29, 2012). "Microfluidic Encapsulation of Cells in Polymer Microgels," *Small* 8(11):1633-1642.

U.S. Appl. No. 16/362,246, filed Mar. 22, 2019 by Kang et al.

Rouse, M. (Nov. 28, 2014). "Bioprinting," Whatis.com.com, retrieved from https://whatis.techtarget.com/definition/bioprinting?vgnextfmt=print, last visited May 15, 2020, 1 page.

* cited by examiner

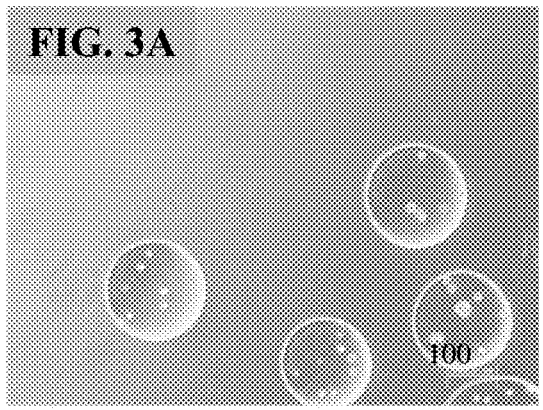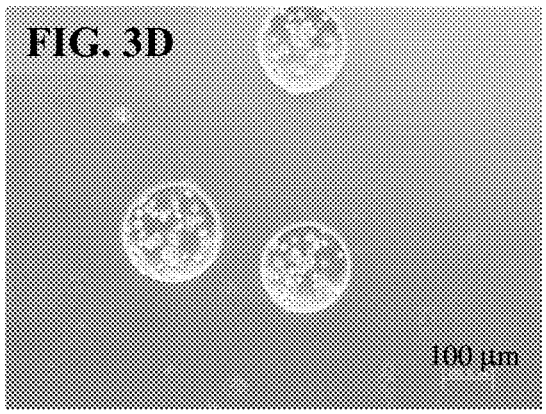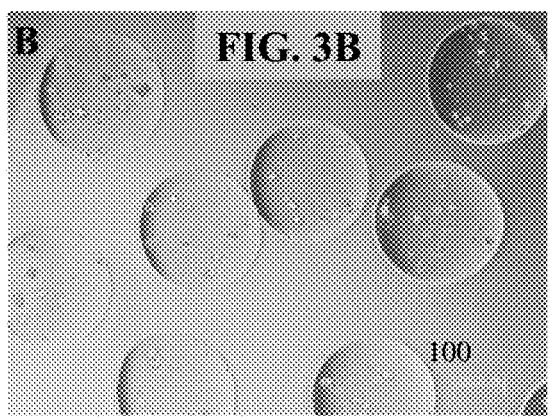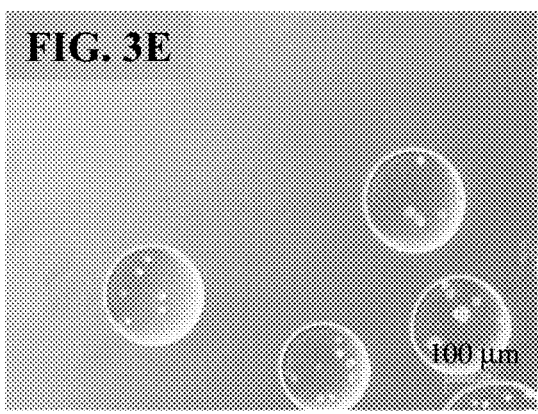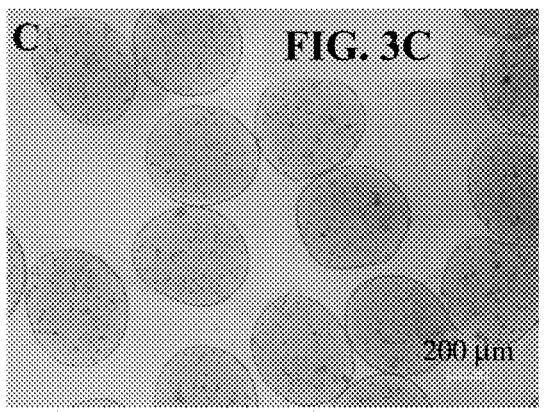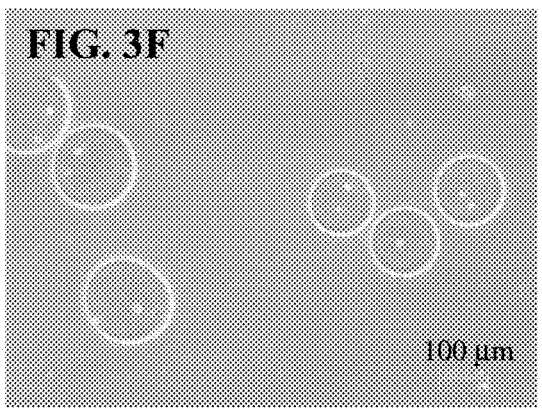

FIG. 4
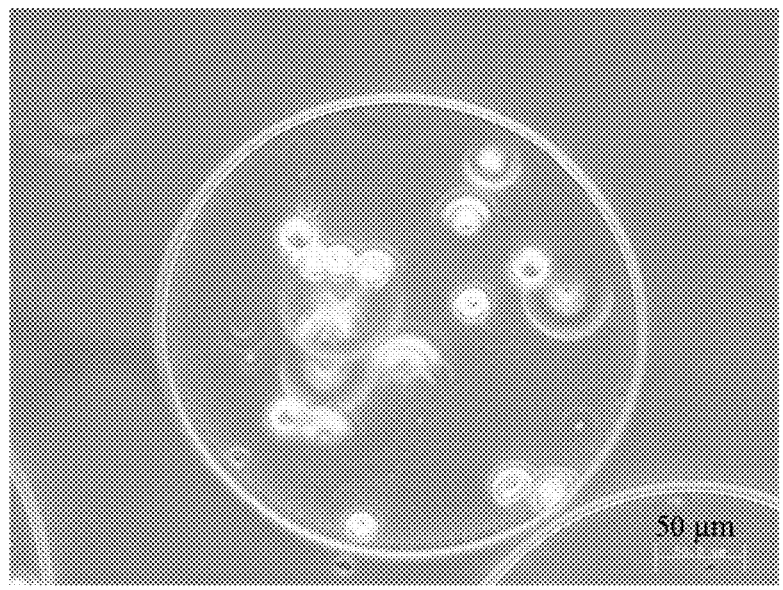
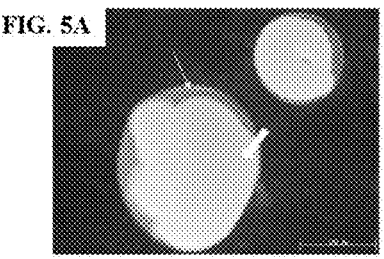
Shell: calcium alginate
Core: starch
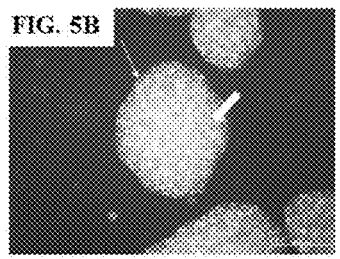
Shell: polylysine
Core: type I collagen
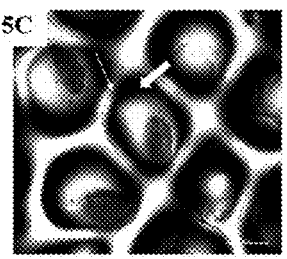
Shell: calcium alginate
Core: type I collagen
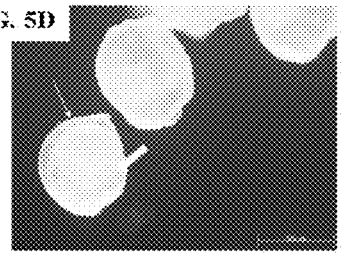
Shell: calcium alginate
Core: polyurethane
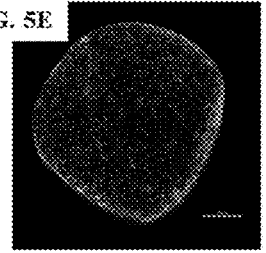
Shell: FITC-polylysine
Core: type I collagen
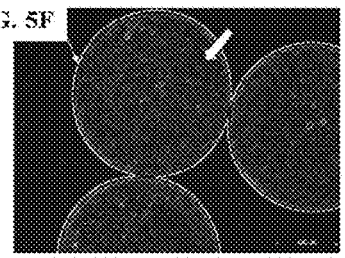
Shell: polylysine
Core: sodium alginate

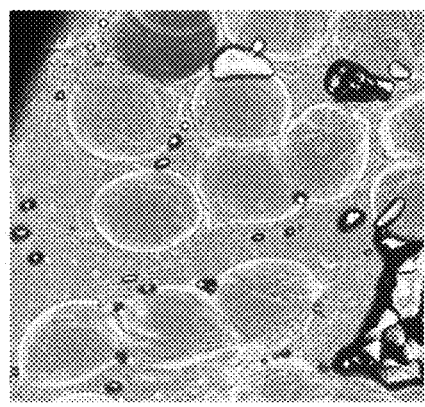
FIG. 6A
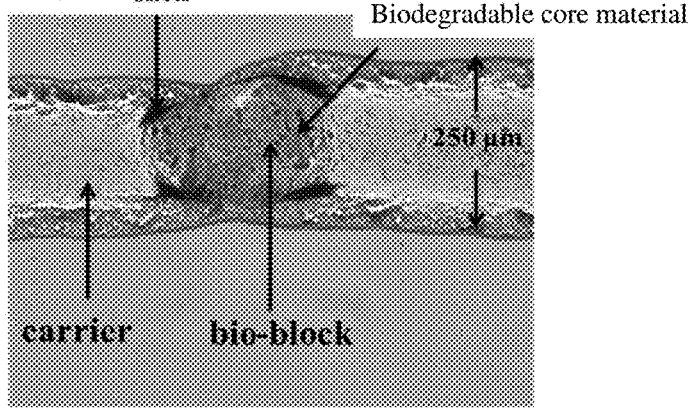
FIG. 6B
FIG. 7
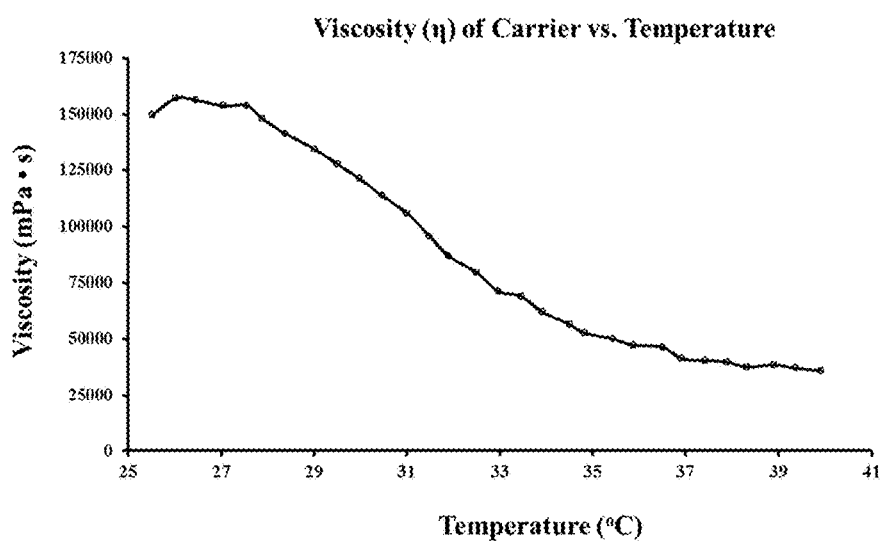

2% alginate     5% alginate     2% alginate + bio-block

FIG. 14A  FIG. 14B  FIG. 14C
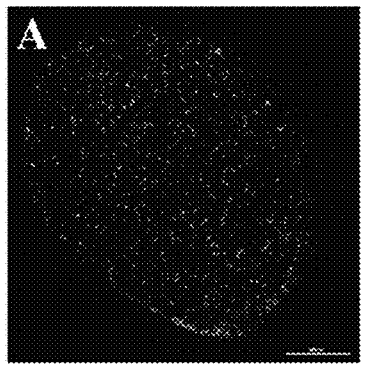 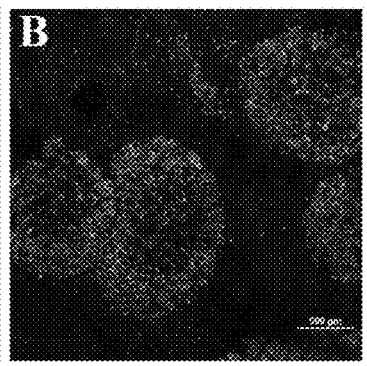 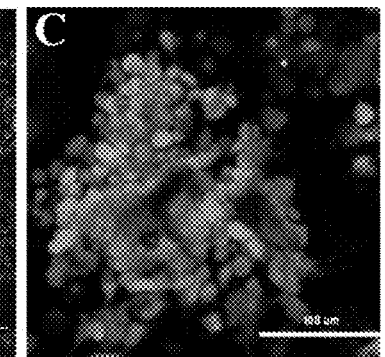
FIG. 14D
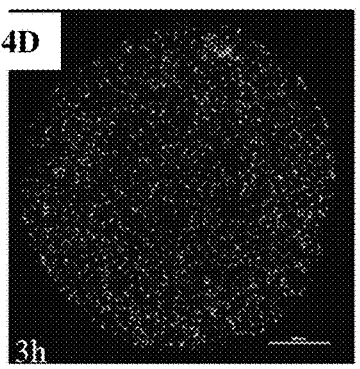 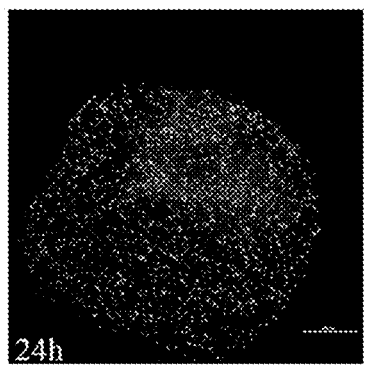 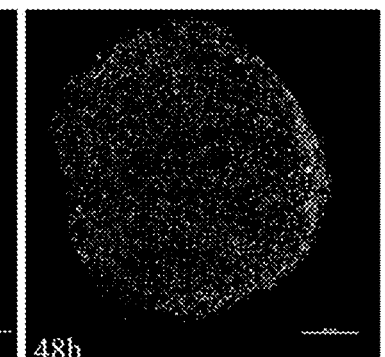
FIG. 14E
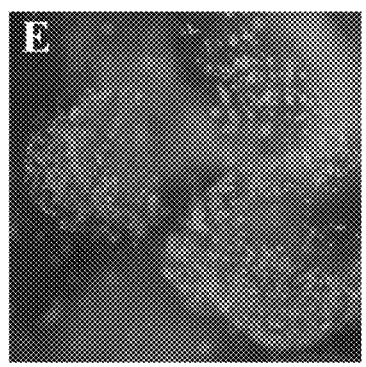

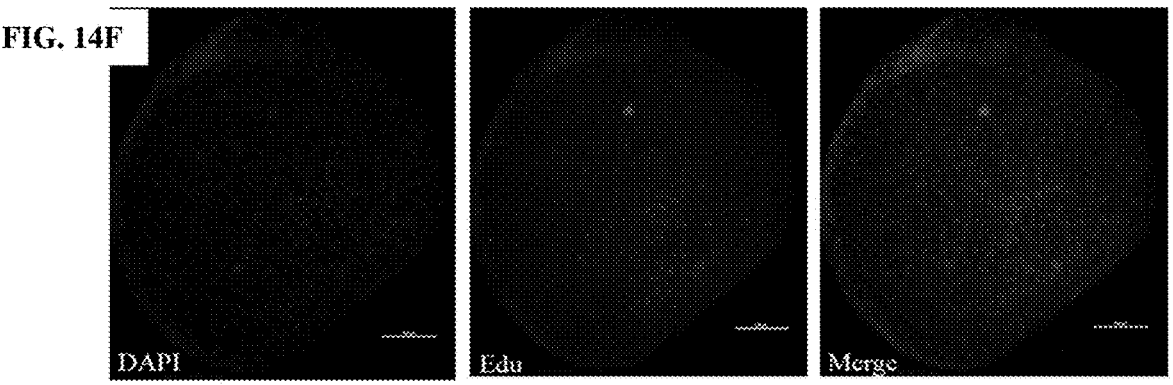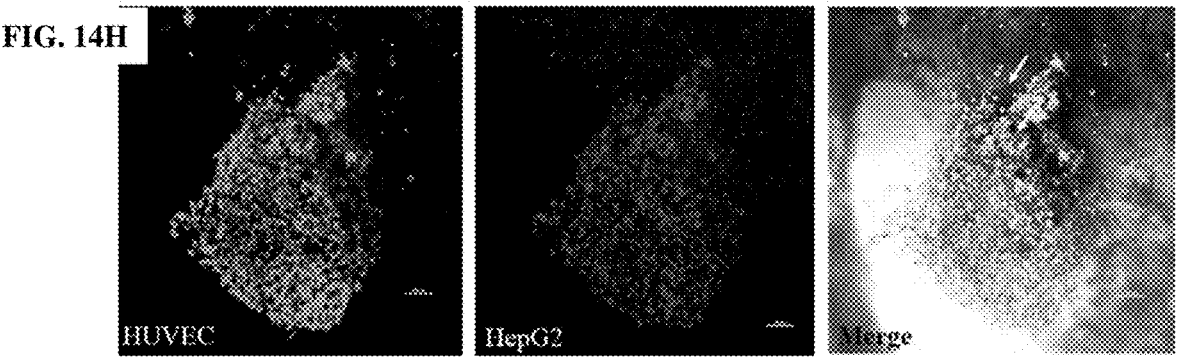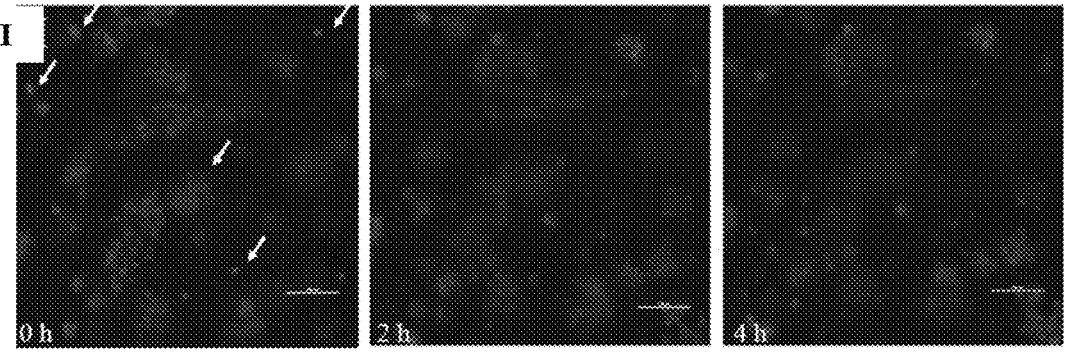

FIG. 15A   FIG. 15B
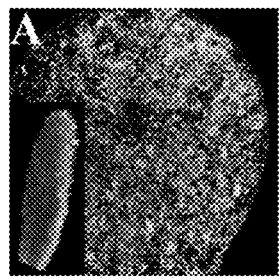
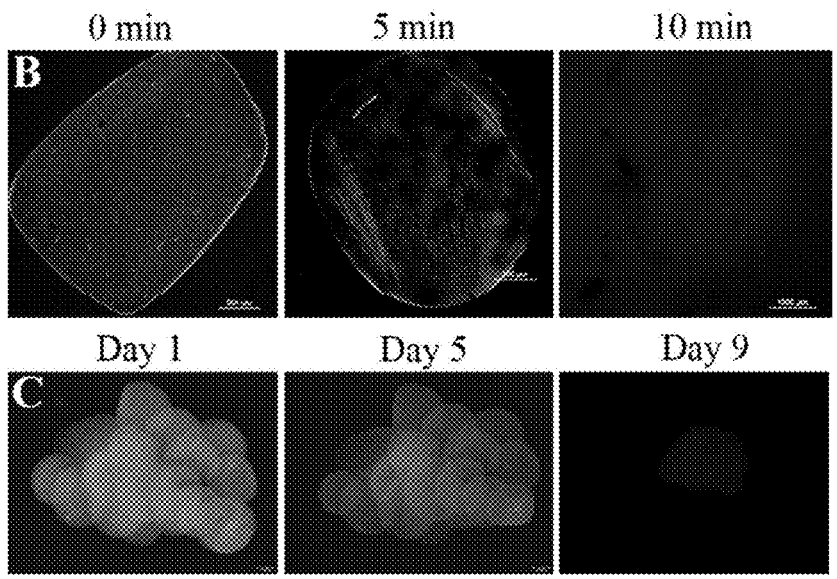
FIG. 15C
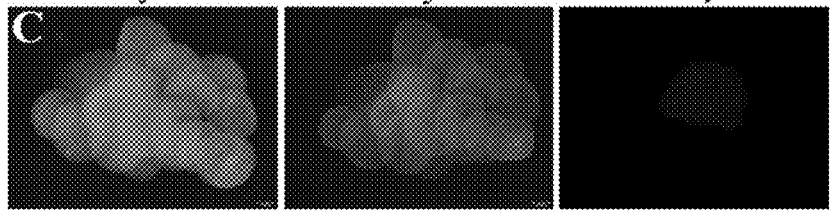
FIG. 15D
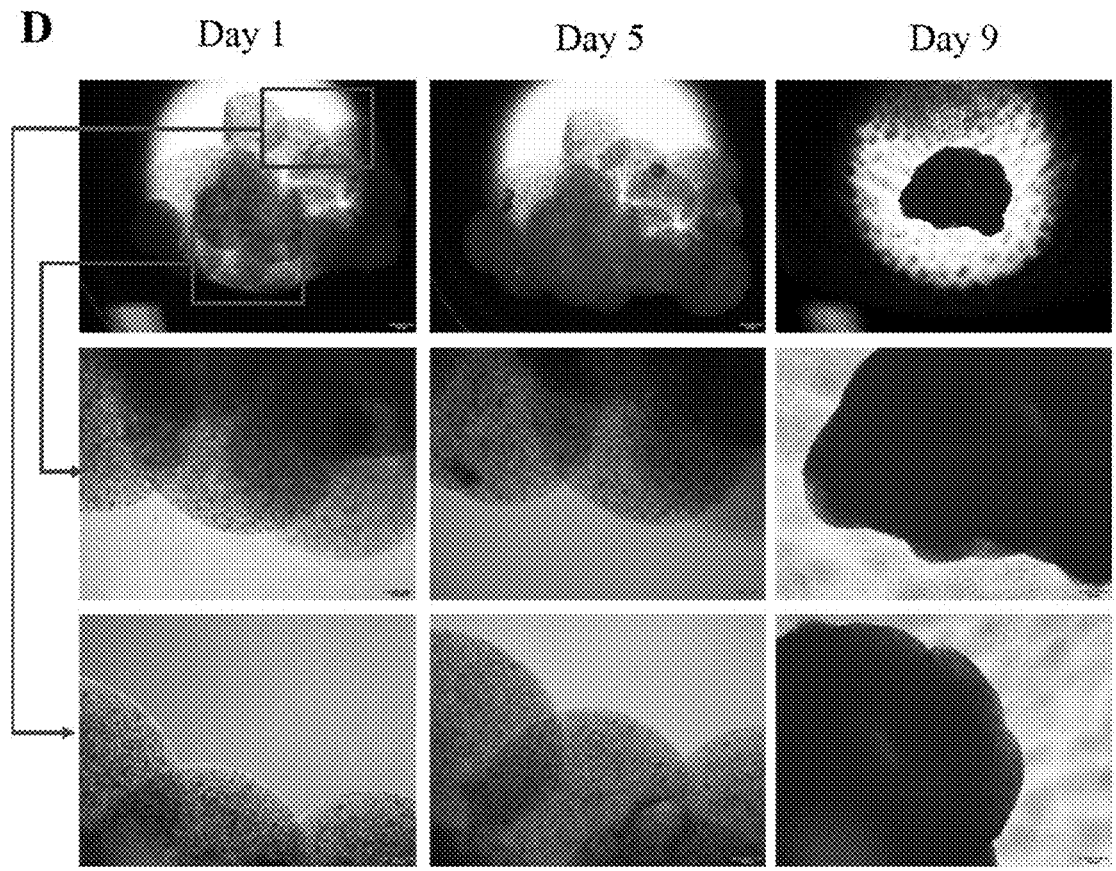

FIG. 17A
FIG. 17B
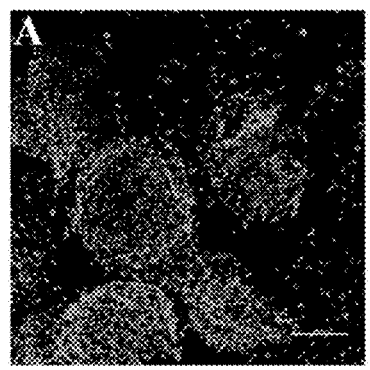
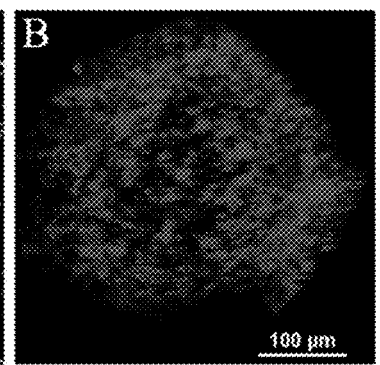
FIG. 17C
FIG. 17D
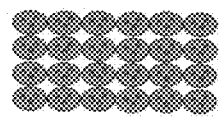
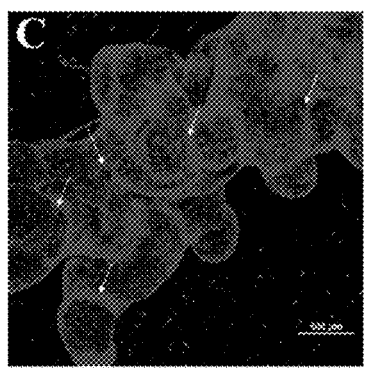
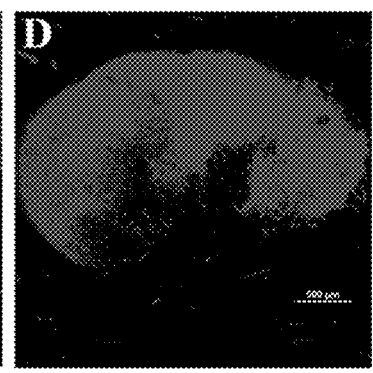
FIG. 17E
FIG. 17F
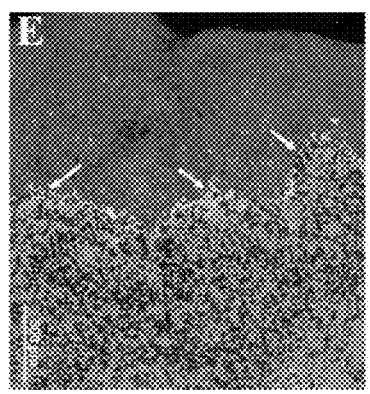
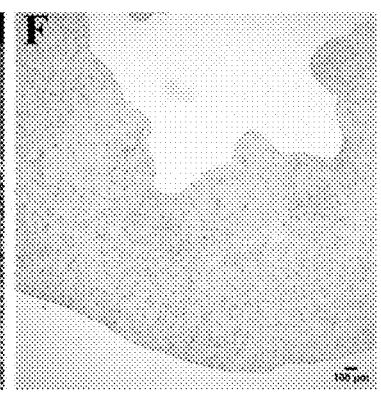

FIG. 17G 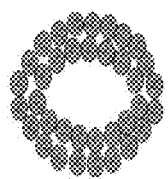 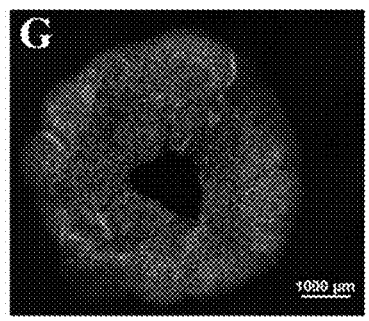

FIG. 17I  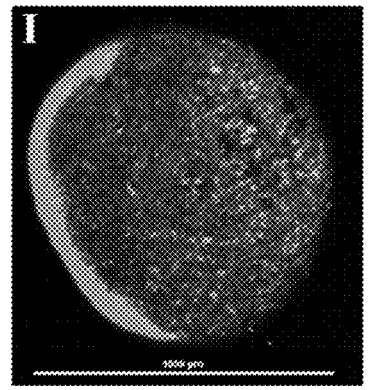

- Bio-block
- MSCs
- Osteoblast differentiation factors
- Chondrocyte differentiation factors

- Bio-block
- MSCs
- Osteoblast differentiation factors
- Chondrocyte differentiation factors

- MSC bio-blocks having a microenvironment for smooth muscle cell differentiation
- MSC bio-blocks having a microenvironment for endothelial cell differentiation

HE          CD31          α-SMA

X 200　　　　　　　　X 400

COMPOSITIONS FOR CELL-BASED THREE DIMENSIONAL PRINTING

CROSS REFERENCE TO RELATED APPLICATIONS

This application is a continuation of International Patent Application No. PCT/CN2016/078678 filed Apr. 7, 2016, which claims priority benefit of International Patent Application No. PCT/CN2015/075967 filed Apr. 7, 2015, International Patent Application No. PCT/CN2015/092549 filed Oct. 22, 2015, Chinese Patent Application No. 201510160942.0 filed Apr. 7, 2015, Chinese Patent Application No. 201510698379.2 filed Oct. 22, 2015, Chinese Patent Application No. 201510690578.9 filed Oct. 22, 2015, and Chinese Patent Application No. 201510689098.1 filed Oct. 22, 2015, the contents of which are incorporated herein by reference in its entirety.

FIELD OF THE INVENTION

The present invention relates to the field of biology, regenerative medicine, bioprinting (such as cell-based three dimensional (3D) bioprinting), and tissue engineering.

BACKGROUND OF THE INVENTION

Human tissues are composed of cells arranged in an orderly manner. Tissues and cells with different physiological functions are usually associated with distinct cellular distribution patterns. For example, epithelial cells are tightly packed as a monolayer to ensure their protective functions. Muscle cells are arranged in a cord-like structure to support their contractile function. Neurons either remain parallel to each other, or interconnect with each other to form a web-like structure to facilitate their function of information delivery.

Abnormalities in cell distribution are manifested as defects in cell morphology, intercellular connections, and/or activities of the cell group. Abnormal cellular distribution patterns commonly arise during pathological transformations of tissues and organs, leading to functional defects of cells and damaging the overall structure and functions of the tissues and organs. For example, hepatic cords in a hepatic tumor tissue are disarranged and lack the lobule structure of a normal liver. Disorder in distribution of epithelial cells of the small intestine compromises the protective functions of the epithelial barrier, leading to increasing levels of endotoxins absorbed through the small intestine, and ultimately causing endotoxemia. Irregular distribution of vascular smooth muscle cells reduces compliance, elasticity and anti-strain capacity of blood vessels. Therefore, precision distribution of cells is a key factor in artificial tissue and organ construction.

The three-dimensional (3D) bioprinting technology emerged in recent years, and there have been attempts to use 3D bioprinting to construct complex tissues and organs. So far, a number of 3D bioprinting technologies has been reported, including the 3D bioprinting technologies proposed by Cyfuse Biomedical K.K. (referred herein after as "Cyfuse technology"; see, for example U.S. Patent Application Publication No. US2014012192A1), and by Organovo Holdings Inc. (referred herein as "Organovo technology"; see, for example, International Patent Application Publication No. WO2013040078A2).

The Cyfuse technology mainly involves the following steps: constructing cell spheroids to form mini-tissues; and depositing the cell spheroids on fine needle arrays according to a pre-determined spatial distribution; and relying on the inherent adhesion properties of cells to fuse the deposited mini-tissues in order to obtain the tissue with the desired structure.

The basic steps of the Organovo technology include the following. First, a bio-ink (i.e., cells) and a bio-sheet (typically gel) are prepared. Then, the bio-ink and bio-sheet are used to 3D print a tissue or organ according to a 3D model as follows" (1) print a layer of bio-ink, i.e., placing a layer of cells on top of another layer of cells or gel; (2) print a bio-sheet, i.e., placing a layer of gel on top of cells; (3) repeat steps (1) and (2) until complete printing the tissue or organ.

However, current bioprinting methods are associated with significant deficiencies. Particularly, none of the currently known bioprinting methods can achieve precise distribution of cells, or construction of mini-tissues and tissue blocks with precise structure. Meanwhile, cells used in the current bioprinting methods lack mechanical protection. As a result, when used directly or in a mixture with hydrogel in 3D bioprinting, cells can be injured or killed due to damage by external pressure or shearing force. This deficiency greatly limits applications of the bioprinting technologies. To overcome the low cell survival rate, some known bioprinting technologies use a large number of cells to build mini-tissues, which further substantially limit applications of such bioprinting technologies.

Therefore, currently known 3D bioprinting technologies cannot construct tissues or organs with complicated three-dimensional structures via methods that have control over cell number and precise cell distribution. The three-dimensional constructs printed thereof also suffer from low cell survival rates, and substantial size limitations. There is a clear need for new cell-based building blocks and bioprinting methods.

The disclosures of all publications, patents, patent applications and published patent applications referred to herein are hereby incorporated herein by reference in their entirety.

BRIEF SUMMARY OF THE INVENTION

The present application provides a bio-block that can serve as a basic building block in cell-based bioprinting or as a research tool. Bio-ink compositions, and methods of bioprinting an artificial tissue or tissue progenitor using the bio-ink compositions, and other methods of using the bio-block or the compositions are further provided.

One aspect of the present application provides a bio-ink composition comprising a plurality of bio-blocks each comprising: a) a core comprising a biodegradable polymeric core material and a cell, and b) a shell comprising a biodegradable polymeric shell material. In some embodiments, the bio-ink composition further comprises a carrier. In some embodiments, the plurality of bio-blocks are suspended homogenously within the carrier. In some embodiments, the carrier is a liquid or a paste. In some embodiments, the carrier comprises a polymer selected from the group consisting of collagen, fibrin, chitosan, alginate, starch, hyaluronic acid, laminin, agarose, gelatin, glucan, elastin, methylcellulose, polyvinyl alcohol, polyamino acid (such as polylysine), acrylate copolymer, and combinations thereof. In some embodiments, the carrier has a viscosity of about 1 Pa·s to about 1000 Pa·s.

In some embodiments according to any one of the bio-ink compositions described above, the bio-ink composition comprises at least about 50% bio-blocks (w/w).

In some embodiments according to any one of the bio-ink compositions described above, the plurality of bio-blocks is of the same type. In some embodiments, the plurality of bio-blocks is of different types.

In some embodiments according to any one of the bio-ink compositions described above, the length of each bio-block is about 30 µm to about 2 mm. In some embodiments, the width of each bio-block is about 30 µm to about 2 mm. In some embodiments, the thickness of each bio-block is about is about 30 µm to about 2 mm. In some embodiments, the ratio between the length and the thickness of each bio-block is no more than about 50:1 (such as no more than about any of 20:1, 10:1, 5:1, or 2:1).

In some embodiments according to any one of the bio-ink compositions described above, the core comprises the cell embedded in the biodegradable polymeric core material. In some embodiments, the core comprises the cell enwrapped by the biodegradable polymeric core material.

In some embodiments according to any one of the bio-ink compositions described above, the core comprise an agent selected from a nutrient, an extracellular matrix factor, a cell factor, and a pharmaceutically active agent. In some embodiments, the core comprises at least 3 different agents. In some embodiments, the core comprises a cell factor that facilitates cell proliferation, and the cell factor is selected from the group consisting of insulin, IGF-I, IGF-II, TGF, VEGF, PDGF, ODGF, SRIH, NGF, EGF, FGF, IL-1, IL-2, IL-3, IL-4, IL-5, IL6, IL-7, IL-8, IL-10, IL-12, CCL, CXC, XCL, MCP, TNF, EPO, CSF, cortisol, T3, T4, and combinations thereof. In some embodiments, the core comprises a cell factor that facilitates cell differentiation, and the cell factor is selected from the group consisting of Oct3/4, Sox2, Klf4, c-Myc, GATA4, TSP1, β-glycerophosphate, dexamethasone, vitamin C, insulin, IBMX, indomethacin, PDGF-BB, 5-azacytidine, and combinations thereof. In some embodiments, the core comprises a cell factor that facilitates cell migration, and the cell factor is selected from the group consisting of cAMP, $PIP_3$, SDF-1, N-cadherin, NF-κB, osteonectin, thromboxane A2, Ras, and combinations thereof. In some embodiments, the core comprises a cell factor that facilitates cell metabolism, and the cell factor is selected from the group consisting of IGF-I, TRIP-Br2, DKK-1, sRANKL, OPG, TRACP-5b, ALP, SIRT1, PGC-1α, PGC-1β, IL-3, IL-4, IL6, TGF-β, PGE2, G-CSF, TNFα, and combinations thereof. In some embodiments, the core comprises a cell factor that facilitates cell secretion, and the cell factor is selected from the group consisting of P600, P110, TCGFIII, BSF-2, glucagon, β-adrenergic agonist, arginine, $Ca^{2+}$, acetyl choline, somatostatin, and combinations thereof. In some embodiments, the core comprises a pharmaceutically active agent, and the pharmaceutically active agent is selected from the group consisting of rhIL-2, rhIL-11, rhEPO, IFN-α, IFN-β, IFN-γ, G-CSF, GM-CSF, rHuEPO, sTNF-R1, rhTNF-α, and combinations thereof.

In some embodiments according to any one of the bio-ink compositions described above, the biodegradable polymeric core material comprises a naturally occurring polymer or derivative thereof. In some embodiments, the naturally occurring polymer is selected from the group consisting of collagen, fibrin, chitosan, alginate, oxidized alginate, starch, hyaluronic acid, laminin, agarose, gelatin, glucan, and combinations thereof. In some embodiments, the biodegradable polymeric core material comprises type I collagen. In some embodiments, the biodegradable polymeric core material consists essentially of type I collagen. In some embodiments, the biodegradable polymeric core material comprises a mixture of type I collagen and alginate.

In some embodiments according to any one of the bio-ink compositions described above, the biodegradable polymeric core material comprises a synthetic polymer. In some embodiments, the synthetic polymer is selected from the group consisting of polyphosphazene, polyacrylic acid, polymethacrylic acid, polylactic acid (PLA), polyglycolic acid (PGA), poly-(lactide-coglycolide acid) (PLGA), poly-orthoester (POE), polycaprolactone (PCL), polyhydroxyrate (PHB), polyamine acid (such as polylysine), degradable polyurethane, copolymers thereof, and combinations thereof.

In some embodiments according to any one of the bio-ink compositions described above, the cell is a stem cell, such as a mesenchymal stem cell (MSC). In some embodiments, the core comprises an agent that induces differentiation of the MSC to an osteoblast or a bone tissue (such as dexamethasone, ascorbic acid, glycerophosphate, or combinations thereof). In some embodiments, the core comprises an agent selected from the group consisting of dexamethasone, ascorbic acid, and glycerophosphate. In some embodiments, the core comprises an agent that induces differentiation of the MSC to a chondrocyte or a cartilage tissue (such as TGF-β3, dexamethasone, ascorbic acid 2-phosphate, sodium pyruvate, proline, insulin, transferrin, selenous acid, or combinations thereof). In some embodiments, the core comprises TGF-β3, dexamethasone, ascorbic acid 2-phosphate, sodium pyruvate, proline, insulin, transferrin, and selenous acid.

In some embodiments according to any one of the bio-ink compositions described above, the core comprises a plurality of cells. In some embodiments, the core comprises at least about 50 cells. In some embodiments, the core comprises about 2 cells to about 50 cells. In some embodiments, the plurality of cells is of the same type. In some embodiments, the plurality of cells is of at least two different types.

In some embodiments according to any one of the bio-ink compositions described above, the plurality of bio-blocks comprises a bio-block comprising at least two cores.

In some embodiments according to any one of the bio-ink compositions described above, the shell is permeable to nutrients. In some embodiments, the shell is permeable to a macromolecule having a molecular weight of at least about 110 kDa.

In some embodiments according to any one of the bio-ink compositions described above, the shell comprises one or more micropores.

In some embodiments according to any one of the bio-ink compositions described above, the shell has a thickness of about 0.1 µm to about 50 µm (such as about 1 µm to about 20 µm).

In some embodiments according to any one of the bio-ink compositions described above, the shell has a modulus of elasticity of about 0.01 MPa to about 100 MPa.

In some embodiments according to any one of the bio-ink compositions described above, the biodegradable polymeric shell material comprises a naturally occurring polymer or derivative thereof. In some embodiments, the naturally occurring polymer is selected from the group consisting of collagen, fibrin, chitosan, alginate, oxidized alginate, starch, hyaluronic acid, laminin, agarose, gelatin, glucan, elastin, and combinations thereof. In some embodiments, the biodegradable polymeric shell material comprises oxidized alginate or alginate. In some embodiments, the oxidation level of the oxidized alginate is about 1% to about 40%. In some embodiments, the biodegradable polymeric shell material comprises at least about 4% oxidized alginate or alginate (w/w). In some embodiments, the biodegradable polymeric shell material comprises a mixture of alginate and oxidized alginate. In some embodiments, the ratio between the alginate and oxidized alginate is about 1:9 to about 9:1.

In some embodiments according to any one of the bio-ink compositions described above, the biodegradable polymeric shell material comprises a synthetic polymer. In some embodiments, the synthetic polymer is selected from the group consisting of polyphosphazene, polyacrylic acid, polymethacrylic acid, polylactic acid (PLA), polyglycolic acid (PGA), poly-(lactide-coglycolide acid) (PLGA), poly-orthoester (POE), polycaprolactone (PCL), polyhydroxyrate (PHB), polyamine acid (such as polylysine), degradable polyurethane, copolymers thereof, and combinations thereof.

In some embodiments according to any one of the bio-ink compositions described above, the biodegradable polymeric shell material is crosslinked.

In some embodiments according to any one of the bio-ink compositions described above, the plurality of bio-blocks comprises a bio-block comprising at least two shells.

In some embodiments according to any one of the bio-ink compositions described above, the bio-block has a hardness of about 0.01 GPa to about 0.4 GPa.

Another aspect of the present application provides a method of preparing an artificial tissue or a tissue progenitor, comprising bioprinting (such as by inkjet or microextrusion) any one of the bio-ink compositions described above to obtain a multi-dimensional construct having a pre-determined pattern. In some embodiments, the bio-ink composition is not bioprinted onto a scaffold.

In some embodiments according to any one of the methods described above, the bioprinting is carried out by inkjet or microextrusion.

In some embodiments according to any one of the methods described above, at least about 80% (such as at least about 90%) of the cells in the plurality of bio-blocks survive after the bioprinting.

In some embodiments according to any one of the methods described above, the method further comprises culturing the multi-dimensional construct in vitro under a condition that allows the cells in the plurality of bio-blocks to proliferate, differentiate, metabolize, migrate, secrete, or any combination thereof. In some embodiments, the shell is at least partially degraded during the culturing.

In some embodiments according to any one of the methods described above, the bioprinting is carried out directly on a subject, such as a human subject. In some embodiments, the bioprinting is carried out directly at a damaged site of a tissue of the subject. In some embodiments, the tissue is a skin tissue. In some embodiments, the method further comprises obtaining cell distribution information of the damaged site of the tissue, wherein the bioprinting is carried out according to the cell distribution information. In some embodiments, the cells in the plurality of bio-blocks are derived from the subject.

Further provided in one aspect of the present application is an artificial tissue or a tissue progenitor prepared by any one of the methods described above. In some embodiments, the length of the artificial tissue or tissue progenitor is at least about 100 µm (such as at least about any of 200 µm, 500 µm, 1 mm or more). In some embodiments, the thickness of the artificial tissue or tissue progenitor is at least about 100 µm (such as at least about any of 200 µm, 500 µm, 1 mm or more). In some embodiments, the cells in the bio-blocks proliferate, differentiate, migrate, or any combination thereof, and optionally wherein the biodegradable polymeric core material is at least partially degraded. In some embodiments, the cells in different bio-blocks are connected to each other, and wherein the biodegradable polymeric core material and/or the biodegradable polymeric shell material are at least partially degraded.

Also provided in one aspect of the present application is a bio-block comprising: a) a core comprising a biodegradable polymeric core material and a cell, and b) a shell comprising a biodegradable polymeric shell material. In some embodiments, the length of the bio-block is about 30 µm to about 2 mm. In some embodiments, the width of the bio-block is about 30 µm to about 2 mm. In some embodiments, the thickness of the bio-block is about 30 µm to about 2 mm. In some embodiments, the ratio between the length and the thickness of the bio-block is no more than about 50:1 (such as no more than about any of 20:1, 10:1, 5:1, or 2:1).

In some embodiments according to any one of the bio-blocks described above, the core comprises the cell embedded in the biodegradable polymeric core material. In some embodiments, the core comprises the cell enwrapped by the biodegradable polymeric core material.

In some embodiments according to any one of the bio-blocks described above, the core comprise an agent selected from a nutrient, an extracellular matrix factor, a cell factor, and a pharmaceutically active agent. In some embodiments, the core comprises at least 3 different agents. In some embodiments, the core comprises a cell factor that facilitates cell proliferation, and the cell factor is selected from the group consisting of insulin, IGF-I, IGF-II, TGF, VEGF, PDGF, ODGF, SRIH, NGF, EGF, FGF, IL-1, IL-2, IL-3, IL-4, IL-5, IL6, IL-7, IL-8, IL-10, IL-12, CCL, CXC, XCL, MCP, TNF, EPO, CSF, cortisol, T3, T4, and combinations thereof. In some embodiments, the core comprises a cell factor that facilitates cell differentiation, and the cell factor is selected from the group consisting of Oct3/4, Sox2, Klf4, c-Myc, GATA4, TSP1, β-glycerophosphate, dexamethasone, vitamin C, insulin, IBMX, indomethacin, PDGF-BB, 5-azacytidine, and combinations thereof. In some embodiments, the core comprises a cell factor that facilitates cell migration, and the cell factor is selected from the group consisting of cAMP, $PIP_3$, SDF-1, N-cadherin, NF-κB, osteonectin, thromboxane A2, Ras, and combinations thereof. In some embodiments, the core comprises a cell factor that facilitates cell metabolism, and the cell factor is selected from the group consisting of IGF-I, TRIP-Br2, DKK-1, sRANKL, OPG, TRACP-5b, ALP, SIRT1, PGC-1α, PGC-1β, IL-3, IL-4, IL6, TGF-β, PGE2, G-CSF, TNFα, and combinations thereof. In some embodiments, the core comprises a cell factor that facilitates cell secretion, and the cell factor is selected from the group consisting of P600, P110, TCGFIII, BSF-2, glucagon, β-adrenergic agonist, arginine, $Ca^{2+}$, acetyl choline, somatostatin, and combinations thereof. In some embodiments, the core comprises a pharmaceutically active agent, and the pharmaceutically active agent is selected from the group consisting of rhIL-2, rhIL-11, rhEPO, IFN-α, IFN-β, IFN-γ, G-CSF, GM-CSF, rHuEPO, sTNF-R1, rhTNF-α, and combinations thereof.

In some embodiments according to any one of the bio-blocks described above, the biodegradable polymeric core material comprises a naturally occurring polymer or derivative thereof. In some embodiments, the naturally occurring polymer is selected from the group consisting of collagen, fibrin, chitosan, alginate, oxidized alginate, starch, hyaluronic acid, laminin, agarose, gelatin, glucan, and combinations thereof. In some embodiments, the biodegradable polymeric core material comprises type I collagen. In some embodiments, the biodegradable polymeric core material consists essentially of type I collagen. In some embodiments, the biodegradable polymeric core material comprises a mixture of type I collagen and alginate.

In some embodiments according to any one of bio-blocks described above, the biodegradable polymeric core material comprises a synthetic polymer. In some embodiments, the synthetic polymer is selected from the group consisting of polyphosphazene, polyacrylic acid, polymethacrylic acid, polylactic acid (PLA), polyglycolic acid (PGA), poly-(lactide-coglycolide acid) (PLGA), polyorthoester (POE), polycaprolactone (PCL), polyhydroxyrate (PHB), polyamino acid (such as polylysine), degradable polyurethane, copolymers thereof, and combinations thereof.

In some embodiments according to any one of the bio-blocks described above, the cell is a stem cell, such as a mesenchymal stem cell (MSC). In some embodiments, the core comprises an agent that induces differentiation of the MSC to an osteoblast or a bone tissue (such as dexamethasone, ascorbic acid, glycerophosphate, or combinations thereof). In some embodiments, the core comprises an agent selected from the group consisting of dexamethasone, ascorbic acid, and glycerophosphate. In some embodiments, the core comprises an agent that induces differentiation of the MSC to a chondrocyte or a cartilage tissue (such as TGF-β3, dexamethasone, ascorbic acid 2-phosphate, sodium pyruvate, proline, insulin, transferrin, selenous acid, or combinations thereof). In some embodiments, the core comprises TGF-β3, dexamethasone, ascorbic acid 2-phosphate, sodium pyruvate, proline, insulin, transferrin, and selenous acid.

In some embodiments according to any one of the bio-blocks described above, the core comprises a plurality of cells. In some embodiments, the core comprises at least about 50 cells. In some embodiments, the core comprises about 2 cells to about 50 cells. In some embodiments, the plurality of cells is of the same type. In some embodiments, the plurality of cells is of at least two different types.

In some embodiments according to any one of the bio-blocks described above, the bio-block comprises at least two cores.

In some embodiments according to any one of the bio-blocks described above, the shell is permeable to nutrients. In some embodiments, the shell is permeable to a macromolecule having a molecular weight of at least about 110 kDa.

In some embodiments according to any one of the bio-blocks described above, the shell comprises one or more micropores.

In some embodiments according to any one of the bio-blocks described above, the shell has a thickness of about 0.1 μm to about 50 μm (such as about 1 μm to about 20 μm).

In some embodiments according to any one of the bio-blocks described above, the shell has a modulus of elasticity of about 0.01 MPa to about 100 MPa.

In some embodiments according to any one of the bio-blocks described above, the biodegradable polymeric shell material comprises a naturally occurring polymer or derivative thereof. In some embodiments, the naturally occurring polymer is selected from the group consisting of collagen, fibrin, chitosan, alginate, oxidized alginate, starch, hyaluronic acid, laminin, agarose, gelatin, glucan, elastin, and combinations thereof. In some embodiments, the biodegradable polymeric shell material comprises oxidized alginate or alginate. In some embodiments, the oxidation level of the oxidized alginate is about 1% to about 40%. In some embodiments, the biodegradable polymeric shell material comprises at least about 4% oxidized alginate or alginate (w/w). In some embodiments, the biodegradable polymeric shell material comprises a mixture of alginate and oxidized alginate. In some embodiments, the ratio between the alginate and oxidized alginate is about 1:9 to about 9:1.

In some embodiments according to any one of the bio-blocks described above, the biodegradable polymeric shell material comprises a synthetic polymer. In some embodiments, the synthetic polymer is selected from the group consisting of polyphosphazene, polyacrylic acid, polymethacrylic acid, polylactic acid (PLA), polyglycolic acid (PGA), poly-(lactide-coglycolide acid) (PLGA), polyorthoester (POE), polycaprolactone (PCL), polyhydroxyrate (PHB), polyamino acid (such as polylysine), degradable polyurethane, copolymers thereof, and combinations thereof.

In some embodiments according to any one of the bio-blocks described above, the biodegradable polymeric shell material is crosslinked.

In some embodiments according to any one of the bio-blocks described above, the bio-block comprises at least two shells.

In some embodiments according to any one of the bio-blocks described above, the bio-block has a hardness of about 0.01 GPa to about 0.4 GPa.

Another aspect of the present application provides a method of preparing a composite construct comprising a first differentiated cell and a second differentiate cell or progenitors thereof, comprising bioprinting a first bio-ink composition and a second bio-ink composition to obtain a multi-dimensional construct having a pre-determined pattern, wherein the first bio-ink composition comprises a plurality of first bio-blocks each comprising: a) a core comprising a biodegradable polymeric core material, a MSC cell, and a first agent or a first cell that induces the MSC to differentiate into the first differentiated cell, and b) a shell comprising a biodegradable polymeric shell material; and wherein the second bio-ink composition comprises a plurality of second bio-blocks each comprising: a) a core comprising a biodegradable polymeric core material, a MSC cell, and a second agent or a second cell that induces the MSC to differentiate into the second differentiated cell, and b) a shell comprising a biodegradable polymeric shell material. In some embodiments, wherein the composite construct comprises artificial bone and cartilage or progenitors thereof, the first bio-blocks each comprises a core comprising an agent that induces the MSC to differentiate into an osteoblast (such as dexamethasone, ascorbic acid, and glycerophosphate), and the second bio-blocks each comprises a core comprising an agent that induces the MSC to differentiate into a chondrocyte (such as TGF-β3, dexamethasone, ascorbic acid 2-phosphate, sodium pyruvate, proline, insulin, transferrin, and selenous acid). In some embodiments, the method further comprises in vitro culturing the multi-dimensional construct for about 1 day to about 19 days. In some embodiments, there is provided a composite construct comprising artificial bone and cartilage or progenitors thereof prepared by any one of the methods of preparing a composite construct described above. In some embodiments, wherein the composite construct comprises endothelial cells and smooth muscle cells or progenitors thereof, the first bio-blocks each comprises a core comprising a MSC and an endothelial cell, and the second bio-blocks each comprises a core comprising a MSC and a smooth muscle cell.

Further provided are kits, commercial batches, and articles of manufacture comprising any one of the bio-blocks, the compositions (such as the pharmaceutical compositions or the bio-ink compositions), the pluralities of bio-blocks, the multi-dimensional constructs (such as composite constructs), the tissue progenitors, or the artificial tissues described above.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE DRAWINGS

FIGS. 3A-3F depict exemplary spherical bio-blocks with different sizes and different number of cells under phase contrast microscopy. The bright outer circles are the shells of the bio-blocks, and the bright spots inside the large circles are the HUVECs in the cores. FIG. 3A shows bio-blocks with a size of 120 µm. FIG. 3B shows bio-blocks with a size of 200 µm. FIG. 3C shows bio-blocks with a size of 450 µm. FIG. 3D shows bio-blocks, each with about 50 cells. FIG. 3E shows bio-blocks, each with about 8 cells. FIG. 3F shows bio-blocks, each with about 2 cells.

FIG. 4 depicts an exemplary bio-block under phase contrast microscopy. One spherical bio-block is shown in the middle of the view. The bright outer circle is the shell of the bio-block, and the bright spots inside are the Human Umbilical Vein Endothelial Cells (HUVECs) in the core.

FIGS. 5A-5F depict bio-blocks of various combinations of polymeric core materials and polymeric shell materials. Scale bar of all figures are 500 µm, unless otherwise stated. Thin white arrows designate locations of shells, and thick white arrows designate locations of cores. FIG. 5A shows bio-blocks with a shell comprising calcium alginate and a core comprising starch. FIG. 5B shows bio-blocks with a shell comprising polylysine and a core comprising type I collagen. FIG. 5C shows bio-blocks with a shell comprising calcium alginate and a core comprising type I collagen. FIG. 5D shows bio-blocks with a shell comprising calcium alginate and a core comprising polyurethane. FIG. 5E shows a bio-block with a shell comprising polylysine-FITC and a core comprising type I collagen stained with tracker CM-DiI (read fluorescence). FIG. 5F shows bio-blocks with a shell comprising polylysine and a core comprising sodium alginate, bar=100 µm.

FIGS. 6A-6B depict an exemplary bio-ink composition for bioprinting. FIG. 6A shows a bio-ink composition comprising a carrier and a plurality of bio-blocks. The dark bio-block further comprises methyl violet in the core to demonstrate integrity of the bio-block after bioprinting. FIG. 6B shows a bioprinted bio-block monolayer with a width of about 250 µm. Shown in the figure is one bio-block surrounded by the carrier, which also serves as a biocompatible (optionally bioadhesive) material to bind the bio-block. The bio-block maintained the structural integrity after bioprinting.

FIG. 7 depicts a plot of viscosity in mPa·s of a carrier comprising sodium alginate and gelatin in an exemplary bio-ink composition as a function of temperature.

FIG. 8A shows HUVECs in bio-blocks immediately after the bio-blocks were prepared. Each large circle shows approximately the boundary of a bio-block. FIG. 8B shows HUVECs in bio-blocks after storage at 4° C. for about 3 hours after preparation. Each large circle shows approximately the boundary of a bio-block. FIG. 8C shows HUVECs in bio-blocks after bioprinting. The white spots with high saturation level, such as the white spot pointed by a white arrow, are dead cells. FIG. 8D shows HUVECs in bio-blocks after culturing at about 37° C. for about 72 hours after preparation. The white spots with high saturation level, such as the white spot pointed by a white arrow, are dead cells. Images were collected using laser scanning confocal microscopy.

FIG. 9A shows HepG2 cells (dark circular spots) inside multiple bio-blocks (large gray circles) on day one of culturing. Cells adopted a circular shape, and did not spread or adhere to other cells. The image was collected under 40 times magnification by phase contrast microscopy. FIG. 9B shows HepG2 cells in a single bio-block on day 5 of culturing. White arrows point to spreading and adherent cells. The image was collected under 200 times magnification by phase contrast microscopy.

FIG. 11A shows cells in capsules immediately after preparation. FIG. 11B shows cells in capsules after culturing for 7 days. FIG. 11C shows cells in bio-blocks immediately after preparation. FIG. 11D shows cells in bio-blocks after culturing for 7 days.

FIG. 12A shows connections among cells of different bio-blocks marked by white circles. FIG. 12B shows connections among cells across the border (marked with an arrow) between two bio-blocks. FIG. 12C shows connections (yellow signal) between HepG2 cells (green) and HUVEC cells (red) across different bio-blocks.

FIGS. 14A-14I depict biological properties of bio-blocks. FIGS. 14A-14D show cell viability in bio-blocks. Living cells were labeled with Calcein AM showing green fluorescence, and dead cells were labeled with propidium iodide showing red fluorescence. FIG. 14A shows HUVECs in a bio-block immediately after the bio-block was prepared. Cell viability was more than 95%. FIG. 14B shows HUVECs in bio-blocks after bioprinting. Cell viability was more than 90%. FIG. 14C shows HUVECs in a bio-block after culturing at about 37° C. with 5% $CO_2$ for about 5 days after preparation. Cell viability was more than 90%. FIG. 14D shows HUVECs in a bio-block after storage at 4° C. for 3 h (left panel), 24 h (middle panel) and 48 h (right panel). Cell viability was more than 90%, 80% and 50%, respectively. FIGS. 14E-14I show cells engaged in normal functions inside bio-blocks. FIG. 14E depicts adhesion and spreading of HUVEC cells inside a bio-block. FIG. 14F depicts proliferation of HepG2 cells inside a bio-block that had been cultured at about 37° C. for about 2 days after preparation of the bio-block. Cell nuclei were stained by DAPI (blue channel), and proliferating cells were stained using EdU (red channel). FIG. 14G shows hepatocytes secreting albumin in bio-blocks. Cell nuclei were stained by DAPI (blue channel), and albumin secreted by hepatocytes was stained by albumin test kit (red channel). FIG. 14H shows connections among cells inside bio-blocks. HUVECs were labeled with cell tracker Green CMFDA showing green fluorescence (left panel), and HepG2 labeled with cell tracker CM-Dil showing red fluorescence (middle panel). Yellow fluorescence in right panel indicates cell connection between HepG2 and HUVEC. FIG. 14I shows BMSC migration in bio-blocks. Arrows indicate the migrated cells.

FIGS. 15A-15D show degradation of bio-block shells and fusion of bio-blocks. FIG. 15A shows a bio-block comprising a polylysine shell and HUVECs. Polylysine was labeled with FITC showing green fluorescence. HUVECs labeled with cell tracker CM-Dil showing red fluorescence. FIG. 15B shows degradation of a bio-block shell using 0.25% trypsin. The shell was degraded partially in 5 min (middle panel), and degraded completely in 10 min (right panel). FIG. 15C shows degradation of a bio-block shell. The shell of the bio-block was partially degraded by the cells in 5 days (middle panel), and completely degraded in 9 days (right panel). FIG. 15D shows fusion of bio-blocks via cell connection after shell degeneration over time.

FIG. 16A shows a REVOTEK B series 3D bioprinter. FIG. 16B shows a bio-block mixed with sodium alginate to be extruded by jet. FIGS. 16C-16F show the shapes of various printed three-dimensional structure. FIG. 16C shows a sheet structure formed by one type of bio-blocks. FIG. 16D shows a sheet structure formed by two types of bio-blocks. FIG. 16E shows a ring-shaped structure formed by two types of bio-blocks. FIG. 16F shows an irregular-shaped structure formed by two types of bio-blocks. FIGS. 16G-16I show accurate distribution of cells in bio-blocks. One type of cells expressed green fluorescence protein. A second type of cells expressed red fluorescence protein.

FIGS. 17A-17J shows that bio-blocks fused into an organic whole to form a tissue-like structure. FIG. 17A shows bio-blocks comprising HepG2 cells labeled with cell tracker Green CMFDA showing green fluorescence. FIG. 17B shows bio-blocks comprising BMSCs labeled with cell tracker CM-Dil showing red fluorescence. FIG. 17C shows that the bio-blocks fused with each other after being cultured at 37° C. with 5% $CO_2$ in H-DMEM media containing about 10% FBS for 3 days. FIG. 17D shows that the bio-blocks fused into a single entity after being cultured at 37° C. with 5% $CO_2$ in H-DMEM media containing about 10% FBS for 9 days. FIG. 17E shows that the bio-blocks fused into a sheet-shaped artificial tissue. Thin arrows designate locations of connection between the two types of bio-blocks. FIG. 17F shows HE staining of the sheet-shaped artificial tissue. FIG. 17G shows that the bio-blocks fused into a ring-shaped artificial tissue. FIG. 17H shows HE staining of the ring-shaped artificial tissue. FIG. 17I shows that the bio-blocks fused into an irregular-shaped artificial tissue. FIG. 17J shows HE staining of the irregular-shaped artificial tissue.

FIG. 25A shows formation of a small number of blood capillaries in an artificial tissue bioprinted using bio-blocks comprising a mixture of BMSC and HUVEC at a ratio of 20:1. FIG. 25B shows formation of a large number of blood capillaries in an artificial tissue bioprinted using bio-blocks comprising a mixture of BMSC and HUVEC at a ratio of 10:1. FIG. 25C shows formation of a small number of blood capillaries in an artificial tissue bioprinted using bio-blocks comprising a mixture of BMSC and HUVEC at a ratio of 3:1. FIG. 25D shows formation of a small number of blood capillaries in an artificial tissue bioprinted using bio-blocks comprising a mixture of BMSC and HUVEC at a ratio of 3:2. FIG. 25E shows formation of a large number of blood capillaries in an artificial tissue bioprinted using bio-blocks comprising a mixture of BMSC, hepatocyte, and HUVEC at a ratio of 10:1:1. FIG. 25F shows formation of a small number of blood capillaries in an artificial tissue bioprinted using bio-blocks comprising a mixture of BMSC, smooth muscle cells, and HUVEC at a ratio of 16:3:1.

DETAILED DESCRIPTION OF THE INVENTION

Figure 1A:
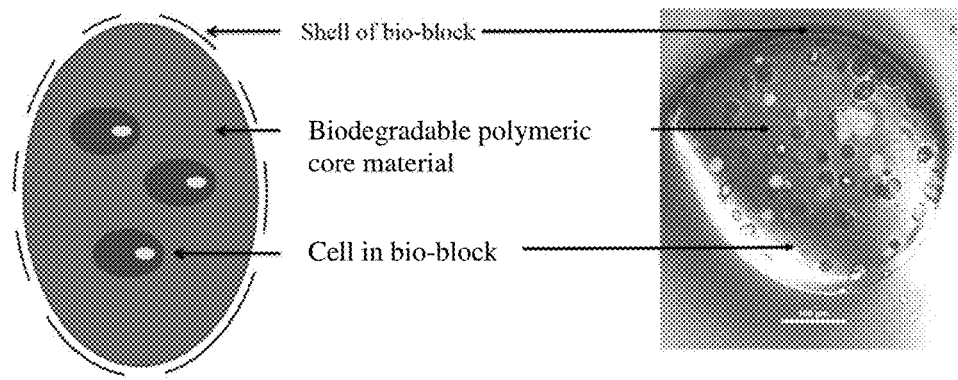
FIG. 1A shows an exemplary bio-block, including a schematic cartoon in the left panel, and an image of a bio-block in the right panel. The core comprises three cells enwrapped by a biodegradable polymeric core material, and the shell has microchannels or micropores for exchange of materials, such as nutrients.

The present application discloses a novel cell-based building block (referred herein as "bio-block") and bio-ink compositions comprising the bio-blocks, which are particularly useful for construction of multi-dimensional biological structures having precise cell distribution patterns. For the first time, a fundamentally unique basic building block (i.e. bio-block) is proposed by the present invention to provide a technical solution to many challenges of current 3-D bioprinting methods for preparing artificial tissues or tissue progenitors. The bio-block of the present application comprises one or more shells each comprising a biodegradable polymeric shell material, and one or more cores each comprising a biodegradable polymeric core material and one or more cells. Each bio-block has a pre-determined number of cells, and cell types. Also, the structure and dimensions of the bio-blocks can be controlled. The polymeric shell material and the polymeric core material of the bio-blocks can further provide favorable and controllable mechanical properties and microenvironments (such as cell factors, nutrients, extracellular matrix, pharmaceutically active agents, etc.) to promote cell activities and functions (such as proliferation, differentiation, migration, metabolism, secretion, etc.). The bio-blocks of the present application can be used to prepare a standardized and controllable bio-ink compatible with many bioprinting systems, allowing precise distribution of cells when used to bioprint an artificial tissue or organ.

Bio-blocks of the present application differ significantly from currently known encapsulated cells due to technical features designed to cater their different uses. Encapsulated cells typically have immobilized cells within or inside a polymeric semi-permeable membrane that shields the cells from immune cells and antibodies of the host, which may otherwise attack and destroy the encapsulated cells. Encapsulated cells can be applied to a site of damaged tissue (such as skin, pancreas, or brain) in a subject in need either directly, or as a mini-tissue comprising encapsulated cells embedded in or deposited on top of a scaffold. The semi-permeable membranes of the transplanted encapsulated cells maintain their integrity over an extended period of time (such as from months to years). Once the semi-permeable membranes are degraded, the encapsulated cells may become non-functional due to immune attacks. By contrast, the bio-blocks of the present application provide effective mechanical protection to the cells to ensure high survival rate (such as 90% or higher) of the cells during bioprinting. The polymeric core material and the polymeric shell material of the bio-blocks can provide sufficient mechanical strength to allow construction of multi-dimensional biological structures (such as tissues or tissue progenitors) without requiring a scaffold. The shell of the bio-block may have microchannels or micropores that allow exchange of a variety of macromolecules to promote cell activities and functions. Furthermore, it is desirable in certain embodiments for the shells of the bio-blocks to have a relatively fast degradation rate (such as complete degradation within about 2 days to about 28 days) to allow fusion of cells from adjacent bio-blocks. In some embodiments, bioprinted multidimensional structures comprising the bio-blocks are cultured in vitro to promote degradation of the shells and formation of an integrated and functional tissue or tissue progenitor before transplantation into a subject in need.

Further provided in the present invention are bio-ink compositions comprising the bio-blocks, and methods of using the bio-blocks and bio-ink compositions, including bioprinting an artificial tissue or tissue progenitor using the bio-ink compositions. Compared to the current bioprinting technologies, the methods described herein provide higher and customizable precision in the positioning of individual cells or groups of cells in a multi-dimensional construct. The precision of the bioprinted construct can be controlled by using bio-blocks having suitable dimensions, structure, and cell compositions. Additionally, cells within each bio-block can be regulated in a highly tailored fashion depending on the cell factors and biopolymers included in the bio-block, which enables fine control among different functional units and regions within a complex tissue or organ. The mechanically robust polymeric shell and core materials of the bio-block ensure high cell viability during the often stressful bioprinting process. Mechanical strength of the bio-blocks in some embodiments obviates the need for a scaffold (such as hydrogel sheets) or a substrate in bioprinted artificial tissues or organs. In some embodiments, a bioprinted multi-dimensional construct can be cultured in vitro prior to use. The culturing step can allow cells to proliferate and undergo cellular activities within and beyond bio-blocks to significantly increase cell density of multi-dimensional construct without breaking down the intended cellular distribution pattern.

Furthermore, in some embodiments, the present application provides a bio-block comprising a shell comprising oxidized alginate, which enables control of the degradation rate of the shell, such as by controlling the oxidation level of the oxidized alginate in the polymeric shell material. The technical effect of using oxidized alginate in the polymeric core and/or polymeric shell material is significant and beneficial. In particular, sodium alginate is a natural polysaccharide, which can dissolve in cold or warm water to form a viscous, homogenous solution. When contacting a calcium solution, a sodium alginate solution can form calcium alginate that can be deposited to form a structure. Therefore, sodium alginate has been used in a variety of cell encapsulation studies. However, because the degradation rate of calcium alginate is relatively slow, cells encapsulated in a shell comprising calcium alginate may have a growth rate that mismatches the degradation rate of calcium alginate, which can result in failure of the proliferated cells to penetrate the shell and to interact intimately with cells outside the shell, thereby inhibiting formation of an integrated tissue. Inventors of the present application surprisingly discovered that the degradation rate of a shell in a bio-block can be regulated, for example, by including oxidized alginate with a suitable oxidation level in the polymeric shell material, thereby allowing the growth rate of cells in a bio-block to match the degradation rate of the shell.

The bio-blocks, as well as the artificial tissues and the tissue progenitors comprising the bio-blocks or prepared by bioprinting of the bio-blocks and the bio-ink compositions disclosed herein are useful for a variety of applications in research and medicine, including tissue engineering, in vitro research, stem cell differentiation, in vivo research, drug screening, drug discovery, tissue regeneration, and regenerative medicine.

Accordingly, in some embodiments, there is provided a bio-ink composition comprising a plurality of bio-blocks each comprising: a) a core comprising a biodegradable polymeric core material and a cell, and b) a shell comprising a biodegradable polymeric shell material (such as oxidized alginate). In some embodiments, the bio-ink composition further comprises a carrier.

In some embodiments, there is provided a method of preparing an artificial tissue or a tissue progenitor, comprising bioprinting a bio-ink composition to obtain a multi-dimensional construct having a pre-determined pattern, wherein the bio-ink composition comprises a plurality of bio-blocks each comprising: a) a core comprising a biodegradable polymeric core material and a cell, and b) a shell comprising a biodegradable polymeric shell material (such as oxidized alginate).

In some embodiments, there is provided a bio-block comprising: a) a core comprising a biodegradable polymeric core material and a cell, and b) a shell comprising a biodegradable polymeric shell material (such as oxidized alginate).

Definitions

Terms are used herein as generally used in the art, unless otherwise defined as follows.

As used herein, "bio-block" refers to a cell-based basic building block that can be used in many fields, such as bioprinting (e.g., 3D bioprinting), tissue engineering, and regenerative medicine. In particular, the bio-block of the present application comprises a one or more cores each comprising one or more cells, and one or more shells each coats at least one core, wherein the one or more cores and the one or more shells each (for example, independently) comprise a biodegradable material. Schematic diagrams showing exemplary core-shell structures of bio-blocks are depicted in FIG. 1B-1F.

As used herein, "MSC bio-block" refers to a bio-block comprising at least one core comprising one or more mesenchymal stem cells (MSC). "Type I MSC bio-block" refers to a MSC bio-block having a microenvironment (including, for example, agents) that is suitable for differentiation of the one or more MSCs towards osteoblasts or bone tissue. "Type II MSC bio-block" refers to a MSC bio-block having a microenvironment (including, for example, agents) that is suitable for differentiation of the one or more MSCs towards chondrocytes or cartilage tissue. "Type III MSC bio-block" refers to a MSC bio-block having a microenvironment (including, for example, agents) that is suitable for differentiation of the one or more MSCs towards endothelial cells. "Type IV MSC bio-block" refers to a MSC bio-block having a microenvironment (including, for example, agents) that is suitable for differentiation of the one or more MSCs towards smooth muscle cells.

As used herein, "bio-ink" refers to a liquid or paste composition suitable for bioprinting, wherein the composition comprises one or more types of bio-blocks. For example, the bio-ink can be a solution, suspension, gel, or concentrate containing bio-blocks. In some embodiments, the bio-ink comprises a plurality of bio-blocks and a carrier, such as a cell-adhesive carrier. The bio-ink can be used for bioprinting to obtain a planar and/or sheet-like structure having pre-determined dimensions. The planar and/or sheet-like structure can be further deposited to form a three-dimensional construct having a pre-determined shape and structure. Cells in the bio-blocks of the bio-ink composition can engage in expected life activities before, during, and/or after bioprinting.

As used herein, "bioprint" refers to printing using a material comprising biological substances, including biological molecules derived from biological sources (e.g. proteins, lipids, carbohydrates, nucleic acids, metabolites, and/or small molecules), cells, subcellular structures (e.g. organelles, membranes, etc.), groups of cells, groups of subcellular structures, or molecules that are related to biological molecules (e.g. synthetic biological molecules or synthetic analogs of biological molecules). "Printing" refers to a process of depositing a material according to a pre-determined pattern, design or scheme. "Printing" (such as bioprinting) described herein can be carried out by a variety of methods, including, but not limited to, printing using a printer (such as a 3D printer or bioprinter), printing using an automated or non-automated mechanical process rather than a printer, and printing by manual deposition (e.g. using a pipette).

As used herein, "tissue" refers to an ensemble of one or more groups of cells each having the same or similar morphology and functions. Tissue typically further comprises non-cell materials known as intercellular substance, such as extracellular matrix and fibers. A tissue may include a single type of cells or multiple types of cells. As used herein, "organ" refers to a structural unit comprising one or more tissues for serving one or more specific bodily functions. In some embodiments, an organ consists of a single tissue. In some embodiments, an organ comprises multiple tissues. "Artificial tissue" refers to a tissue that is not formed through natural tissue generation or development processes inside a biological organism. In some embodiments, an artificial tissue is a man-made tissue, such as a bioprinted tissue. "Artificial tissue" and "tissue construct" are used interchangeably herein. "Tissue progenitor" refers to an ensemble of cells that are capable of forming a tissue that can carry out a specific function, upon culturing, induction, or other manipulation steps. In some embodiments, a tissue progenitor is a man-made (i.e. "artificial") tissue progenitor. In some embodiments, the cells in the tissue progenitor are not connected to each other. In some embodiments, the cells in the tissue progenitor are partially connected to each other.

As used herein, "multi-dimensional construct" refers to a structure of at least one dimension, and typically no more than three dimensions. In some embodiments, the multi-dimensional construct is a two-dimensional structure. In some embodiments, the multi-dimensional construct is a three-dimensional structure.

As used herein, "composite construct" refers to a multi-dimensional construct having at least two types of cells, or a progenitor thereof. For example, the composite construct may have a mixture of two or more cell types, which may be arranged in a specific distribution pattern. Alternatively, the composite construct may have a single type of progenitor cells (such as stem cell, for example, MSC) under two or more types of microenvironments for differentiation, whereby culturing the composite construct may produce a mature composite construct having two or more types of differentiated cell types derived from the progenitor cells.

As used herein, "biodegradable" material refers to material that can be degraded and/or absorbed by cells or organisms, and the degradation materials are biocompatible. Biodegradable material can be obtained from a natural source (such as from animals or plants), modified from a naturally-occurring material, or synthesized. "Biocompatible" material refers to non-cytotoxic material (including degradation products thereof). Biocompatible material can be transplanted into a host (such as human) without causing significant or severe adverse effects. For example, the biocompatible material does not cause cytotoxic effects to the host (such as human tissue), or induce immune rejection, allergy, or inflammation in the host.

As used herein, "mechanical protection" refers to reduction or avoidance of external mechanical or physical damage (such as damage due to shearing force or pressure generated in a 3D bioprinting process) to cells, for example, as provided by shells having a suitable hardness and elastic modulus in bio-blocks.

As used herein, "agent" refers to a chemical, molecule, biochemical, or drug, including, but not limited to a small molecule compound, a hormone, a peptide (such as an oligopeptide, or a protein), a nucleic acid (such as an oligonucleotide, a DNA, an RNA, or a chemically modified nucleic acid), or the like, which can have an effect on cellular activities, functions, and/or behaviors. The agent may be derived from a natural source, produced using recombinant methods, or synthesized chemically. The agents can have the same molecular identity as factors or molecules secreted or produced by cells in the bio-blocks, but the agents described herein are obtained from exogenous sources other than the cells in the bio-blocks.

As used herein, "cell factor" refers to an agent that mediates signaling inside or among cells. A cell factor may maintain, promote, improve or regulate proliferation, differentiation, migration, metabolism, and/or secretion of a cell.

As used herein, "stimulus" refers to a chemical factor (such as agent, acid, base, oxygen concentration, etc.) or a physical factor (such as temperature, light, mechanical force, etc.), which can have an effect on cellular activities, functions, and/or behaviors.

As used herein, a "subject" refers to an animal, such as vertebrates. In some embodiments, the subject is a mammal, including, but not limited to, human, bovine, horse, feline, canine, rodent, or primate. In some embodiments, the subject is a human. "Patient", "subject", and "individual" are used herein interchangeably.

As used herein, "length" of a three-dimensional object (such as bio-block, three-dimensional construct, artificial tissue, or tissue progenitor) is defined as the longest line within the body of the object. "Width" of the three-dimensional object is defined as the longest line in the body of the object that is orthogonal to the length. "Thickness" of the three-dimensional object is defined as the longest line in the body of the object that is orthogonal to both length and width, wherein the thickness is shorter or equal to the width. For a spherical object, the length, width, and thickness of the object equal to the diameter. The direction of the length of the object is defined as the "x-axis," the direction of the width of the object is defined as the "y-axis," and the direction of the thickness of the object is defined as the "z-axis."

Unless otherwise stated, "percentage" used herein refers to weight by weight (i.e., w/w) percentage.

Unless otherwise stated, "ratio" used herein refers to weight by weight (i.e., w/w) ratio.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

Bio-Blocks

The present invention provides bio-blocks useful for making multi-dimensional constructs of a pre-determined pattern, tissue progenitors, and ultimately artificial tissues.

The present application in one aspect provides a bio-block comprising a core comprising a biodegradable core material (such as a polymeric material) and a cell, and a shell comprising a biodegradable shell material (such as a polymeric material). In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, the bio-block has one or more (such as any of 1, 2, 3, 4, 5, or 6) of the following properties or characteristics: (1) the core is in a gel state; (2) the shell provides mechanical support to the core; (3) the core further comprises an agent that regulates (such as facilitates) cell proliferation, differentiation, migration, metabolism, or secretion; (4) the biodegradable polymeric core material comprises a mixture of type I collagen and alginate; (5) the shell comprises one or more micropores; and (6) the biodegradable polymeric shell material comprises alginate (such as comprising alginate, gelatin and elastin). In some embodiments, the size of the bio-block is about 30 μm to about 800 μm. In some embodiments, the biodegradable polymeric core material comprises a naturally occurring polymer. In some embodiments, the core comprises about 1 cell to about 5000 cells (such as about 2 cells to about 50 cells, or about 100 cells to about 5000 cells). In some embodiments, the shell has a thickness of about 0.1 μm to about 50 μm, such as about 1 μm to about 20 μm. In some embodiments, the biodegradable polymeric shell material comprises a naturally occurring polymer. In some embodiments, the biodegradable polymeric shell material comprises calcium.

Embodiments of the bio-blocks described herein may have one or more technical advantages including, but not limited to:

(1) The core comprises a controllable number, types, and ratios of cells, which is suitable as a standardized, controllable bioprinting material;

(2) The biodegradable polymeric materials, as well as the agents (such as cell factors) in the core and/or the shell provides a specific microenvironment (including, for example, growth factors and nutrients for cell growth and differentiation, space for cell proliferation and differentiation, physical factor and mechanical stimulus for promoting biological functions of the cell, feeder cells for cooperating or regulating stem cell differentiation, etc.) to regulate activities and function of the cell;

(3) The core-shell structure of the bio-block allows the bio-block to have suitable hardness, mechanical strength, and elastic modulus to provide mechanical protection and stable physical space for cell survival and growth in the bio-blocks;

(4) The bio-block enables precise cell distribution in multi-dimensional structures constructed thereof (such as by bioprinting). Specifically, different types of bio-blocks, which may have different structures, different types of cells, different types of cell factors, and/or different biodegradable polymeric material, can be prepared according to the need. The different types of bio-blocks can then be used in bioprinting, and optionally be cultured to proliferate without disrupting the pre-determined cell distribution pattern, in order to obtain an artificial tissue with precise cell distribution patterns;

(5) The cell can be regulated using one or more cell factors or pharmaceutically active agents that are supplemented in the bio-block to promote proliferation, differentiation, migration, metabolism, and/or secretion;

(6) The shell is degradable, such as by including oxidized alginate in the biodegradable polymeric shell material, and the degradation rate of the shell can be controlled (such as by choosing a suitable oxidation level of the oxidized alginate) to match the growth rate of cells in the bio-block.

Thus, in some embodiments, there is provided a bio-block comprising a core comprising a biodegradable polymeric core material and a cell, and a shell comprising a biodegradable polymeric shell material. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%). In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 μm to about 50 μm (such as about 1 μm to about 20 μm). In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a modulus of elasticity of about 0.01 MPa to about 100 MPa. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell is permeable to a macromolecule having a molecular weight larger than about 110 kDa. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), and wherein the shell has a thickness of about 0.1 μm to about 50 μm (such as about 1 μm to about 20 μm). In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), and wherein the shell has a modulus of elasticity of about 0.01 MPa to about 100 MPa. In some embodiments, the biodegradable polymeric core material comprises a naturally occurring polymer. In some embodiments, the core comprises about 1 cell to about 5000 cells (such as about 2 cells to about 50 cells, or about 100 cells to about 5000 cells). In some embodiments, the biodegradable polymeric shell material comprises a naturally occurring polymer. In some embodiments, the biodegradable polymeric shell material is crosslinked (such as by a divalent ion, for example, $Ca^{2+}$). In some embodiments, the bio-block comprises one or more micropores. In some embodiments, the bio-block has a hardness of about 0.01 GPa to about 0.4 GPa.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), and wherein the shell is permeable to a macromolecule having a molecular weight larger than about 110 kDa. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), and wherein the shell has a modulus of elasticity of about 0.01 MPa to about 100 MPa. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), and wherein the shell is permeable to a macromolecule having a molecular weight larger than about 110 kDa. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a modulus of elasticity of about 0.01 MPa to about 100 MPa, and wherein the shell is permeable to a macromolecule having a molecular weight larger than about 110 kDa. In some embodiments, the length of the bio-block is about 30

µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a modulus of elasticity of about 0.01 MPa to about 100 MPa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a modulus of elasticity of about 0.01 MPa to about 100 MPa, and wherein the biodegradable polymeric core material comprises type I collagen. In some embodiments, the length of the bio-block is about 30 µm to about 2 mm. In some embodiments, the ratio between the length and the thickness of the bio-block is no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell is permeable to a macromolecule having a molecular weight larger than about 110 kDa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell is permeable to a macromolecule having a molecular weight larger than about 110 kDa, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 µm to about 50 µm (such as about 1 µm to about 20 µm), and wherein the shell has a modulus of elasticity of about 0.01 MPa to about 100 MPa. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 µm to about 50 µm (such as about 1 µm to about 20 µm), and wherein the shell is permeable to a macromolecule having a molecular weight larger than about 110 kDa. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 µm to about 50 µm (such as about 1 µm to about 20 µm), and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 µm to about 50 µm (such as about 1 µm to about 20 µm), and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a modulus of elasticity of about 0.01 MPa to about 100 MPa, and wherein the shell is permeable to a macromolecule having a molecular weight larger than about 110 kDa. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a modulus of elasticity of about 0.01 MPa to about 100 MPa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a modulus of elasticity of about 0.01 MPa to about 100 MPa, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell is permeable to a macromolecule having a molecular weight larger than about 110 kDa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell is permeable to a macromolecule having a molecular weight larger than about 110 kDa, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the shell is permeable to a macromolecule having a molecular weight larger than about 110 kDa. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), wherein the shell has a modulus of elasticity of about 0.01 MPa to about 100 MPa, and wherein the shell is permeable to a macromolecule having a molecular weight larger than about 110 kDa. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), wherein the shell has a modulus of elasticity of about 0.01 MPa to about 100 MPa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), wherein the shell has a modulus of elasticity of about 0.01 MPa to about 100 MPa, and wherein the biodegradable polymeric core material comprises type I collagen. In some embodiments, the biodegradable polymeric shell material comprises oxidized alginate (such as with an oxidation level of about 1% to about 40%, and/or a weight percentage of at least about 5%). In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), wherein the shell is permeable to a macromolecule having a molecular weight larger than about 110 kDa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), wherein the shell is permeable to a macromolecule having a molecular weight larger than about 110 kDa, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 µm to about 50 µm (such as about 1 µm to about 20 µm), wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a modulus of elasticity of about 0.01 MPa to about 100 MPa, wherein the shell is permeable to a macromolecule having a molecular weight larger than about 110 kDa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a modulus of elasticity of about 0.01 MPa to about 100 MPa, wherein the shell is permeable to a macromolecule having a molecular weight larger than about 110 kDa, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a modulus of elasticity of about 0.01 MPa to about 100 MPa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a modulus of elasticity of about 0.01 MPa to about 100 MPa, wherein the shell is permeable to a macromolecule having a molecular weight larger than about 110 kDa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 μm to about 50 μm (such as about 1 μm to about 20 μm), wherein the shell is permeable to a macromolecule having a molecular weight larger than about 110 kDa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 μm to about 50 μm (such as about 1 μm to about 20 μm), wherein the shell has a modulus of elasticity of about 0.01 MPa to about 100 MPa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 μm to about 50 μm (such as about 1 μm to about 20 μm), wherein the shell has a modulus of elasticity of about 0.01 MPa to about 100 MPa, wherein the shell is permeable to a macromolecule having a molecular weight larger than about 110 kDa, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 μm to about 50 μm (such as about 1 μm to about 20 μm), wherein the shell has a modulus of elasticity of about 0.01 MPa to about 100 MPa, wherein the shell is permeable to a macromolecule having a molecular weight larger than about 110 kDa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the core is in a gel state. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell is permeable to a macromolecule having a molecular weight larger than about 110 kDa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a modulus of elasticity of about 0.01 MPa to about 100 MPa, wherein the shell is permeable to a macromolecule having a molecular weight larger than about 110 kDa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a modulus of elasticity of about 0.01 MPa to about 100 MPa, wherein the shell is permeable to a macromolecule having a molecular weight larger than about 110 kDa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 µm to about 50 µm (such as about 1 µm to about 20 µm), wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 µm to about 50 µm (such as about 1 µm to about 20 µm), wherein the shell is permeable to a macromolecule having a molecular weight larger than about 110 kDa, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 µm to about 50 µm (such as about 1 µm to about 20 µm), wherein the shell is permeable to a macromolecule having a molecular weight larger than about 110 kDa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 µm to about 50 µm (such as about 1 µm to about 20 µm), wherein the shell has a modulus of elasticity of about 0.01 MPa to about 100 MPa, and wherein the biodegradable polymeric core material comprises type I collagen. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 µm to about 50 µm (such as about 1 µm to about 20 µm), wherein the shell has a modulus of elasticity of about 0.01 MPa to about 100 MPa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 μm to about 50 μm (such as about 1 μm to about 20 μm), wherein the shell has a modulus of elasticity of about 0.01 MPa to about 100 MPa, and wherein the shell is permeable to a macromolecule having a molecular weight larger than about 110 kDa. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 μm to about 50 μm (such as about 1 μm to about 20 μm), wherein the shell has a modulus of elasticity of about 0.01 MPa to about 100 MPa, wherein the shell is permeable to a macromolecule having a molecular weight larger than about 110 kDa, and wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 μm to about 50 μm (such as about 1 μm to about 20 μm), wherein the shell has a modulus of elasticity of about 0.01 MPa to about 100 MPa, wherein the shell is permeable to a macromolecule having a molecular weight larger than about 110 kDa, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 μm to about 50 μm (such as about 1 μm to about 20 μm), wherein the shell has a modulus of elasticity of about 0.01 MPa to about 100 MPa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 μm to about 50 μm (such as about 1 μm to about 20 μm), wherein the shell is permeable to a macromolecule having a molecular weight larger than about 110 kDa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a modulus of elasticity of about 0.01 MPa to about 100 MPa, wherein the shell is permeable to a macromolecule having a molecular weight larger than about 110 kDa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two cores and/or at least two shells.

In some embodiments, there is provided a bio-block comprising a core comprising a biodegradable polymeric core material and a cell, and a shell comprising a biodegradable polymeric shell material, wherein the shell has a thickness of about 0.1 μm to about 50 μm (such as about 1 μm to about 20 μm), wherein the shell has a modulus of elasticity of about 0.01 MPa to about 100 MPa, wherein the shell is permeable to a macromolecule having a molecular weight larger than about 110 kDa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 μm to about 50 μm (such as about 1 μm to about 20 μm), wherein the shell has a modulus of elasticity of about 0.01 MPa to about 100 MPa, wherein the shell is permeable to a macromolecule having a molecular weight larger than about 110 kDa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, and wherein the biodegradable polymeric core material comprises type I collagen. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block comprising a core comprising a biodegradable polymeric core material and a cell, and a shell comprising a biodegradable polymeric shell material, wherein the biodegradable polymeric shell material comprises oxidized alginate (such as with an oxidation level of about 1% to about 40%, and/or a weight percentage of at least about 5%), wherein the shell has a thickness of about 0.1 μm to about 50 μm (such as about 1 μm to about 20 μm), wherein the shell has a modulus of elasticity of about 0.01 MPa to about 100 MPa, wherein the shell is permeable to a macromolecule having a molecular weight larger than about 110 kDa, wherein the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent, wherein the biodegradable polymeric core material comprises type I collagen, wherein the length of the bio-block is about 30 μm to about 2 mm, wherein the ratio between the length and the thickness of the bio-block is no more than about 50:1 (such as no more than about any of 20:1, 10:1, 5:1, or 2:1), wherein the core comprises about 1 cell to about 5000 cells (such as about 2 cells to about 50 cells, or about 100 cells to about 5000 cells), wherein the bio-block comprises one or more micropores (such as with a size of more than about 50 nm), wherein the bio-block has a hardness of about 0.01 GPa to about 0.4 GPa.

Many properties of the bio-block can be customized to satisfy the different needs in constructing artificial tissues with different multi-dimensional constructs and cell distribution patterns. It is intended that any of the properties (such as composition, ratio, physical and chemical properties, etc.) of one component (such as cell, biodegradable material, agent, core, shell, etc.) of the bio-block as described herein can be combined with any of the properties of another component of the bio-block as described herein, as if each and every combination is individually described. Descriptions of the properties and components below apply to each core and shell, or subcomponents (such as cell) thereof, of the bio-block.

Structure

In some embodiments, there is provided a bio-block comprising a core comprising a biodegradable polymeric core material and a cell, and a shell comprising a biodegradable polymeric shell material. In some embodiments, the core comprises the cell embedded in the biodegradable polymeric core material. In some embodiments, the core comprises the cell enwrapped by the biodegradable polymeric core material. In some embodiments, the cells are evenly distributed within the core. In some embodiments, the cells are aggregated in the center or another location inside the core. In some embodiments, the cells are immobilized in the core. In some embodiments, the cells can diffuse freely in the core. In some embodiments, the shell provides mechanical support to the core. FIG. 1A shows a schematic cartoon of an exemplary embodiment of a bio-block, wherein the shell of the bio-block is the exterior layer of the bio-block that surrounds and mechanically protects the core in the interior, which comprises at least one cell.

In some embodiments, there is provided a bio-block comprising a core and a shell, wherein the core comprises a cell, and wherein the shell coats the core. "Coat" or "coating" refers to the structural relationship of two adjacent structural layers, wherein the outer structural layer covers, surrounds, enwraps, or embeds (i.e. coats) the inner structural layer. In some embodiments, the shell does not comprise a cell. In some embodiments, the core comprises a biodegradable core material. In some embodiments, the shell comprises a biodegradable shell material. In some embodiments, the biodegradable core material and the biodegradable shell material are identical. In some embodiments, the biodegradable core material and the biodegradable shell material are different.

The bio-block may have a combination of any number of cores (such as any one of 1, 2, 3, 4, 5, 6, 7, 8, 9, 10, or more) and any number of shells (such as any one of 1, 2, 3, 4, 5, 6, 7, 8, 9, 10, or more). The bio-block of the present invention may adopt a variety of structures, including, but not limited to the structures illustrated in FIGS. 1B-1F. Typically, the most interior structural layer of the bio-block is a core, and the most exterior structural layer of the bio-block is a shell. Each core may be coated (such as surrounded, enwrapped, or embedded) by a shell, or a second core. A shell may be coated (such as surrounded, enwrapped, or embedded) by a second shell or a core, or a shell may be the most exterior structural layer of the bio-block. The bio-block may contain consecutive structural layers being all cores, or being all shells. The bio-block may also contain alternating structural layers, wherein core and shell alternates in at least three consecutive structural layers, e.g., in the order of core-shell-core or shell-core-shell. The bio-block may also comprise a combination of consecutive structural layers and alternating structural layers. In some embodiments, a shell coats two or more cores.

Figure 1B:
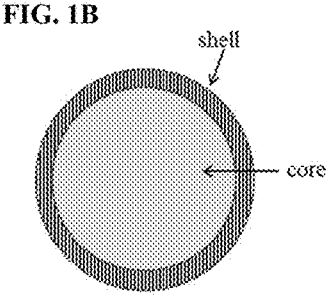
FIG. 1B depicts an exemplary bio-block structure having a single shell and a single core, wherein the shell coats the core.

In some embodiments, the bio-block consists of (including consists essentially of) a single core and a single shell. In some embodiments, the bio-block consists (including consists essentially of) of a single shell coating a single core. In some embodiments, the bio-block has a structure as shown in FIG. 1B.

Figure 1C:
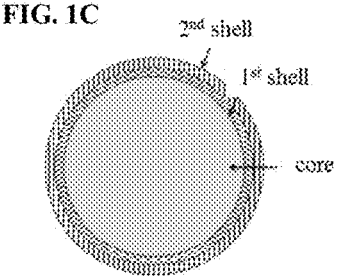
FIG. 1C depicts an exemplary bio-block structure having a single core coated by a first shell, and the first shell coated by a second shell.
Figure 1D:
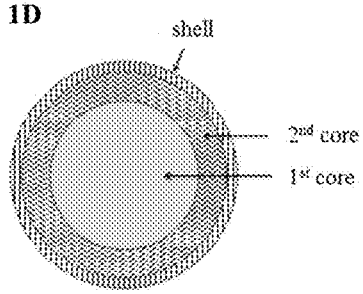
FIG. 1D depicts an exemplary bio-block structure having a first core coated by a second core, and the second core coated by a single shell.

In some embodiments, the bio-block comprises at least two (such as at least about any of 2, 3, 4, 5, 6, 7, 8, 9, 10, or more) cores. In some embodiments, the bio-block comprises at least two (such as at least about any of 2, 3, 4, 5, 6, 7, 8, 9, 10, or more) shells. In some embodiments, the bio-block comprises a single core and at least two (such as at least about any of 2, 3, 4, 5, 6, 7, 8, 9, 10, or more) shells, wherein the single core is the most interior structural layer of the bio-block. In some embodiments, the at least two shells are consecutive with respect to each other. In some embodiments, the bio-block comprises a first shell, a second shell and a single core, wherein the first shell coats the single core, and the second shell coats the first shell. In some embodiments, the bio-block has a structure as shown in FIG. 1C. In some embodiments, the bio-block comprises at least two (such as at least about any of 2, 3, 4, 5, 6, 7, 8, 9, 10, or more) cores and a single shell, wherein the single shell is the most exterior structural layer of the bio-block. In some embodiments, the at least two cores are consecutive with respect to each other. In some embodiments, the bio-block comprises a first core, a second core and a single shell, wherein the second core coats the first core, and the single shell coats the second core. In some embodiments, the bio-block has a structure as shown in FIG. 1D.

Figure 1E:
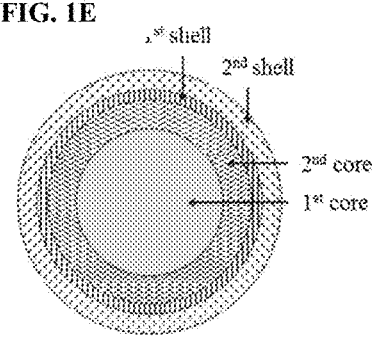
FIG. 1E depicts an exemplary bio-block structure having a first core coated by a second core, the second core coated by a first shell, and the first shell coated by a second shell.
Figure 1F:
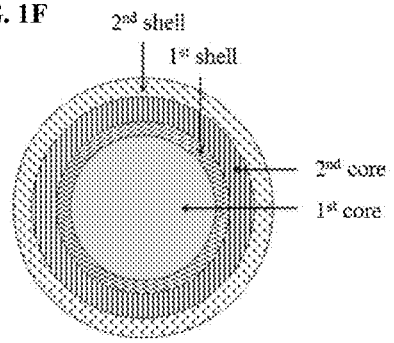
FIG. 1F depicts an exemplary bio-block structure having a first core coated by a first shell, the first shell coated by a second core, and the second core coated by a second shell.

In some embodiments, the bio-block comprises at least two (such as at least about any of 2, 3, 4, 5, 6, 7, 8, 9, 10, or more) cores and at least two (such as at least about any of 2, 3, 4, 5, 6, 7, 8, 9, 10, or more) shells. In some embodiments, the at least two cores are on the interior side of the bio-block with respect to the at least two shells. In some embodiments, the at least two cores are consecutive with respect to each other, and the at least two shells are consecutive with respect to each other. For example, in some embodiments, the bio-block comprises a first core, a second core, a first shell, and a second shell, wherein the second core coats the first core, the first shell coats the second core, and the second shell coats the first shell. In some embodiments, the bio-block has a structure as shown in FIG. 1E. In some embodiments, the bio-block has an alternating core-shell structure. For example, in some embodiments, the bio-block comprises a first core, a second core, a first shell, and a second shell, wherein the first shell coats the first core, the second core coats the first shell, and the second shell coats the second core. In some embodiments, the bio-block has a structure as shown in FIG. 1F.

In some embodiments, each core independently enwraps or embeds a cell or a plurality of cells. For example, wherein the bio-block has two cores, both cores may enwrap or embeds the same cell or plurality of cells, or each core may comprise a different cell or cell composition. In some embodiments, wherein the bio-block has three cores, all three cores may comprise the same cell or plurality of cells; or each of the three cores may comprise a different cell or plurality of cells; or two of the three cores may comprise the same cell or plurality of cells, and the third core may comprise a different cell or plurality of cells.

The bio-blocks can be of any suitable shape. In some embodiments, the bio-block is spherical, cubical, rectangular prism, hexagonal prism, cylindrical, or of irregular shape. In some embodiments, the bio-block is spherical. Different shapes can be chosen to tailor to the specific need for a given tissue. For example, some shapes (such as spherical, cubical, or hexagonal prism) may allow tight packing of the bio-blocks in a tissue construct. Some shapes (such as irregular shape) may allow construction of special structural features in a tissue or tissue progenitor.

The dimensions of the bio-block can be pre-determined according to the desired precision in cell distribution within an artificial tissue. In some embodiments, the length of the bio-block is at least about any of 20, 30, 50, 100, 120, 150, 200, 250, 300, 350, 400, 450, 500, 600, 700, 800, 900, 1000, 1500, or 2000 µm. In some embodiments, the length of the bio-block is about any of 20-30, 30-50, 50-100, 100-150, 150-200, 200-250, 250-300, 300-350, 350-400, 400-450, 450-500, 500-600, 600-700, 700-800, 800-900, 900-1000, 1000-1500, 1500-2000, 20-50, 20-100, 100-200, 200-400, 500-600, 600-800, 800-1000, 1000-2000, 20-100, 100-500, 100-800, 500-1000, 300-800, 30-50, 30-200, 30-500, 30-800, 30-1000, 30-2000, or 20-2000 µm. In some embodiments, the width of the bio-block is at least about any of 20, 30, 50, 100, 120, 150, 200, 250, 300, 350, 400, 450, 500, 600, 700, 800, 900, 1000, 1500, or 2000 µm. In some embodiments, the width of the bio-block is about any of 20-30, 30-50, 50-100, 100-150, 150-200, 200-250, 250-300, 300-350, 350-400, 400-450, 450-500, 500-600, 600-700, 700-800, 800-900, 900-1000, 1000-1500, 1500-2000, 20-50, 20-100, 100-200, 200-400, 500-600, 600-800, 800-1000, 1000-2000, 20-100, 100-500, 100-800, 500-1000, 300-800, 30-50, 30-200, 30-500, 30-800, 30-1000, 30-2000, or 20-2000 µm. In some embodiments, the thickness of the bio-block is at least about any of 20, 30, 50, 100, 120, 150, 200, 250, 300, 350, 400, 450, 500, 600, 700, 800, 900, 1000, 1500, or 2000 µm. In some embodiments, the thickness of the bio-block is about any of 20-30, 30-50, 50-100, 100-150, 150-200, 200-250, 250-300, 300-350, 350-400, 400-450, 450-500, 500-600, 600-700, 700-800, 800-900, 900-1000, 1000-1500, 1500-2000, 20-50, 20-100, 100-200, 200-400, 500-600, 600-800, 800-1000, 1000-2000, 20-100, 100-500, 100-800, 500-1000, 300-800, 30-50, 30-200, 30-500, 30-800, 30-1000, 30-2000, or 20-2000 µm. In some embodiments, the ratio between the length and the width of the bio-block is no more than about any of 10:1, 9:1, 8:1, 7:1, 6:1, 5:1, 4:1, 3:1, 2:1, 1.5:1, or 1:1. In some embodiments, the ratio between the length and the width of the bio-blocks is any of about 1:1 to about 1.5:1, about 1:1 to about 2:1, about 1:1 to about 3:1, about 1:1 to about 4:1, about 1:1 to about 5:1, about 1:1 to about 6:1, about 1:1 to about 7:1, about 1:1 to about 8:1, about 1:1 to about 9:1, or about 1:1 to about 10:1. In some embodiments, the ratio between the length and the thickness of the bio-block is no more than about any of 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, or 1:1. In some embodiments, the ratio between the length and the thickness of the bio-block is any of about 1:1 to about 2:1, about 1:1 to about 3:1, about 1:1 to about 4:1, about 1:1 to about 5:1, about 1:1 to about 10:1, about 1:1 to about 20:1, about to about 50:1, or about 1:1 to about 100:1. In some embodiments, the length of the bio-block is equal to the width of the bio-block. In some embodiments, the width of the bio-block is equal to the thickness of the bio-block. In some embodiments, the bio-block is not a fiber. In some embodiments, the bio-block is not a sheet.

As used herein, the "size" of a spherical bio-block is the diameter of the spherical bio-block. The term "diameter" with its strict geometric definition does not apply to non-spherical bio-blocks. However, a volume-based particle diameter can be defined as the diameter of the sphere that has the same volume as a given non-spherical bio-block, which can be used to quantitatively define the size of non-spherical bio-blocks. In some embodiments, the size of the bio-block (i.e. the diameter of the spherical bio-block or the volume-based particle diameter of the non-spherical bio-block) is at least about any of 20, 30, 50, 100, 120, 150, 200, 250, 300, 350, 400, 450, 500, 600, 700, 800, 900, 1000, 1500, or 2000 µm. In some embodiments, the size of the bio-block (i.e. the diameter of the spherical bio-block or the volume-based particle diameter of the non-spherical bio-block) is about any of 20-30, 30-50, 50-100, 100-150, 150-200, 200-250, 250-300, 300-350, 350-400, 400-450, 450-500, 500-600, 600-700, 700-800, 800-900, 900-1000, 1000-1500, 1500-2000, 20-50, 20-100, 100-200, 200-400, 500-600, 600-800, 800-1000, 1000-2000, 20-100, 100-500, 100-800, 500-1000, 300-800, 30-50, 30-200, 30-500, 30-800, 30-1000, 30-2000, or 20-2000 µm. In some embodiments, the size of the bio-block (i.e. the diameter of the spherical bio-block or the volume-based particle diameter of the non-spherical bio-block) is about 20 µm to about 2 mm, including for example about any of 20-100, 100-500, 500-1000 or 1000-2000 µm. In some embodiments, the size of the bio-block (i.e. the diameter of the spherical bio-block or the volume-based particle diameter of the non-spherical bio-block) is about 30 µm to about 800 µm, including for example about any of 30-100, 100-200, or 200-800 µm.

Bio-blocks described herein can be prepared using a variety of methods, including those known in the art for manufacturing microspheriods and microcapsules, such as using an encapsulator as described in Example 1. The shape, dimensions and size of the bio-blocks can be precisely controlled during the preparation process using an encapsulator. In some embodiments, the bio-block is prepared under sterile conditions. In some embodiments, the bio-block is prepared in a GMP workshop. In some embodiments, the bio-block is freshly prepared prior to use. In some embodiments, the bio-block can be stored under refrigerated conditions (such as about 4° C.) for at least about any of 3 hours, 6 hours, 12 hours, 1 day, 2 days, or 3 days prior to use.

Biodegradable Polymeric Material

In some embodiments, the shell consists of a single material layer. In some embodiments, the shell comprises more than one material layers. In some embodiments, the core consists of at least one cell embedded or enwrapped in a single material layer. In some embodiments, the core comprises more than one material layers. In some embodiments, such as the bio-block illustrated in FIG. 1A, the core comprises a cell-enwrapping or cell-embedding material layer comprising a biodegradable polymeric core material. In some embodiments, the core comprises at least one additional material layer placed between the cell-enwrapping or cell-embedding material layer of the core and the shell. In some embodiments, the at least one additional material layer of the core enwraps the core, and provides further mechanical support to the core. In some embodiments, the shell and the material layer(s) in the core maintain a space with a pre-determined volume and structure for the cell(s) to spread, grow, proliferate, attach (or adhere), differentiate, metabolize, secrete and/or migrate.

The shell and the core of the bio-block, including any material layer or combinations of material layers thereof, as well as each shell of the bio-block comprising more than one shell, and each core of the bio-block comprising more than one core, may independently comprise a biodegradable material (such as biodegradable polymer) or composition. For example, wherein the bio-block has two cores, both cores may comprise the same biodegradable material or composition, or each core may comprise a different biodegradable material or composition. In some embodiments, wherein the bio-block has three cores, all three cores may comprise the same biodegradable material or composition; or each of the three cores may comprise a different biodegradable material or composition; or two of the three cores may comprise the same biodegradable material or composition, and the third core may comprise a different biodegradable material or composition. In some embodiments, each core of the bio-block comprises a different composition.

The biodegradable core material may be selected independently from the cell in the core. Thus, different cores of the bio-block may: (1) comprise the same biodegradable material or composition, and the same cell or cell composition; (2) comprise the same biodegradable material or composition, but different cell or cell composition; (3) comprise different biodegradable material or composition, and different cell or cell composition. In preferred embodiments, suitable biodegradable core material is selected to prepare the core to provide optimal conditions for the growth, proliferation, differentiation, migration, and/or secretion of the cell.

The biodegradable polymers (for example, the biodegradable polymeric shell material or the biodegradable polymeric core material) and their degradation products thereof are non-toxic and compatible with the cell(s) in the bio-block. In some embodiments, the biodegradable polymers (for example, the biodegradable polymeric shell material or the biodegradable polymeric core material) and their degradation products are non-immunogenic. In some embodiments, the biodegradable polymers (for example, the biodegradable polymeric shell material or the biodegradable polymeric core material) are degradable by enzymes, such as enzymes secreted from the cells (for example, trypsin). In some embodiments, the biodegradable polymers are degraded completely in no more than about 28 days. In some embodiments, the biodegradable polymers are degraded completely within no more than about any of 21, 14, 12, 10, 9, 8, 7, 6, 5, 4, 3, or 2 days. In some embodiments, the biodegradable polymers are degraded completely within no more than about any of 2-5, 2-6, 2-8, 2-10, 2-12, or 2-14 days. In some embodiments, the degradation products of the biodegradable polymers (for example, the biodegradable polymeric shell material or the biodegradable polymeric core material) provide nutrients for the cell.

In some embodiments, the rate of degradation of the biodegradable polymeric core and/or shell material is predetermined using any one or any combination of a variety of methods according to actual application of the bio-block. For example, different biopolymers have different rates of degradation. In some embodiments, to achieve a desirable overall degradation rate of the biodegradable polymeric core and/or shell material, a specific biodegradable polymer of a known degradation rate, or a composition comprising specific biodegradable polymers mixed at a pre-determined weight ratio is used. In some embodiments, a low percentage (such as less than about any of 0.5%, 1%, 2%, 5%, 10%, 15%, 20%, or 25%) of a biodegradable polymer with a slow degradation rate (such as with a degradation half-life longer than about any of 1 day, 3 days, 1 week, 2 weeks, 3 weeks, 1 months, 2 months, 3 months, 6 months or a year) is used in the biodegradable polymeric core and/or shell material to achieve a fast overall degradation rate (such as with a half-life of shorter than about any of 1 hour, 5 hours, 10 hours, 1 day, 3 days, 1 week, 2 weeks, 3 weeks, 1 months, 3 months, 6 months, or a year). In some embodiments, a high percentage (such as more than about any of 0.5%, 1%, 2%, 5%, 10%, 15%, 20%, or 25%) of a biodegradable polymer with slow degradation rate (such as with a degradation half-life longer than about any of 1 day, 3 days, 1 week, 2 weeks, 3 weeks, 1 months, 2 months, 3 months, 6 months or a year) is used in the biodegradable polymeric core and/or shell material to achieve a slow overall degradation rate (such as with a half-life of longer than about any of 1 hour, 5 hours, 10 hours, 1 day, 3 days, 1 week, 2 weeks, 3 weeks, 1 months, 3 months, 6 months, or a year). The degradation rate of a biodegradable polymer typically depends on its (average) molecular weight. In some embodiments, to achieve a fast degradation rate, a low-molecule weight (such as less than about any of 500 Da, 1 kDa, 2 kDa, 3 kDa, 5 kDa, or 10 kDa) species of a biodegradable polymer is used in the biodegradable polymeric core and/or shell material. In some embodiments, to achieve a slow degradation rate, a high-molecule weight (such as more than any of 5 kDa, 10 kDa, 20 kDa, 50 kDa, 100 kDa, 200 kDa, 500 kDa, 1000 kDa or more) species of a biodegradable polymer is used in the biodegradable polymeric core and/or shell material. Additional exemplary methods to control the degradation rate of the biodegradable polymeric core and/or shell material include, but are not limited to, adopting particular parameters for the bio-block (such as number of cell-enwrapping or cell-embedding layers, number, spacing and density of micropores on the shell, surface area of the shell, etc.), and manipulations of the preparation process of the biodegradable polymers (such as method of polymerization, ratio of copolymers, crosslinking of polymers, etc.).

Many biodegradable materials are known in the art, and their degradation properties have been studied. See, for example, Alexander D. Augst, Hyun Joon Kong, David J. Mooney, "Alginate Hydrogels as biomaterial," *Macromol. Biosci.* 2006, 623-633. Suitable biodegradable materials can be selected to prepare the shell based on actual needs.

In some embodiments, the biodegradable polymer (for example, the biodegradable polymeric shell material or the biodegradable polymeric core material) is biocompatible and selected from the group consisting of naturally occurring polymer, synthetic polymer, recombinant polymer, and combinations thereof.

In some embodiments, the biodegradable polymers (for example, the biodegradable polymeric shell material or the biodegradable polymeric core material) comprise naturally occurring polymers, such as biopolymers derived from animals (such as human) and/or plants, or derivatives thereof. Naturally occurring polymers have excellent compatibility profile with cells of all types, are almost always biodegradable on a biologically reasonable timescale, and their degradation products are non-toxic. Derivatives of naturally occurring polymers include modified naturally occurring polymers, which are obtained by modification of a naturally-occurring polymer using chemical and/or physical methods to alter the chemical and/or physical properties of the naturally-occurring polymer. In some embodiments, atoms, functional groups or interactions in the main chain or side chains of a naturally-occurring polymer may be modified chemically to obtain a modified naturally-occurring biodegradable polymeric material. For example, sodium alginate may be oxidized to obtain modified sodium alginate, i.e., oxidized sodium alginate.

Naturally occurring polymers and derivatives contemplated herein include, but are not limited to, collagen (such as (such as type I collagen, type II collagen or type III collagen), fibrin, chitosan, alginate, oxidized alginate, starch, hyaluronic acid, laminin, agarose, gelatin, glucan, elastin and combinations thereof. The naturally occurring polymers also include salts of any of the naturally occurring polymers described above, including, but not limited to, sodium salt, potassium salt, calcium salt, strontium salt, and barium salt.

In some embodiments, the biodegradable polymers (for example, the biodegradable polymeric shell material or the biodegradable polymeric core material) comprise synthetic biodegradable polymers. Synthetic polymers contemplated herein include, but are not limited to, polypohosphazene, polyacrylic acid, polymethacrylic acid, acrylate copolymer (such as copolymer of acrylic acid and polymethacrylic acid), polylactic acid (PLA), polyglycolic acid (PGA), poly-(lactide-coglycolide acid) (PLGA), polyorthoester (POE), polycaprolactone (PCL), polyhydroxyrate (PHB), polyamine acid (such as polylysine), degradable polyurethane, copolymers thereof, and combinations thereof. The synthetic polymers also include salts of any of the synthetic polymers described above.

In some embodiments, the biodegradable polymers (for example, the biodegradable polymeric shell material or the biodegradable polymeric core material) comprise naturally occurring polymers and synthetic polymers. In some embodiments, the biodegradable polymeric shell material comprises a naturally occurring polymer and a synthetic polymer. In some embodiments, the biodegradable polymeric core material comprises a naturally occurring polymer and a synthetic polymer.

In some embodiments, the biodegradable polymeric shell material and the biodegradable polymeric core material comprise different biodegradable polymers. In some embodiments, the biodegradable polymeric shell material and the biodegradable polymeric core material comprise the same biodegradable polymers with different weight ratios. For example, in some embodiments, the biodegradable polymeric core material comprises no more than about 2% (such as no about 1.5%) sodium alginate, and the biodegradable polymeric shell material comprises more than about 4% (such as about 5%) sodium alginate. In some embodiments, different material layers within the shell comprise different biodegradable polymers. In some embodiments, different material layers within the core comprise different biodegradable polymers. In some embodiments, different material layers within the shell comprise the same biodegradable polymers with different weight ratios. In some embodiments, different material layers within the core comprise the same biodegradable polymers with different weight ratios.

Depending on the chemical and physical properties of the biodegradable polymers, the core, the shell and/or the bio-block may be in a solid or semi-solid state. In some embodiments, the bio-block is in a gel state. In some embodiments, the core is in a gel state. In some embodiments, the bio-block comprises a hydrogel. In some embodiments, the hydrogel comprises alginate, oxidized alginate, agarose, gelatin, chitosan, or other water-soluble or hydrophilic polymers. In some embodiments, the hydrogel comprises a synthetic hydrophilic polymer, such as polyethylene glycol, polyacrylic acid, or derivatives thereof (e.g. polymethylacrylic acid, polyacrylamide, or poly-N-substituted-acrylamide).

Oxidized Alginate

Alginate is a suitable biodegradable polymeric material for use in the core and/or the shell. Alginic acid is a naturally occurring polysaccharide, comprising a random block copolymer of β-1,4-D-mannuronic acid (M unit) and α-1,4-L-guluronic acid (G unit). Typically, the M unit and G unit of an alginic acid are connected through 1,4-glucosidic bond in the combination of M-M, G-G, or M-G to from a block copolymer. Naturally occurring alginic acids has an empirical formula of $(C_6H_8O_6)_n$, with a typical molecular weight of about 4 kDa-1500 kDa. Alginic acid can be extracted from brown algae. Alginate is a salt derived from alginic acid, including but not limited to, sodium alginate, calcium alginate, strontium alginate, and barium alginate. As used herein, the term "G/M value" refers to the molar ratio of α-1,4-L-guluronic acid (G unit) and β-1,4-D-mannuronic acid (M unit) within an alginate or oxidized alginate.

Oxidized alginate is the product of an oxidation reaction of alginate (such as sodium alginate). Typically, oxidation reactions convert the hydroxyl groups of a portion of the uronic acid units in alginate (such as sodium alginate) into aldehyde groups. Inventors of the application surprisingly discovered that oxidized alginate (such as oxidized sodium alginate and/or oxidized calcium alginate) can be used in the core and/or shell, and the degradation rate of the core and/or shell can thereby be controlled by including oxidized alginate of a suitable oxidation level in the core and/or shell. As used herein, "oxidation level" refers to the molar percentage of oxidized uronic acid units among total uronic acid units in an alginic acid or alginate. The degradation rate of a core or shell comprising alginate or oxidized alginate may further depend on the molecular mass and relative amount of the alginate or oxidized alginate, as well as the number of cells in the bio-block.

In some embodiments, there is provided a method of controlling the degradation rate of a bio-block, comprising assessing degradation rates of a plurality of bio-blocks each comprising a shell comprising oxidized alginate having an oxidation level between about 1% to about 40%, and preparing the bio-block comprising the shell comprising oxidized alginate having the oxidation level that yields the desired degradation rate. In some embodiments, the method further comprises varying the relative amount of the oxidized alginate in the biodegradable polymeric shell material in the plurality of bio-blocks between about 1% to about 25%. In some embodiments, the method further comprises varying the molecular weight of the oxidized alginate in the plurality of bio-blocks between about 4 kDa to about 1500 kDa. In some embodiments, the method further comprises varying the number of cells in the plurality of bio-blocks.

Alginate and oxidized alginate suitable for use in the bio-blocks have a molecular weight of about 4 kDa to about 1500 kDa. In some embodiments, the molecular weight of the alginate or oxidized alginate in the bio-blocks is about any of 4-10 kDa, 10-20 kDa, 20-30 kDa, 30-40 kDa, 40-50 kDa, 50-60 kDa, 60-70 kDa, 70-80 kDa, 80-90 kDa, 90-100 kDa, 100-200 kDa, 200-300 kDa, 300-400 kDa, 400-500 kDa, 500-600 kDa, 700-800 kDa, 800-900 kDa, 900-1000 kDa, 1100-1200 kDa, 1200-1300 kDa, 1300-1400 kDa, or 1400-1500 kDa. In some embodiments, the molecular weight of the alginate or oxidized alginate is about 32 kDa to about 250 kDa. In some embodiments, the alginate or oxidized alginate is soluble in water.

Alginate and oxidized alginate suitable for use in the bio-blocks have a G/M value of about 0.2 to about 5. In some embodiments, the G/M value of the alginate or oxidized alginate in the bio-blocks is about any of 0.2-0.3, 0.3-0.4, 0.4-0.5, 0.5-0.6, 0.6-0.7, 0.7-0.8, 0.8-0.9, 0.9-1.0, 1.0-1.5, 1.5-2.0, 2.0-2.5, 2.5-3.0, 3.0-3.5, 3.5-4.0, 4.0-4.5, or 4.5-5.0. In some embodiments, the G/M value of the alginate or oxidized alginate in the bio-blocks is about 0.2-2.5.

In some embodiments, the alginate or oxidized alginate has a viscosity of about 100-3000 mPa·s. In some embodiments, the alginate or oxidized alginate has a viscosity of about any of 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2600, 2600-2700, 2700-2800, 2800-2900, or 2900-3000 mPa·s. In some embodiments, the alginate or oxidized alginate has a viscosity of about 200-2000 mPa·s.

Suitable oxidation level of the oxidized alginate for use in the bio-blocks is about 1% to about 40%. In some embodiments, the oxidation level of the oxidized alginate in the bio-blocks is about any one of 1-2%, 2-3%, 3-4%, 4-5%, 5-6%, 6-7%, 7-8%, 8-9%, 9-10%, 11-12%, 12-13%, 13-14%, 14-15%, 15-16%, 16-17%, 17-18%, 18-19%, 19-20%, 20-25%, 25-30%, 30-35%, or 35-40%. In some embodiments, the oxidation level of the oxidized alginate in the bio-blocks is about any one of 2.5-4.4%, 4.4-8.8%, 8.8%-17.6%, or 17.6-22%.

Oxidized alginate may be obtained from oxidation reactions of alginate, for example, by reacting alginate salt with sodium periodate or other oxidative agents known in the art. In some embodiments, the oxidized alginate is obtained from oxidation reaction of an alginate obtained form an algae, such as brown algae, for example, kelp and *Sargassum*.

In some embodiments, the biodegradable polymeric material (such as a the biodegradable polymeric shell material or the biodegradable polymeric core material) comprises a mixture of alginate and oxidized alginate. In some embodiments, the percentage (by weight) of oxidized alginate in the mixture of alginate and oxidized alginate is at least about any one of 5%, 10%, 15%, 20%, 25%, 30%, 35%, 40%, 45%, 50%, 55%, 60%, 65%, 70%, 75%, 80%, 85%, 90%, 95%, 98%, or more. In some embodiments, the percentage of oxidized alginate in the mixture of alginate and oxidized alginate is any one of about 1% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 1% to about 10%, about 20% to about 40%, about 40% to about 60%, about 1% to about 50%, about, about 25% to about 50%, about 50% to about 75%, about 75% to about 100%, about 40% to about 60%, about 60% to about 80%, about 80% to about 100%, or about 50% to about 100%. In some embodiments, the ratio between the oxidized alginate and alginate is at least about any one of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, or more. In some embodiments, the ratio between the oxidized alginate and alginate is any one of about 1:10 to about 1:9, about 1:9 to about 1:8, about 1:8 to about 1:7, about 1:7 to about 1:6, about 1:6 to about 1:5 about 1:5 to about 1:4 about 1:4 to about 1:3, about 1:3 to about 1:2, about 1:2 to about 1:1, about 1:1 to about 2:1, about 2:1 to about 3:1, about 3:1 to about 4:1, about 4:1, to about 5:1, about 5:1 to about 6:1, about 6:1 to about 7:1, about 7:1 to about 8:1, about 8:1 to about 9:1, about 9:1 to about 10:1, about 1:10 to about 10:1, about 1:8 to about 8:1, about 1:7 to about 7:1, about 1:6 to about 6:1, about 1:5 to about 5:1, about 1:4 to about 4:1, about 1:3 to about 3:1, about 1:2 to about 2:1, about 1:9 to about 1:1, about 1:1 to about 1:9, about 1:9 to about 1:4, about 1:4 to about 1:2, about 2:1 to about 4:1, or about 4:1 to about 9:1.

Shell

In some embodiments, the bio-block comprises a single shell comprising a polymeric shell material (such biodegradable polymeric shell material). In some embodiments, the bio-block comprises at least two shells each independently comprising a polymeric shell material (such biodegradable polymeric shell material). In some embodiments, the at least two shells comprise the same polymeric shell material (such as biodegradable polymeric shell material). In some embodiments, each of the at least two shells comprise a distinct polymeric shell material (such as biodegradable polymeric shell material). In some embodiments, each of the at least two shells serve distinct functions. Functions served by the shells include, but are not limited to, providing mechanical support, providing nutrients to the cell, providing a microenvironment for the cell, providing physical space for the cell, and combinations thereof.

In some embodiments, the biodegradable polymeric shell material comprises a naturally occurring polymer or derivative thereof. In some embodiments, the naturally occurring polymer is selected from the group consisting of collagen (such as type I, type II or type III collagen), fibrin, chitosan, alginate (such as sodium alginate or calcium alginate), oxidized alginate, starch, hyaluronic acid, laminin, agarose, gelatin, glucan, elastin and combinations thereof.

In some embodiments, the biodegradable polymeric shell material comprises a synthetic polymer. In some embodiments, the synthetic polymer is selected from the group consisting of polypohosphazene, polyacrylic acid, polymethacrylic acid, polyacrylic acid, polymethacrylic acid, acrylate copolymer (such as copolymer of acrylic acid and polymethacrylic acid), polylactic acid (PLA), polyglycolic acid (PGA), poly-(lactide-coglycolide acid) (PLGA), polyorthoester (POE), polycaprolactone (PCL), polyhydroxyrate (PHB), polyamino acid (such as polylysine), degradable polyurethane, copolymers thereof, and combinations thereof.

In some embodiments, the biodegradable polymeric shell material comprises alginate, oxidized alginate, or combination thereof. In some embodiments, the percentage of the alginate, oxidized alginate, or combination thereof in the biodegradable polymeric shell material is at least about any one of 1%, 1.25%, 1.5%, 2%, 2.5%, 3%, 4%, 5%, 7.5%, 10%, 15%, 20%, or 25%. In some embodiments, the percentage of the alginate, oxidized alginate, or combination thereof in the biodegradable polymeric core material is about any one of 1%-1.25%, 1.25%-1.5%, 1.5%-2%, 2%-3%, 3%-4%, 4%-5%, 5%-6%, 6%-7%, 7%-8%, 8%-9%, 9%-10%, 1%-1.5%, 1%-2%, 1-2.5%, 1%-5%, 5-10%, 10%-15%, 15%-20%, 20%-25%, or 1%-25%.

In some embodiments, the shell comprises oxidized alginate. In some embodiments, the shell comprises about 1-25% oxidized alginate, such as about any of 1-2%, 2-3%, 3%-4%, 4%-5%, 5%-6%, 6%-7%, 7%-8%, 8%-9%, 9%-10%, 10%-15%, 15%-20%, or 20%-25%. In some embodiments, the shell comprises at least 4% (such as at least about any of 5%, 6%, 7%, 8%, 9%, 10%, 15%, 20%, or 25%) oxidized alginate.

In some embodiments, the shell comprises a mixture of alginate and oxidized alginate. In some embodiments, the weight ratio of the alginate to the oxidized alginate is about 1:9 to about 9:1, such as 1:9, 2:8, 3:7, 4:6, 5:5, 6:4, 7:3, 8:2 and 9:1. In some embodiments, the weight ratio of the alginate to the oxidized alginate is any of about 1:10 to about 1:9, about 1:9 to about 1:8, about 1:8 to about 1:7, about 1:7 to about 1:6, about 1:6 to about 1:5 about 1:5 to about 1:4 about 1:4 to about 1:3, about 1:3 to about 1:2, about 1:2 to about 1:1, about 1:1 to about 2:1, about 2:1 to about 3:1, about 3:1 to about 4:1, about 4:1, to about 5:1, about 5:1 to about 6:1, about 6:1 to about 7:1, about 7:1 to about 8:1, about 8:1 to about 9:1, about 9:1 to about 10:1, about 1:10 to about 10:1, about 1:8 to about 8:1, about 1:7 to about 7:1, about 1:6 to about 6:1, about 1:5 to about 5:1, about 1:4 to about 4:1, about 1:3 to about 3:1, about 1:2 to about 2:1, about 1:9 to about 1:1, about 1:1 to about 1:9, about 1:9 to about 1:4, about 1:4 to about 1:2, about 2:1 to about 4:1, or about 4:1 to about 9:1. In some embodiments, the percentage of oxidized alginate in the biodegradable polymeric shell material is at least about any one of 1%, 1.25%, 1.5%, 2%, 2.5%, 3%, 4%, 5%, 7.5%, 10%, 15%, 20%, or 25%. In some embodiments, the percentage of oxidized alginate in the biodegradable polymeric shell material is about any one of 1%-1.25%, 1.25%-1.5%, 1.5%-2%, 2%-3%, 3%-4%, 4%-5%, 5%-6%, 6%-7%, 7%-8%, 8%-9%, 9%-10%, 1%-1.5%, 1%-2%, 1-2.5%, 1%-5%, 5-10%, 10%-15%, 15%-20%, 20%-25%, or 1%-25%. In some embodiments, the percentage of alginate in the biodegradable polymeric shell material is at least about any one of 1%, 1.25%, 1.5%, 2%, 2.5%, 3%, 4%, 5%, 7.5%, 10%, 15%, 20%, or 25%. In some embodiments, the percentage of alginate in the biodegradable polymeric shell material is about any one of 1%-1.25%, 1.25%-1.5%, 1.5%-2%, 2%-3%, 3%-4%, 4%-5%, 5%-6%, 6%-7%, 7%-8%, 8%-9%, 9%-10%, 1%-1.5%, 1%-2%, 1-2.5%, 1%-5%, 5-10%, 10%-15%, 15%-20%, 20%-25%, or 1%-25%.

In some embodiments, the biodegradable polymeric shell material is crosslinked. Crosslinking of the biodegradable polymeric shell material may enhance the elastic properties, mechanical strength, and stability of the core and/or shell comprising the biodegradable polymer. In some embodiments, the biodegradable polymeric shell material is crosslinked covalently. In some embodiments, the biodegradable polymeric shell material is crosslinked non-covalently (such as by formation of ionic bonds). In some embodiments, the crosslinking is reversible. In some embodiment, the biodegradable polymeric shell material is crosslinked by oxidation, such as oxidation of disulfide bonds. In some embodiment, the biodegradable polymeric shell material is crosslinked by a chemical reaction. In some embodiments, the biodegradable polymeric shell material is crosslinked by a physical process, such as heating or cooling. In some embodiments, the biodegradable polymeric shell material is crosslinked by In some embodiments, biodegradable polymeric shell material (such as alginate or oxidized alginate) is crosslinked by a divalent ion, such as $Ca^{2+}$, $Sr^{2+}$, and $Ba^{2+}$. In some embodiments, the shell is solidified by the crosslinking.

In some embodiments, at least one shell is solidified, e.g., by crosslinking. In some embodiments, each shell is solidified, such as by crosslinking. In some embodiments, wherein the bio-block comprises more than one shell, the outermost shell (such as only the outermost shell) is solidified. The solidified (such as crosslinked) shell may have improved mechanical properties.

In some embodiments, the biodegradable polymeric shell material further comprises a cation with a +2 charge, including, but not limited to, $Ca^{2+}$, $Ba^{2+}$ and $Sr^{2+}$. In some embodiments, the biodegradable polymeric shell material further comprises calcium (such as $Ca^{2+}$). In some embodiments, the shell comprises calcium alginate. In some embodiments, the cation (such as $Ca^{2+}$) serves to crosslink the polymers in the biodegradable polymeric shell material. In some embodiments, the crosslinked polymers form a hydrogel. In some embodiments, crosslinking of the polymers using the cation (such as $Ca^{2+}$) yields favorable mechanical properties of the shell, such as increasing elasticity and hardness of the shell.

In some embodiments, the biodegradable polymeric shell material comprises (including consists of or consists essentially of) a polyamino acid (such as polylysine), such as polylysine. In some embodiments, the percentage of the polylysine in the biodegradable polymeric shell material is at least about any one of 0.1%, 0.2%, 0.5%, 0.6%, 0.7%, 0.8%, 0.9%, 1%, 1.2%, 1.5%, 2%, 3%, 4%, 5% or more. In some embodiments, the percentage of the alginate in the biodegradable polymeric core material is about any one of 0.1%-0.2%, 0.2%-0.5%, 0.5%-0.6%, 0.6%-0.7%, 0.7%-0.8%, 0.8%-0.9%, 0.9%-1%, 1%-1.2%, 1.2%-1.5%, 1.5%-2%, 2%-3%, 3%-5%, 0.1%-1%, 1%-2%, or 0.1%-5%. In some embodiments, the percentage of polylysine in the biodegradable polymeric shell material is no more than about 5%.

In some embodiments, the biodegradable polymeric shell material comprises a mixture of alginate and agarose. The weight ratio of the alginate to the agarose depends on the actual application of the bio-block. In some embodiments, the weight ratio of the agarose to the alginate in the biodegradable polymeric shell material is at least about any of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1. In some embodiments, the weight ratio of the agarose to the alginate in the biodegradable polymeric shell material is any one of about 1:10 to about 1:9, about 1:9 to about 1:8, about 1:8 to about 1:7, about 1:7 to about 1:6, about 1:6 to about 1:5, about 1:5 to about 1:4, about 1:4 to about 1:3, about 1:3 to about 1:2, about 1:2 to about 1:1, about 1:1 to about 2:1, about 2:1 to about 3:1, about 3:1 to about 4:1, about 4:1 to about 5:1, about 5:1 to about 6:1, about 6:1 to about 7:1, about 7:1 to about 8:1, about 8:1 to about 9:1, about 9:1 to about 10:1, about 1:10 to about 1:5, about 1:5 to about 1:1, about 1:1 to about 5:1, about 5:1 to about 10:1, about 1:5 to about 5:1, or about 1:10 to about 10:1. In some embodiments, the weight ratio of the agarose and the alginate in the biodegradable polymeric shell material is about 1:4. In some embodiments, the percentage of the alginate in the biodegradable polymeric shell material is at least about any of 0.5%, 1%, 1.5%, 2%, 2.5%, 3%, 4%, 5%, 7.5%, or 10%. In some embodiments, the percentage of the alginate in the biodegradable polymeric shell material is about any one of 0.5%-1%, 1%-1.5%, 1.5%-2%, 2%-2.5%, 2.5%-3%, 3%-4%, 4%-5%, 5%-7.5%, 7.5%-10%, 0.5%-2%, 2%-3%, 1.5%-3%, 0.5%-4%, 1%-5%, 5-10% or 0.5%-10%. In some embodiments, the percentage of alginate in the biodegradable polymeric core material is at least about 4% (including for example, at least about 5%, at least about 7.5%, or at least about 10%). In some embodiments, the percentage of the agarose in the biodegradable polymeric shell material is at least about any of 0.5%, 1%, 1.5%, 2%, 2.5%, 3%, 4%, 5%, 7.5%, or 10%. In some embodiments, the percentage of the agarose in the biodegradable polymeric shell material is about any one of 0.5%-1%, 1%-1.5%, 1.5%-2%, 2%-2.5%, 2.5%-3%, 3%-4%, 4%-5%, 5%-7.5%, 7.5%-10%, 0.5%-2%, 2%-3%, 1.5%-3%, 0.5%-4%, 1%-5%, 5-10% or 0.5%-10%.

In some embodiments, the biodegradable polymeric shell material comprises a mixture of alginate (such as sodium alginate) and elastin. The weight ratio of the alginate to the elastin depends on the actual application of the bio-block. In some embodiments, the weight ratio of the alginate to the elastin in the biodegradable polymeric shell material is at least about any of 50:1, 100:1, 200:1, 300:1, 400:1, 500:1, 600:1, 700:1, 800:1, 900:1, 1000:1, 2000:1, or 5000:1. In some embodiments, the weight ratio of the alginate to the elastin in the biodegradable polymeric shell material is any of about 50:1 to about 100:1, about 100:1 to about 200:1, about 200:1 to about 300:1, about 300:1 to about 400:1, about 400:1 to about 500:1, about 500:1 to about 600:1, about 600:1 to about 700:1, about 700:1 to about 800:1, about 800:1 to about 900:1, about 900:1 to about 1000:1, about 1000:1 to about 2000:1, about 2000:1 to about 5000:1, about 50:1 to about 300:1, about 300:1 to about 500:1, about 500:1 to about 1000:1, about 800:1 to about 5000:1, about 400:1 to about 600:1, or about 200:1 to about 800:1. In some embodiments, the weight ratio of the alginate to the elastin in the biodegradable polymeric shell material is about 500:1. In some embodiments, the percentage of the alginate in the biodegradable polymeric shell material is at least about any of 0.5%, 1%, 1.5%, 2%, 2.5%, 3%, 4%, 5%, 7.5%, or 10%. In some embodiments, the percentage of the alginate in the biodegradable polymeric shell material is about any of 0.5%-1%, 1%-1.5%, 1.5%-2%, 2%-2.5%, 2.5%-3%, 3%-4%, 4%-5%, 5%-7.5%, 7.5%-10%, 0.5%-2%, 2%-3%, 1.5%-3%, 0.5-4%, 1%-5%, 5-10% or 0.5%-10%. In some embodiments, the percentage of alginate in the biodegradable polymeric core material is at least about 4% (including for example, at least about 5%, at least about 7.5%, or at least about 10%). In some embodiments, the percentage of elastin in the biodegradable polymeric shell material is at least about any of 0.01%, 0.02%, 0.03%, 0.04%, 0.05%, 0.06%, 0.07%, 0.08%, 0.1%, 0.15%, 0.2%, or 0.5%. In some embodiments, the percentage of elastin in the biodegradable polymeric shell material is about any of 0.01%-0.02%, 0.02%-0.03%, 0.03%-0.04%, 0.04%-0.05%, 0.05%-0.06%, 0.06%-0.07%, 0.07%-0.08%, 0.08%-0.1%, 0.1%-0.15%, 0.15%-0.2%, 0.2%, 0.2%-0.5%, 0.01%-0.03%, 0.03%-0.05%, 0.05%-0.08%, 0.08%-0.15%, 0.01%-0.05%, 0.05%-0.1%, 0.03%-0.07%, 0.04%-0.06%, 0.01%-0.1%, 0.1%-0.5%, or 0.01%-0.5%.

In some embodiments, the biodegradable polymeric shell material comprises alginate (such as sodium alginate or calcium alginate) and gelatin. The weight ratios of the alginate, and the gelatin depend on the actual application of the bio-block. In some embodiments, the weight ratio of the alginate to the gelatin in the biodegradable polymeric shell material is at least about any of 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the weight ratio of the alginate to the gelatin in the biodegradable polymeric shell material is about any of 10:1 to about 9:1, about 9:1 to about 8:1, about 8:1 to about 7:1, about 7:1 to about 6:1, about 6:1 to about 5:1, about 5:1 to about 4:1, about 4:1 to about 3:1, about 3:1 to about 2:1, about 2:1 to about 1:1, about 1:1 to about 1:2, about 1:2 to about 1:3, about 1:3 to about 1:4, about 1:4 to about 1:5, about 1:5 to about 1:6, about 1:6 to about 1:7, about 1:7 to about 1:8, about 1:8 to about 1:9, about 1:9 to about 1:10, about 10:1 to about 5:1, about 5:1 to about 1:1, about 1:1 to about 1:5, about 1:5 to about 1:10, about 2:1 to about 1:2, about 4:1 to about 1:4, or about 10:1 to about 1:10. In some embodiments, the weight ratio of the gelatin and the alginate in the biodegradable polymeric shell material is about 15:85. In some embodiments, the percentage of the alginate in the biodegradable polymeric shell material is at least about any of 0.1%, 0.5%, 1%, 1.25%, 1.5%, 2%, 3%, 4%, 5%, 7.5%, or 10%. In some embodiments, the percentage of alginate in the biodegradable polymeric shell material is about any of 0.1%-0.5%, 0.5%-1%, 1%-1.25%, 1.25%-1.5%, 1.5%-2%, 2%-3%, 3%-4%, 4%-5%, 5%-7.5%, 7.5%-10%, 0.1%-1%, 1%-1.5%, 1%-2%, 0.5-2.5%, 1%-3%, 5-10% or 0.5%-5%. In some embodiments, the percentage of alginate in the biodegradable polymeric core material is at least about 4% (including for example, at least about 5%, at least about 7.5%, or at least about 10%). In some embodiments, the percentage of gelatin in the biodegradable polymeric shell material is at least about any of 0.1%, 0.5%, 1%, 1.25%, 1.5%, 2%, 3%, 4%, 5%, 7.5%, or 10%. In some embodiments, the percentage of gelatin in the biodegradable polymeric shell material is about any of 0.1%-0.5%, 0.5%-1%, 1%-1.25%, 1.25%-1.5%, 1.5%-2%, 2%-3%, 3%-4%, 4%-5%, 5%-7.5%, 7.5%-10%, 0.1%-1%, 1%-1.5%, 1%-2%, 0.5-2.5%, 1%-3%, 5-10% or 0.5%-5%.

In some embodiments, the biodegradable polymeric shell material comprises alginate (such as sodium alginate), gelatin, and elastin. The weight ratios of the alginate, the gelatin and the elastin depend on the actual application of the bio-block. In some embodiments, the weight ratio of the alginate to the gelatin in the biodegradable polymeric shell material is about any of 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the weight ratio of the alginate to the gelatin in the biodegradable polymeric shell material is about any of 10:1 to about 9:1, about 9:1 to about 8:1, about 8:1 to about 7:1, about 7:1 to about 6:1, about 6:1 to about 5:1, about 5:1 to about 4:1, about 4:1 to about 3:1, about 3:1 to about 2:1, about 2:1 to about 1:1, about 1:1 to about 1:2, about 1:2 to about 1:3, about 1:3 to about 1:4, about 1:4 to about 1:5, about 1:5 to about 1:6, about 1:6 to about 1:7, about 1:7 to about 1:8, about 1:8 to about 1:9, about 1:9 to about 1:10, about 10:1 to about 5:1, about 5:1 to about 1:1, about 1:1 to about 1:5, about 1:5 to about 1:10, about 2:1 to about 1:2, about 4:1 to about 1:4, or about 10:1 to about 1:10. In some embodiments, the weight ratio of the alginate to the elastin in the biodegradable polymeric shell material is at least about any of 1000:1, 500:1, 400:1, 300:1, 250:1, 200:1, 100:1, 50:1, or 10:1. In some embodiments, the weight ratio of the alginate to the elastin in the biodegradable polymeric shell material is about any of 10:1 to about 50:1, about 50:1 to about 100:1, about 100:1 to about 200:1, about 200:1 to about 250:1, about 250:1 to about 300:1, about 300:1 to about 400:1, about 400:1 to about 500:1, about 500:1 to about 1000:1, about 10:1 to about 100:1, about 100:1 to about 200:1, about 200:1 to about 300:1, about 300:1 to about 400:1, about 400:1 to about 1000:1, or about 100:1 to about 500:1. The weight ratio of the gelatin to the elastin in the biodegradable polymeric shell material is at least about any of 1000:1, 500:1, 400:1, 300:1, 250:1, 200:1, 100:1, 50:1, or 10:1. In some embodiments, the weight ratio of the gelatin to the elastin in the biodegradable polymeric shell material is about any of 10:1 to about 50:1, about 50:1 to about 100:1, about 100:1 to about 200:1, about 200:1 to about 250:1, about 250:1 to about 300:1, about 300:1 to about 400:1, about 400:1 to about 500:1, about 500:1 to about 1000:1, about 10:1 to about 100:1, about 100:1 to about 200:1, about 200:1 to about 300:1, about 300:1 to about 400:1, about 400:1 to about 1000:1, or about 100:1 to about 500:1. In some embodiments, the weight ratio of the gelatin, the alginate and the elastin in the biodegradable polymeric shell material is about 250:250:1. In some embodiments, the percentage of the alginate in the biodegradable polymeric shell material is at least about any of 0.1%, 0.5%, 1%, 1.25%, 1.5%, 2%, 3%, 4%, 5%, 7.5%, or 10%. In some embodiments, the percentage of alginate in the biodegradable polymeric shell material is about any of 0.1%-0.5%, 0.5%-1%, 1%-1.25%, 1.25%-1.5%, 1.5%-2%, 2%-3%, 3%-4%, 4%-5%, 5%-7.5%, 7.5%-10%, 0.1%-1%, 1%-1.5%, 1%-2%, 0.5-2.5%, 1%-3%, 5-10% or 0.5%-5%. In some embodiments, the percentage of alginate in the biodegradable polymeric core material is at least about 4% (including for example, at least about 5%, at least about 7.5%, or at least about 10%). In some embodiments, the percentage of gelatin in the biodegradable polymeric shell material is at least about any of 0.1%, 0.5%, 1%, 1.25%, 1.5%, 2%, 3%, 4%, 5%, 7.5%, or 10%. In some embodiments, the percentage of gelatin in the biodegradable polymeric shell material is about any of 0.1%-0.5%, 0.5%-1%, 1%-1.25%, 1.25%-1.5%, 1.5%-2%, 2%-3%, 3%-4%, 4%-5%, 5%-7.5%, 7.5%-10%, 0.1%-1%, 1%-1.5%, 1%-2%, 0.5-2.5%, 1%-3%, 5-10% or 0.5%-5%. In some embodiments, the percentage of elastin in the biodegradable polymeric shell material is at least about any of 0.01%, 0.02%, 0.03%, 0.04%, 0.05%, 0.06%, 0.07%, 0.08%, 0.1%, 0.15%, 0.2%, or 0.5%. In some embodiments, the percentage of elastin in the biodegradable polymeric shell material is about any of 0.01%-0.02%, 0.02%-0.03%, 0.03%-0.04%, 0.04%-0.05%, 0.05%-0.06%, 0.06%-0.07%, 0.07%-0.08%, 0.08%-0.1%, 0.1%-0.15%, 0.15%-0.2%, 0.2%, 0.2%-0.5%, 0.01%-0.03%, 0.03%-0.05%, 0.05%-0.08%, 0.08%-0.15%, 0.01%-0.05%, 0.05%-0.1%, 0.03%-0.07%, 0.04%-0.06%, 0.01%-0.1%, 0.1%-0.5%, or 0.01%-0.5%.

Many physical properties of the shell affect the level of mechanical support and protection that can be provided by the shell. The composition of the biodegradable polymeric shell material contributes to the physical properties of the shell, and one skilled in the art can choose a composition according to actual need. In some embodiments, the shell provides mechanical support and/or protection to the core, including the cell.

In some embodiments, the shell degrades completely within no more than about 28 days. In some embodiments, the shell degrades completely within no more than about any of 21 days, 14 days, 12 days, 10 days, 9 days, 8 days, 7 days, 6 days, 5 days, 4 days, 3 days, or 2 days. In some embodiments, the shell degrades completely within about any of 2-5 days, 2-6 days, 2-8 days, 2-10 days, 2-12 days, 2-14 days, 14-21 days, 21-28 days, 7-14 days, 5-10 days, or 2-28 days.

In some embodiments, the shell has a viscosity of about 100-3000 mPa·s. In some embodiments, the shell has a viscosity of about any one of 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2600, 2600-2700, 2700-2800, 2800-2900, or 2900-3000 mPa·s. In some preferred embodiments, the shell has a viscosity of about 200-2000 mPa·s.

In some embodiments, the shell has a thickness of about any of 0.1, 0.5, 1, 2, 5, 10, 15, 20, 25, 30, 50, 100, or 200 µm. In some embodiments, the shell has a thickness of about any of 0.1-0.5, 0.5-1, 1-2, 2-5, 5-10, 10-15, 15-20, 20-25, 25-30, 30-50, 0.1-1, 1-5, 1-10, 5-10, 10-20, 10-30, 5-20, 1-20, 0.1-50, 1-20, 1-100, or 1-200 µm. In some embodiments, the shell has a thickness of about 0.1 µm to about 50 µm, such as about 1 µm to about 20 µm.

The hardness and elasticity of the bio-block are typically reflective of the hardness and elasticity of the shell of the bio-block. The capacity of mechanical protection provided by the shell is dependent on the hardness and elasticity of the shell or the bio-block, which can be controlled by adjusting the composition (such as the biodegradable polymeric shell material, including components and relative amount of each component) of the shell. In some embodiments, the bio-block or the shell has a hardness of at least about any of 0.01, 0.05, 0.1, 0.15, 0.18, 0.2, 0.22, 0.25, 0.3, or 0.4 GPa. In some embodiments, the bio-block or the shell has a hardness of about any one of 0.01-0.05, 0.05-0.1, 0.1-0.15, 0.14-0.16, 0.16-0.18, 0.18-0.2, 0.2-0.22, 0.2-0.3, 0.3-0.4, 0.01-0.4, 0.01-1, 0.1-0.2, 0.2-0.4, 0.15-0.25, 0.04-0.22, 0.01-0.02, 0.02-0.03, 0.03-0.04, 0.04-0.05, 0.05-0.06, 0.06-0.07, 0.07-0.08, 0.08-0.09, 0.09-0.1, 0.15-0.2, 0.05-0.15, or 0.06-0.1 GPa. In some embodiments, the bio-block or the shell has a modulus of elasticity of at least about any of 0.01, 0.1, 0.5, 1, 1.5, 2, 2.5, 2.8, 3, 3.2, 3.4, 3.6, 4, 10, 20, 50, 75, or 100 MPa. In some embodiments, the bio-block or the shell has an elasticity of about any one of 0.01-0.05, 0.05-0.1, 0.1-0.5, 0.5-0.8, 0.8-1, 0.5-1, 1-1.2, 1.2-1.4, 1.4-1.6, 1.6-1.8, 1.8-2, 1-1.5, 1.5-2, 2-2.4, 2.4-2.8, 2.8-3, 3-3.2, 3.2-3.4, 3.4-3.6, 3.6-4, 4-10, 10-20, 20-30, 30-40, 40-50, 20-50, 50-75, 75-100, 50-80, 80-100, 0.5-4, 1-1.5, 1.5-2, 2-3, 0.8-1.6, 1.4-2.4, 0.8-3.2, 1-100, 10-100, 0.5-6, 1.5-2.5, 2.5-3, 2.8-3.2, 3.2-3.6, 2.9-3.6, 0.01-1, 1-5, 5-10, 10-50, 50-100, 0.01-10, 0.01-25, 0.01-50, 0.01-75, 1-25, 1-50, 10-50, 10-75, or 0.01-100 MPa.

In some embodiments, the bio-block has mechanical strength to endure elastic deformation during three-dimensional deposition. In some embodiments, the bio-block endures elastic deformation during handling and tissue-manufacturing (such as bioprinting) process. In some embodiments, the bio-block reduces mechanical damage of the cell in the bio-block during bioprinting by at least about any of 5%, 10%, 15%, 20%, 25%, 30%, 40%, 50%, 70%, 80%, or 90% compared to bioprinting of the same type of cell using the same bioprinter and under similar conditions. In some embodiments, the bio-block reduces heating of the cell in the bio-block during bioprinting by at least about any of 5%, 10%, 15%, 20%, 25%, 30%, 40%, 50%, 70%, 80%, or 90% compared to bioprinting of the same type of cell using the same bioprinter and under similar conditions. In some embodiments, the bio-block preserves activities (such as metabolism, proliferation, differentiation, migration, and/or secretion) of the cell in the bio-block during bioprinting. In some embodiments, more than about any of 80%, 85%, 87.5%, 90%, 92.5%, 95%, or 98% of the plurality of cells in the bio-block survives about 24 hours after bioprinting. In some embodiments, more than about 90% of the plurality of cells in the bio-block survives at least about any of 3 hours, 6 hours, 12 hours, 24 hours, 2 days, 4 days, or 1 week after bioprinting. In some embodiments, more than about any of 80%, 85%, 87.5%, 90%, 92.5%, 95%, or 98% of the plurality of cells in the bio-block is capable of proliferation about 24 hours after bioprinting. In some embodiments, more than about any of 80%, 85%, 87.5%, 90%, 92.5%, 95%, or 98% of the plurality of cells in the bio-block is capable of differentiation about 24 hours after bioprinting. In some embodiments, more than about any of 80%, 85%, 87.5%, 90%, 92.5%, 95%, or 98% of the plurality of cells in the bio-block has normal metabolism about 24 hours after bioprinting. In some embodiments, more than about any of 80%, 85%, 87.5%, 90%, 92.5%, 95%, or 98% of the plurality of cells in the bio-block is capable of migration about 24 hours after bioprinting. In some embodiments, more than about any of 80%, 85%, 87.5%, 90%, 92.5%, 95%, or 98% of the plurality of cells in the bio-block is capable of secretion about 24 hours after bioprinting.

Core

In some embodiments, the bio-block comprises a single core comprising a polymeric core material (such biodegradable polymeric core material). In some embodiments, the bio-block comprises at least two cores each independently comprising a polymeric core material (such biodegradable polymeric core material). In some embodiments, the bio-block comprises at least two cores. In some embodiments, the at least two cores comprise the same polymeric core material (such as biodegradable polymeric core material). In some embodiments, each of the at least two cores comprise a distinct polymeric core material (such as biodegradable polymeric core material).

In some embodiments, the biodegradable polymeric core material comprises a naturally occurring polymer or derivative thereof. In some embodiments, the naturally occurring polymer is selected from the group consisting of collagen (such as type I, type II or type III collagen), fibrin, chitosan, alginate (such as sodium alginate or calcium alginate), oxidized alginate, starch, hyaluronic acid, laminin, agarose, gelatin, glucan, elastin and combinations thereof.

In some embodiments, the biodegradable polymeric core material comprises a synthetic polymer. In some embodiments, the synthetic polymer is selected from the group consisting of polypohosphazene, polyacrylic acid, polymethacrylic acid, polyacrylic acid, polymethacrylic acid, acrylate copolymer (such as copolymer of acrylic acid and polymethacrylic acid), polylactic acid (PLA), polyglycolic acid (PGA), poly-(lactide-coglycolide acid) (PLGA), polyorthoester (POE), polycaprolactone (PCL), polyhydroxyrate (PHB), polyamine acid (such as polylysine), degradable polyurethane, copolymers thereof, and combinations thereof.

In some embodiments, the biodegradable polymeric core material comprises (including consists of or consists essentially of) alginate (such as sodium alginate). In some embodiments, the biodegradable polymeric core material comprises (including consists of or consists essentially of) type I collagen. In some embodiments, biodegradable polymeric core material comprises (including consists of or consists essentially of) laminin. In some embodiments, the biodegradable polymeric core material comprises (including consists of or consists essentially of) starch. In some embodiments, the biodegradable polymeric core material comprises (including consists of or consists essentially of) degradable polyurethane.

In some embodiments, the bio-block comprises a core comprising alginate (such as sodium alginate, for example, no more than about 2%) and a cell, and a shell comprising alginate (such as calcium alginate, such as at least about 4%). In some embodiments, the bio-block comprises a core comprising type I collagen (such as at least about 0.4%), alginate (such as sodium alginate, for example, no more than about 2.5% or 2%) and a cell, and a shell comprising alginate (such as calcium alginate, such as at least about 2.5% or 4%) and elastin. In some embodiments, the bio-block comprises a core comprising alginate (such as sodium alginate, for example, no more than about 2%) and a cell, and a shell comprising polylysine (such as at least about 1%). In some embodiments, the bio-block comprises a core comprising starch (such as at least about 50%) and a cell, and a shell comprising alginate (such as calcium alginate, for example, at least about 4%). In some embodiments, the bio-block comprises a core comprising starch (such as at least about 50%) and a cell, and a shell comprising oxidized alginate (such as oxidized calcium alginate, for example, at least about 4%). In some embodiments, the bio-block comprises a core comprising starch (such as at least about 50%) and a cell, and a shell comprising alginate (such as calcium alginate) and oxidized alginate (such as oxidized calcium alginate). In some embodiments, the bio-block comprises a core comprising type I collagen (such as at least about 0.4%) and a cell, and a shell comprising polylysine (such as at least about 1%). In some embodiments, the bio-block comprises a core comprising type I collagen (such as at least about 0.4%) and a cell, and a shell comprising alginate (such as calcium alginate, for example, at least about 0.4%). In some embodiments, the bio-block comprises a core comprising type I collagen (such as at least about 0.4%) and a cell, and a shell comprising oxidized alginate (such as oxidized calcium alginate, for example, at least about 0.4%). In some embodiments, the bio-block comprises a core comprising type I collagen (such as at least about 0.4%) and a cell, and a shell comprising alginate (such as calcium alginate) and oxidized alginate (such as oxidized calcium alginate). In some embodiments, the bio-block comprises a core comprising polyurethane (such as at least about 40%) and a cell, and a shell comprising alginate (such as calcium alginate, for example, at least about 4%). In some embodiments, the bio-block comprises a core comprising polyurethane (such as at least about 40%) and a cell, and a shell comprising oxidized alginate (such as oxidized calcium alginate, for example, at least about 4%). In some embodiments, the bio-block comprises a core comprising polyurethane (such as at least about 40%) and a cell, and a shell comprising alginate (such as calcium alginate) and oxidized alginate (such as oxidized calcium alginate). In some embodiments, the bio-block comprises a core comprising polyurethane (such as at least about 40%) and a cell, and a shell comprising alginate (such as calcium alginate) and gelatin. In some embodiments, the bio-block comprises a core comprising laminin and a cell, and a shell comprising alginate (such as calcium alginate) and agarose.

In some embodiments, the biodegradable polymeric core material comprises alginate, oxidized alginate, or combination thereof. In some embodiments, the percentage of the alginate, oxidized alginate, or combination thereof in the biodegradable polymeric core material is at least about any of 0.1%, 0.5%, 1%, 1.25%, 1.5%, 2%, 3%, 4%, 5%, 7.5%, or 10%. In some embodiments, the percentage of the alginate, oxidized alginate, or combination thereof in the biodegradable polymeric core material is about any of 0.1%-0.5%, 0.5%-1%, 1%-1.25%, 1.25%-1.5%, 1.5%-2%, 2%-3%, 3%-4%, 4%-5%, 5%-7.5%, 7.5%-10%, 0.1%-1%, 1%-1.5%, 1%-2%, 0.5-2.5%, 1%-3%, 5-10% or 0.5%-5%. In some embodiments, the percentage of the alginate, oxidized alginate, or combination thereof in the biodegradable polymeric core material is no more than about 2.5% (including for example, no more than about any of 2%, 1.5%, 1%, or 0.5%).

In some embodiments, the biodegradable polymeric core material comprises (such as consists essentially of) type I collagen. In some embodiments, the concentration of the type I collagen in the biodegradable polymeric core material is at least about any of 0.1 mg/mL, 0.5 mg/mL, 1 mg/mL, 1.5 mg/mL, 2 mg/mL, 3 mg/mL, 4 mg/mL, 5 mg/mL, 10 mg/mL or more. In some embodiments, the concentration of the type I collagen in the biodegradable polymeric core material is about any one of 0.1-0.5, 0.5-1, 1-1.5, 1-2, 2-3, 3-4, 4-5, 5-10, 0.1-2, 0.1-5, or 1-10 mg/mL. In some embodiments, the weight percentage of type I collagen in the biodegradable polymeric core material is at least about any of 0.01%, 0.05%, 0.1%, 0.125%, 0.15%, 0.175%, 0.2%, 0.25%, 0.3%, 0.4%, 0.5%, 0.6%, 0.7%, 0.8%, 0.9%, 1%, 2%, 3%, 4%, 5%, 10%, or more. In some embodiments, the percentage of type I collagen in the biodegradable polymeric core material is about any of 0.01%-0.05%, 0.05%-0.1%, 0.1%-0.125%, 0.125%-0.15%, 0.15%-0.175%, 0.175%-0.2%, 0.2%-0.25%, 0.25%-0.3%, 0.3%-0.4%, 0.4%-0.5%, 0.5%-0.6%, 0.6%-0.7%, 0.7%-0.8%, 0.8%-0.9%, 0.2%-0.8%, 0.5%-1%, 1%-2%, 2%-3%, 3%-4%, 4%-5%, 0.01%-0.1%, 0.1%-0.2%, 0.2%-0.5%, 0.1%-0.5%, 0.1%-1%, 0.05%-5%, or 5%-10%.

In some embodiments, the biodegradable polymeric core material comprises a mixture of type I collagen and alginate (such as sodium alginate). The weight ratio between the type I collagen to the alginate depends on the actual application of the bio-block. In some embodiments, the weight ratio between the type I collagen to the alginate in the biodegradable polymeric core material is at least about any of 50:1, 30:1, 20:1, 10:1, 9:1, 8:1, 6:1, 4:1, 2:1, 1:1, 1:2, 1:4, 1:6, 1:8, 3:25, 1:9, 1:10, 1:20, 1:30, or 1:50. In some embodiments, the weight ratio between the type I collagen to the alginate in the biodegradable polymeric core material is any of about 50:1 to about 30:1, about 30:1 to about 20:1, about 20:1 to about 10:1, about 10:1 to about 9:1, about 9:1 to about 8:1, about 8:1 to about 6:1, about 6:1 to about 4:1, about 4:1 to about 2:1, about 2:1 to about 1:1, about 1:1 to about 1:2, about 1:2 to about 1:4, about 1:4 to about 1:6, about 1:6 to about 1:8, about 1:8 to about 1:9, about 1:9 to about 1:10, about 1:10 to about 1:20, about 1:20 to about 1:30, about 1:30 to about 1:50, about 10:1 to about 5:1, about 5:1 to about 1:1, about 1:1 to about 1:5, about 1:5 to about 1:10, about 1:7 to about 1:10, or about 1:8 to about 1:9. In some embodiments, the percentage of type I collagen in the biodegradable polymeric core material is at least about any of 0.01%, 0.05%, 0.1%, 0.125%, 0.15%, 0.175%, 0.2%, 0.25%, 0.3%, 0.4%, 0.5%, 0.6%, 0.7%, 0.8%, 0.9%, 1%, 2%, 3%, 4%, 5%, 10%, or more. In some embodiments, the percentage of type I collagen in the biodegradable polymeric core material is about any of 0.01%-0.05%, 0.05%-0.1%, 0.1%-0.125%, 0.125%-0.15%, 0.15%-0.175%, 0.175%-0.2%, 0.2%-0.25%, 0.25%-0.3%, 0.3%-0.4%, 0.4%-0.5%, 0.5%-0.6%, 0.6%-0.7%, 0.7%-0.8%, 0.8%-0.9%, 0.2%-0.8%, 0.5%-1%, 1%-2%, 2%-3%, 3%-4%, 4%-5%, 0.01%-0.1%, 0.1%-0.2%, 0.2%-0.5%, 0.1%-0.5%, 0.1%-1%, 0.05%-5%, or 5%-10%. In some embodiments, the percentage of the alginate in the biodegradable polymeric core material is at least about any of 0.1%, 0.5%, 1%, 1.25%, 1.5%, 2%, 3%, 4%, 5%, 7.5%, or 10%. In some embodiments, the percentage of the alginate in the biodegradable polymeric core material is about any of 0.1%-0.5%, 0.5%-1%, 1%-1.25%, 1.25%-1.5%, 1.5%-2%, 2%-3%, 3%-4%, 4%-5%, 5%-7.5%, 7.5%-10%, 0.1%-1%, 1%-1.5%, 1%-2%, 0.5-2.5%, 1%-3%, 5-10% or 0.5%-5%. In some embodiments, the percentage of alginate in the biodegradable polymeric core material is no more than about 2.5% (including for example, no more than about any of 2%, 1.5%, 1%, or 0.5%).

In some embodiments, the biodegradable polymeric core material comprises type I collagen and laminin. The weight ratio of the type I collagen to the laminin depends on the actual application of the bio-block. In some embodiments, the weight ratio of the type I collagen to the laminin in the biodegradable polymeric core material is at least about any of 50:1, 30:1, 20:1, 10:1, 9:1, 8:1, 6:1, 4:1, 2:1, 1:1, 1:2, 1:4, 1:6, 1:8, 1:9, 1:10, 1:20, 1:30, or 1:50. In some embodiments, the weight ratio of the type I collagen to the laminin in the biodegradable polymeric core material is any of about 50:1 to about 30:1, about 30:1 to about 20:1, about 20:1 to about 10:1, about 10:1 to about 9:1, about 9:1 to about 8:1, about 8:1 to about 6:1, about 6:1 to about 4:1, about 4:1 to about 2:1, about 2:1 to about 1:1, about 1:1 to about 1:2, about 1:2 to about 1:4, about 1:4 to about 1:6, about 1:6 to about 1:8, about 1:8 to about 1:9, about 1:9 to about 1:10, about 1:10 to about 1:20, about 1:20 to about 1:30, about 1:30 to about 1:50, about 10:1 to about 5:1, about 5:1 to about 1:1, about 1:1 to about 1:5, about 1:5 to about 1:10, about 1:7 to about 1:10, or about 1:8 to about 1:9. In some embodiments, the percentage of type I collagen in the biodegradable polymeric core material is at least about any of 0.01%, 0.05%, 0.1%, 0.125%, 0.15%, 0.175%, 0.2%, 0.25%, 0.3%, 0.4%, 0.5%, 0.6%, 0.7%, 0.8%, 0.9%, 1%, 2%, 3%, 4%, 5%, 10%, or more. In some embodiments, the percentage of type I collagen in the biodegradable polymeric core material is about any of 0.01%-0.05%, 0.05%-0.1%, 0.1%-0.125%, 0.125%-0.15%, 0.15%-0.175%, 0.175%-0.2%, 0.2%-0.25%, 0.25%-0.3%, 0.3%-0.4%, 0.4%-0.5%, 0.5%-0.6%, 0.6%-0.7%, 0.7%-0.8%, 0.8%-0.9%, 0.2%-0.8%, 0.5%-1%, 1%-2%, 2%-3%, 3%-4%, 4%-5%, 0.01%-0.1%, 0.1%-0.2%, 0.2%-0.5%, 0.1%-0.5%, 0.1%-1%, 0.05%-5%, or 5%-10%. In some embodiments, the percentage of the laminin in the biodegradable polymeric core material is at least about any of 0.1%, 0.5%, 1%, 1.25%, 1.5%, 2%, 3%, 4%, 5%, 7.5%, or 10%. In some embodiments, the percentage of the laminin in the biodegradable polymeric core material is about any of 0.1%-0.5%, 0.5%-1%, 1%-1.25%, 1.25%-1.5%, 1.5%-2%, 2%-3%, 3%-4%, 4%-5%, 5%-7.5%, 7.5%-10%, 0.1%-1%, 1%-1.5%, 1%-2%, 0.5-2.5%, 1%-3%, 5-10% or 0.5%-5%.

In some embodiments, the biodegradable polymeric core material comprises starch. In some embodiments, the percentage of starch in the biodegradable polymeric core material is at least about any of 5%, 10%, 20%, 30%, 40%, 50%, 60%, 70%, 80%, or more. In some embodiments, the percentage of starch in the biodegradable polymeric core material is about any of 5%-10%, 10%-20%, 20%-30%, 30%-40%, 40%-50%, 50%-60%, 60%-80%, 10%-80%, 20%-70%, 30%-60%, or 40%-60%.

In some embodiments, the biodegradable polymeric core material comprises polyurethane. In some embodiments, the percentage of polyurethane in the biodegradable polymeric core material is at least about any of 5%, 10%, 20%, 30%, 40%, 50%, 60%, 70%, 80%, or more. In some embodiments, the percentage of polyurethane in the biodegradable polymeric core material is about any of 5%-10%, 10%-20%, 20%-30%, 30%-40%, 40%-50%, 50%-60%, 60%-70%, 10%-80%, 20%-70%, 30%-60%, or 40%-80%.

Microenvironment

In some embodiments, the bio-block, including the shell and/or the core, provides a suitable spatial structure for cell adhesion and spreading, as well as a microenvironment for the cell. "Microenvironment" refers to the appropriate environment comprising a combination of suitable microenvironmental factors for a cell to carry out its life activities. "Microenvironmental factors" include, but are not limited to, physical factors (e.g., physical space, mechanical strength, mechanical factors, temperature, humidity, osmotic pressure, etc.); chemical factors (e.g., pH, ionic concentrations, etc.); biological factors (e.g., cells, cell factors, such as cytokines, growth factors, etc.). The microenvironment may dynamically regulate one or more activities of the cell, including, but not limited to, proliferation, differentiation, migration, metabolism, and secretion. In some embodiments, the core provides a microenvironment (such as nutrients) for the cell.

In some embodiments, the shell provides one or more microenvironmental factors to the cell. In some embodiments, the core provides one or more microenvironmental factors to the cell. In some embodiments, the shell and the core provide one or more microenvironmental factors to the cell. In some embodiments, the one or more microenvironmental factors comprise growth factors for the cell to grow and to differentiate. In some embodiments, the one or more microenvironmental factors comprise a structure and space for the cell to proliferate and to differentiate. In some embodiments, the one or more microenvironmental factors comprise physical factors (such as mechanical stimuli) for the cell to carry out its biological functions. In some embodiments, the one or more microenvironmental factors comprise feeder cells to facilitate or to regulate differentiation of the cell, wherein the cell is a stem cell. In some embodiments, the biodegradable polymeric core and/or shell material provides one or more microenvironmental factors (such as space, nutrients, ECM, etc.) for the cell. In some embodiments, bio-blocks having a core consisting essentially of type I collagen (such as at least about 0.4%) provides a suitable microenvironment for the cell.

In some embodiments, the core comprises an agent selected from the group consisting of nutrients, extracellular matrix, cell factors, pharmaceutically active agents, and combinations thereof. In some embodiments, the core comprises an agent that regulates (such as facilitates) cell proliferation, differentiation, migration, metabolism, secretion, or any combination thereof. In some embodiments, the cell factors regulate (such as facilitate) cell proliferation, differentiation, migration, metabolism, secretion, or any combination thereof.

In some embodiments, the shell comprises an agent selected from the group consisting of nutrients, extracellular matrix, cell factors, pharmaceutically active agents, and combinations thereof. In some embodiments, the shell comprises an agent that regulates (such as facilitates) cell proliferation, differentiation, migration, metabolism, secretion, or any combination thereof. In some embodiments, the cell factors regulate (such as facilitate) cell proliferation, differentiation, migration, metabolism, secretion, or any combination thereof.

In some embodiments, the agent is a protein. In some embodiments, the agent is a human protein. In some embodiments, the agent is a small molecule. In some embodiments, the agent is a small molecule that naturally occurs in human tissues. In some embodiments, the biodegradable polymeric core material comprises the agent. In some embodiments, the biodegradable polymeric core material binds to the agent to allow controlled release of the agent to the cell(s). In some embodiments, the nutrients comprise nucleotides, amino acids, peptides, carbohydrates (such as monosaccharides, oligosaccharides or polysaccharides), lipids, or vitamins. In some embodiments, the extracellular matrix molecule comprises polysaccharide, glycosaminoglycan, glycoprotein, structural protein (such as collagen or elastin), or adhesion protein (such as fibronectin or laminin). Agents (such as cell factors) that facilitate cell proliferation include, but are not limited to, insulin, insulin growth factor (IGF, such as IGF-I or IGF-II), transforming growth factor (TGF, such as TGFα and TGFβ), vascular epidermal growth factor (VEGF), epidermal growth factor (EGF), fibroblast growth factor (FGF), platelet-derived growth factor (PDGF), osteosarcoma source growth factor (ODGF), somatostatin (SRIH), nerve growth factor (NGF), interleukin (IL, such as IL-1, IL-2, IL-3, IL-4, IL-5, IL-6, IL-7, IL-8, IL-10, IL-12), erythropoietin (EPO), colony stimulating factor (CSF), cortisol, thyroid hormones (such as T3 or T4), chemokines (such as CCL, CXC, XCL, or MCP), Tumor Necrosis Factor (TNF), and combinations thereof. Agents (such as cell factors) that facilitate cell differentiation include, but are not limited to, Oct3/4, Sox2, Klf4, c-Myc, GATA4, TSP1, β-glycerophosphate, dexamethasone, vitamin C, insulin, IBMX, indomethacin, PDGF-BB, 5-azacytidine, and combinations thereof. Agents (such as cell factors) that facilitate cell migration include, but are not limited to, cAMP, $PIP_3$, SDF-1, N-cadherin, NF-κB, osteonectin, thromboxane A2, Ras, and combinations thereof. Agents (such as cell factors) that facilitate cell metabolism include, but are not limited to, IGF-I, TRIP-Br2, DKK-1, sRANKL, OPG, TRACP-5b, ALP, SIRT1(2-7), PGC-1α, PGC-1β, IL-3, IL-4, IL6, TGF-β, PGE2, G-CSF, TNFα, and combinations thereof. Agents (such as cell factors) that facilitate cell secretion include, but are not limited to, P600, P110, TCGFIII, BSF-2, glucagon, 3-adrenergic agonist, arginine, $Ca^{2+}$, acetyl choline (ACH), somatostatin, and combinations thereof. In some embodiments, the pharmaceutically active agent regulates (such as facilitates) cell proliferation, differentiation, migration, secretion and/or metabolism. In some embodiments, the pharmaceutically active agent is selected from the group consisting of rhIL-2, rhIL-11, rhEPO, IFN-α, IFN-β, IFN-γ, G-CSF, GM-CSF, rHuEPO, sTNF-R1, rhTNF-α, and combinations thereof.

The core may comprise any number of agents, such as at least about any of 1, 2, 3, 4, 5, 6, 7, 8, 9, 10, or more agents. In some embodiments, the core comprises about any of 1-3, 3-5, 1-5, 1-8, 1-10, 2-5, 5-10, or 10-20 agents. In some embodiments, the core comprises at least one (including at least about any of 1, 2, 3, 4, 5, 6, 7, 8, or more) agent from each of the groups described above of (1) agents that facilitate cell proliferation, (2) agents that facilitate differentiation, (3) agents that facilitate migration, (4) agents that facilitate metabolism, and (5) agents that facilitate secretion. In some embodiments, the core comprises at least one (including at least about any of 1, 2, 3, 4, 5, 10, 15, or 20) agent that regulates (such as facilitates) cell proliferation, differentiation, migration, metabolism, and/or secretion, selected from the group consisting of insulin, IGF-I, IGF-II, TGFα, TGFβ, VEGF, PDGF, ODGF, SRIH, NGF, IL-1, IL-2, IL-3, IL-4, IL-5, IL6, IL-7, EPO, CSF, cortisol, T3, T4, Oct3/4, Sox2, Klf4, c-Myc, GATA4, TSP1, β-glycerophosphate, dexamethasone, vitamin C, insulin, IBMX, indomethacin, PDGF-BB, 5-azacytidine, cAMP, $PIP_3$, SDF-1, N-cadherin, NF-κB, osteonectin, thromboxane A2, Ras, TRIP-Br2, DKK-1, sRANKL, OPG, TRACP-5b, ALP, SIRT1, PGC-1α, PGC-1β, PGE2, G-CSF.

A suitable concentration of the agent in the core depends on the efficacy, stability, and function of the agent, and composition of the core and/or shell. In some embodiments, the agent is present in the bio-block at a concentration of about 0.01 ng/mL to about 100 mg/mL.

In some embodiments, the core and/or the shell comprises at least one nutrient for the cell. In some embodiments, the biodegradable polymeric core material and/or the biodegradable polymeric shell material further comprises at least one nutrient for the cell. In some embodiments, the biodegradable polymers in the core and/or the shell bind to the at least one nutrient to allow controlled release of nutrients to the cell. In some embodiments, the degradation products of the biodegradable polymers in the core and/or the shell provide at least one nutrient for the cell. Nutrients contemplated herein include, but are not limited to nucleotides, amino acids, peptides (including proteins), nucleic acids (including DNA, RNA, and oligonucleotides), carbohydrates (including mono-, oligo-, and poly-saccharides), lipids, vitamins, salts, and oxygen. The percentage of nutrients in the bio-block depends on the actual application of the bio-block. In some embodiments, the weight percentage of nutrients in the bio-block is at least about any of 5%, 10%, 20%, 30%, 40%, 50%, 60%, 70%, 80%, 90%, or 95%. In some embodiments, the weight percentage of nutrients in the bio-block is about any of 0-5%, 5%-10%, 10%-20%, 20%-30%, 30%-40%, 40%-50%, 50%-60%, 60%-70%, 70%-80%, 80%-90%, 90%-95%, 95%-100%, 0-10%, 10%-50%, 5%-25%, 0-50%, 25%-75%, or 50%-100%.

In some embodiments, the core and/or the shell comprises an extracellular matrix (ECM) molecule. In some embodiments, the biodegradable polymeric core material or the biodegradable polymeric shell material comprises an ECM molecule. In some embodiments, the biodegradable polymeric core material binds to the ECM molecule to allow controlled release of the ECM molecule to the cell. ECM molecules contemplated herein include, but are not limited to, polysaccharides, proteins, and glycoproteins, such as glycosaminoglycans, proteoglycan, structural proteins (e.g. collagen and elastin), and adhesion proteins (e.g. fibronectin and laminin). In some embodiments, the degradation products of the biopolymers in the core and/or the shell provide at least one precursor of extracellular matrix (ECM) material for the cell(s). Precursors of ECM molecules contemplated herein include, but are not limited to amino acids, carbohydrates (including monosaccharides and polysaccharides), and lipids. The amount of ECM molecule in the bio-block depends on the actual application of the bio-block. In some embodiments, the weight percentage of ECM molecule in the bio-block is at least about any of 0.1%, 1%, 5%, 10%, 15%, 20%, 25%, 30%, 40%, 50%, 60%, 70%, or 80%.

In some embodiments, the shell is permeable to nutrients, such as nutrients provided to the bio-blocks in the media or to the biocompatible material surrounding the bio-blocks. In some embodiments, the nutrients are selected from the group consisting of water, oxygen, carbohydrates, lipids, proteins, amino acids, peptides, minerals, vitamins, cell factors, nucleic acids, and combinations thereof. In some embodiments, the biodegradable polymeric core and/or shell material has a plurality of microchannels that allow exchange of nutrients or waste materials between the interior and exterior of the bio-block. In some embodiments, the nutrients (such as amino acids, nucleotides, oxygen, carbohydrates, lipids, vitamins, inorganic salt and other small molecules) diffuse through the plurality of microchannels in the biodegradable polymeric shell material.

In some embodiments, the shell comprises one or more micropores. In some embodiments, the shell comprises a plurality of microchannels and micropores. The exemplary bio-block illustrated in FIG. 1A shows micropores in the shell. Unlike microchannels that are inherent structural components of certain biodegradable polymers, micropores are fabricated pores scattered in the shell according to the design and preparation process of the bio-block. Micropores may have a larger size than microchannels, and allow exchange of larger nutrients or macromolecules, such as proteins and nucleic acids. In some embodiments, the average diameter (or size) of the microchannels in the shell is at least about any of 10, 20, 50, 100, 150, 200, 250, 300, 350, 400, or 500 nm. In some embodiments, the average diameter (or size) of the microchannels in the shell is about any one of 10-20, 20-50, 50-100, 100-150, 150-200, 200-250, 250-300, 300-400, 400-500, 10-50, 50-100, 100-500, 10-100, or 10-500 nm. In some embodiments, the average diameter (or size) of the micropores in the shell is at least about any of 50, 75, 100, 200, 400, 600, 800, 1000, 1500, 2000, 4000, or 5000 nm. In some embodiments, the average diameter (or size) of the micropores in the shell is about any one of 50-100, 100-200, 200-400, 400-600, 600-1000, 1000-5000, 50-200, 50-500, or 50-5000 nm.

In some embodiments, the shell is permeable to macromolecules of a molecular weight larger than about any of 100 kDa, 110 kDa, 120 kDa, 130 kDa, 150 kDa, 200 kDa, 250 kDa, 300 kDa, 500 kDa, 1 MDa, 2 MDa, 5 MDa or more. In some embodiments, the shell is permeable to macromolecules of a molecular weight of about any one of 100 kDa to 150 kDa, 110 kDa to 200 kDa, 200 kDa to 300 kDa, 300 kDa to 500 kDa, 500 kDa to 1 MDa, 100 kDa to 200 kDa, 100 kDa to 250 kDa, 100 kDa to 300 kDa, 100 kDa to 500 kDa, 100 kDa to 1 Mda, 100 kDa to 5 MDa, 150 kDa to 300 kDa, 200 kDa to 500 kDa, 200 kDa to 1 Mda, or 200 kDa to 5 MDa.

In some embodiments, the shell is permeable to immune-related molecules. In some embodiments, the shell is permeable to cytokines. In some embodiments, the shell is permeable to chemokines. In some embodiments, the shell is permeable to immunoglobulin, such as IgG, IgM, IgA, IgD, IgE.

Any of the bio-blocks described herein can be present in a mixture, wherein the bio-block is allowed to contact, or to fuse with another bio-block in the mixture. In some embodiments, the bio-block is isolated, i.e. the bio-block is not in direct contact with another bio-block. In some embodiments, the isolated bio-block is provided in a container.

Cell

The cell in the core of the bio-block is customizable in terms of the number of cells in each bio-block and the cell type. In some embodiments, the core comprises one cell. In some embodiments the core comprises a plurality of cells. In some embodiments, the core comprises at least about any of 1, 2, 4, 6, 8, 10, 15, 20, 25, 30, 40, 50, 60, 70, 80, 90, 100, 150, 200, 300, 400, 500, 600, 700, 800, 900, 1000, 2000, 3000, 4000, 5000, 10000, 20000, 30000, 40000, 50000, 100000, 200000, 500000, or 1000000 cells. In some embodiments, the core comprises no more than about any of 2, 5, 10, 20, 30, 40, 50, 100, 200, 300, 500, 600, 700, 800, 900, 1000, 2000, 3000, 4000, 5000, 10000, 20000, 30000, 40000, 50000, 100000, 200000, 500000, or 1000000 cells. In some embodiments, the core comprises about any of 1-2, 2-4, 4-6, 6-8, 8-10, 10-15, 15-20, 20-25, 25-30, 30-40, 40-50, 50-60, 60-70, 70-80, 80-90, 90-100, 100-150, 150-200, 200-300, 300-400, 400-500, 500-1000, 1000-2000, 1-10, 2-10, 2-5, 5-10, 10-20, 20-30, 30-50, 2-25, 25-50, 2-50, 50-100, 100-200, 50-250, 250-500, 500-2000, 2-100, 2-500, 2-2000, 2000-3000, 3000-4000, 4000-5000, 5000-10000, 10000-20000, 20000-30000, 30000-40000, 40000-50000, 50000-100000, 2-5000, 100-5000, 100-1500, 100-1000, 500-5000, 500-10000, 1000-5000, 1-2000, 10-900, 20-800, 30-700, 40-600, 50-500, 60-400, 70-300, 80-200, 10-100, 1-50000, 1-100000, 100000-200000, 200000-500000, 500000-1000000, or 1-1000000 cells. In some embodiments, the core comprises about 1 cell to about 1000000 cells. In some embodiments, the core comprises at least 50 cells. In some embodiments, the core comprises about 1 cell to about 5000 cells, including, for example, about 2 cells to about 50 cells, or about 100 cells to about 5000 cells.

In some embodiments, the plurality of cells is of about any of 1, 2, 3, 4, 5, 6, 7, 8, 9, 10, 15, 20, or more types. In some embodiments, the plurality of cells is of the same type. In some embodiments, the plurality of cells is of at least two different types. Cells may be classified into different types based on their sources, tissues of origin, morphologies, functions, histological markers, expression profiles, or the like.

In some embodiments, the cell is a bacterium, a yeast cell, a plant cell, or an animal cell. In some embodiments, the cell is a mammalian cell. In some embodiments, the cell is a human cell. In some embodiments, the cell is isolated from natural sources, such as a tissue biopsy. In some embodiments, the cell is isolated from an in vitro cultured cell line. In some embodiments, the cell is a genetically engineered cell. In some embodiments, the cell is a seed cell that undergoes proliferation, differentiation, or both in the core.

In some embodiments, the cell is derived from a primary cell. In some embodiments, the cell is derived from a cell line. In some embodiments, the cell is an adherent cell. In some embodiments, the cell is a differentiated adherent cell. In some embodiments, the cell is an undifferentiated adherent cell. In some embodiments, the cell is a pluripotent stem cell. In some embodiments, the cell is a non-adherent cell.

In some embodiments, the cell is derived from an epithelial, muscular, nervous, or connective tissue, or any combination thereof. In some embodiments, the cell is derived from a tissue selected from the group consisting of liver, gastrointestinal, pancreatic, kidney, lung, tracheal, vascular, skeletal muscle, cardiac, skin, smooth muscle, connective tissue, corneal, genitourinary, breast, reproductive, endothelial, epithelial, fibroblast, neural, Schwann, adipose, bone, bone marrow, cartilage, pericytes, mesothelial, endocrine, stromal, lymph, blood, endoderm, ectoderm, mesoderm and combinations thereof. In some embodiments, the cell is derived from a tumor. In some embodiments, the cell is derived from a bone tissue, cartilage tissue, and/or a joint tissue. In some embodiments, the cell is a smooth muscle cell. In some embodiments, the cell is an endothelial cell. In some embodiments, the cell is a hepatocyte.

In some embodiments, the cell is selected from the group consisting of liver cell, gastrointestinal cell, pancreatic cell, kidney cell, lung cell, tracheal cell, vascular cell, skeletal muscle cell, cardiac cell, skin cell, smooth muscle cell, connective tissue cell, corneal cell, genitourinary cell, breast cell, reproductive cell, endothelial cell, epithelial cell, fibroblast, neural cell, Schwann cell, adipose cell, bone cell, bone marrow cell, cartilage cell, pericyte, mesothelial cell, cell derived from endocrine tissue, stromal cell, stem cell, progenitor cell, lymph cell, blood cell, endoderm-derived cell, ectoderm-derived cell, mesoderm-derived cell, undifferentiated cell (such as stem cell, or progenitor cell), and combinations thereof.

In some embodiments, the cell is a stem cell. In some embodiments, the core comprises a plurality of cells comprising a stem cell. In some embodiments, the stem cell is unipotent. In some embodiments, the stem cell is multipotent. In some embodiments, the stem cell is pluripotent. In some embodiments, the stem cell is totipotent. In some embodiments, the stem cell is an induced pluripotent stem cell (iPS). In some embodiments, the stem cell is an embryonic stem cell. In some embodiments, the stem cell is an adult stem cell. In some embodiments, the stem cell is derived from a primary cell. In some embodiments, the stem cell is derived from a cell line. In some embodiments, the stem cell is a progenitor cell. In some embodiments, the core comprises more than one (such as any of 2, 3, 4, 5, 6, or more) type of stem cells. In some embodiments, the stem cell is a hematopoietic stem cell. In some embodiments, the stem cell is a mesenchymal stem cell (MSC). In some embodiments, the stem cell is derived from the bone marrow. In some embodiments, the stem cell is derived from a non-marrow source, such as the umbilical cord, placental tissue, peripheral blood, adipose tissue, teeth, or skin.

Cells of appropriate type(s) can be chosen for bio-blocks to tailor to the specific composition of a given artificial tissue. For example, in some embodiments, the bio-block comprises a cardiomyocyte, wherein the bio-block is useful for preparing a cardiac tissue. In some embodiments, the bio-block comprises a cell selected from the group consisting of endothelial cell, smooth muscle cell, and a fibroblast, wherein the bio-block is useful for preparing a blood vessel. In some embodiments, the bio-block comprises an endothelial cell, wherein the bio-block is useful for preparing a skin tissue.

MSC Bio-Blocks

One aspect of the present application provides bio-blocks comprising one or more mesenchymal stem cells (MSCs; herein after such bio-blocks are referred to as "MSC bio-blocks").

Thus, in some embodiments, there is provided a bio-block comprising a core comprising a biodegradable polymeric core material and an MSC, and a shell comprising a biodegradable polymeric shell material. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

The MSC bio-blocks may have any of the components and/or properties of the bio-blocks described above, provided that the core of the MSC bio-block comprises at least one MSC. In some embodiments, the MSC is a bone marrow stromal cell or a bone marrow-derived mesenchymal stem cell (BMSC). In some embodiments, the MSC is derived from the umbilical cord tissue, such as Wharton's jelly or the umbilical cord blood. In some embodiments, the MSC is derived from the amniotic fluid. In some embodiments, the MSC is derived from an adipose tissue. In some embodiments, the MSC is derived from a dental pulp tissue. In some embodiments, the MSC is derived from skin or hair follicles. In some embodiments, the MSC is derived from adult muscle. In some embodiments, the MSC is derived from corneal stroma. In some embodiments, the MSC is derived from the synovial membrane. In some embodiments, the MSC is derived from joint-related tissues, such as meniscus, intra-articular ligament, and infrapatellar fat pad.

The core may comprise any number of MSCs, including, for example, at least about any of 1, 2, 4, 6, 8, 10, 15, 20, 25, 30, 40, 50, 60, 70, 80, 90, 100, 150, 200, 300, 400, 500, 600, 700, 800, 900, 1000, 2000, 3000, 4000, 5000, 10000, 20000, 30000, 40000, 50000, 100000, 200000, 500000, or 1000000 MSCs. In some embodiments, the core comprises about any of 1-10, 10-900, 20-800, 30-700, 40-600, 50-500, 60-400, 70-300, 80-200, 10-100, 10-1000, 10-10000, 10-100000, or 1-1000000 MSCs. The MSC may be present at a suitable percentage of the total number of cells in the core. In some embodiments, the number of MSCs is at least about any of 10%, 20%, 30%, 40%, 50%, 60%, 70%, 80%, 90%, 95%, or more of the total number of cells in the core. In some embodiments, the number of MSCs is about any one of 10%-20%, 20%-30%, 30%-40%, 40%-50%, 50%-60%, 60%-70%, 70%-80%, 80%-90%, 90%-100%, 10%-40%, 40%-80%, 10%-50%, 50%-100%, or 20%-100% of the total number of cells in the core.

The MSCs in the MSC bio-blocks described herein may be induced to differentiate towards various cell fates. Four types of exemplary MSC bio-blocks are described herein, including MSC bio-blocks that provide microenvironments for differentiation of the MSCs towards osteoblasts or bone tissue (referred hereinafter as "Type I MSC bio-blocks"), towards chondrocytes or cartilage tissue (referred hereinafter as "Type II MSC bio-blocks"), towards endothelial cells (referred hereinafter as "Type III MSC bio-blocks"), or towards smooth muscle cells (referred hereinafter as "Type IV MSC bio-blocks"). The microenvironments may include suitable physical (such as space, mechanical protection, and stimuli, etc.), chemical (such as pH, nutrients, etc.), and biological (such as cell factors, and ECM, etc.) for MSC differentiation, which are provided by the components of the MSC bio-blocks as a whole. In some embodiments, the microenvironment comprises growth factors and/or nutrients for the proliferation and differentiation of the MSC. In some embodiments, the microenvironment comprises space for the proliferation and differentiation of the MSC. In some embodiments, the microenvironment comprises physical stimuli (such as mechanical stimulation, or hypoxia) to maintain or facilitate biological functions of the MSC. In some embodiments, the microenvironment comprises feeder cells that coordinate or regulate MSC differentiation. By providing different microenvironments, the MSC in the MSC bio-block can be differentiated into different cell types. In some embodiments, the core and/or the shell comprise one or more agents that induce differentiation of the MSC towards an osteoblast. In some embodiments, the core and/or the shell comprise one or more agents that induce differentiation of the MSC towards a chondrocyte. In some embodiments, the core and/or the shell comprise one or more agents that induce differentiation of the MSC towards an endothelial cell. In some embodiments, the core and/or the shell comprise one or more agents that induce differentiation of the MSC towards a smooth muscle cell.

Thus, in some embodiments, there is provided a bio-block (i.e., a Type I MSC bio-block) comprising: (a) a core comprising a biodegradable polymeric core material, an MSC, and an agent that induces the MSC to differentiate into an osteoblast; and (b) a shell comprising a biodegradable polymeric shell material. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core further comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block (i.e., a Type I MSC bio-block) comprising: (a) a core comprising a biodegradable polymeric core material, an MSC, dexamethasone, ascorbic acid, and glycerophosphate; and (b) a shell comprising a biodegradable polymeric shell material. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core further comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block (i.e., a Type II MSC bio-block) comprising: (a) a core comprising a biodegradable polymeric core material, an MSC, and an agent that induces the MSC to differentiate into a chondrocyte; and (b) a shell comprising a biodegradable polymeric shell material. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core further comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block (i.e., a Type II MSC bio-block) comprising: (a) a core comprising a biodegradable polymeric core material, an MSC, TGF-β3, dexamethasone, ascorbic acid 2-phosphate, sodium pyruvate, proline, insulin, transferrin, and selenous acid; and (b) a shell comprising a biodegradable polymeric shell material. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core further comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, the microenvironment includes an agent that induces, promotes, or regulates differentiation of the MSC to an osteoblast (referred hereinafter as "osteoblast differentiation agent"). Any one or combinations of osteoblast differentiation agents known in the art can be used in the Type I MSC bio-blocks. Exemplary osteoblast differentiation agents include, but are not limited to, vitamin $D_3$, ascorbic acid, β-glycerophosphate, dexamethasone, type I collagen, Wnt (such as Wnt3a, Wnt4, Wnt5a, and Wnt10b), BMP (such as BMP-2, BMP-4, BMP-7); stimulators of transcription factors β-catenin, Runx2, SATB2, TAZ, osterix, Smads, C/EBPs, and ATF4; and inhibitors of transcription factors PPARγ, and Twist1. See, for example, Fakhry M. et al. "Molecular mechanisms of mesenchymal stem cell differentiation towards osteoblasts" *World J. Stem Cells*. 2013, 5(4): 136-148, which is incorporated herein by reference. In some embodiments, the core of the Type I MSC bio-block comprises vitamin $D_3$, ascorbic acid, and β-glycerophosphate. In some embodiments, the core of the Type I MSC bio-block comprises dexamethasone, ascorbic acid, and β-glycerophosphate. In some embodiments, the biodegradable polymeric core material of the Type I MSC bio-block comprises (including consisting essentially of) type I collagen.

Suitable concentrations of the osteoblast differentiation agents depend on the nature of the agent, and may be in the range of about 1 nM to about 100 mM, or about 1 ng/mL to 10 mg/mL. In some embodiments, the concentration of dexamethasone in the core of the Type I MSC bio-block is at least about any of 0.01 µM, 0.02 µM, 0.05 µM, 0.1 µM, 0.2 µM, 0.5 µM, or 1 mM. In some embodiments, the concentration of dexamethasone in the core of the Type I MSC bio-block is about any of 0.01 µM-0.05 µM, 0.05 µM-0.1 µM, 0.1 µM-0.2 µM, 0.2 µM-0.5 µM, 0.05 µM-0.2 µM, 0.01 µM-0.2 µM, or 0.1 µM-1 mM. In some embodiments, the concentration of ascorbic acid in the core of the Type I MSC bio-block is at least about any of 0.005 mM, 0.01 mM, 0.02 mM, 0.05 mM, 0.1 mM, 0.2 mM, or 0.5 mM. In some embodiments, the concentration of ascorbic acid in the core of the Type I MSC bio-block is about any of 0.005 mM-0.01 mM, 0.01 mM-0.02 mM, 0.02 mM-0.05 mM, 0.05 mM-0.1 mM, 0.1 mM-0.5 mM, 0.01 mM-0.1 mM, or 0.01 mM-0.5 mM. In some embodiments, the concentration of β-glycerophosphate in the core of the Type I MSC bio-block is at least about any of 0.1 mM, 1 mM, 2 mM, 5 mM, 10 mM, 15 mM, 20 mM, 50 mM, or more. In some embodiments, the concentration of β-glycerophosphate in the core of the Type I MSC bio-block is about any of 0.1 mM-1 mM, 1 mM-5 mM, 5 mM-10 mM, 5 mM-15 mM, 1 mM-20 mM, or 1 mM-50 mM.

In some embodiments, the microenvironment includes an agent that induces, promotes, or regulates differentiation of the MSC to a chondrocyte (referred hereinafter as "chondrocyte differentiation agent"). Any one or combinations of chondrocyte differentiation agents known in the art can be used in the Type II MSC bio-blocks. Exemplary chondrocyte differentiation agents include, but are not limited to N-cadherin, dexamethasone, ascorbate, insulin, transferrin, and selenous acid, TGF-b (such as TGF-b1, TGF-b2, and/or TGF-b3), BMP (such as BMP2, BMP4, BMP6), and IGF1. See, for example, Boeuf S. and Richter W. "Chondrogenesis of mesenchymal stem cells: role of tissue source and inducing factors." *Stem Cell Research & Therapy* 2010, 1:31, which is incorporated herein by reference. In some embodiments, the core of the Type II MSC bio-block comprises dexamethasone, ascorbate, insulin, transferrin, and selenous acid. In some embodiments, the core of the Type II MSC bio-block further comprises TFG-β. In some embodiments, the core of the Type II MSC bio-block comprises TFG-β3, dexamethasone, ascorbic acid 2-phosphate, sodium pyruvate, proline, insulin, transferrin, and selenous acid. In some embodiments, an ITS+ tissue culture supplement solution comprising insulin, transferrin, and selenous acid is included in the core of the Type II MSC bio-block. ITS+ Premix Tissue Culture supplements are commercially available from various sources, such as Corning, Collaborative Biomedical, Thermo Fisher Scientific, or Sigma-Aldrich. In some embodiments, the biodegradable polymeric core material of the Type II MSC bio-block comprises (including consisting essentially of) type I collagen.

Suitable concentrations of the osteoblast differentiation agents depend on the nature of the agent, and may be in the range of about 1 nM to about 100 mM, or about 1 ng/mL to 10 mg/mL. In some embodiments, the concentration of dexamethasone in the core of the Type II MSC bio-block is at least about any of 0.01 µM, 0.02 µM, 0.05 µM, 0.1 µM, 0.2 µM, 0.5 µM, or 1 mM. In some embodiments, the concentration of dexamethasone in the core of the Type II MSC bio-block is about any of 0.01 µM-0.05 µM, 0.05 µM-0.1 µM, 0.1 µM-0.2 µM, 0.2 µM-0.5 µM, 0.05 µM-0.2 µM, 0.01 µM-0.2 µM, or 0.1 µM-1 mM. In some embodiments, the concentration of ascorbic acid 2-phosphate in the core of the Type II MSC bio-block is at least about any of 5, 10, 20, 50, 100, 200 or 500 µg/mL. In some embodiments, the concentration of ascorbic acid 2-phosphate in the core of the Type II MSC bio-block is about any of 5-10, 10-50, 5-50, 20-100, 10-200, 20-200, 100-500, or 10-200 µg/mL. In some embodiments, the concentration of sodium pyruvate in the core of the Type II MSC bio-block is at least about any of 10, 20, 50, 100, 200, 500, or 1000 µg/mL. In some embodiments, the concentration of sodium pyruvate in the core of the Type II MSC bio-block is about any of 10-20, 20-50, 20-100, 10-200, 20-200, 50-500, or 50-1000 µg/mL. In some embodiments, the concentration of proline in the core of the Type II MSC bio-block is at least about any of 4, 10, 20, 40, 100, 200 or 400 µg/mL. In some embodiments, the concentration of proline in the core of the Type II MSC bio-block is about any of 4-10, 10-40, 5-50, 20-100, 10-200, 20-200, 100-400, or 10-200 µg/mL. In some embodiments, the concentration of TGF-β (such as TGF-β3) in the core of the Type II MSC bio-block is at least about any of 1, 2, 5, 10, 20, 50, or 100 ng/mL. In some embodiments, the concentration of proline in the core of the Type II MSC bio-block is about any of 1-5, 2-10, 5-20, 5-50, 50-100, or 1-100 ng/mL. In some embodiments, the percentage (v/v) of the ITS+ tissue culture supplement solution in the core of the Type II MSC bio-block is at least about any of 1%, 2%, 5%, 10%, 20%, 30%, or more. In some embodiments, the percentage (v/v) of the ITS+ tissue culture supplement solution in the core of the Type II MSC bio-block is about any of 1%-5%, 5%-10%, 5%-15%, 10%-20%, 5%-25%, or 1%-30%.

In some embodiments, the MSC bio-block further comprises a differentiated cell. In some embodiments, the differentiated cell provides a microenvironment for the MSC to differentiate towards the differentiated cell. In some embodiments, the core of the MSC bio-block comprises the MSC and the differentiated cell. In some embodiments, the MSC bio-block comprises a first core comprising the MSC, and a second core comprising the differentiated cell. In some embodiments, the differentiated cell is an endothelial cell, such as HUVEC. In some embodiments, the differentiated cell is a smooth muscle cell. In some embodiments, the MSC and the differentiated cell are derived from the same organism, such as a mammal, for example, human, rat, mice, or non-human primate. In some embodiments, the MSC and the differentiated cell are derived from the same source, such as the same subject. In some embodiments, the MSC and the differentiated cell are derived from different organisms. For example, in some embodiments, the MSC is derived from rat, and the differentiated cell is derived from rat.

Thus, in some embodiments, there is provided a bio-block (i.e., a Type III MSC bio-block) comprising: (a) a core comprising a biodegradable polymeric core material, an MSC, and an endothelial cell; and (b) a shell comprising a biodegradable polymeric shell material. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core further comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 2 cells to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells. In some embodiments, the bio-block is subjected to a fluid shear force, such as at about 115-5 dyn/cm².

In some embodiments, there is provided a bio-block (i.e., a Type III MSC bio-block) comprising: (a) a core comprising a biodegradable polymeric core material, an MSC, and an agent that induces differentiation of the MSC to an endothelial cell (such as VEGF and ECGS, or VEGF and bFGF); and (b) a shell comprising a biodegradable polymeric shell material. In some embodiments, the core comprises at least about 50 ng/mL VEGF and at least about 30 ng/mL ECGS. In some embodiments, the core comprises at least about 10 ng/mL VEGF and at least about 2 ng/mL bFGF. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core further comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 2 cells to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells. In some embodiments, the bio-block is subjected to a fluid shear force, such as at about 115-5 dyn/cm².

In some embodiments, there is provided a bio-block (i.e., a Type IV MSC bio-block) comprising: (a) a core comprising a biodegradable polymeric core material, an MSC, and a smooth muscle cell; and (b) a shell comprising a biodegradable polymeric shell material. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core further comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 2 cells to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-block (i.e., a Type IV MSC bio-block) comprising: (a) a core comprising a biodegradable polymeric core material, an MSC, and an agent that induces differentiation of the MSC to a smooth muscle cell (such as angiotensin II); and (b) a shell comprising a biodegradable polymeric shell material. In some embodiments, there is provided a bio-block (i.e., a Type IV MSC bio-block) comprising: (a) a core comprising a biodegradable polymeric core material comprising poly(lactide/ε-caprolactone) (i.e., PLCL), and an adipose-derived MSC; and (b) a shell comprising a biodegradable polymeric shell material. In some embodiments, there is provided a bio-block (i.e., a Type IV MSC bio-block) comprising: (a) a core comprising a biodegradable polymeric core material comprising type IV collagen, and an embryonic stem cell; and (b) a shell comprising a biodegradable polymeric shell material. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core further comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 2 cells to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

The ratio between the number of the differentiated cell (such as endothelial cell, or smooth muscle cell) and the number of the MSC in the Type III or Type IV MSC bio-block can be optimized to provide a suitable microenvironment for the differentiation of the MSC. In some embodiments, the ratio between the number of the number of the differentiated cell (such as endothelial cell, or smooth muscle cell) and the number of the MSC is at least about any of 1:20, 1:19, 1:18, 1:17, 1:16, 1:15, 1:14, 1:13, 1:12, 1:11, 1:10.5, 1:10, 1:9.5, 1:9, 1:8.5, 1:8, 1:7, 1:6, 1:5, 1:4, 1:3, 1:2, 2:3, or 1:1. In some embodiments, the ratio between the number of the differentiated cell (such as endothelial cell, or smooth muscle cell) and the number of the MSC is about 1:20 to about 1:1, such as about any one of 1:20 to 1:15, 1:15 to 1:10, 1:10 to 1:5, 1:5 to 1:1, 1:20 to 1:18, 1:18 to 1:16, 1:16 to 1:14, 1:14 to 1:12, 1:12 to 1:10, 1:10 to 1:8, 1:8 to 1:6, 1:6 to 1:4, 1:4 to 1:2, 1:10.5 to 1:9.5, 1:11 to 1:9, 1:12 to 1:8, 1:13 to 1:7, 1:14 to 1:6, 1:15 to 1:5, or 1:20 to 2:3. In some embodiments, the ratio between the number of the endothelial cell and the number of the MSC is about 1:10. In some embodiments, the ratio between the number of the smooth muscle cell and the number of the MSC is about 1:3.

In some embodiments, there is provided a bio-block (i.e., a Type I MSC bio-block) comprising: a MSC cell, a core enwrapping the MSC cell, and a shell coating the core, wherein the core and the shell each independently comprises a biodegradable material, and the core provides a microenvironment that induces the MSC to differentiate into an osteoblast or a bone tissue (for example, the core comprises a cell factor that induces the MSC to differentiate into an osteoblast or a bone tissue). In some embodiments, the shell provides a microenvironment that induces the MSC to differentiate into an osteoblast or a bone tissue (for example, the core comprises a cell factor that induces the MSC to differentiate into an osteoblast or a bone tissue). In some embodiments, the cell factor comprises dexamethasone, ascorbic acid, and glycerophosphate. In some embodiments, the shell does not comprise a cell.

In some embodiments, there is provided a bio-block (i.e., a Type II MSC bio-block) comprising: a MSC cell, a core enwrapping the MSC cell, and a shell coating the core, wherein the core and the shell each independently comprises a biodegradable material, and wherein the core provides a microenvironment that induces the MSC to differentiate into a chondrocyte or a cartilage tissue (for example, the core comprises a cell factor that induces the MSC to differentiate into a chondrocyte or a cartilage tissue). In some embodiments, the shell provides a microenvironment that induces the MSC to differentiate into a chondrocyte or a cartilage tissue (for example, the core comprises a cell factor that induces the MSC to differentiate into a chondrocyte or a cartilage tissue). In some embodiments, the cell factor comprises TFG-β3, dexamethasone, ascorbic acid 2-phosphate, sodium pyruvate, proline, and an insulin-transferrin-selenous acid solution. In some embodiments, the shell does not comprise a cell.

In some embodiments, there is provided a bio-block (i.e., a Type III MSC bio-block) comprising: a MSC cell, a core enwrapping the MSC cell, and a shell coating the core, wherein the core and the shell each independently comprises a biodegradable material, and wherein the core provides a microenvironment that induces the MSC to differentiate into an endothelial cell. In some embodiments, the core comprises an endothelial cell. In some embodiments, the core comprises VEGF and ECGS. In some embodiments, the core comprises VEGF and bFGF.

In some embodiments, there is provided a bio-block (i.e., a Type III MSC bio-block) comprising: a MSC cell, a core enwrapping the MSC cell, and a shell coating the core, wherein the core and the shell each independently comprises a biodegradable material, and wherein the core provides a microenvironment that induces the MSC to differentiate into a smooth muscle cell. In some embodiments, the core comprises angiotensin II. In some embodiments, wherein the MSC is derived from an adipose tissue, the core comprises poly(lactide/ε-caprolactone) (i.e., PLCL). In some embodiments, the core comprises Type IV collagen.

In some embodiments of any one of the Type I, II, III, or IV MSC bio-blocks described above, the core provides a microenvironment (such as nutrients) for cellular activities of the MSC. In some embodiments, each core independently comprises a biodegradable material, wherein the biodegradable material is biocompatible. In some embodiments, the biodegradable material of the core is naturally occurring (such as a naturally occurring biodegradable material from plants or animals), synthetic, recombinant, modified, or any combination thereof. In some embodiments, the biodegradable material of the core comprises a naturally occurring biodegradable polymer, such as collagen, fibrin, chitosan, alginate, starch, hyaluronic acid, laminin, agarose, gelatin, glucan, elastin, or a combination thereof; a modified biodegradable polymer, such as modified alginate, for example, oxidized alginate (e.g., oxidized sodium alginate); and/or a synthetic biodegradable polymer, such as polypohosphazene, polyacrylic acid, polymethacrylic acid, acrylate copolymer (such as copolymer of acrylic acid and polymethacrylic acid), polylactic acid (PLA), polyglycolic acid (PGA), poly-(lactide-coglycolide acid) (PLGA), poly-orthoester (POE), polycaprolactone (PCL), polyhydroxyrate (PHB), polyamino acid (such as polylysine), degradable polyurethane, copolymer thereof, or a combination thereof. In some embodiments, the biodegradable polymer of the core can be degraded by an enzyme (such as an enzyme secreted by the MSC). In some embodiments, the degradation product of the core provides nutrients that maintain or promote cellular activities of the MSC. In some embodiments, the biodegradable polymer is selected from the group consisting of collagen (such as type I, type II, or type III collagen), fibrin, chitosan, alginate (such as sodium alginate), oxidized alginate (such as oxidized sodium alginate), starch, hyaluronic acid, laminin, elastin, gelatin, glucan, polyamino acid (such as polylysine), agarose, biodegradable polyurethane, and combinations thereof. In some embodiments, the core comprises type I collagen and/or alginate, such as type I collagen and sodium alginate. In some embodiments, the core comprises laminin. In some embodiments, the core comprises starch. In some embodiments, the core comprises biodegradable polyurethane. In some embodiments, the core comprises alginate (such as sodium alginate or calcium alginate), and oxidized alginate (such as oxidized sodium alginate). In some embodiments, the core is in a gel state.

In some embodiments of any one of the Type I, II, III, or IV MSC bio-blocks described above, the shell provides mechanical protection for the MSC cell. In some embodiments, each shell independently has a hardness of about 0.01-0.4 GPa, such as about any of 0.01-0.02, 0.02-0.03, 0.03-0.04, 0.04-0.05, 0.05-0.06, 0.06-0.07, 0.07-0.08, 0.08-0.09, 0.09-0.1, 0.1-0.15, 0.15-0.2, 0.2-0.3, 0.3-0.4, 0.01-0.4, 0.01-0.05, 0.05-0.1, 0.1-0.2, 0.2-0.4, 0.05-0.15, or 0.06-0.1 GPa; and/or a modulus of elasticity of about 0.01-100 MPa, such as about any of 0.01-0.05, 0.05-0.1, 0.1-0.5, 0.5-0.8, 0.8-1, 1-1.2, 1.2-1.4, 1.4-1.6, 1.6-1.8, 1.8-2, 2-2.4, 2.4-2.8, 2.8-3.2, 3.2-4, 4-10, 10-20, 20-30, 30-40, 40-50, 50-80, 80-100, 0.5-4, 0.5-1, 1-1.5, 1.5-2, 2-3, 0.8-1.6, 1.4-2.4, 0.8-3.2, 0.01-100, 1-100, 10-100, or 0.5-50 MPa. In some embodiments, the shell provides a microenvironment (such as nutrients) for cellular activities of the MSC. In some embodiments, each shell independently comprises a biodegradable material, wherein the biodegradable material is biocompatible. In some embodiments, the biodegradable material of the shell is naturally occurring (such as a naturally occurring biodegradable material from plants or animals), synthetic, recombinant, modified, or any combination thereof. In some embodiments, the biodegradable material of the shell comprises a naturally occurring biodegradable polymer, such as collagen, fibrin, chitosan, alginate, starch, hyaluronic acid, laminin, agarose, gelatin, glucan, elastin, or a combination thereof; a modified biodegradable polymer, such as modified alginate, for example, oxidized alginate (e.g., oxidized sodium alginate); and/or a synthetic biodegradable polymer, such as polypohosphazene, polyacrylic acid, polymethacrylic acid, acrylate copolymer (such as copolymer of acrylic acid and polymethacrylic acid), polylactic acid (PLA), polyglycolic acid (PGA), poly-(lactide-coglycolide acid) (PLGA), poly-orthoester (POE), polycaprolactone (PCL), polyhydroxyrate (PHB), polyamino acid (such as polylysine), degradable polyurethane, copolymer thereof, or a combination thereof. In some embodiments, the biodegradable polymer of the shell can be degraded by an enzyme (such as an enzyme secreted by the MSC). In some embodiments, the degradation product of the shell provides nutrients that maintain or promote cellular activities of the MSC. In some embodiments, the biodegradable polymer is selected from the group consisting of collagen (such as type I, type II, or type III collagen), fibrin, chitosan, alginate (such as sodium alginate), oxidized alginate (such as oxidized sodium alginate), starch, hyaluronic acid, laminin, elastin, gelatin, glucan, polyamino acid (such as polylysine), agarose, biodegradable polyurethane, and combinations thereof. In some embodiments, the shell comprises alginate (such as sodium alginate or calcium alginate), for example, calcium alginate and gelatin, and optionally elastin. In some embodiments, the shell comprises oxidized alginate (such as oxidized sodium alginate). In some embodiments, the shell comprises alginate (such as sodium alginate and calcium alginate) and oxidized alginate (such as oxidized sodium alginate). In some embodiments, the shell comprises alginate (such as sodium alginate or calcium alginate) and agarose.

In some embodiments of any one of the Type I, II, III, or IV MSC bio-blocks described above, each shell is independently processed (such as using a solidifying or crosslinking solution, for example, to improve the mechanical properties of the shell). In some embodiments, each core is independently permeable. For example, the shell is permeable to water, oxygen and nutrients, including, saccharides, such as glucose, lipids, proteins, amino acids, peptides, minerals, vitamins, cell factors, and nucleic acids. In some embodiments, each shell independently has one or more microchannels or micropores for exchange of materials inside and outside the bio-block. In some embodiments, the diameter of the one or more microchannels is at least about any of 10, 20, 50, 100, 150, 200, 250, 300, 350, 400, or 500 nm. In some embodiments, the diameter of the one or more micropores is at least about any one of 100, 200, 400, 600, 800, 1000, 1500, 2000, 4000, or 5000 nm. In some embodiments, each shell independently has a thickness of about 0.1-50 µm, such as about any one of 0.1-0.5, 0.5-1, 1-2, 2-5, 5-10, 10-15, 15-20, 20-25, 25-30, 30-50, 50-100, 100-200, 200-300, 300-400, 400-500, 0.1-1, 1-5, 1-10, 5-10, 10-20, 10-30, 5-20, or 1-20 µm.

In some embodiments of any one of the Type I, II, III, or IV MSC bio-blocks described above, each core and/or shell independently further comprises an additional agent, such as a nutrient, an ECM molecule, a cell factor, and/or a pharmaceutically active agent. In some embodiments, the additional agent can regulate (such as promote) proliferation, migration, secretion, and/or metabolism of the MSC. In some embodiments, the nutrient is selected from the group consisting of nucleic acids, amino acids, polypeptides, carbohydrates (such as monosaccharides, oligosaccharides, polysaccharides), lipids, and vitamins. In some embodiments, the ECM molecule is selected from the group consisting of polysaccharides (such as glycosaminoglycans, proteoglycans), structural proteins (such as collagen and elastin), adhesion proteins (such as fibronectin and laminin). In some embodiments, the cell factor can regulate proliferation, migration, secretion and/or metabolism of the cell. Suitable cell factors include, but are not limited to: cell factors related to cell proliferation, such as insulin, insulin growth factor (IGF, such as IGF-I or IGF-II), transforming growth factor (TGF, such as TGFα and TGFβ), vascular epidermal growth factor (VEGF), epidermal growth factor (EGF), fibroblast growth factor (FGF), platelet-derived growth factor (PDGF), osteosarcoma source growth factor (ODGF), somatostatin (SRIH), nerve growth factor (NGF), interleukin (IL, such as IL-1, IL-2, IL-3, IL-4, IL-5, IL-6, IL-7, IL-8, IL-10, IL-12), erythropoietin (EPO), colony stimulating factor (CSF), cortisol, thyroid hormones (such as T3 or T4), chemokines (such as CCL, CXC, XCL, or MCP), Tumor Necrosis Factor (TNF), and combinations thereof; cell factors related to cell migration, such as cAMP, $PIP_3$, SDF-1, N-cadherin, NF-κB, osteonectin, thromboxane A2, Ras, and combinations thereof; cell factors related to cell metabolism, such as IGF-I, TRIP-Br2, DKK-1, sRANKL, OPG, TRACP-5b, ALP, SIRT1(2-7), PGC-1α, PGC-1β, IL-3, IL-4, IL6, TGF-β, PGE2, G-CSF, TNFα, and combinations thereof. In some embodiments, the pharmaceutically active agent regulates (such as facilitates) cell proliferation, differentiation, migration, secretion and/or metabolism. In some embodiments, the pharmaceutically active agent is selected from the group consisting of rhIL-2, rhIL-11, rhEPO, IFN-α, IFN-β, IFN-γ, G-CSF, GM-CSF, rHuEPO, sTNF-R1, rhTNF-α, and combinations thereof.

In some embodiments of any one of the Type I, II, III, or IV MSC bio-blocks described above, each core independently comprises one or more MSCs, such as about $1\text{-}10^6$ MSCs, including, about any one of 10-900, 20-800, 30-700, 40-600, 50-500, 60-400, 70-300, 80-200, 10-100, $10\text{-}10^3$, $10\text{-}10^4$, $10\text{-}10^5$, $10\text{-}10^6$ cells. In some embodiments, the size of the bio-block is about 20-2000 µm, such as about any of 30-1900 µm, 40-1800 µm, 50-1700 µm, 60-1600 µm, 70-1500 µm, 80-1400 µm, 90-1300 µm, 100-1200 µm, 200-1000 µm, 300-800 µm, 400-600 µm, or 100-500 µm. In some embodiments, the bio-block is spherical, or of any other suitable shape (such as cubical, rectangular prism, cylindrical, or of irregular shape). In some embodiments, the bio-block is solid or semi-solid, such as in a gel state. In some embodiments, the bio-block is present in a composition. In some embodiments, the bio-block is isolated. In some embodiments, the bio-block is provided in a container.

Bio-Ink Compositions and Pharmaceutical Compositions

The present application further provides compositions (such as bio-ink compositions, pharmaceutical compositions) comprising a plurality of any of the bio-blocks (including MSC bio-blocks, such as Type I, II, III, or IV MSC bio-blocks) described herein or a plurality of isolated bio-blocks. It is intended that any of the properties (such as composition, ratio, physical and chemical properties, etc.) of the bio-block (including MSC bio-block, such as Type I, II, III, or IV MSC bio-block) as described herein can be combined with any of the properties (such as carrier properties, etc.) of the bio-ink composition as described herein, as if each and every combination is individually described.

The bio-ink compositions differ significantly from other bio-ink compositions currently used for 3D bioprinting, which typically comprise cells suspended in a carrier. Because the core and/or shell of the bio-blocks have suitable mechanical and physical properties, the bio-ink compositions described herein has at least the following advantages: (1) providing mechanical protection for the cells; (2) promoting cell survival; and (3) no need for a scaffold.

In addition to the many unique properties of the bio-blocks, the bio-ink compositions also differ significantly from compositions comprising encapsulated cells. For example, the bio-ink composition is suitable for extrusion, such as by inkjet or microextrusion bioprinting. In some embodiments, the bio-ink composition is essentially free of liquid. In some embodiments, the bio-ink composition is a liquid or a paste. In some embodiments, the bio-ink composition comprises a carrier that is suitable for extrusion. Thus, the carrier in the bio-ink composition must comprise material having suitable viscosity for extrusion. Furthermore, the bio-ink composition may comprise any number of types of bio-blocks, which can be homogenously suspended within the carrier. By contrast, encapsulated cells are typically prepared in a solution, or embedded in or deposited on top of a solid or semi-solid scaffold. The weight percentage of bio-blocks and cell density in the bio-ink composition of the present application may also differ from those in compositions comprising encapsulated cells.

Accordingly, one aspect of the present application provides a bio-ink composition comprising a plurality of bio-blocks each comprising: a) a core comprising a biodegradable polymeric core material and a cell (such as MSC), and b) a shell comprising a biodegradable polymeric shell material. In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks each comprising: a) a core comprising a biodegradable polymeric core material and a cell, and b) a shell comprising a biodegradable polymeric shell material, wherein the bio-ink composition comprises at least about 50% bio-blocks (w/w). In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks and a carrier (such as a liquid or a paste), wherein the plurality of bio-blocks each comprises: a) a core comprising a biodegradable polymeric core material and a cell, and b) a shell comprising a biodegradable polymeric shell material, wherein the bio-ink composition comprises at least about 50% bio-blocks (w/w). In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks and a carrier (such as a liquid or a paste), wherein the plurality of bio-blocks each comprises: a) a core comprising a biodegradable polymeric core material and a cell, and b) a shell comprising a biodegradable polymeric shell material, and wherein the plurality of bio-blocks are suspended homogenously within the carrier. In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks and a carrier (such as a liquid or a paste), wherein the plurality of bio-blocks each comprises: a) a core comprising a biodegradable polymeric core material and a cell, and b) a shell comprising a biodegradable polymeric shell material, wherein the plurality of bio-blocks are suspended homogenously within the carrier, and wherein the bio-ink composition comprises at least about 50% bio-blocks (w/w). In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks and a carrier (such as a liquid or a paste), wherein the plurality of bio-blocks each comprises: a) a core comprising a biodegradable polymeric core material and a cell, and b) a shell comprising a biodegradable polymeric shell material, and wherein the carrier has a viscosity of about 1 Pa·s to about 1000 Pa·s. In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks and a carrier (such as a liquid or a paste), wherein the plurality of bio-blocks each comprises: a) a core comprising a biodegradable polymeric core material and a cell, and b) a shell comprising a biodegradable polymeric shell material, wherein the carrier has a viscosity of about 1 Pa·s to about 1000 Pa·s, and wherein the bio-ink composition comprises at least about 50% bio-blocks (w/w). In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks and a carrier (such as a liquid or a paste), wherein the plurality of bio-blocks each comprises: a) a core comprising a biodegradable polymeric core material and a cell, and b) a shell comprising a biodegradable polymeric shell material, wherein the plurality of bio-blocks are suspended homogenously within the carrier, and wherein the carrier has a viscosity of about 1 Pa·s to about 1000 Pa·s. In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks and a carrier (such as a liquid or a paste), wherein the plurality of bio-blocks each comprises: a) a core comprising a biodegradable polymeric core material and a cell, and b) a shell comprising a biodegradable polymeric shell material, wherein the plurality of bio-blocks are suspended homogenously within the carrier, wherein the carrier has a viscosity of about 1 Pa·s to about 1000 Pa·s, and wherein the bio-ink composition comprises at least about 50% bio-blocks (w/w). In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks each comprising: a) a core comprising a biodegradable polymeric core material, a MSC, and an agent induces the MSC to differentiate into an osteoblast; and b) a shell comprising a biodegradable polymeric shell material. In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks each comprising: a) a core comprising a biodegradable polymeric core material, a MSC, and an agent induces the MSC to differentiate into a chondrocyte; and b) a shell comprising a biodegradable polymeric shell material. In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks each comprising: a) a core comprising a biodegradable polymeric core material, a MSC, dexamethasone, ascorbic acid, and glycerophosphate; and b) a shell comprising a biodegradable polymeric shell material. In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a bio-ink composition comprising a plurality of bio-blocks each comprising: a) a core comprising a biodegradable polymeric core material, a MSC, TGF-β3, dexamethasone, ascorbic acid 2-phosphate, sodium pyruvate, proline, insulin, transferrin, and selenous acid; and b) a shell comprising a biodegradable polymeric shell material. In some embodiments, the plurality of bio-blocks is of the same type. In some embodiments, the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a composition (such as bio-ink composition), comprising a plurality of any one of the Type I and/or Type II MSC bio-blocks described herein. In some embodiments, the composition comprises a carrier. In some embodiments, the carrier comprises a bio-adhesive material. In some embodiments, the carrier (such as bioadhesive material) and its degradation product is non-cytotoxic, and/or is non-immunogenic to a host. In some embodiments, the carrier (such as bioadhesive material) comprises a biodegradable material. In some embodiments, the carrier (such as bioadhesive material) is biocompatible. In some embodiments, the degradation product of the biodegradable material of the carrier provides nutrients that can maintain or promote cellular activities of the MSC. In some embodiments, the biodegradable material of the carrier (such as bioadhesive material) is naturally occurring (such as a naturally occurring biodegradable material from plants or animals), synthetic, recombinant, modified, or any combination thereof. In some embodiments, the biodegradable material of the carrier (such as bioadhesive material) comprises a naturally occurring biodegradable polymer, such as collagen, fibrin, chitosan, alginate, starch, hyaluronic acid, laminin, agarose, gelatin, glucan, elastin, or a combination thereof; a modified biodegradable polymer, such as modified alginate, for example, oxidized alginate (e.g., oxidized sodium alginate); and/or a synthetic biodegradable polymer, such as polypophosphazene, polyacrylic acid, polymethacrylic acid, acrylate copolymer (such as copolymer of acrylic acid and polymethacrylic acid), polylactic acid (PLA), polyglycolic acid (PGA), poly-(lactide-coglycolide acid) (PLGA), polyorthoester (POE), polycaprolactone (PCL), polyhydroxyrate (PHB), polyamino acid (such as polylysine), degradable polyurethane, copolymer thereof, or a combination thereof. In some embodiments, the biodegradable polymer of the carrier (such as bioadhesive material) is selected from the group consisting of collagen, fibrin, chitosan, alginate (such as sodium alginate or calcium alginate), oxidized alginate (such as oxidized sodium alginate), starch, hyaluronic acid, laminin, elastin, gelatin, polyamino acid (such as polylysine), agarose, glucan, methyl cellulose, polyvinyl alcohol, polyacrylic acid and derivatives thereof (e.g., polyacrylic acid or an ester thereof, polymethacrylic acid or ester thereof), polyacrylamide, N-substituted acrylamides, and combinations thereof. In some embodiments, the carrier (such as bioadhesive material) comprises sodium alginate and/or oxidized sodium alginate. In some embodiments, the carrier (such as bioadhesive material) comprises alginate (such as sodium alginate or calcium alginate) and oxidized alginate (such as oxidized sodium alginate). In some embodiments, the carrier further comprises water, inorganic salt, pH buffer, stabilizer, preservative, or any combination thereof. In some embodiments, the carrier (such as bioadhesive material) is liquid or semi-liquid (such as gel). In some embodiments, the viscosity of the carrier (such as bioadhesive material) is about 1-1000 Pa·s, such as about any of 1-2, 2-3, 3-4, 4-5, 5-6, 6-7, 7-8, 8-9, 9-10, 10-12, 12-14, 14-16, 16-18, 18-20, 20-25, 25-30, 30-50, 50-80, 80-100, 100-200, 200-300, 300-400, 400-500, 500-800, 800-1000, 1-3, 3-8, 8-16, 3-10, 10-20, 20-50, 50-160, or 30-160 Pa·s. In some embodiments, the carrier (such as bioadhesive material) further comprises an additional agent, such as a nutrient, an ECM molecule, an anti-apoptotic agents, an antioxidant, a cell factor, a pharmaceutically active agent, or any combination thereof. In some embodiments, the additional agent can regulate (such as promote) proliferation, migration, secretion, and/or metabolism of the MSC. In some embodiments, the nutrient is selected from the group consisting of nucleic acids, amino acids, polypeptides, carbohydrates (such as monosaccharides, oligosaccharides, polysaccharides), lipids, and vitamins. In some embodiments, the ECM molecule is selected from the group consisting of polysaccharides (such as glycosaminoglycans, proteoglycans), structural proteins (such as collagen and elastin), adhesion proteins (such as fibronectin and laminin). In some embodiments, the cell factor can regulate proliferation, migration, secretion and/or metabolism of the cell. Suitable cell factors include, but are not limited to: cell factors related to cell proliferation, such as insulin, insulin growth factor (IGF, such as IGF-I or IGF-II), transforming growth factor (TGF, such as TGF$\alpha$ and TGF$\beta$), vascular epidermal growth factor (VEGF), epidermal growth factor (EGF), fibroblast growth factor (FGF), platelet-derived growth factor (PDGF), osteosarcoma source growth factor (ODGF), somatostatin (SRIH), nerve growth factor (NGF), interleukin (IL, such as IL-1, IL-2, IL-3, IL-4, IL-5, IL-6, IL-7, IL-8, IL-10, IL-12), erythropoietin (EPO), colony stimulating factor (CSF), cortisol, thyroid hormones (such as T3 or T4), chemokines (such as CCL, CXC, XCL, or MCP), Tumor Necrosis Factor (TNF), and combinations thereof; cell factors related to cell differentiation, such as Oct3/4, Sox2, Klf4, c-Myc, GATA4, TSP1, $\beta$-glycerophosphate, dexamethasone, vitamin C, insulin, IBMX, indomethacin, PDGF-BB, 5-azacytidine, and combinations thereof; cell factors related to cell migration, such as cAMP, $PIP_3$, SDF-1, N-cadherin, NF-$\kappa$B, osteonectin, thromboxane A2, Ras, and combinations thereof; cell factors related to cell metabolism, such as IGF-I, TRIP-Br2, DKK-1, sRANKL, OPG, TRACP-5b, ALP, SIRT1(2-7), PGC-1$\alpha$, PGC-1$\beta$, IL-3, IL-4, IL6, TGF-$\beta$, PGE2, G-CSF, TNF$\alpha$, and combinations thereof. In some embodiments, the pharmaceutically active agent regulates (such as facilitates) cell proliferation, differentiation, migration, secretion and/or metabolism. In some embodiments, the pharmaceutically active agent is selected from the group consisting of rhIL-2, rhIL-11, rhEPO, IFN-$\alpha$, IFN-$\beta$, IFN-$\gamma$, G-CSF, GM-CSF, rHuEPO, sTNF-R1, rhTNF-$\alpha$, and combinations thereof. In some embodiments, the composition (such as bio-ink composition) comprises at least about any of 10%, 20%, 30%, 40%, 50%, 60%, 80%, or 90% (w/w) of the Type I and/or Type II MSC bio-blocks. In some embodiments, the composition (such as bio-ink composition) is liquid, semi-liquid (such as gel), or solid, including, for example, suspension, gel, or concentrate. In some embodiments, the composition (such as bio-ink composition) is extrudable. In some embodiments, the composition (such as bio-ink composition) is used for bio-printing, and/or building a construct (such as three-dimensional construct, tissue progenitor, tissue, or organ).

Components and Properties of the Bio-Ink Composition

In some embodiments, the bio-ink composition comprises a carrier. The carrier, including its degradation products, is typically non-toxic to the cells. In some embodiments, the carrier is non-immunogenic. In some embodiments, the carrier is a biocompatible material. In some embodiments, the carrier is a bioadhesive material. As used herein, "bioadhesive material" refers to a biodegradable and biocompatible material that can serve to agglutinate. "Agglutinate" refers to fusion or adhesion of cells, cell aggregates, multicellular aggregates, multicellular bodies, and/or multicellular layers. The terms, "agglutinate", "fuse", and "adhere" are used herein interchangeably. Suitable bioadhesive materials include, but are not limited to, collagen, fibrin, chitosan, alginate, starch, hyaluronic acid, laminin, agarose, gelatin, glucan, elastin, methylcellulose, polyvinyl alcohol, polyamino acid (such as polylysine), polyacrylic acid, polymethacrylic acid, acrylate copolymer (such as copolymer of acrylic acid and polymethacrylic acid), and combinations thereof. In some embodiments, the biocompatible material comprises a protein or a carbohydrate that adheres to other bio-blocks. In some embodiments, the biocompatible material binds the bio-blocks within a multi-dimensional construct, an artificial tissue, or a tissue progenitor. In some embodiments, the carrier comprises a biodegradable polymer. In some embodiments, the degradation product of the biodegradable polymer provides at least one nutrient or ECM precursor to the cells in the bio-blocks. In some embodiments, the carrier further comprises an ECM molecule or at least one nutrient.

In some embodiments, the carrier comprises a naturally occurring polymer or a derivative thereof. In some embodiments, the carrier comprises a polymer selected from the group consisting of collagen, fibrin, chitosan, alginate, oxidized alginate, starch, hyaluronic acid, laminin, agarose, gelatin, glucan, and combinations thereof.

In some embodiments, the carrier comprises alginate (such as sodium alginate). In some embodiments, the carrier comprises oxidized alginate. Any of the alginates and oxidized alginates described in the section "oxidized alginate" can be used in the carrier. Suitable percentage of the alginate, oxidized alginate, or combination thereof in the carrier is at least about any of 0.1%, 0.5%, 1%, 1.25%, 1.5%, 2%, 3%, 4%, 5%, 7.5%, or 10%. In some embodiments, the percentage of the alginate, oxidized alginate, or combination thereof in the carrier is about any of 0.1%-0.5%, 0.5%-1%, 1%-1.25%, 1.25%-1.5%, 1.5%-2%, 2%-3%, 3%-4%, 4%-5%, 5%-7.5%, 7.5%-10%, 0.1%-1%, 1%-1.5%, 1%-2%, 0.5-2.5%, 1%-3%, 5-10% or 0.5%-5%. In some embodiments, the percentage of the alginate, oxidized alginate, or combination thereof in the carrier is no more than about 5% (including for example, no more than about any of 4%, 2.5%, 1.5%, or 1%).

In some embodiments, the carrier comprises gelatin. In some embodiments, the percentage of gelatin in the carrier is at least about any of 0.1%, 0.5%, 1%, 1.25%, 1.5%, 2%, 3%, 4%, 5%, 7.5%, or 10%. In some embodiments, the percentage of gelatin in the carrier is about any of 0.1%-0.5%, 0.5%-1%, 1%-1.25%, 1.25%-1.5%, 1.5%-2%, 2%-3%, 3%-4%, 4%-5%, 5%-7.5%, 7.5%-10%, 0.1%-1%, 1%-1.5%, 1%-2%, 0.5-2.5%, 1%-3%, 5-10% or 0.5%-5%.

In some embodiments, the carrier comprises alginate (such as sodium alginate) and gelatin. In some embodiments, the weight ratio of the alginate to the gelatin in the carrier is at least about any of 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the weight ratio of the alginate to the gelatin in the carrier is about any of 10:1 to about 9:1, about 9:1 to about 8:1, about 8:1 to about 7:1, about 7:1 to about 6:1, about 6:1 to about 5:1, about 5:1 to about 4:1, about 4:1 to about 3:1, about 3:1 to about 2:1, about 2:1 to about 1:1, about 1:1 to about 1:2, about 1:2 to about 1:3, about 1:3 to about 1:4, about 1:4 to about 1:5, about 1:5 to about 1:6, about 1:6 to about 1:7, about 1:7 to about 1:8, about 1:8 to about 1:9, about 1:9 to about 1:10, about 10:1 to about 5:1, about 5:1 to about 1:1, about 1:1 to about 1:5, about 1:5 to about 1:10, about 2:1 to about 1:2, about 4:1 to about 1:4, or about 10:1 to about 1:10. In some embodiments, the weight ratio of the gelatin and the alginate in the carrier is about 15:85.

In some embodiments, the carrier comprises a synthetic polymer. In some embodiments, the carrier comprises a polymer selected from the group consisting of polypohosphazene, polyacrylic acid, polymethacrylic acid, acrylate copolymer (such as copolymer of acrylic acid and polymethacrylic acid), polylactic acid (PLA), polyglycolic acid (PGA), poly-(lactide-coglycolide acid) (PLGA), polyorthoester (POE), polycaprolactone (PCL), polyhydroxyrate (PHB), polyamine acid (such as polylysine), degradable polyurethane, copolymers thereof, and combinations thereof.

In some embodiments, the carrier comprises the same polymer at different concentration or same composition of polymers with different weight ratios as the shell and/or the core of the bio-blocks. In some embodiments, the carrier comprises a different polymer as the shell and/or the core of the bio-blocks. In some embodiments, the carrier further comprises water, inorganic salt, pH buffer, stabilizer, or preservatives.

In some embodiments, the carrier degrades completely within no more than about 28 days. In some embodiments, the carrier degrades completely within no more than about any of 21 days, 14 days, 12 days, 10 days, 9 days, 8 days, 7 days, 6 days, 5 days, 4 days, 3 days, or 2 days. In some embodiments, the carrier degrades completely within about any of 2-5 days, 2-6 days, 2-8 days, 2-10 days, 2-12 days, 2-14 days, 14-21 days, 21-28 days, 7-14 days, 5-10 days, or 2-28 days.

In some embodiments, the carrier in the bio-ink composition is a paste. In some embodiments, the carrier in the bio-ink composition is semi-solid (such as a hydrogel). In some embodiments, the carrier in the bio-ink composition is a liquid. In some embodiments, the bio-ink composition is essentially free of liquid.

In some embodiments, the carrier is viscous. In some embodiments, the carrier has a viscosity of at least about any of 0.01, 0.1, 0.5, 1, 5, 10, 20, 30, 40, 50, 60, 70, 80, 90, 100, 150, 200, 300, 400, 500, 600, 700, 800, 900, 1000 Pa·s. In some embodiments, the carrier has a viscosity of about any of 0.01-0.1, 0.1-0.5, 0.5-1, 1-5, 5-10, 10-20, 20-25, 25-30, 30-40, 40-50, 50-60, 60-70, 70-80, 80-90, 90-100, 100-200, 200-300, 300-400, 400-500, 500-600, 600-700, 700-800, 800-900, 900-1000, 0.01-1, 1-10, 25-50, 10-30, 30-50, 50-100, 30-160, 1-50, 1-100, 1-200, 25-200, 50-150, 100-500, 500-1000, 1-250, 250-750, 1-500, or 1-1000 Pa·s. In some embodiments, the carrier has a viscosity of about 1 Pa·s to about 1000 Pa·s. In some embodiments, the carrier has a viscosity of about 30 Pa·s to about 160 Pa·s.

In some embodiments, the carrier or the bio-ink composition (with or without carrier) is extrudable. "Extrudable" refers to the state of a composition, which can be forced (such as under pressure) to pass through a nozzle or an orifice to form a structure. In some embodiments, the carrier or the bio-ink composition (with or without carrier) is suitable for jetting through an inkjet nozzle. In some embodiments, the carrier or the bio-ink composition (with or without carrier) is suitable for forming microdroplets or a stream by inkjet. In some embodiments, the carrier or the bio-ink composition (with or without carrier) is suitable for extrusion by a microextrusion dispensing system.

In some embodiments, the bio-ink composition further comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the agent is a protein. In some embodiments, the agent is a human protein. In some embodiments, the agent is a small molecule. In some embodiments, the agent is a small molecule that naturally occurs in human tissues. In some embodiments, the biodegradable polymeric core material comprises the agent. In some embodiments, the biodegradable polymeric core material binds to the agent to allow controlled release of the agent to the cell(s). In some embodiments, the nutrients comprise nucleotides, amino acids, peptides, carbohydrates (such as monosaccharides, oligosaccharides or polysaccharides), lipids, or vitamins. In some embodiments, the extracellular matrix molecule comprises polysaccharide, glycosaminoglycan, glycoprotein, structural protein (such as collagen or elastin), or adhesion protein (such as fibronectin or laminin). Agents (such as cell factors) that facilitate cell proliferation include, but are not limited to, insulin, insulin growth factor (IGF, such as IGF-I or IGF-II), transforming growth factor (TGF, such as TGFα and TGFβ), vascular epidermal growth factor (VEGF), epidermal growth factor (EGF), fibroblast growth factor (FGF), platelet-derived growth factor (PDGF), osteosarcoma source growth factor (ODGF), somatostatin (SRIH), nerve growth factor (NGF), interleukin (IL, such as IL-1, IL-2, IL-3, IL-4, IL-5, IL-6, IL-7, IL-8, IL-10, IL-12), erythropoietin (EPO), colony stimulating factor (CSF), cortisol, thyroid hormones (such as T3 or T4), chemokines (such as CCL, CXC, XCL, or MCP), Tumor Necrosis Factor (TNF), and combinations thereof. Agents (such as cell factors) that facilitate cell differentiation include, but are not limited to, Oct3/4, Sox2, Klf4, c-Myc, GATA4, TSP1, β-glycerophosphate, dexamethasone, vitamin C, insulin, IBMX, indomethacin, PDGF-BB, 5-azacytidine, and combinations thereof. Agents (such as cell factors) that facilitate cell migration include, but are not limited to, cAMP, $PIP_3$, SDF-1, N-cadherin, NF-κB, osteonectin, thromboxane A2, Ras, and combinations thereof. Agents (such as cell factors) that facilitate cell metabolism include, but are not limited to, IGF-I, TRIP-Br2, DKK-1, sRANKL, OPG, TRACP-5b, ALP, SIRT1(2-7), PGC-1α, PGC-1β, IL-3, IL-4, IL6, TGF-β, PGE2, G-CSF, TNFα, and combinations thereof. Agents (such as cell factors) that facilitate cell secretion include, but are not limited to, P600, P110, TCGFIII, BSF-2, glucagon, β-adrenergic agonist, arginine, $Ca^{2+}$, acetyl choline (ACH), somatostatin, and combinations thereof. In some embodiments, the pharmaceutically active agent regulates (such as facilitates) cell proliferation, differentiation, migration, secretion and/or metabolism. In some embodiments, the pharmaceutically active agent is selected from the group consisting of rhIL-2, rhIL-11, rhEPO, IFN-α, IFN-β, IFN-γ, G-CSF, GM-CSF, rHuEPO, sTNF-R1, rhTNF-α, and combinations thereof.

In some embodiments, the bio-ink composition is used for bioprinting of a multi-dimensional construct, an artificial tissue or a tissue-progenitor. In some embodiments, the bio-ink composition is used with other biocompatible materials, inks or compositions in bioprinting. In some embodiments, the bio-ink composition is used for inkjet printing. In some embodiments, the bio-ink composition is used for microextrusion.

Pharmaceutical Compositions, and Isolated Bio-Blocks

In some embodiments, there is provided a pharmaceutical composition comprising one or more bio-blocks (including the MSC bio-blocks) described herein and a pharmaceutically acceptable carrier. In some embodiments, the one or more bio-blocks further comprise a therapeutic agent, such as a therapeutic protein, or a targeting agent. In some embodiments, the pharmaceutical composition further comprises a pharmaceutically acceptable carrier, excipients, stabilizing agents, and/or other agents, which are known in the art, to provide favorable properties for administration of the pharmaceutical composition to a subject (such as a human subject). Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also comprise adjuvants such as preserving stabilizing, wetting, emulsifying agents and the like together with the penetration enhancer. The final form may be sterile and may also be able to pass readily through an injection device such as a hollow needle. The proper viscosity may be achieved and maintained by the proper choice of solvents or excipients.

The pharmaceutical compositions described herein may include other agents, excipients, or stabilizers to improve properties of the composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. In some embodiments, the pharmaceutical composition is formulated to have a pH in the range of about 4.5 to about 9.0, including for example pH ranges of about any one of 5.0 to about 8.0, about 6.5 to about 7.5, or about 6.5 to about 7.0. In some embodiments, the pharmaceutical composition can also be made to be isotonic with blood by the addition of a suitable tonicity modifier, such as glycerol.

In some embodiments, the pharmaceutical composition is used in cell therapy. In some embodiments, the pharmaceutical composition is used in regenerative medicine.

In some embodiments, there is provided a plurality of isolated bio-blocks according to any one of the bio-blocks (including the MSC bio-blocks) described above, and wherein the bio-blocks are isolated from each other. In some embodiments, each of the isolated bio-blocks in the plurality of the isolated bio-blocks is provided in a separate container. In some embodiments, the plurality of isolated bio-blocks is provided in a single container. Suitable container includes, but is not limited to, a dish (such as tissue culture or cell culture dish), a flask, a vial, a tube (such a test tube, a microcentrifuge tube, a centrifuge tube etc.), a well of a multi-well plate (such as a microtiter plate having any of 6, 12, 24, 96, 384, 1536, or more wells), or the like. In some embodiments, the plurality of isolated bio-blocks is analyzed in parallel (e.g. simultaneously), and/or in a high throughput screening context.

In some embodiments, there is provided a container comprising a plurality of isolated bio-blocks according any of the bio-blocks (including the MSC bio-blocks) described above. In some embodiments, the container further comprises a liquid or semi-liquid composition comprising agents, inorganic salt, culturing media, buffers, or other components useful for culturing or conducting experiments on the plurality of isolated bio-blocks. In some embodiments, the liquid or semi-liquid composition further comprises an agent or combination of agents that regulates (such as facilitates) cell activities, comprising cell proliferation, differentiation, migration, metabolism, secretion, or signaling. In some embodiments, the liquid or semi-liquid composition further comprises a compound (such as a surfactant) that helps to keep the bio-blocks isolated. In some embodiments, the liquid or semi-liquid composition further comprises stabilizer, or preservatives. In some embodiments, the plurality of isolated bio-blocks is dispensed in the liquid or semi-liquid composition.

In some embodiments of the plurality of isolated bio-blocks or the container, at least two of the isolated bio-blocks are different. Different bio-blocks may differ in the size and/or shape of the bio-blocks, number of cells and/or types of cells in the core of the bio-blocks, compositions of the biodegradable polymeric core material, compositions of the biodegradable polymeric shell material, agent(s) that facilitate activities (such as proliferation, differentiation, migration, metabolism and/or secretion) of the cells and incorporated in the core of the bio-blocks, nutrients and/or ECM molecules incorporated in the bio-blocks, and/or any of the other parameters described in the previous section. In some embodiments, each of the at least two isolated bio-blocks comprises a different agent or combination of agents that regulates (such as facilitates) cell proliferation, differentiation, migration, metabolism, secretion, or any combination thereof.

In some embodiments, there is provided a plurality of isolated bio-blocks or a container comprising a plurality of isolated bio-blocks, wherein each isolated bio-block comprises at least one stem cell (such as MSC). In some embodiments, at least two isolated bio-blocks in the plurality of isolated bio-blocks or the container are different. In some embodiments, each of the at least two isolated bio-blocks comprises a different type of stem cell. In some embodiments, the isolated bio-blocks comprise the same type of stem cell. In some embodiments, each of the at least two isolated bio-blocks comprises a different agent or combination of agents that regulates (such as facilitates) cell proliferation, differentiation, migration, metabolism, secretion, signaling, or any combination thereof.

In some embodiments, the plurality of isolated bio-blocks or the container is used for tissue engineering. In some embodiments, the plurality of isolated bio-blocks or the container is used as a research tool in in vitro research or in vivo research. In some embodiments, the plurality of isolated bio-blocks or the container is used to study cell signaling. In some embodiments, the plurality of isolated bio-blocks or the container is used to study stem cell differentiation.

In some embodiments, the composition (such as the bio-ink composition or the pharmaceutical composition) consists of or consists essentially of the bio-blocks. In some embodiments, the composition (such as the bio-ink composition, or the pharmaceutical composition) or the plurality of isolated bio-blocks comprises at least about 50% of bio-blocks by weight. In some embodiments, the composition (such as the bio-ink composition or the pharmaceutical composition) or the plurality of isolated bio-blocks comprises at least about any of 10%, 20%, 30%, 40%, 50%, 55%, 60%, 65%, 70%, 75%, 80%, 85%, 90%, 95%, 98%, or 99% of bio-blocks by weight. In some embodiments, the composition (such as the bio-ink composition or the pharmaceutical composition) or the plurality of isolated bio-blocks comprises about any of 10%-20% 20%-30%, 30%-40%, 40%-50%, 50%-55%, 55%-60%, 60%-65%, 65%-70%, 70%-75%, 75%-80%, 80%-85%, 85%-90%, 90%-95%, 95%-100%, 10%-50%, 50%-60%, 60%-70%, 70%-80%, 80%-90%, 90%-100%, 50%-75%, 75%-100%, 10%-75%, or 50%-100% of bio-blocks by weight. In some embodiments, the composition (such as the bio-ink composition or the pharmaceutical composition) or the plurality of isolated bio-blocks is essentially free of liquid, such as having less than about any of 1%, 2.5%, 5%, 7.5%, or 10% of liquid except for the liquid contained in the bio-blocks.

In some embodiments, the composition (such as the bio-ink composition or the pharmaceutical composition) or the plurality of isolated bio-blocks comprises a plurality of any of the bio-blocks as described in the previous section. In some embodiments, the plurality of bio-blocks is of the same type. In some embodiments, the plurality of bio-blocks is of different types. In some embodiments, the plurality of bio-blocks is of about any of 1, 2, 3, 4, 5, 6, 7, 8, 9, or 10 types. Different types of bio-blocks may differ in the size and/or shape of the bio-blocks, number of cells and/or types of cells in the core of the bio-blocks, compositions of the biodegradable polymeric core material, compositions of the biodegradable polymeric shell material, agent(s) that facilitate activities (such as proliferation, differentiation, migration, metabolism and/or secretion) of the cells and incorporated in the core of the bio-blocks, nutrients and/or ECM molecules incorporated in the bio-blocks, and/or any of the other parameters described in the previous section. In some embodiments, the average size of the bio-blocks in the composition (such as the bio-ink composition or the pharmaceutical composition) or the plurality of isolated bio-blocks is at least about any of 10, 20, 30, 50, 100, 120, 150, 200, 250, 300, 350, 400, 450, 500, 600, 700, 800, 900, 1000, 1500, or 2000 µm. In some embodiments, the average size of the bio-blocks in the composition (such as the bio-ink composition or the pharmaceutical composition) or the plurality of isolated bio-blocks is about any of 10-20, 20-30, 30-50, 50-100, 100-150, 150-200, 200-250, 250-300, 300-350, 350-400, 400-450, 450-500, 500-600, 600-700, 700-800, 800-900, 900-1000, 1000-1500, 1500-2000, 10-50, 20-100, 100-200, 200-400, 500-600, 600-800, 800-1000, 1000-2000, 10-100, 100-500, 100-800, 500-1000, 300-800, 30-50, 30-200, 30-500, 30-800, 30-1000, 30-2000, or 20-2000 µm. In some embodiments, the average size of the bio-blocks in the composition (such as the bio-ink composition or the pharmaceutical composition) or the plurality of isolated bio-blocks is about 30 µm to about 800 µm. In some embodiments, the average size of the bio-blocks in the composition (such as the bio-ink composition or the pharmaceutical composition) or the plurality of isolated bio-blocks is about 100 to about 500 µm. In some embodiments, the variation of the size of the same type of bio-blocks in the composition (such as the bio-ink composition or the pharmaceutical composition) or the plurality of isolated bio-blocks is less than about any of 1%, 5%, 10%, 15%, 20%, 25%, 30%, or 35% of the average size of the same type of bio-blocks. In some embodiments, the average length of the bio-blocks in the composition (such as the bio-ink composition or the pharmaceutical composition) or the plurality of isolated bio-blocks is at least about any of 10, 20, 30, 50, 100, 120, 150, 200, 250, 300, 350, 400, 450, 500, 600, 700, 800, 900, 1000, 1500, or 2000 µm. In some embodiments, the average length of the bio-blocks in the composition (such as the bio-ink composition or the pharmaceutical composition) or the plurality of isolated bio-blocks is about any of 10-20, 20-30, 30-50, 50-100, 100-150, 150-200, 200-250, 250-300, 300-350, 350-400, 400-450, 450-500, 500-600, 600-700, 700-800, 800-900, 900-1000, 1000-1500, 1500-2000, 10-50, 20-100, 100-200, 200-400, 500-600, 600-800, 800-1000, 1000-2000, 10-100, 100-500, 100-800, 500-1000, 300-800, 30-50, 30-200, 30-500, 30-800, 30-1000, 30-2000, or 20-2000 µm. In some embodiments, the average length of the bio-blocks in the composition (such as the bio-ink composition or the pharmaceutical composition) or the plurality of isolated bio-blocks is about 30 μm to about 800 μm. In some embodiments, the average length of the bio-blocks in the composition (such as the bio-ink composition or the pharmaceutical composition) or the plurality of isolated bio-blocks is about 100 to about 500 μm. In some embodiments, the variation of the dimensions (such as length, width, and/or thickness) of the same type of bio-blocks in the composition (such as the bio-ink composition or the pharmaceutical composition) or the plurality of isolated bio-blocks is less than about any of 1%, 5%, 10%, 15%, 20%, 25%, 30%, or 35% of the average size of the same type of bio-blocks. In some embodiments, each bio-block in the composition (such as the bio-ink composition or the pharmaceutical composition) or the plurality of isolated bio-blocks has a single cell. In some embodiments, the average number of cells in the bio-blocks of the composition (such as the bio-ink composition or the pharmaceutical composition) or the plurality of isolated bio-blocks is at least about any of 2, 5, 10, 20, 30, 40, 50, 100, 200, 300, 500, 1000, 2000, 3000, 4000, 5000, 10000, 20000, 30000, 40000, 50000, 100000, 200000, 500000, or 1000000 cells. In some embodiments, the average number of cells in the bio-blocks of the composition (such as the bio-ink composition or the pharmaceutical composition) or the plurality of isolated bio-blocks is about any of 1-2, 2-4, 4-6, 6-8, 8-10, 10-15, 15-20, 20-25, 25-30, 30-40, 40-50, 50-60, 60-70, 70-80, 80-90, 90-100, 100-150, 150-200, 200-300, 300-400, 400-500, 500-1000, 1000-2000, 1-10, 2-10, 2-5, 5-10, 10-20, 20-30, 30-50, 2-25, 25-50, 2-50, 50-100, 100-200, 50-250, 250-500, 500-2000, 2-100, 2-500, 2-2000, 2000-3000, 3000-4000, 4000-5000, 5000-10000, 10000-20000, 20000-30000, 30000-40000, 40000-50000, 50000-100000, 2-5000, 100-5000, 100-1500, 100-1000, 500-5000, 500-10000, 1000-5000, 1-50000, 1-100000, 100000-200000, 200000-500000, 500000-1000000, or 1-1000000 cells. In some embodiments, the average number of cells in the bio-blocks of the composition (such as the bio-ink composition or the pharmaceutical composition) or the plurality of isolated bio-blocks is about 1 cell to about 1000000 cells. In some embodiments, the average number of cells in the bio-blocks of the composition (such as the bio-ink composition or the pharmaceutical composition) or the plurality of isolated bio-blocks is at least 50 cells. In some embodiments, the average number of cells in the bio-blocks of the composition (such as the bio-ink composition or the pharmaceutical composition) or the plurality of isolated bio-blocks is about 1 cell to about 5000 cells, including, for example, about 2 cells to about 50 cells, or about 100 cells to about 5000 cells. In some embodiments, the variation in number of cells per bio-block among the same type of bio-blocks in the composition (such as the bio-ink composition or the pharmaceutical composition) or the plurality of isolated bio-blocks is less than about any of 1%, 5%, 10%, 15%, 20%, 25%, 30%, or 35% of the average number of cells among the same type of bio-blocks.

In some embodiments, the composition (such as the bio-ink composition or the pharmaceutical composition) is prepared by mixing a plurality of bio-blocks (including MSC bio-blocks, such as Type I, II, III, or IV MSC bio-blocks). In some embodiments, the bio-ink composition is prepared by mixing a plurality of bio-blocks (including MSC bio-blocks, such as Type I, II, III, or IV MSC bio-blocks) with a carrier. In some embodiments, the composition (such as the bio-ink composition or the pharmaceutical composition) or the plurality of isolated bio-blocks is prepared under sterile conditions. In some embodiments, the composition (such as the bio-ink composition or the pharmaceutical composition) or the plurality of isolated bio-blocks is prepared in a GMP workshop. In some embodiments, the composition (such as the bio-ink composition or the pharmaceutical composition) or the plurality of isolated bio-blocks is prepared immediately before use. In some embodiments, the composition (such as the bio-ink composition or the pharmaceutical composition) or the plurality of isolated bio-blocks can be stored under refrigerated conditions (such as about 4° C.) for at least about any of 3 hours, 6 hours, 12 hours, 1 day, 2 days, or 3 days prior to use.

Methods of Preparing Multi-Dimensional Constructs, Tissue Progenitors, and Tissues The present application further provides methods of preparing an artificial tissue or the tissue progenitor, comprising bioprinting any of the bio-ink compositions described herein to obtain a multi-dimensional construct having a pre-determined pattern. It is intended that any of the properties (such as composition, ratio, physical and chemical properties, etc.) of the bio-ink composition as described herein can be combined with any of the properties (such as steps, conditions, etc.) of the methods of preparing an artificial tissue or tissue progenitor as described herein, as if each and every combination is individually described.

Because bio-blocks are used as the basic building units in the methods described herein, the methods of preparing an artificial tissue or tissue progenitor described herein have many advantages over currently known bioprinting methods, including, but not limited to: (1) higher precision in cell distribution (including cell number, type and position); (2) higher precision in microenvironments of cells; (3) higher cell survival rate; (4) no need for scaffold or a substrate; (5) promotion of cell proliferation, differentiation, migration, metabolism and/or secretion during optional culturing step; (6) degradation of shell and at least partial connection among cells in neighboring bio-blocks during optional culturing step; and (7) dimensions and/or complexity of the prepared tissue or progenitor.

Methods of Preparing an Artificial Tissue or Tissue Progenitor

Thus, in some embodiments, there is provided a method of preparing an artificial tissue or tissue progenitor, comprising bioprinting (such as inkjet or microextrusion) a bio-ink composition to obtain a multi-dimensional construct having a pre-determined pattern, wherein the bio-ink composition comprises a plurality of bio-blocks each comprising: a) a core comprising a biodegradable polymeric core material and a cell, and b) a shell comprising a biodegradable polymeric shell material. In some embodiments, at least about 80% (such as at least about any of 85%, 90%, 95%, or more) of the cells in the plurality of bio-blocks survive after the bioprinting. In some embodiments, the length of the artificial tissue or tissue progenitor is at least about 100 μm (such as at least about any of 200 μm, 500 μm, 1 mm or more). In some embodiments, the thickness of the artificial tissue or tissue progenitor is at least about 100 μm (such as at least about any of 200 μm, 500 μm, 1 mm or more). In some embodiments, the bio-ink composition has one or more (such as any of 1, 2, 3, 4, or 5) of the following properties or characteristics: (1) the bio-ink composition comprises a carrier (such as a liquid or a paste); (2) the plurality of bio-blocks are suspended homogenously within the carrier; (3) the carrier has a viscosity of about 1 Pa·s to about 1000 Pa·s; (4) the bio-ink composition comprises at least about 50% bio-blocks (w/w); and (5) the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 800 µm. In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa.

In some embodiments, there is provided a method of preparing an artificial tissue or the tissue progenitor, comprising bioprinting (such as inkjet or microextrusion) a bio-ink composition to obtain a multi-dimensional construct having a pre-determined pattern, wherein the bio-ink composition comprises a plurality of bio-blocks each comprising: a) a core comprising a biodegradable polymeric core material and a cell, and b) a shell comprising a biodegradable polymeric shell material; and wherein the bio-ink composition is not bioprinted onto a scaffold. In some embodiments, at least about 80% (such as at least about any of 85%, 90%, 95%, or more) of the cells in the plurality of bio-blocks survive after the bioprinting. In some embodiments, the length of the artificial tissue or tissue progenitor is at least about 100 µm (such as at least about any of 200 µm, 500 µm, 1 mm or more). In some embodiments, the thickness of the artificial tissue or tissue progenitor is at least about 100 µm (such as at least about any of 200 µm, 500 µm, 1 mm or more). In some embodiments, the bio-ink composition has one or more (such as any of 1, 2, 3, 4, or 5) of the following properties or characteristics: (1) the bio-ink composition comprises a carrier (such as a liquid or a paste); (2) the plurality of bio-blocks are suspended homogenously within the carrier; (3) the carrier has a viscosity of about 1 Pa·s to about 1000 Pa·s; (4) the bio-ink composition comprises at least about 50% bio-blocks (w/w); and (5) the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a method of preparing an artificial tissue or the tissue progenitor, comprising bioprinting (such as inkjet or microextrusion) a bio-ink composition to obtain a multi-dimensional construct having a pre-determined pattern, and culturing the multi-dimensional construct in vitro under a condition that allows the cells in the plurality of bio-blocks to proliferate, differentiate, metabolize, migrate, secrete, or any combination thereof, wherein the bio-ink composition comprises a plurality of bio-blocks each comprising: a) a core comprising a biodegradable polymeric core material and a cell, and b) a shell comprising a biodegradable polymeric shell material. In some embodiments, at least about 80% (such as at least about any of 85%, 90%, 95%, or more) of the cells in the plurality of bio-blocks survive after the bioprinting. In some embodiments, the shell is at least partially degraded (such as at least about any of 20%, 50%, or 80%, or fully degraded) during the culturing. In some embodiments, the length of the artificial tissue or tissue progenitor is at least about 100 µm (such as at least about any of 200 µm, 500 µm, 1 mm or more). In some embodiments, the thickness of the artificial tissue or tissue progenitor is at least about 100 µm (such as at least about any of 200 µm, 500 µm, 1 mm or more). In some embodiments, the bio-ink composition has one or more (such as any of 1, 2, 3, 4, or 5) of the following properties or characteristics: (1) the bio-ink composition comprises a carrier (such as a liquid or a paste); (2) the plurality of bio-blocks are suspended homogenously within the carrier; (3) the carrier has a viscosity of about 1 Pa·s to about 1000 Pa·s; (4) the bio-ink composition comprises at least about 50% bio-blocks (w/w); and (5) the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 µm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

In some embodiments, there is provided a method of preparing an artificial tissue or the tissue progenitor, comprising bioprinting (such as inkjet or microextrusion) a bio-ink composition to obtain a multi-dimensional construct having a pre-determined pattern, and culturing the multi-dimensional construct in vitro under a condition that allows the cells in the plurality of bio-blocks to proliferate, differentiate, metabolize, migrate, secrete, or any combination thereof, wherein the bio-ink composition comprises a plurality of bio-blocks each comprising: a) a core comprising a biodegradable polymeric core material and a cell, and b) a shell comprising a biodegradable polymeric shell material; and wherein the bio-ink composition is not bioprinted onto a scaffold. In some embodiments, at least about 80% (such as at least about any of 85%, 90%, 95%, or more) of the cells in the plurality of bio-blocks survive after the bioprinting. In some embodiments, the shell is at least partially degraded (such as at least about any of 20%, 50%, or 80%, or fully degraded) during the culturing. In some embodiments, the length of the artificial tissue or tissue progenitor is at least about 100 μm (such as at least about any of 200 μm, 500 μm, 1 mm or more). In some embodiments, the thickness of the artificial tissue or tissue progenitor is at least about 100 μm (such as at least about any of 200 μm, 500 μm, 1 mm or more). In some embodiments, the bio-ink composition has one or more (such as any of 1, 2, 3, 4, or 5) of the following properties or characteristics: (1) the bio-ink composition comprises a carrier (such as a liquid or a paste); (2) the plurality of bio-blocks are suspended homogenously within the carrier; (3) the carrier has a viscosity of about 1 Pa·s to about 1000 Pa·s; (4) the bio-ink composition comprises at least about 50% bio-blocks (w/w); and (5) the plurality of bio-blocks is of different types. In some embodiments, the bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 μm to about 50 μm (such as about 1 μm to about 20 μm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, differentiation, migration, metabolism, and/or secretion), and a pharmaceutically active agent. In some embodiments, the length of the bio-block is about 30 μm to about 2 mm. In some embodiments, the ratio between the length and the thickness of the bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the bio-block comprises one or more micropores (such as with a size of more than about 50 nm). In some embodiments, the bio-block has a hardness of about 0.01 GPa to about 0.4 GPa. In some embodiments, the bio-block comprises at least two cores and/or at least two shells.

Figure 2:
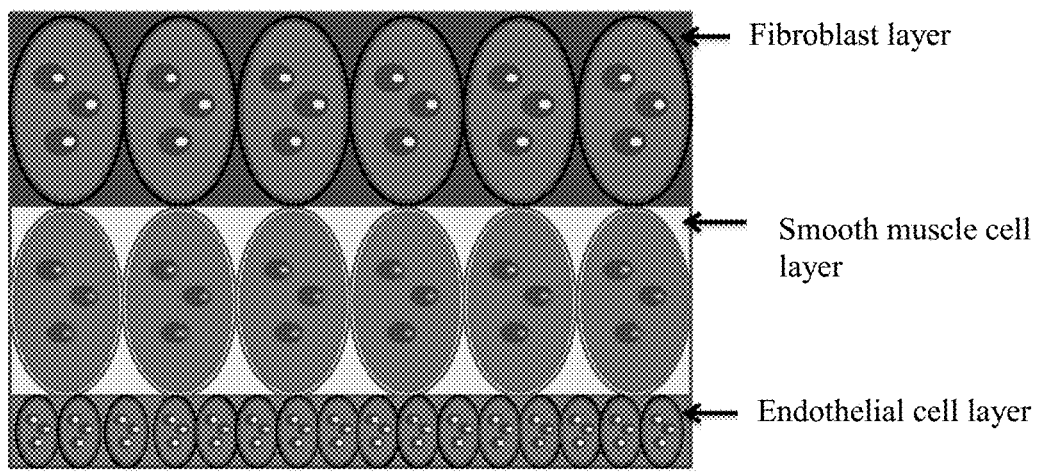
FIG. 2 shows a cross-section layout of a blood vessel progenitor comprising three different layers, each with a different type of bio-blocks deposited in a biocompatible (such as bioadhesive) material. The fibroblast layer comprises bio-blocks having fibroblasts in their cores. The smooth muscle cell layer comprises bio-blocks having smooth muscle cells in their cores. The endothelial cell layer comprises bio-blocks having endothelial cells in their cores. The biocompatible material in each layer may be in a hydrogel state, and may provide appropriate nutrients and culturing conditions for the cells in the bio-blocks.

In some embodiments, the method uses a single bio-ink composition. In some embodiments, the method uses at least two (including at least about any of 2, 3, 4, 5, 6, 7, 8, 9, or 10) bio-ink compositions. The different bio-ink compositions may comprise different carriers, different types of bio-blocks, and/or different ratios of the types of bio-blocks. In some embodiments, the bioprinting is continuous or essentially continuous. In some embodiments, the method comprises bioprinting sequentially a plurality of layers to obtain a multi-dimensional construct having a pre-determined pattern comprising the plurality of layers, wherein each layer is bioprinted with a bio-ink composition according to the pre-determined pattern of the layer. In some embodiments, the method comprises bioprinting sequentially a plurality of segments to obtain a multi-dimensional construct having a pre-determined pattern comprising the plurality of segments, wherein each segment is bioprinted with a bio-ink composition according to the pre-determined pattern of the segment. In some embodiments, the carrier of the bio-ink composition provides a biocompatible (optionally bioadhesive) material to bind the bio-blocks in the layer, segment, and/or multi-dimensional construct. FIG. 2 illustrates a schematic cartoon of an exemplary artificial blood vessel progenitor having three layers, wherein each layer is bioprinted using a different bio-ink composition having different types of bio-blocks, and wherein the carriers of the bio-ink compositions comprise biocompatible (optionally bioadhesive) materials to secure the positions of the bio-blocks within the layers. For example, the artificial blood vessel progenitor comprises an endothelial layer, a smooth muscle layer, and a fibroblast layer; the inner-most layer of the artificial blood vessel progenitor is bioprinted using endothelial cell bio-blocks, the middle layer of the construct is bioprinted using the smooth muscle cell bio-blocks, and the outer-most layer of the construct is bioprinted using the fibroblast bio-blocks. The carriers of the bio-ink compositions may further comprise one or more agents that maintain, promote, improve or regulate cell activities of the cells in the bio-blocks. For example, carrier in the bio-ink for bioprinting the endothelial layer may further comprise a cell factor that promotes proliferation or differentiation of endothelial cells; carrier in the bio-ink for bioprinting the smooth muscle layer may further comprise a cell factor that promotes proliferation or differentiation of smooth muscle cells; carrier in the bio-ink for bioprinting the fibroblast layer may further comprise a cell factor that promotes proliferation or differentiation of fibroblast cells. FIG. 13 illustrates a schematic cartoon of an exemplary cardiac muscle tissue progenitor comprising a single type of bio-blocks, wherein each bio-block comprises two different types of cells.

In some embodiments, the method uses a bio-ink composition that is essentially free of liquid. In some embodiments, the method comprises bioprinting a liquid-free bio-ink composition onto a surface comprising a biocompatible (optionally bioadhesive) material to obtain a multi-dimensional construct having a pre-determined pattern. In some embodiments, the method comprises bioprinting a liquid-free bio-ink composition and bioprinting a biocompatible (optionally bioadhesive) material to obtain a multi-dimensional construct having a pre-determined pattern.

In some embodiments, the method further comprises preparing a bio-ink composition from a plurality of bio-blocks and optionally a carrier. In some embodiments, the method further comprises bioprinting other biocompatible materials, inks or compositions.

The bioprinting can be carried out using any known methods in the art, including, but not limited to using bioprinters, and manual deposition methods (such as using a pipette). In some embodiments, the bioprinting is carried out by a rapid prototyping method. In some embodiments, the rapid prototyping method uses a three-dimensional delivery device (such as bioprinter) to deposit the bio-blocks or bio-ink compositions on a biocompatible surface (such as hydrogel and/or porous membrane) in a three-dimensional, automated, computer-aided fashion. In some embodiments, the bio-printing is carried out by an engineered process. The term "engineered process" refers to a process of depositing cells, cell solution, cell suspension, gel or slurry containing cells, cell concentrates, multicellular aggregates, and/or bio-blocks, etc., in a three dimensional structure according to a computer script using a computer-aided device. In some embodiments, the computer script is one or more computer programs, computer applications, or computer modules. In some embodiments, the bio-blocks fused after the bio-printing to form a three-dimensional construct. Bioprinting using automated, computer-aided devices (such as bioprinters) may be preferred in certain embodiments of the methods described herein. Advantages of methods using such devices include, for example, rapid, precise, and reproducible placement of the bio-blocks, and using a pre-determined plan and/or pattern to build the multidimensional construct having different types of cells, bio-blocks, and/or layers thereof.

Any of the known bioprinters, such as the bioprinters developed by Cyfuse, Organovo EnvisionTEC, and Revotek can be used in the bioprinting process. There are currently three main types of bioprinters, including inkjet bioprinters, microextrusion bioprinters, and laser-assisted bioprinters, as described in Murph S V and Atala A. (2014) Nature Biotechnology, 32 (8): 773-785, incorporated herein by reference. The present invention contemplates use of any of the known bioprinters or bioprinters specially developed by the inventors in the method of preparing a tissue construct or the tissue progenitor using the bio-ink composition described herein.

In some embodiments, the bioprinting is carried out by inkjet. In some embodiments, the ink-jet bioprinters are Drop-On-Demand inkjet bioprinters. In some embodiments, the ink-jet bioprinters are continuous ink-jet bioprinters. In some embodiments, the inkjet bioprinter is a thermal ink-jet bioprinter, which heats the printer head to produce air pressure to force the bio-ink out of the inkjet nozzle. In some embodiments, the nozzle heats up the bio-blocks in the bio-ink by at least about any of 0.1° C., 0.2° C., 0.5° C., 0.75° C., 1° C., 1.5° C., 2° C., or more. In some embodiments, the inkjet bioprinter is an acoustic bioprinter, which uses pulses formed by piezoelectric or ultrasound pressure to force the bio-ink out of the inkjet nozzle. In some embodiments, each droplet of the bio-ink forced out of the inkjet nozzle has a single bio-block. In some embodiments, each droplet of the bio-ink forced out of the inkjet nozzle comprises no more than about any of 2, 3, 4, 5, 10, 15, 20, 25, 50, 100, or more bio-blocks.

In some embodiments, the bioprinting is carried out by microextrusion. In some embodiments, the bio-ink composition is extruded by a pneumatic dispensing system. In some embodiments, the bio-ink composition is extruded by a mechanical (such as piston or screw) dispensing system.

In some embodiments, the pressure on the bio-ink composition during bio-printing is at least about any of 5 KPa, 10 KPa, 20 KPa, 40 KPa, 60 KPa, 80 KPa, 100 KPa, 120 KPa, 150 KPa, 200 KPa or more. In some embodiments, the speed of the bioprinting is about at least any of 50 mm/min, 100 mm/min, 150 mm/min, 200 mm/min, 250 mm/min, 300 mm/min, 400 mm/min, 500 mm/min or more. In some embodiments, the pressure and/or shearing force exerted by the bioprinter (such as the inkjet nozzle, or the microextrusion dispensing system) is not suitable for bioprinting cells suspended in the carrier (rather than as a bio-ink composition of the present application). For example, more than about any of 10%, 20%, 30%, 40%, 50%, or more cells are damaged or killed when bioprinted as a suspension in the carrier (rather than as a bio-ink composition of the present application) using the bioprinters.

In addition to inkjet bioprinting, the methods described herein may use any of the low-temperature deposition technologies, or UV curing technologies known in the art to prepare the multi-dimensional construct using the bio-ink compositions. Examples of inkjet bioprinting, low-temperature deposition, and UV curing technologies have been described, for example, in Malda, Jos, et al. "25th anniversary article: engineering hydrogels for biofabrication." Advanced Materials 25.36 (2013): 5011-5028, which is incorporated herein by reference in its entirety.

In some embodiments, the bioprinting is carried out in a successive layer-by-layer fashion for an artificial tissue or tissue progenitor comprising multiple structural layers. "Layer" as used in reference to a multi-layered, bioprinted tissue or construct, refers to a planar structure having the thickness of a single building block (such as a bio-block), wherein two or more of the planar structures can be stacked along the z-axis (i.e., the vertical axis) to achieve the total thickness of the bioprinted tissue or construct. In some embodiments, each of the layers in the tissue or construct have substantially the same structure and/or composition. In some embodiments, each of the layers in the tissue or construct have unique structures and/or compositions. Additionally, in the x-y plane of each layer (i.e., the horizontal plane), a plurality of bio-blocks (or cells herein) and/or the void space therebetween are arranged according to a pre-determined spatial pattern. As the bio-blocks of the present application comprise one or more cells (such as at least about any of 10, 100, or 1000), each layer in a multi-layered tissue or construct may have the thickness of one or more cells. In some embodiments, each layer has the thickness of a single cell. In some embodiments, each layer has the thickness of more than (such as at least about any of 10, 100, or 1000) one cells. In some embodiments, the method comprises bioprinting the bio-ink composition to deposit one layer at a time. In some embodiments, the method comprises bioprinting the bio-ink composition to deposit multiple (such as about any of 2, 3, 4, 5, 10 or more) layers at a time. In some embodiments, each layer comprises more than one (such as about any of 2, 3, 4, 5, 10 or more) cell types. In some embodiments, as the bio-blocks are bioprinted according to the pre-determined pattern of the multi-dimensional construct, cells within each layer are distributed in a pre-determined pattern in the x-y plane (i.e. horizontal plane), and/or in a pre-determined pattern along the z-axis (i.e. vertical axis).

The multi-dimensional constructs can be of any pre-determined pattern, including any pre-determined shape. For example, the multi-dimensional construct may be a sheet (such as a rectangular, square, circular, elliptical, or hexagonal sheet, or a sheet of irregular shape), a hollow tube, a hollow multi-dimensional construct (such as a hollow cube, a hollow sphere, a hollow rectangular prism, a hollow cylinder, or a hollow multi-dimensional construct of irregular shape), or a solid multi-dimensional construct (such as a solid cube, a solid sphere, a solid rectangular prism, a solid cylinder, or a solid multi-dimensional construct of irregular shape), or any combination thereof. In some embodiments, the multi-dimensional construct has a shape that mimics the natural shape of a tissue or an organ.

In some embodiments, the bioprinting is continuous or substantially continuous. In some embodiments, continuous bioprinting is carried out as follows: dispense the bio-ink composition via a dispensing end (such as syringe, capillary tube, etc.) that is connected to a reservoir containing the bio-ink composition. In some embodiments, the continuous bioprinting dispenses the bio-ink composition according to a repeating pattern of basic functional units in the multi-dimensional construct. The repeating functional units may have any suitable geometric shapes, including, for example, circle, square, rectangle, triangle, polygon, and irregular shapes, in order to form one or more layers having a specific planar geometry to realize the unique deposition pattern of the bio-ink composition and/or void space. In some embodiments, the repeating functional unit has one layer, and consecutively bioprinting (such as depositing) multiple layers of the repeating functional units can provide a multi-layered artificial tissue or tissue progenitor having a specific geometric shape. In some embodiments, consecutively bioprinting (such as depositing) any of 2, 3, 4, 5, 6, 7, 8, 9, 10, 11, 12, 13, 14, 15, or more layers provides the artificial tissue or tissue progenitor. In some embodiments, the artificial tissue or tissue progenitor having a shape in which the x-y plane of the shape is the planar geometric shape of the repeating functional unit.

The multi-dimensional construct can have any dimensions or sizes. In some embodiments, the multi-dimensional construct has a size of at least about any of 30 µm, 50 µm, 100 µm, 200 µm, 500 µm, 1 mm, 2 mm, 5 mm, 1 cm, 2 cm, 5 cm, 10 cm, 20 cm, or 50 cm. In some embodiments, the multi-dimensional construct has a length of at least about any of 30 µm, 50 µm, 100 µm, 200 µm, 500 µm, 1 mm, 2 mm, 5 mm, 1 cm, 2 cm, 5 cm, 10 cm, 20 cm, or 50 cm. In some embodiments, the multi-dimensional construct has a width of at least about any of 30 µm, 50 µm, 100 µm, 200 µm, 500 µm, 1 mm, 2 mm, 5 mm, 1 cm, 2 cm, 5 cm, 10 cm, 20 cm, or 50 cm. In some embodiments, the multi-dimensional construct has a thickness of at least about any of 30 µm, 50 µm, 100 µm, 200 µm, 500 µm, 1 mm, 2 mm, 5 mm, 1 cm, 2 cm, 5 cm, 10 cm, 20 cm, or 50 cm. In some embodiments, the multi-dimensional construct has a thickness comprising at least about any of 2, 5, 10, 15, 20, 30, 40, 50, 60, 70, 80, 90, 100, or more layers of the bio-blocks. In some embodiments, the ratio between the length and the width of the multi-dimensional construct is no more than about any of 10:1, 9:1, 8:1, 7:1, 6:1, 5:1, 4:1, 3:1, 2:1, 1.5:1, or 1:1. In some embodiments, the ratio between the length and the width of the multi-dimensional construct is any of about 1:1 to about 1.5:1, about 1:1 to about 2:1, about 1:1 to about 3:1, about 1:1 to about 4:1, about 1:1 to about 5:1, about 1:1 to about 6:1, about 1:1 to about 7:1, about 1:1 to about 8:1, about 1:1 to about 9:1, or about 1:1 to about 10:1. In some embodiments, the ratio between the length and the thickness of the multi-dimensional construct is no more than about any of 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, or 1:1. In some embodiments, the ratio between the length and the thickness of the multi-dimensional construct is any of about 1:1 to about 2:1, about 1:1 to about 3:1, about 1:1 to about 4:1, about 1:1 to about 5:1, about 1:1 to about 10:1, about 1:1 to about 20:1, about to about 50:1, or about 1:1 to about 100:1. In some embodiments, the method further comprises designing a model of the multi-dimensional construct according to the natural shape and/or cell distribution pattern of a tissue or an organ, wherein the tissue or the organ can be derived from the artificial tissue or the tissue progenitor being prepared.

In some embodiments, the pre-determined pattern is defined by a scaffold. In some embodiments, the bio-ink composition is bioprinted onto a scaffold having a pre-determined pattern. In some embodiments, the scaffold is an artificial structure comprising biodegradable polymers, which is capable of supporting the bio-blocks in the bio-ink to form a multi-dimensional artificial tissue or tissue progenitor. In some embodiments, the method of preparing an artificial tissue or a tissue progenitor does not use a scaffold.

In some embodiments, the method does not mechanically damage the cells in the bio-ink composition. In some embodiments, more than about any of 80%, 85%, 87.5%, 90%, 92.5%, 95%, or 98% of the cells in the bio-ink composition survives after the bioprinting. In some embodiments, more than about 90% of the cells in the bio-ink composition survives at least about any of 3 hours, 6 hours, 12 hours, 24 hours, 2 days, 4 days, or 1 week after the bioprinting. In some embodiments, more than about any of 80%, 85%, 87.5%, 90%, 92.5%, 95%, or 98% of the cells in the bio-ink composition is capable of proliferation after the bioprinting. In some embodiments, more than about any of 80%, 85%, 87.5%, 90%, 92.5%, 95%, or 98% of the cells in the bio-ink composition is capable of differentiation after the bioprinting. In some embodiments, more than about any of 80%, 85%, 87.5%, 90%, 92.5%, 95%, or 98% of the cells in the bio-ink composition have normal metabolism after the bioprinting. In some embodiments, more than about any of 80%, 85%, 87.5%, 90%, 92.5%, 95%, or 98% of the cells in the bio-ink composition is capable of migration after the bioprinting. In some embodiments, more than about any of 80%, 85%, 87.5%, 90%, 92.5%, 95%, or 98% of the cells in the bio-ink composition is capable of secretion after the bioprinting.

In some embodiments, the bioprinting is carried out in vitro. In some embodiments, the bioprinting is carried out directly on a subject. In some embodiments, the subject is a human. In some embodiments, the bioprinting is carried out directly at a damaged site of a tissue of the subject. In some embodiments, the tissue of the subject is damaged by injury, an infection, a disease, or as a consequence of the aging process. In some embodiments, the tissue is a skin tissue. In some embodiments, the bioprinting directly at the damaged site of the tissue of the subject is according to the cell distribution information of the damaged site of the tissue or of the tissue. The cell distribution information includes, but is not limited to, distinct layers of cells in the damaged site or the tissue, the type of cells of each layer, the ratio of different cells in each layer, the multi-dimensional distribution pattern of the cells in each layer, or any combination thereof. In some embodiments, the cell distribution information of the damaged site of the tissue is obtained prior to the bioprinting. In some embodiments, the cells in the bio-ink composition for bioprinting on the subject are derived from the subject. In some embodiments, the cells in the bio-ink composition for bioprinting on the subject are derived from a subject having similar characteristics (such as species, age, gender, disease, genetics information, etc.)

as the subject. In some embodiments, the cells in the bio-ink composition for bioprinting on the subject are derived from existing cell lines.

In some embodiments, the method further comprises culturing the multi-dimensional construct under a condition that allows the cells within the bio-blocks to proliferate, differentiate, metabolize, migrate, and/or secrete. The culturing condition depends on the type of cells, the types of bio-blocks used, the structure and design of the artificial tissue or tissue progenitor, and the physiology of the artificial tissue or tissue progenitor. A person skilled in the art should be able to choose proper culturing conditions, such as media, pH, temperature, $CO_2$ levels, and duration. Typical tissue and cell culture conditions have been described in the art, for example, see Doyle, Alan, and J. Bryan Griffiths, eds. Cell and tissue culture: laboratory procedures in biotechnology. New York: Wiley, 1998. In some embodiments, the multi-dimensional construct is cultured for at least about any of 1 hour, 3 hours, 6 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 25 days, or 30 days to obtain the artificial tissue or the tissue progenitor. In some embodiments, the multi-dimensional construct is cultured for about any of 1 hour to 3 hours, 3 hours to 6 hours, 6 hours to 12 hours, 12 hours to 1 day, 1 day to 3 days, 3 days to 5 days, 5 days to 7 days, 7 days to 10 days, 10 days to 14 days, 14 days to 21 days, 21 days to 28 days, 1 hour to 1 days, 1 day to 7 days, 7 days to 14 days, 1 days to 14 days, 14 days to 28 days, or 1 hour to 30 days to obtain the artificial tissue or the tissue progenitor. In some embodiments, the multi-dimensional construct is cultured in a 3D-culturing incubator. In some embodiments, the multi-dimensional construct is cultured in a bioreactor. In some embodiments, the multi-dimensional construct is cultured at about 37° C. in about 5% $CO_2$. In some embodiments, a physical stimulus (such as stretching, shearing, light, heating or cooling, etc.) is applied to the multi-dimensional construct during the culturing step. In some embodiments, a chemical stimulus (such as a hormone, a chemical gradient etc.) is applied to the multi-dimensional construct during the culturing step. In some embodiments, the biodegradable polymers in the bio-blocks (such as the biodegradable polymeric core material and/or the biodegradable polymeric shell material), and/or the carrier, degrade during the culturing step to provide nutrients for the cells in the bio-blocks. In some embodiments, the biodegradable polymers in the bio-blocks (such as the biodegradable polymeric core material and/or the biodegradable polymeric shell material), and/or the carrier, degrade during the culturing step to provide ECM molecules for the cells. In some embodiments, secretion from the cells during the culturing step integrates with the ECM in the multi-dimensional construct. In some embodiments, the cells in the bio-blocks connect to each other during the culturing step. In some embodiments, the cells from different bio-blocks connect to each other during the culturing step. In some embodiments, a high cell density (such as at least about any of 100, 200, 500, 1000, 2000, 5000, 10000, 20000, 50000, or 100000 cells/mm$^3$) is achieved in the multi-dimensional construct after the culturing step. In some embodiments, the cells proliferate to yield a more than about any of 2, 5, 10, 20, 50, 100, 200, 500, 1000, 2000, 5000, 10000, 20000, 50000, or 100000 fold increase in the cell number of the multi-dimensional construct during the culturing step.

Artificial Tissue and Tissue Progenitor

Further provided by the present application is an artificial tissue, a tissue progenitor, or a multi-dimensional construct prepared by any of the methods described in this section. In some embodiments, the artificial tissue, tissue progenitor or multi-dimensional construct is partially (such as at least about any of 10%, 20%, 30%, 40%, 50%, 60%, 70%, 80%, 90%, 95%, or more) prepared by any of the methods described herein. In some embodiments, the artificial tissue, tissue progenitor, or multi-dimensional construct comprises a plurality of layers. In some embodiments, the artificial tissue forms by fusion of cells in the bio-blocks.

Artificial tissues contemplated herein include, but are not limited to, connective tissue (for example, loose connective tissue, dense connective tissue, elastic tissue, reticular connective tissue and adipose tissue), muscle tissue (for example, skeletal muscle, smooth muscle and cardiac muscle), urogenital tissue, gastrointestinal tissue, lung tissue, bone tissue, cartilage tissue, nerve tissue and epithelial tissue (for example, a single layer of epithelial and stratified epithelium), endoderm-derived tissue, mesoderm-derived tissue and ectoderm-derived tissue, or any combination thereof. In some embodiments, the artificial tissue is a bone tissue, a cartilage tissue, or a joint tissue.

In some embodiments, there is provided an artificial tissue, tissue progenitor, or multi-dimensional construct comprising a plurality of any one of the bio-blocks provided herein. In some embodiments, the bio-blocks are arranged in a pre-determined pattern. In some embodiments, the pre-determined pattern is based on the natural structure and cell distribution pattern of a tissue or an organ. In some embodiments, the plurality of bio-blocks comprises at least about any of 1, 2, 3, 4, 5, 6, 7, 8, 9, or 10 types of bio-blocks. In some embodiments, the plurality of bio-blocks comprises at least about any of 1, 2, 3, 4, 5, 6, 7, 8, 9, or 10 different cell types.

In some embodiments, the artificial tissue, the tissue progenitor, or the multi-dimensional construct has a size of at least about any of 30 µm, 50 µm, 100 µm, 200 µm, 300 µm, 400 µm, 500 µm, 600 µm, 800 µm, 1 mm, 2 mm, 5 mm, 1 cm, 2 cm, 5 cm, 10 cm, 20 cm, or 50 cm. In some embodiments, the artificial tissue, the tissue progenitor, or the multi-dimensional construct has a size of any of about 1 µm to about 50 cm, about 100 µm to about 50 cm, about 10 µm to about 10 cm, about 50 µm to about 1 cm, about 100 µm to about 800 µm, or about 300 µm to about 600 µm. In some embodiments, the artificial tissue, the tissue progenitor, or the multi-dimensional construct has a length of at least about any of 1 µm, 10 µm, 30 µm, 50 µm, 100 µm, 200 µm, 300 µm, 400 µm, 500 µm, 600 µm, 800 µm, 1 mm, 2 mm, 5 mm, 1 cm, 2 cm, 5 cm, 10 cm, 20 cm, or 50 cm. In some embodiments, the artificial tissue, the tissue progenitor, or the multi-dimensional construct has a length of any of about 1 µm to about 50 cm, about 100 µm to about 50 cm, about 10 µm to about 10 cm, about 50 µm to about 1 cm, about 100 µm to about 800 µm, or about 300 µm to about 600 µm. In some embodiments, the artificial tissue, the tissue progenitor, or the multi-dimensional construct has a thickness of at least about any of 1 µm, 10 µm, 30 µm, 50 µm, 100 µm, 200 µm, 300 µm, 400 µm, 500 µm, 600 µm, 800 µm, 1 mm, 2 mm, 5 mm, 1 cm, 2 cm, 5 cm, 10 cm, 20 cm, or 50 cm. In some embodiments, the artificial tissue, the tissue progenitor, or the multi-dimensional construct has a thickness of any of about 1 µm to about 50 cm, about 100 µm to about 50 cm, about 10 µm to about 10 cm, about 50 µm to about 1 cm, about 100 µm to about 800 µm, or about 300 µm to about 600 µm. In some embodiments, the artificial tissue, the tissue progenitor, or the multi-dimensional construct has a thickness of at least about any of 2, 5, 10, 15, 20, 30, 40, 50, 60, 70, 80, 90, 100, or more layers of the bio-blocks. In some embodiments, the artificial tissue, the tissue progenitor, or the multi-dimensional construct has a thickness of about any of 1, 1-5, 5-10, 10-15, 15-20, 20-30, 30-40, 40-50, 50-100, 1-10, 1-20, 1-50, or 1-100 layers of the bio-blocks. In some embodiments, the artificial tissue, the tissue progenitor, or the multi-dimensional construct is further cultured to give rise to an organ or a functional unit of an organ, such as heart, liver, or kidney.

In some embodiments, there is provided a tissue progenitor prepared by any of the methods described herein. Accordingly, there is provided a method of preparing a tissue progenitor, comprising bioprinting a bio-ink composition to obtain a multi-dimensional construct having a pre-determined pattern, and optionally culturing the multi-dimensional construct under a condition that allows the cells to proliferate, differentiate, metabolize, and/or secrete. In some embodiments, the tissue progenitor is further cultured to give rise to a mini-tissue (i.e. a functional building block of a tissue), a tissue, or an organ upon culturing. In some embodiments, the tissue progenitor is implanted in vivo to allow development into a tissue. In some embodiments, the tissue progenitor is bioprinted directly in a subject to allow development of the tissue progenitor into a tissue.

Unlike bioprinted mini-tissues or tissue progenitors known in the art, the cells in the bio-block-based tissue progenitor described herein are not directly in contact with each other, especially cells in different bio-blocks, immediately after the bioprinting step. Culturing of the bioprinted multi-dimensional construct results in activities (such as proliferation, differentiation, migration, metabolism, secretion, etc.) of the cells first within the shell of the bio-blocks, and sometimes beyond the shell of the bio-blocks as the biodegradable polymeric materials of the bio-blocks (for example, the biodegradable polymeric core material and/or the biodegradable polymeric shell material) degrade over the course of culturing. Consequently, precise cell distribution and regulation of cell activities can be achieved in a bio-block-based tissue progenitor, enabling production of more complicated tissues or organs, especially those with structural and cellular heterogeneity (such as cell type and/or composition) within the final tissue or organ product.

In some embodiments, the cells in the different bio-blocks of the tissue progenitor proliferate, differentiate, migrate, or any combination thereof, and optionally the biodegradable polymeric core material is at least partially degraded. In some embodiments, the shell of the bio-blocks is completely degraded after culturing the multidimensional construct for about 2 days to about 28 days, such as any of about 2-3 days, about 3-4 days, about 4-7 days, or about 8-10 days. In some embodiments, the cells in the different bio-blocks of the tissue progenitor proliferate for more than about any of 1.5, 2, 5, 10, 20, 50, 100, 200, 500, 1000, 2000, 5000, 10000, 20000, 50000, or 100000 fold. In some embodiments, the proliferated cells penetrate the shell of the bio-blocks as the biodegradable polymeric core and/or shell material degrades. In some embodiments, the tissue progenitor comprises bio-blocks with stem cells, wherein the stem cells differentiate to give rise to at least about any of 1, 2, 3, 4, 5, 6, 7, 8, 9, or 10 different cell types in the tissue progenitor. In some embodiments, the biodegradable polymeric core material is at least degraded for about any of 10%, 20%, 30%, 40%, 50%, 60%, 70%, 80%, or 90%. In some embodiments of the tissue progenitor, the cells in different bio-blocks are connected to each other, and wherein the biodegradable polymeric core material and/or the biodegradable polymeric shell material are at least partially degraded. In some embodiments, more than about any of 10%, 20%, 30%, 40%, 50%, 60%, 70%, 80%, or 90% of the cells in different bio-blocks are connected to each other. In some embodiments, the biodegradable polymeric shell material is at least degraded for about any of 10%, 20%, 30%, 40%, 50%, 60%, 70%, 80%, or 90%. In some embodiments, the carrier, or the biocompatible (optionally bioadhesive) material is at least degraded for about any of 10%, 20%, 30%, 40%, 50%, 60%, 70%, 80%, or 90%. In some embodiments, the degradation products of the biodegradable polymeric core material, the biodegradable polymeric shell material, the carrier, and/or the biocompatible (optionally bioadhesive) material provide nutrients and/or ECM molecules for the cells.

In some embodiments, there is provided a method of preparing a mini-tissue, an artificial tissue, or an artificial organ, comprising bioprinting a bio-ink composition to obtain a multi-dimensional construct having a pre-determined pattern, optionally culturing the multi-dimensional construct under a condition that allows the cells to proliferate, differentiate, metabolize, and/or secrete to obtain a tissue progenitor, and culturing the tissue progenitor under a condition that allows connection of the cells in different bio-blocks, and allows degradation of the biodegradable polymeric core material and biodegradable polymeric shell material to obtain the mini-tissue, the artificial tissue, or the artificial organ. In some embodiments, the tissue progenitor is cultured for at least about any of 1, 2, 3, 4, 5, 6, 7, 8, 9, 10, 11, 12, 13, 14, 15, 16, 17, 18, 19, 20, 21, 25, or 30 days to obtain the mini-tissue, the artificial tissue, or the artificial organ. In some embodiments, the tissue progenitor is cultured in a 3D-culturing incubator or bioreactor. In some embodiments, a physical and/or chemical stimulus is applied to the tissue progenitor during the culturing step. In some embodiments, the artificial tissue is a blood vessel. In some embodiments, the artificial tissue is a cardiac muscle tissue.

Methods of Preparing Composite Constructs

Using any of the bio-ink compositions comprising any of the MSC bio-blocks (such as Type I MSC bio-blocks and/or Type II MSC bio-blocks, or Type III MSC bio-blocks and/or Type IV MSC bio-blocks) described herein, any of the methods described above can be used to prepare an artificial tissue, a composite construct, or a tissue progenitor thereof. For example, Type I MSC bio-blocks may be used to prepare an artificial bone tissue or progenitor thereof; Type II MSC bio-blocks may be used to prepare an artificial cartilage tissue or progenitor thereof; Type I MSC bio-blocks and Type II MSC bio-blocks may be used to prepare a composite construct comprising artificial bone and cartilage, or progenitor thereof; and Type III MSC bio-blocks and Type IV MSC bio-blocks may be used to prepare a composite construct comprising endothelial cells and smooth muscle cells, or progenitor thereof.

Compared to currently known methods of preparing composite constructs comprising artificial bone and cartilage for implantation, embodiments of the present methods of preparing such composite constructs using the Type I MSC bio-blocks and/or Type II MSC bio-blocks may have one or more of the following advantages, including, but not limited to:

(1) Instead of growing seed cells on a scaffold, the methods of the present application constructs an artificial implant directly using MSC bio-blocks;

(2) The methods of the present application do not require significant proliferation of MSCs prior to using the MSCs. The MSCs in the bio-blocks of the composite construct of the present application can proliferate inside the bio-blocks and eventually form an integrated implant;

(3) The methods of the present application do not need multiple culturing systems. The MSCs in the composite construct can differentiate into osteoblasts and chondrocytes under the same culturing system;

(4) Through precise distribution of the MSC bio-blocks, the methods of the present application can achieve precise distribution of osteoblasts and chondrocytes, thereby providing an artificial implant (i.e., composite construct having bone and cartilage) with complete structures and functions.

Thus, in some embodiments, there is provided a method of preparing an artificial bone tissue or tissue progenitor, comprising bioprinting (such as inkjet or microextrusion) a bio-ink composition to obtain a multi-dimensional construct having a pre-determined pattern, wherein the bio-ink composition comprises a plurality of Type I MSC bio-blocks each comprising: a) a core comprising a biodegradable polymeric core material, a MSC cell, and an agent that induces the MSC to differentiate into an osteoblast, or a bone tissue (such as dexamethasone, ascorbic acid, and glycerophosphate); and b) a shell comprising a biodegradable polymeric shell material. In some embodiments, at least about 80% (such as at least about any of 85%, 90%, 95%, or more) of the MSCs in the plurality of Type I MSC bio-blocks survive after the bioprinting. In some embodiments, the length of the artificial bone or tissue progenitor is at least about 100 µm (such as at least about any of 200 µm, 500 µm, 1 mm or more). In some embodiments, the thickness of the artificial bone or tissue progenitor is at least about 100 µm (such as at least about any of 200 µm, 500 µm, 1 mm or more). In some embodiments, the bio-ink composition has one or more (such as any of 1, 2, 3, 4, or 5) of the following properties or characteristics: (1) the bio-ink composition comprises a carrier (such as a liquid or a paste); (2) the plurality of Type I MSC bio-blocks are suspended homogenously within the carrier; (3) the carrier has a viscosity of about 1 Pa·s to about 1000 Pa·s; (4) the bio-ink composition comprises at least about 50% Type I MSC bio-blocks (w/w); and (5) the plurality of bio-blocks is of different types. In some embodiments, the Type I MSC bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the Type I MSC bio-block is about 30 µm to about 2 mm. In some embodiments, the ratio between the length and the thickness of the Type I MSC bio-block is no more than about 50:1 (such as no more than about any of 20:1, 10:1, 5:1, or 2:1). In some embodiments, the core comprises about 1 MSC to about 5000 MSCs (such as about 2 MSCs to about 50 MSCs, or about 100 MSCs to about 5000 MSCs). In some embodiments, the Type I MSC bio-block comprises one or more micropores (such as with a size of more than about 50 nm). In some embodiments, the Type I MSC bio-block has a hardness of about 0.01 GPa to about 0.4 GPa. In some embodiments, the Type I MSC bio-block comprises at least two cores and/or at least two shells.

In some embodiments, there is provided a method of preparing an artificial cartilage tissue or tissue progenitor, comprising bioprinting (such as inkjet or microextrusion) a bio-ink composition to obtain a multi-dimensional construct having a pre-determined pattern, wherein the bio-ink composition comprises a plurality of Type II MSC bio-blocks each comprising: a) a core comprising a biodegradable polymeric core material, a MSC cell, and an agent that induces the MSC to differentiate into a chondrocyte, or a cartilage tissue (such as TGF-β3, dexamethasone, ascorbic acid 2-phosphate, sodium pyruvate, proline, insulin, transferrin, and selenous acid); and b) a shell comprising a biodegradable polymeric shell material. In some embodiments, at least about 80% (such as at least about any of 85%, 90%, 95%, or more) of the MSCs in the plurality of Type II MSC bio-blocks survive after the bioprinting. In some embodiments, the length of the artificial cartilage or tissue progenitor is at least about 100 µm (such as at least about any of 200 µm, 500 µm, 1 mm or more). In some embodiments, the thickness of the artificial cartilage or tissue progenitor is at least about 100 µm (such as at least about any of 200 µm, 500 µm, 1 mm or more). In some embodiments, the bio-ink composition has one or more (such as any of 1, 2, 3, 4, or 5) of the following properties or characteristics: (1) the bio-ink composition comprises a carrier (such as a liquid or a paste); (2) the plurality of Type II MSC bio-blocks are suspended homogenously within the carrier; (3) the carrier has a viscosity of about 1 Pa·s to about 1000 Pa·s; (4) the bio-ink composition comprises at least about 50% Type II MSC bio-blocks (w/w); and (5) the plurality of Type II MSC bio-blocks is of different types. In some embodiments, the Type II MSC bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the Type II MSC bio-block is about 30 µm to about 2 mm. In some embodiments, the ratio between the length and the thickness of the Type II MSC bio-block is no more than about 50:1 (such as no more than about any of 20:1, 10:1, 5:1, or 2:1). In some embodiments, the core comprises about 1 MSC to about 5000 MSCs (such as about 2 MSCs to about 50 MSCs, or about 100 MSCs to about 5000 MSCs). In some embodiments, the Type II MSC bio-block comprises one or more micropores (such as with a size of more than about 50 nm). In some embodiments, the Type II MSC bio-block has a hardness of about 0.01 GPa to about 0.4 GPa. In some embodiments, the Type II MSC bio-block comprises at least two cores and/or at least two shells.

In some embodiments, there is provided a method of preparing a composite construct comprising a first differentiated cell and a second differentiate cell, comprising bioprinting (such as inkjet or microextrusion) a first bio-ink composition and a second bio-ink composition to obtain a multi-dimensional construct having a pre-determined pattern, wherein the first bio-ink composition comprises a plurality of first bio-blocks each comprising: a) a core comprising a biodegradable polymeric core material, a MSC cell, and a first agent or a first cell that induces the MSC to differentiate into the first differentiated cell; and b) a shell comprising a biodegradable polymeric shell material; and wherein the second bio-ink composition comprises a plurality of second bio-blocks each comprising: a) a core comprising a biodegradable polymeric core material, a MSC cell, and a second agent or a second cell that induces the MSC to differentiate into the second differentiated cell; and b) a shell comprising a biodegradable polymeric shell material. In some embodiments, at least about 80% (such as at least about any of 85%, 90%, 95%, or more) of the MSCs in the plurality of the first bio-blocks and/or the second bio-blocks survive after the bioprinting. In some embodiments, the length of the composite construct is at least about 100 µm (such as at least about any of 200 µm, 500 µm, 1 mm or more). In some embodiments, the thickness of the composite construct is at least about 100 µm (such as at least about any of 200 µm, 500 µm, 1 mm or more). In some embodiments, the first bio-ink composition and/or the second bio-ink composition has one or more (such as any of 1, 2, 3, 4, or 5) of the following properties or characteristics: (1) the first/second bio-ink composition comprises a carrier (such as a liquid or a paste); (2) the plurality of the first/second bio-blocks in are suspended homogenously within the carrier; (3) the carrier has a viscosity of about 1 Pa·s to about 1000 Pa·s; (4) the first/second bio-ink composition comprises at least about 50% the first/second bio-blocks (w/w); and (5) the plurality of the first/second bio-blocks is of different types. In some embodiments, the first bio-block and/or the second bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the first bio-block and/or the second bio-block is about 30 µm to about 2 mm. In some embodiments, the ratio between the length and the thickness of the first bio-block and/or the second bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the first bio-block and/or the second bio-block comprises one or more micropores (such as with a size of more than about 50 nm). In some embodiments, the first bio-block and/or the second bio-block has a hardness of about 0.01 GPa to about 0.4 GPa. In some embodiments, the first bio-block and/or the second bio-block comprises at least two cores and/or at least two shells.

In some embodiments, there is provided a method of preparing a composite construct comprising artificial bone and cartilage (or progenitors thereof), comprising bioprinting (such as inkjet or microextrusion) a first bio-ink composition and a second bio-ink composition to obtain a multi-dimensional construct having a pre-determined pattern, wherein the first bio-ink composition comprises a plurality of Type I MSC bio-blocks each comprising: a) a core comprising a biodegradable polymeric core material, a MSC cell, and an agent that induces the MSC to differentiate into an osteoblast, or a bone tissue (such as dexamethasone, ascorbic acid, and glycerophosphate); and b) a shell comprising a biodegradable polymeric shell material; and wherein the second bio-ink composition comprises a plurality of Type II MSC bio-blocks each comprising: a) a core comprising a biodegradable polymeric core material, a MSC cell, and an agent that induces the MSC to differentiate into a chondrocyte, or a cartilage tissue (such as TGF-β3, dexamethasone, ascorbic acid 2-phosphate, sodium pyruvate, proline, insulin, transferrin, and selenous acid); and b) a shell comprising a biodegradable polymeric shell material. In some embodiments, at least about 80% (such as at least about any of 85%, 90%, 95%, or more) of the MSCs in the plurality of Type I and/or Type II MSC bio-blocks survive after the bioprinting. In some embodiments, the length of the composite construct is at least about 100 µm (such as at least about any of 200 µm, 500 µm, 1 mm or more). In some embodiments, the thickness of the composite construct is at least about 100 µm (such as at least about any of 200 µm, 500 µm, 1 mm or more). In some embodiments, the first bio-ink composition and/or the second bio-ink composition has one or more (such as any of 1, 2, 3, 4, or 5) of the following properties or characteristics: (1) the first/second bio-ink composition comprises a carrier (such as a liquid or a paste); (2) the plurality of Type I/II MSC bio-blocks in are suspended homogenously within the carrier; (3) the carrier has a viscosity of about 1 Pa·s to about 1000 Pa·s; (4) the first/second bio-ink composition comprises at least about 50% Type I/Type II MSC bio-blocks (w/w); and (5) the plurality of Type I/II MSC bio-blocks is of different types. In some embodiments, the Type I MSC bio-block and/or Type II MSC bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the Type I MSC bio-block and/or Type II MSC bio-block is about 30 µm to about 2 mm. In some embodiments, the ratio between the length and the thickness of the Type I MSC bio-block and/or Type II MSC bio-block is no more than about 50:1 (such as no more than about any of 20:1, 10:1, 5:1, or 2:1). In some embodiments, the core comprises about 1 cell to about 5000 cells (such as about 2 cells to about 50 cells, or about 100 cells to about 5000 cells). In some embodiments, the Type I MSC bio-block and/or Type II MSC bio-block comprises one or more micropores (such as with a size of more than about 50 nm). In some embodiments, the Type I MSC bio-block and/or Type II MSC bio-block has a hardness of about 0.01 GPa to about 0.4 GPa. In some embodiments, the Type I MSC bio-block and/or Type II MSC bio-block comprises at least two cores and/or at least two shells.

Figure 19A:
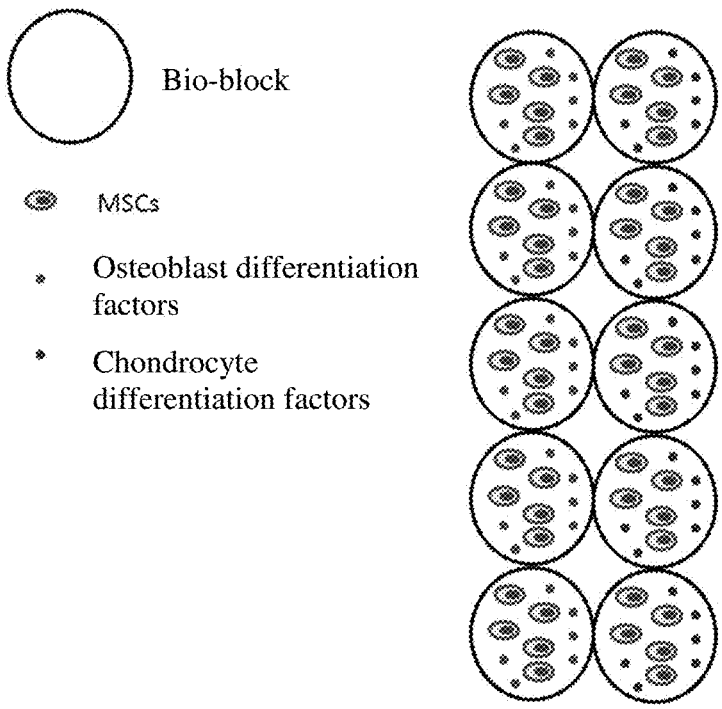
FIG. 19A shows the side view (i.e., along the length) of an exemplary composite construct comprising two layers, namely an osteoblast progenitor layer comprising Type I MSC bio-blocks, and a chondrocyte progenitor layer comprising Type II MSC bio-blocks. Depending on the number of cells in the bio-blocks, the osteoblast progenitor layer and the chondrocyte progenitor layer may each comprise one or more layers of cells. The space among the bio-blocks is filled with a bioadhesive material. In some embodiments, the bioadhesive material further comprises an agent that maintains, promotes, improves or regulates cellular activities inside the bio-blocks. In some embodiments, the composite construct of is prepared by three-dimensional bioprinting of the Type I MSC bio-blocks or the Type II MSC bio-blocks of the present application. In some embodiments, the composite construct is prepared using any other known methods (such as manual deposition) to deposit the Type I MSC bio-blocks or the Type II MSC bio-blocks of the present application.
Figure 19B:
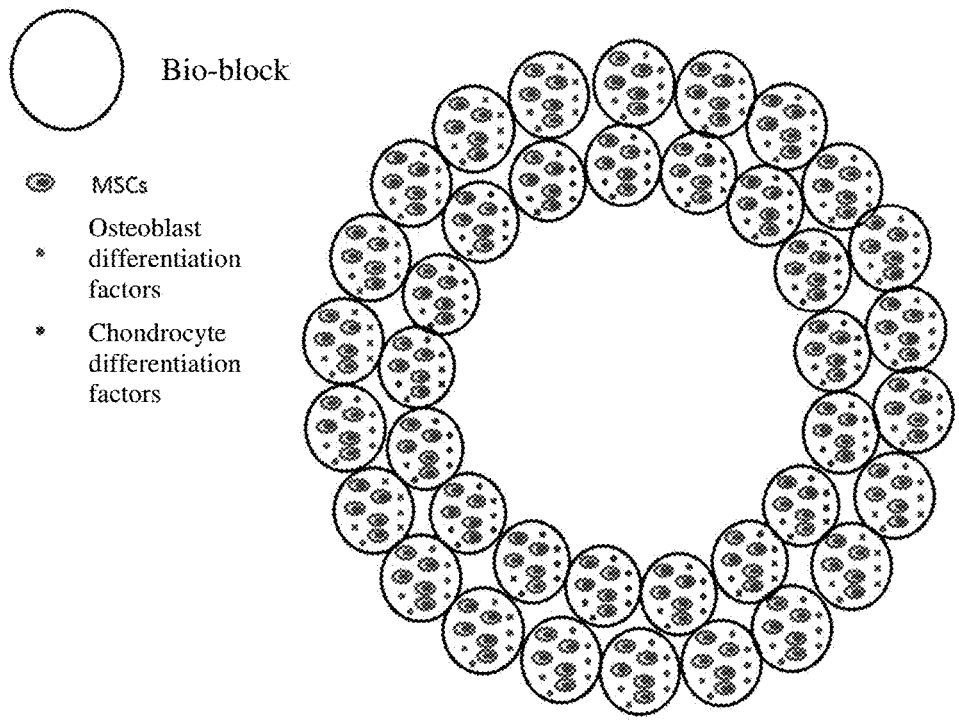
FIG. 19B shows the cross-section of an exemplary composite construct comprising two layers, namely an osteoblast progenitor layer comprising Type I MSC bio-blocks, and a chondrocyte progenitor layer comprising Type II MSC bio-blocks.

In some embodiments, there is provided a method of preparing a construct (such as three-dimensional construct, artificial tissue, organ, a composite construct comprising artificial bone and cartilage, or progenitors thereof), comprising bio-printing a bio-ink composition comprising a plurality of any one of the Type I MSC bio-blocks and/or Type II MSC bio-blocks described herein, or any of the bio-ink compositions comprising the Type I MSC bio-blocks and/or Type II MSC bio-blocks described herein. In some embodiments, the method produces a construct having a pre-determined pattern (such as any pre-determined shape), for example, a three-dimensional construct, artificial tissue, or tissue progenitor, such as a composite construct comprising artificial bone and cartilage. In some embodiments, the method further comprises preparing a bio-ink composition comprising any one of the Type I MSC bio-blocks and/or Type II MSC bio-blocks and a carrier (such as a bioadhesive material). In some embodiments, the composite construct has two layers, namely a first layer comprising the first bio-blocks comprising MSCs that can differentiate into a bone tissue, and a second layer comprising the second bio-blocks comprising MSCs that can differentiate into a cartilage tissue. An exemplary composite construct having two layers is depicted in FIGS. 19A-19B.

In some embodiments, there is provided a method of preparing a composite construct comprising endothelial cells and smooth muscle cells (or progenitors thereof), comprising bioprinting (such as inkjet or microextrusion) a first bio-ink composition and a second bio-ink composition to obtain a multi-dimensional construct having a pre-determined pattern, wherein the first bio-ink composition comprises a plurality of Type III MSC bio-blocks each comprising: a) a core comprising a biodegradable polymeric core material, a MSC cell, and an endothelial cell; and b) a shell comprising a biodegradable polymeric shell material; and wherein the second bio-ink composition comprises a plurality of Type IV MSC bio-blocks each comprising: a) a core comprising a biodegradable polymeric core material, a MSC cell, and a smooth muscle cell; and b) a shell comprising a biodegradable polymeric shell material. In some embodiments, at least about 80% (such as at least about any of 85%, 90%, 95%, or more) of the MSCs, and/or the endothelial cells or the smooth muscle cells in the plurality of Type III and/or Type IV MSC bio-blocks survive after the bioprinting. In some embodiments, the length of the composite construct is at least about 100 µm (such as at least about any of 200 µm, 500 µm, 1 mm or more). In some embodiments, the thickness of the composite construct is at least about 100 µm (such as at least about any of 200 µm, 500 µm, 1 mm or more). In some embodiments, the first bio-ink composition and/or the second bio-ink composition has one or more (such as any of 1, 2, 3, 4, or 5) of the following properties or characteristics: (1) the first/second bio-ink composition comprises a carrier (such as a liquid or a paste); (2) the plurality of Type III/IV MSC bio-blocks in are suspended homogenously within the carrier; (3) the carrier has a viscosity of about 1 Pa·s to about 1000 Pa·s; (4) the first/second bio-ink composition comprises at least about 50% Type III/IV MSC bio-blocks (w/w); and (5) the plurality of Type III/IV MSC bio-blocks is of different types. In some embodiments, the Type III MSC bio-block and/or Type IV MSC bio-block has one or more (such as any of 1, 2, 3, 4, 5, or 6) of the following properties or characteristics: (1) the biodegradable polymeric shell material comprises oxidized alginate (such as with an oxidation level of about 1% to about 40%, and/or a weight percentage of at least about 5%); (2) the shell has a thickness of about 0.1 µm to about 50 µm (such as about 1 µm to about 20 µm); (3) the shell has a modulus of elasticity of about 0.01 MPa to about 100 MPa; (4) the shell is permeable to a macromolecule having a molecular weight larger than about 110 kDa; (5) the biodegradable polymeric core material comprises type I collagen (such as type I collagen only, or type I collagen and alginate); and (6) the core comprises an agent (such as at least 3 different agents) selected from a nutrient, an extracellular matrix molecule, a cell factor (such as factor that facilitates cell proliferation, migration, metabolism, and/or secretion), and a pharmaceutically active agent. In some embodiments, the length of the Type III MSC bio-block and/or Type IV MSC bio-block is about 30 µm to about 2 mm. In some embodiments, the ratio between the length and the thickness of the Type III MSC bio-block and/or Type IV MSC bio-block is no more than about 50:1 (such as no more than about any of 20:1, 10:1, 5:1, or 2:1). In some embodiments, the core comprises about 2 cells to about 5000 cells (such as about 2 cells to about 50 cells, or about 100 cells to about 5000 cells). In some embodiments, the Type III MSC bio-block and/or Type IV MSC bio-block comprises one or more micropores (such as with a size of more than about 50 nm). In some embodiments, the Type III MSC bio-block and/or Type IV MSC bio-block has a hardness of about 0.01 GPa to about 0.4 GPa. In some embodiments, the Type III MSC bio-block and/or Type IV MSC bio-block comprises at least two cores and/or at least two shells.

In some embodiments, there is provided a method of preparing a composite construct comprising m types of cells arranged in a cell distribution pattern, wherein m is an integer equal to or greater than 2 (such as any of 2, 3, 4, 5, 6, 8, 10 or more), and wherein the method comprises: (1) providing m types of bio-blocks, wherein each bio-block comprises one type of the m types of cells, or the cell in each bio-block can differentiate to one type of the m types of cells; (2) arranging the m types of bio-blocks according to the cell distribution pattern of the composite construct to obtain a progenitor construct; and (3) culturing the progenitor construct to obtain the composite construct. In some embodiments, the method further comprises obtaining the cell distribution pattern of the composite construct. In some embodiments, the m types of cells are differentiated form the same type of stem cell, wherein each of the m types of bio-blocks comprise the stem cell, and one or more agents that induce differentiation of the stem cell to one of the m types of cells. In some embodiments, the stem cell is MSC. In some embodiments, the m types of bio-blocks are arranged by bioprinting (such as three-dimensional bioprinting).

In some embodiments, there is provided a method of preparing a composite construct comprising artificial bone and cartilage having a cell distribution pattern, comprising: (1) preparing a first bio-block comprising a MSC and one or more agents that induce differentiation of the MSC to an osteoblast or bone tissue, and a second bio-block comprising a MSC and one or more agents that induce differentiation of the MSC to a chondrocyte or cartilage tissue; (2) arranging a plurality of the first bio-block and a plurality of the second bio-block according to the cell distribution pattern of the composite construct to obtain a progenitor construct; and (3) culturing the progenitor construct to obtain the composite construct. In some embodiments, the method further comprises obtaining the cell distribution pattern of the composite construct. In some embodiments, the one or more agents in the first bio-block comprise dexamethasone, ascorbic acid, and glycerophosphate. In some embodiments, the one or more agents in the second bio-block comprise TGF-β3, dexamethasone, ascorbic acid 2-phosphate, sodium pyruvate, proline, and an insulin-transferrin-selenous acid solution. In some embodiments, the cell distribution pattern comprises the position and type of each cell layer, cell types and ratio of number of cells for each cell type, cell distribution pattern of each cell layer, or combinations thereof. In some embodiments, the first bio-blocks and the second bio-blocks are arranged by bioprinting (such as three-dimensional bioprinting). In some embodiments, the composite construct has two layers, namely a first layer comprising the first bio-blocks comprising MSCs that can differentiate into a bone tissue, and a second layer comprising the second bio-blocks comprising MSCs that can differentiate into a cartilage tissue. An exemplary composite construct having a layer of progenitors for bone tissue and a layer of progenitors for cartilage tissue is depicted in FIGS. 19A-19B.

Figure 22:
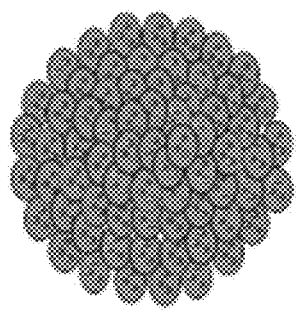
FIG. 22A shows a schematic cross-section layout of an exemplary tissue comprising two types of MSC bio-blocks.
FIG. 22B shows immunohistochemical staining results of the exemplary artificial tissue prepared by bioprinting two types of MSC bio-blocks.

In some embodiments, there is provided a method of preparing a composite construct comprising endothelial cells and smooth muscle cells having a cell distribution pattern, comprising: (1) preparing a first bio-block comprising a MSC and an endothelial cell, and a second bio-block comprising a MSC and a smooth muscle cell; (2) arranging a plurality of the first bio-block and a plurality of the second bio-block according to the cell distribution pattern of the composite construct to obtain a progenitor construct; and (3) culturing the progenitor construct to obtain the composite construct. In some embodiments, the method further comprises obtaining the cell distribution pattern of the composite construct. In some embodiments, the cell distribution pattern comprises the position and type of each cell layer, cell types and ratio of number of cells for each cell type, cell distribution pattern of each cell layer, or combinations thereof. In some embodiments, the first bio-blocks and the second bio-blocks are arranged by bioprinting (such as three-dimensional bioprinting). In some embodiments, the composite construct has two layers, namely a first layer comprising the first bio-blocks that can develop into a tissue comprising endothelial cells, and a second layer that can develop into a tissue comprising smooth muscle cells. An exemplary composite construct having a layer of endothelial cells and progenitors, and a layer of smooth muscle cells and progenitors is depicted in FIG. 22A.

In some embodiments, the construct (such as three-dimensional construct, artificial tissue, tissue progenitor, composite construct, or organ) has a sheet structure (e.g., rectangular, square, circular, oval, hexagonal, or irregular shaped sheet structure), or a hollow tube structure (such as hollow cube, hollow sphere, hollow rectangular prism, hollow cylinder, or irregularly shaped hollow three-dimensional structure), or a solid three-dimensional structure (such as a solid cube, a solid sphere, a solid rectangular prism, a solid cylinder, a solid irregular shaped three dimensional structure), or any combination thereof. In some embodiments, the construct mimics the shape of a natural tissue (such as bone, cartilage, or joint tissue) or organ. In some embodiments, the construct is a live construct. In some embodiments, at least part of the construct is bioprinted. In some embodiments, the bioprinting is continuous or substantially continuous. In some embodiments, the method comprises continuously bioprint a plurality of layers to obtain a multi-layered three-dimensional construct having a pre-determined pattern, wherein each layer is bio-printed using the bio-ink composition according to the pre-determined pattern. In some embodiments, the method comprises continuously bioprinting a plurality of segments to obtain a multi-segmented three-dimensional construct having a pre-determined pattern, wherein each segment is bio-printed using the bio-ink composition according to the pre-determined pattern. In some embodiments, the method further comprises building a structural model of the construct (such as three-dimensional construct) according to the shape and/or cell distribution patter of the natural tissue or organ (such as bone, cartilage, or joint tissue). In some embodiments, the method does not mechanically damage the cells inside the bio-ink composition or the bio-blocks. In some embodiments, at least about any of 80%, 85%, 87.5%, 90%, 92.5%, 95%, or 98% of cells can survive, proliferate, differentiate, secrete, migrant and/or undergo normal metabolism after the bioprinting. In some embodiments, the bioprinting does not use a scaffold.

In some embodiments, the method further comprises culturing the construct under conditions that allow proliferation, differentiation, migration, secretion and/or metabolism of the cells in the bio-blocks. In some embodiments, the construct is cultured for at least about 1, 2, 3, 4, 5, 6, 7, 8, 9, 10, 11, 12, 13, 14, 15, 16, 17, 18, 19, 20, 21, 25 or 30 days. In some embodiments, the construct is cultured for about any of 1-5 days, 5-10 days, 10-15 days, 15-20 days, 7-14 days, 4-16 days, 2-18 days, 1-19 days, or 2-20 days. It was surprisingly found that in some embodiments, in vitro culture of the composite construct provides differentiated cells having calcium nodes in no more than about 10 days. By contrast, without being present in bio-blocks, MSCs cultured in a typical cell culture system and similar amount of osteoblast differentiation agents (e.g., dexamethasone, ascorbic acid, and glycerophosphate) normally requires about 20 days to differentiate into cells having calcium nodes.

In some embodiments, the construct is cultured in a 3D incubator or bioreactor. In some embodiments, the construct is subjected to a physical stimulus (such as pressure, shearing force, light, heating, etc.) and/or a chemical stimulus (such as hormone, cell factor, chemical reagents, etc.) during the culturing. In some embodiments, the biodegradable material in the core and/or shell and/or carrier is at least partially degraded. In some embodiments, the cells inside and/or among the bio-blocks are connected to each other during the culturing. In some embodiments, the size of the construct is at least about any of 30 μm, 50 μm, 100 μm, 200 μm, 500 μm, 1 mm, 2 mm, 5 mm, 1 cm, 2 cm, 5 cm, 10 cm, 20 cm or 50 cm.

Further provided are artificial tissues (such as bone, cartilage, or joint tissue), composite constructs, or tissue progenitors thereof prepared using any one of the methods described herein using MSC bio-blocks (such as Type I MSC bio-blocks and/or Type II MSC bio-blocks, or Type III MSC bio-blocks and/or Type IV MSC bio-blocks) and bio-ink compositions thereof.

In some embodiments, there is provided a composite construct, comprising a first layer of bio-blocks each comprising an osteoblast or progenitor thereof (such as MSC), and a second layer of bio-blocks each comprising a chondrocyte or progenitor thereof (such as MSC). In some embodiments, the first layer of bio-blocks each comprises a core comprising a MSC and one or more agents that induces differentiation of the MSC to an osteoblast or a bone tissue, such as dexamethasone, ascorbic acid, and glycerophosphate. In some embodiments, the second layer of bio-blocks each comprises a core comprising a MSC and one or more agents that induces differentiation of the MSC to a chondrocyte or a cartilage tissue, such as TGF-β3, dexamethasone, ascorbic acid 2-phosphate, sodium pyruvate, proline, insulin, transferrin, and selenous acid. In some embodiments, the first layer of bio-blocks and/or the second layer of bio-blocks each comprises a plurality of MSCs. In some embodiments, the first layer of bio-blocks and/or the second layer of bio-blocks each comprises no more than about any one of 2, 3, 4, 5, 10, 20, 50, 100, 200, 500, 1000, $10^4$, $10^5$ or $10^6$ MSCs. In some embodiments, the composite construct comprises at least about any of 2, 3, 4, 5, 6, 7, or more first layers of bio-blocks. In some embodiments, the composite construct comprises at least about any of 2, 3, 4, 5, 6, 7, or more second layers of bio-blocks. In some embodiments, cells in the first layer of bio-blocks are connected to the cells in the second layer of bio-blocks. In some embodiments, the shell of the bio-blocks of the first layer and/or the bio-blocks of the second layer are at least about any of 10%, 20%, 30%, 40%, 50%, 60%, 70%, 80%, 90%, or more degraded. In some embodiments, the composite construct does not comprise a scaffold.

In some embodiments, there is provided a composite construct, comprising a first layer of bio-blocks each comprising a plurality of endothelial cells or progenitors thereof (such as MSC), and a second layer of bio-blocks each comprising a plurality of smooth muscle cells or progenitors thereof (such as MSC). In some embodiments, the first layer of bio-blocks each comprises a core comprising a MSC and an endothelial cell. In some embodiments, the second layer of bio-blocks each comprises a core comprising a MSC and a smooth muscle cell. In some embodiments, the first layer of bio-blocks and/or the second layer of bio-blocks each comprises a plurality of MSCs. In some embodiments, the first layer of bio-blocks and/or the second layer of bio-blocks each comprises no more than about any one of 2, 3, 4, 5, 10, 20, 50, 100, 200, 500, 1000, $10^4$, $10^5$ or $10^6$ MSCs. In some embodiments, the composite construct comprises at least about any of 2, 3, 4, 5, 6, 7, or more first layers of bio-blocks. In some embodiments, the composite construct comprises at least about any of 2, 3, 4, 5, 6, 7, or more second layers of bio-blocks. In some embodiments, cells in the first layer of bio-blocks are connected to the cells in the second layer of bio-blocks. In some embodiments, the shell of the bio-blocks of the first layer and/or the bio-blocks of the second layer are at least about any of 10%, 20%, 30%, 40%, 50%, 60%, 70%, 80%, 90%, or more degraded. In some embodiments, the composite construct does not comprise a scaffold.

Methods of Preparing Bio-Blocks

One aspect of the present invention provides methods of preparing any of the bio-blocks (including MSC bio-blocks, such as Type I, II, III, or IV MSC bio-blocks) as described above, including bio-blocks of various structures, such as bio-blocks with a single core and a single shell, bio-blocks having at least two cores, bio-blocks having at least two shells, and bio-blocks having at least two cores and at least two shells.

Thus, in some embodiments, there is provided a method of preparing a bio-block, comprising the steps of: (1) obtaining at least one core by each independently mixing a cell composition with a polymeric core material; and (2) coating the at least one core with at least one shell each independently comprising a polymeric shell material to obtain the bio-block. In some embodiments, step (1) further comprises granulation of the innermost core.

In some embodiments, there is provided a method of preparing a bio-block, comprising the steps of: (1) obtaining at least one core by each independently mixing a cell composition with a polymeric core material; (2) coating the at least one core with at least one shell each independently comprising a polymeric shell material; (3) coating the at least one shell with at least one additional core, wherein each of the at least one additional core independently comprises a polymeric core material and a cell composition; and (4) coating the at least one additional core with at least one additional shell each independently comprising a polymeric shell material to obtain the bio-block. In some embodiments, step (1) further comprises granulation of the innermost core.

In some embodiments, there is provided a method of preparing a bio-block, comprising the steps of: (1) obtaining at least one core by each independently mixing a cell composition with a polymeric core material; (2) coating the innermost core with at least one different core, wherein each of the at least one different core independently comprises a polymeric core material and a cell composition; and (3) coating the at least one different core with at least one shell each independently comprising a polymeric shell material to obtain the bio-block. In some embodiments, step (1) further comprises granulation of the innermost core.

In some embodiments, there is provided a method of preparing a bio-block, comprising the steps of: (1) obtaining at least one core by each independently mixing a cell composition with a polymeric core material; (2) coating the innermost core with at least one different core, wherein each of the at least one different core independently comprises a polymeric core material and a cell composition; (3) coating the at least one different core with at least one shell each independently comprising a polymeric shell material; (4) coating the at least one shell with at least one additional core, wherein each of the at least one additional core independently comprises a polymeric core material and a cell composition; and (5) coating the at least one additional core with at least one additional shell each independently comprising a polymeric shell material to obtain the bio-block. In some embodiments, the steps (4) and (5) are repeated for one or more times. In some embodiments, step (1) further comprises granulation of the innermost core.

For example, in some embodiments, there is provided a method of preparing a bio-block, comprising the steps of: (1) mixing a cell composition with a polymeric core material to obtain a core; and (b) coating the core with a shell comprising a polymeric shell material to obtain the bio-block. In some embodiments, step (1) further comprises granulation of the core.

In some embodiments, there is provided a method of preparing a bio-block, comprising the steps of: (1) mixing a cell composition with a polymeric core material to obtain a core; (2) coating the core with a first shell comprising a first polymeric shell material; (3) coating the first shell with a second shell comprising a second polymeric shell material to obtain the bio-block. In some embodiments, step (1) further comprises granulation of the core.

In some embodiments, there is provided a method of preparing a bio-block, comprising the steps of: (1) mixing a first cell composition with a first polymeric core material to obtain a first core; (2) mixing a second cell composition with a second polymeric core material to obtain a second core; (3) coating the first core with the second core; (4) coating the second core with a shell comprising a polymeric shell material to obtain the bio-block. In some embodiments, step (1) further comprises granulation of the first core.

In some embodiments, there is provided a method of preparing a bio-block, comprising the steps of: (1) mixing a first cell composition with a first polymeric core material to obtain a first core; (2) mixing a second cell composition with a second polymeric core material to obtain a second core; (3) coating the first core with the second core; (4) coating the second core with a first shell comprising a first polymeric shell material; (5) coating the first shell with a second shell comprising a second polymeric shell material to obtain the bio-block. In some embodiments, step (1) further comprises granulation of the first core.

In some embodiments, there is provided a method of preparing a bio-block, comprising the steps of: (1) mixing a first cell composition with a first polymeric core material to obtain a first core; (2) coating the first core with a first shell comprising a first polymeric shell material; (3) mixing a second cell composition with a second polymeric core material to obtain a second core; (4) coating the first shell with the second core; (5) coating the second core with a second shell comprising a second polymeric shell material to obtain the bio-block. In some embodiments, step (1) further comprises granulation of the first core.

In some embodiments, there is provided a method of preparing a bio-block, comprising: (1) mixing a cell and a biodegradable core material to obtain a core material enwrapping the cell; and (2) granulating the core material, and coating the core material with a biodegradable shell material to obtain the bio-block. In some embodiments, step (1) further comprises mixing the cell, the biodegradable core material, and a suitable additional agent (such as a nutrient, ECM molecule, cell factor and/or pharmaceutically active agent). In some embodiments, in step (2), a device for preparing microspheroids or microcapsules, such as an encapsulator is used for granulation and coating. In some embodiments, the method further comprises processing the shell of the bio-block (such as using a shell solidifying or crosslinking solution, for example, to improve the mechanical properties of the shell) after step (2). In some embodiments, the method is carried out under sterile conditions. In some embodiments, the method is carried out in a GMP workshop. In some embodiments, the bio-block can be stored under refrigerated conditions (such as about 4° C.) after preparation, for at least about any of 3 hours, 6 hours, 12 hours, 1 day, 2 days, or 3 days.

The polymeric core material and the polymeric shell material used in the methods described above may comprise any one or combinations of the materials suitable for use in bio-blocks as described in the "Bio-blocks" section, including naturally occurring polymers and synthetic polymers. The cell composition may comprise any number of cells (such as about 1 to about 1000000 cells) of any type or combination of types as described in the "Bio-blocks" sections. Each core may comprise the same or different polymeric core material and/or the cell composition. Each shell may comprise the same or different polymeric shell material. In some embodiments, the polymeric core material of one or more (including all) cores is biodegradable. In some embodiments, the polymeric shell material of one or more (including all) shells is biodegradable. In some embodiments, the polymeric core material of all cores and the polymeric shell material of all shells are biodegradable.

Any one or more (including all) of the cores prepared in the methods described above may further comprise an additional agent selected from a nutrient, extracellular matrix, cell factor, pharmaceutically active agent, and combinations thereof. In some embodiments, step (1) comprises obtaining at least one core by each independently and mixing the cell composition, the polymeric core material and an additional agent comprising a nutrient, extracellular matrix, cell factor, or pharmaceutically active agent. Any nutrient, extracellular matrix, cell factor, or pharmaceutically active agent as described in the "Bio-blocks" section may be used in the methods of preparing the bio-blocks.

Any one or more (including all) of the shells (or the polymeric shell materials) may be further processed after the coating step(s). In some embodiments, the outermost shell is processed. In some embodiments, only the outermost shell is processed. Processing of the shell may comprise any steps known in the art to alter or improve the properties (such as chemical properties and/or mechanical properties) of the polymeric shell material. In some embodiments, the processing comprises solidifying the shell to improve mechanical properties (such as hardness and/or elasticity) of the shell. In some embodiments, wherein the polymeric shell material comprises alginate, the processing comprises treating the polymeric shell material with calcium (such as $Ca^{2+}$) to crosslink the alginate.

The coating and/or granulation steps may be carried out using any method and apparatus known in the art, such as using an encapsulator, a micropipette (e.g., using an extrusion method), or a microinjection pump. In some embodiments, the coating and/or granulation steps are carried out on a hydrophobic surface. In some embodiments, the method is carried out under sterile conditions. In some embodiments, the method is carried out in a GMP workshop. In some embodiments, the method is carried out at about 4° C.

The bio-blocks prepared any of the methods described herein may further be stored at appropriate conditions prior to use. In some embodiments, the bio-block can be stored under refrigerated conditions (such as about 4° C.) for about 3 hours to about 3 days. In some embodiments, the bio-block can be stored under refrigerated conditions (such as about 4° C.) for at least about any of 3 hours, 6 hours, 12 hours, 1 day, 2 days, or 3 days.

Further provided is a bio-block prepared by any one of the methods described herein.

Methods of Preparing MSC Bio-Blocks

In some embodiments, there is provided a method of preparing an MSC bio-block, such as a Type I MSC bio-block, comprising: (1) mixing a MSC, one or more agents that induce the MSC to differentiate into an osteoblast or a bone tissue, and a biodegradable core material to obtain a core material enwrapping the MSC; (2) granulating the core material, and coating the core material with a biodegradable shell material to obtain the MSC bio-block. In some embodiments, step (1) further comprises mixing the MSC, the biodegradable core material, the one or more agents that induce the MSC to differentiate into an osteoblast or a bone tissue, and an additional agent (such as a nutrient, ECM molecule, cell factor and/or pharmaceutically active agent).

In some embodiments, there is provided a method of preparing an MSC bio-block, such as a Type II MSC bio-block, comprising: (1) mixing a MSC, one or more agents that induce the MSC to differentiate into a chondrocyte or a cartilage tissue, and a biodegradable core material to obtain a core material enwrapping the MSC; (2) granulating the core material, and coating the core material with a biodegradable shell material to obtain the MSC bio-block. In some embodiments, step (1) further comprises mixing the MSC, the biodegradable core material, the one or more agents that induce the MSC to differentiate into a chondrocyte or a cartilage tissue, and an additional agent (such as a nutrient, ECM molecule, cell factor and/or pharmaceutically active agent).

In some embodiments, there is provided a method of preparing an MSC bio-block, such as a Type III MSC bio-block, comprising: (1) mixing a MSC, an endothelial cell, and a biodegradable core material to obtain a core material enwrapping the MSC; (2) granulating the core material, and coating the core material with a biodegradable shell material to obtain the MSC bio-block. In some embodiments, step (1) further comprises mixing the MSC, the biodegradable core material, the endothelial cell, and an additional agent (such as a nutrient, ECM molecule, cell factor and/or pharmaceutically active agent).

In some embodiments, there is provided a method of preparing an MSC bio-block, such as a Type IV MSC bio-block, comprising: (1) mixing a MSC, a smooth muscle cell, and a biodegradable core material to obtain a core material enwrapping the MSC; (2) granulating the core material, and coating the core material with a biodegradable shell material to obtain the MSC bio-block. In some embodiments, step (1) further comprises mixing the MSC, the biodegradable core material, the smooth muscle cell, and an additional agent (such as a nutrient, ECM molecule, cell factor and/or pharmaceutically active agent).

In some embodiments according to any of the above methods of preparing MSC bio-blocks described above, in step (2), a device for preparing microspheroids or microcapsules, such as an encapsulator is used for granulation and coating. In some embodiments, the method further comprises processing the shell of the bio-block (such as using a shell solidifying or crosslinking solution, for example, to improve the mechanical properties of the shell) after step (2). In some embodiments, the method is carried out under sterile conditions. In some embodiments, the method is carried out in a GMP workshop. In some embodiments, the bio-block can be stored under refrigerated conditions (such as about 4° C.) after preparation, for at least about any of 3 hours, 6 hours, 12 hours, 1 day, 2 days, or 3 days.

Further provided is an MSC bio-block (such as Type I, II, III, or IV MSC bio-block) prepared by any one of the methods described herein.

Use of Bio-Blocks, Pluralities of Bio-Blocks, Compositions, Tissue Progenitors, and Artificial Tissues Any of the bio-blocks (including MSC bio-blocks, such as Type I, II, III, or IV MSC bio-blocks), the compositions (such as the bio-ink compositions or the pharmaceutical compositions), the pluralities of isolated bio-blocks, the tissue progenitors, the artificial tissues, the artificial organs or the multi-dimensional constructs described in the present application may be useful for a variety of applications, such as tissue engineering, in vitro research, stem cell differentiation, in vivo research, drug screening, drug discovery, tissue regeneration, and regenerative medicine.

Thus, in some embodiments, there is provided use of any of the bio-blocks (including MSC bio-blocks, such as Type I, II, III, or IV MSC bio-blocks), the multi-dimensional constructs, the tissue progenitors, or the artificial tissues described herein for stem cell differentiation research; drug discovery; drug screening; in vivo or in vitro assay; transplantation into a host; tissue engineering; tissue regeneration; analysis of cellular functions in response to a stimulus or an agent; study of in vivo effects of microenvironments; treating an individual in need thereof; evaluation of efficacy of a composition on a tissue or cells in a tissue; 3-dimensional tissue culture; or repair of a damaged tissue in an individual.

In some embodiments, the bio-block (including MSC bio-block, such as Type I, II, III, or IV MSC bio-block) is useful for tissue engineering. In some embodiments, the bio-block provides a unique microenvironment for the cell(s) inside the bio-block to allow study of culturing (such as three-dimensional culturing) conditions that allow cellular activities, including, but not limited to, proliferation, differentiation, metabolism, migration, secretion, signaling, tissue development and organogenesis.

As it is known in the art, tissue engineering is an interdisciplinary field that applies and combines the principles of engineering and life sciences. In some embodiments, tissue engineering refers to use of biological alternatives (such as the bio-blocks of the present application) to restore, maintain, or improve tissue functions. Without being bound by any theory or hypothesis, the basic principle of classical tissue engineering involves obtaining a small amount of live tissue form an individual, isolating cells (also known as seed cells) from the live tissue using a special enzyme or other methods, culturing the isolated cells in vitro to proliferate the isolated cells, and mixing the proliferated cells with biocompatible, degradable, and absorbable biomaterials (i.e., scaffold) at a pre-determined ratio so that the cells adhere to the biomaterial (i.e., scaffold) to provide a cell-scaffold composition, and implanting the composition into a damaged site of a tissue or organ in the individual. As the biomaterial gradually degrades and becomes absorbed in vivo, the implanted cells continuously proliferate and secrete extracellular matrix molecules, and eventually form the corresponding tissue or organ, thereby achieving the purposes of tissue repair and reconstruction. The bio-blocks of the present application have one or more of the following advantages: the types and numbers of the cells in the bio-blocks can be controlled; the dimensions of the bio-blocks can be controlled; the core and shell of the bio-blocks each (such as independently) comprise biodegradable materials; and the degradation rate of the shells of the bio-blocks can be controlled. Therefore, the bio-blocks of the present application are especially suitable for tissue engineering.

In some embodiments, there is provided a method of providing a microenvironment comprising a plurality of microenvironmental factors to a cell comprising providing a bio-block comprising the cell and the plurality of microenvironmental factors, and culturing the bio-block under appropriate conditions. Exemplary microenvironmental factors include, but are not limited to, physical factors (e.g., mechanical factors, temperature, humidity, osmotic pressure, etc.); chemical factors (e.g., pH, ionic concentrations, etc.); biological factors (e.g., cells, cytokines, etc.). The microenvironmental factors may dynamically regulate one or more activities of the cell, including, but not limited to, proliferation, differentiation, migration, metabolism, and secretion. In some embodiments, the plurality of microenvironmental factors comprises growth factors for the cell to grow and to differentiate. In some embodiments, the plurality of microenvironmental factors comprises a structure and space for the cell to proliferate and to differentiate. In some embodiments, the plurality of microenvironmental factors comprises physical factors (such as mechanical stimuli) for the cell to carry out its biological functions. In some embodiments, the plurality of microenvironmental factors comprises feeder cells to facilitate or to regulate differentiation of the cell, wherein the cell is a stem cell.

In some embodiments, there is provided a method of three-dimensional tissue culturing comprising providing a bio-block comprising a cell or a plurality of bio-blocks to be cultured, agents, or other components useful for the tissue culturing, and culturing the bio-block under appropriate conditions. In some embodiments, the cell in the bio-block can give rise to the cells naturally found in a tissue. In some embodiments, the cell is a stem cell. In some embodiments, a plurality of isolated bio-blocks, such as any of the pluralities of isolated bio-blocks described above, is used to investigate of three-dimensional tissue culturing conditions. In some embodiments, the plurality of isolated bio-blocks is analyzed in parallel (e.g. simultaneously), and/or in a high throughput screening context. In some embodiments, at least two of the isolated bio-blocks in the plurality of isolated bio-blocks are different, allowing simultaneous investigation of at least two tissue culturing conditions. In some embodiments, the plurality of isolated bio-blocks is provided in a container. In some embodiments, any of the containers comprising a plurality of bio-blocks (such as isolated bio-blocks as described above) is used for the method of three-dimensional culturing.

In some embodiments, the bio-block (including MSC bio-block, such as Type I, II, III, or IV MSC bio-block), the plurality of isolated bio-blocks, the multi-dimensional construct (such as the composite construct), the tissue progenitor or the artificial tissue is useful for in vitro research, including a variety of in vitro assays. In some embodiments, the in vitro assay is a procedure for testing or measuring the presence or activity of a substance (e.g., a chemical, molecule, biochemical, drug, etc.) in an organic or biologic sample (e.g., cell aggregate, tissue, organ, organism, etc.). In some embodiments, the in vitro assay is qualitative. In some embodiments, the in vitro assay is quantitative. In some embodiments, the quantitative in vitro assay measures the amount of a substance in a sample. Exemplary in vitro assays contemplated by the present application include, but are not limited to, image-based assays, measurement of secreted proteins, expression of markers, and production of proteins. In some embodiments, the in vitro assay is used to detect or measure one or more of: molecular binding (including radioligand binding), molecular uptake, activity (e.g., enzymatic activity and receptor activity, etc.), gene expression, protein expression, receptor agonism, receptor antagonism, cell signaling, apoptosis, chemosensitivity, transfection, cell migration, chemotaxis, cell viability, cell proliferation, safety, efficacy, metabolism, toxicity, and abuse liability. In some embodiments, the in vitro assay is an immunoassay, including competitive immunoassays or non-competitive immunoassays. In some embodiments, the in vitro assay is an enzyme-linked immunosorbent assay (ELISA). In some embodiments, the bio-block, the multi-dimensional construct, the artificial tissue or the tissue progenitor provides molecules, cells, groups of cells, or tissues that are measured or detected in the in vitro assays.

In some embodiments, there is provided a method of analyzing cellular functions in response to a stimulus or an agent, comprising exposing the cells in the bio-block (including MSC bio-block, such as Type I, II, III, or IV MSC bio-block) according to any one of the bio-blocks described above to the stimulus or the agent, and assessing a change in the cellular functions in the bio-block. The cellular functions contemplated herein include, but are not limited to cell activities, cell behaviors, subcellular organelle dynamics and activities, and functions and activities of molecules inside cells. Examples of cellular functions include, but are not limited to, proliferation, differentiation, metabolism, migration, secretion, signaling, apoptosis, necrosis, death, chemotaxis, localization of molecules, binding of molecules, and the like. In some embodiments, the stimulus or the agent is provided in the core of the bio-block. In some embodiments, the bio-block is an isolated bio-block. In some embodiments, the bio-block is provided in a container. In some embodiments, the stimulus or the agent is provided in the container. In some embodiments, any one of the pluralities of isolated bio-blocks or the containers as described above is used in the method of analyzing cellular functions. In some embodiments, the stimulus or agent is a drug. In some embodiments, the method is used for determining the efficacy of the drug. In some embodiments, the method is used for screening the drug.

In some embodiments, the bio-block is useful for studying stem cell differentiation. In some embodiments, there is provided a method of studying MSC differentiation using any one of the MSC bio-blocks described herein (such as Type I, II, III, or IV MSC bio-blocks). In some embodiments, any one of the pluralities of isolated bio-blocks, or the containers comprising a plurality of isolated bio-blocks as described in the previous sections is used to study stem cell differentiation, wherein each of the isolated bio-blocks comprises at least one stem cell. In some embodiments, at least two of the isolated bio-blocks in the plurality of the isolated bio-blocks or the container are different, allowing simultaneous investigation of the effects of at least two different conditions on stem cell differentiation. In some embodiments, each of the at least two isolated bio-blocks comprises a different type of stem cell. In some embodiments, the isolated bio-blocks comprise the same type of stem cell. In some embodiments, each of the at least two isolated bio-blocks comprises a different agent or combination of agents that regulates (such as facilitates) cell proliferation, differentiation, migration, metabolism, secretion, signaling, or any combination thereof. In some embodiments, the plurality of isolated bio-blocks is analyzed in parallel (e.g. simultaneously), and/or in a high throughput screening context.

In some embodiments, the bio-block (including MSC bio-blocks, such as Type I, II, III, or IV MSC bio-block), the bio-ink composition, the multi-dimensional construct (such as the composite construct), the artificial tissue or the tissue progenitor is useful for in vivo research. In some embodiments, the bio-block, the multi-dimensional construct, the tissue progenitor or the artificial tissue is used as a xenograph in a subject. In some embodiment, there is provided a method of analyzing cellular functions in response to a stimulus or agent, comprising exposing the cells in a bio-block, and assessing a change of the cellular functions in the bio-block, wherein the bio-block is positions inside a subject. In some embodiments, the multi-dimensional construct, the tissue progenitor, or the artificial tissue, is used for in vivo transplant in a subject. In some embodiments of the in vivo research, the bio-block or the bio-ink composition is bioprinted directly in a subject. In some embodiments, the bio-ink composition is bioprinted according to cellular distribution pattern of a tissue. In some embodiments, the bio-ink composition is bioprinted onto a scaffold in the subject. In some embodiments, the subject is an animal model. In some embodiments, the effects of the in vivo microenvironment of the bio-block are studied as the cells in the bio-block proliferate, differentiate migrate, metabolize, secrete, or develop in the subject. In some embodiments, the in vivo research is used to assess the in vivo effect of a compound (such as a drug) on the cells in the bio-block, the tissue progenitor or the artificial tissue.

In some embodiments, the in vitro and/or in vivo research is useful to discover, develop, or study any molecule, cells, or biological structures and their mechanisms in any area including, but not limited to, molecular biology, cell biology, developmental biology, translational biology, medicinal biology, or tissue engineering. Exemplary applications of the in vitro and in vivo research include, but are not limited to, development of multi-dimensional culturing systems, signaling pathways, stem cell induction and differentiation, embryogenesis and development, immunology, interactions between cells and materials, cell therapy, tissue regeneration, and regenerative medicine.

In some embodiments, the bio-block, the plurality of isolated bio-blocks, the multi-dimensional construct, the tissue progenitor, or the artificial tissue is useful for drug screening or drug discovery. In some embodiments, there is provided a method of analyzing cellular functions in response to a drug, comprising exposing the cells in the bio-block to the drug, and assessing a change in cellular functions (such as proliferation, survival, signaling, gene expression, detoxification, toxicity, etc.). In some embodiments, the method is used to determine the efficacy of the drug. In some embodiments, the method is used to screen for the drug. In some embodiments, the cells in the bio-block are derived from a subject in need of the drug.

In some embodiments, there is provided a method of assessing the effect of a factor (such as chemical reagent, for example, compound; or physical stimulus, for example, radiation or heating) on a tissue, comprising exposing the artificial tissue or the tissue progenitor to the factor, and evaluating activities of the cells in the artificial tissue, or the tissue progenitor in response to the factor. In some embodiments, there is provided a method of assessing the effect of a compound on a tissue, comprising exposing the artificial tissue or the tissue progenitor to the compound, and evaluating activities of the cells in the artificial tissue, or the tissue progenitor in response to the compound. In some embodiments, the compound is a drug. In some embodiments, the method is used to determine the efficacy of the drug. In some embodiments, the method is used to screen for the drug. In some embodiments, the cells in the bio-block are derived from a subject in need of the drug.

In some embodiments, the bio-block, the plurality of isolated bio-blocks, the multi-dimensional construct, the artificial tissue or the tissue progenitor is used to prepare an array, microarray or chip of cells, multicellular aggregates or tissues for drug screening or drug discovery. In some embodiments, an array, microarray, or chip of tissues is used as part of a kit for drug screening of drug discovery. In some embodiments, each bio-block, plurality of isolated bio-blocks, multi-dimensional construct, tissue progenitor or artificial tissue exists within a well of a biocompatible multi-well container, wherein the container is compatible with one or more automated drug screening procedures and/or devices. In some embodiments, automated drug screening procedures and/or devices include any suitable procedure or device that is computer or robot-assisted.

In some embodiments, the bio-block, the plurality of isolated bio-blocks, the multi-dimensional construct, the tissue progenitor, the artificial tissue, or any of the methods described herein is useful for drug screening or drug discovery to research or develop drugs potentially useful in any therapeutic area. In some embodiments, suitable therapeutic areas include, by way of non-limiting examples, infectious disease, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, and immunology. In some embodiments, the MSC bio-blocks, the plurality of isolated MSC bio-blocks, the composite construct, the tissue progenitor, the artificial tissue, or any of the methods described herein using the MSC bio-blocks are suitable for treating an orthopedic disease or condition.

In some embodiments, the bio-block is useful for tissue regeneration. In some embodiments, the pharmaceutical composition comprising the bio-block is useful for treating a subject in need of protecting, repairing, or replacing a tissue by administering an effective amount the pharmaceutical composition to the subject. In some embodiments, there is provided a method of protecting a tissue comprising administering to a subject in need thereof an effective amount of the pharmaceutical composition. In some embodiments, there is provided a method of repairing a damaged tissue comprising administering to a subject in need thereof an effective amount of the pharmaceutical composition. In some embodiments, there is provided a method of replacing a tissue (such as a defective or missing tissue) comprising administering to a subject in need thereof an effective amount of the pharmaceutical composition. In some embodiments, the tissue is a skin tissue. In some embodiments, the tissue is a bone, cartilage, or joint tissue.

In some embodiments, there is provided a method of cell therapy comprising administering to a subject in need thereof an effective amount of the pharmaceutical composition. The effective amount of the pharmaceutical composition to be administered depends on actual need. In some embodiments, the effective amount of the pharmaceutical composition is enough to improve the tissue condition (such as integrity, health, appearance, etc.) by at least about any of 10%, 20%, 30%, 40%, 50%, 60%, 70%, 80%, or 90%. In some embodiments, the effective amount of the pharmaceutical composition is more than about any of 1, 5, 10, 20, 50, 100, 200, 500, or 1000 bio-blocks.

In some embodiments, the pharmaceutical composition is administered topically. In some embodiments, the pharmaceutical composition is administered by surgical implantation. Other exemplary routes of administration include, but are not limited to, intravenous, intra-arterial, intraperitoneal, intrapulmonary, intravesicular, intramuscular, intra-tracheal, subcutaneous, intraocular, intrathecal, or transdermal. In some embodiments, the pharmaceutical composition is administered for a single time. In some embodiments, the pharmaceutical composition is administered for multiple times. In some embodiments, the pharmaceutical composition is administered at an interval of any of three times per day, two times per day, once per day, once per two days, once per three days, once per week, once per two weeks, once per three weeks, once per month, once per two months, once per three months, once per six months, or once per year.

In some embodiments, the bio-block, the bio-ink composition, the multi-dimensional construct, the tissue progenitor, or the artificial tissue is useful for tissue regeneration. In some embodiments, the multi-dimensional construct, the tissue progenitor, or the artificial tissue is used for in vivo tissue or organ transplantation. In some embodiments, the bio-block, the bio-ink composition, the multi-dimensional construct, the artificial tissue or the tissue progenitor is used to replace a damaged, diseased, or failing tissue or organ in a subject. In some embodiments, the MSC bio-block, the MSC bio-ink composition, the composite construct, the artificial bone or cartilage, or progenitor thereof is used to replace or repair a damaged bone, cartilage, or joint in a subject. In some embodiments, the subject is a human subject.

In some embodiments, there is provided a method of repairing a damaged site of a tissue in a subject, comprising bioprinting a bio-ink composition directly at the damaged site of the tissue of the subject. In some embodiments, the bio-ink composition is bioprinted onto a scaffold placed at the damaged site of the tissue. In some embodiments, the tissue is a skin tissue. In some embodiments, the method further comprises obtaining cell distribution information of the damaged site of the tissue, wherein the bioprinting is carried out according to the cell distribution information. In some embodiments, the cells in the bio-ink composition for bioprinting on the subject are derived from a subject having similar characteristics (such as species, age, gender, disease, genetics information, etc.) as the subject. In some embodiments, the cells in the bio-ink composition for bioprinting on the subject are derived from existing cell lines. In some embodiments, the bio-ink composition comprises at least one bio-block comprising a stem cell.

In some embodiments, the bio-block, the plurality of isolated bio-blocks, the multi-dimensional construct, the tissue progenitor or the artificial tissue is used to isolate cells (including stem cells, progenitor cells, immune cells, or other cells) for use in cell therapy. In some embodiments, the bio-block, the multi-dimensional construct, the tissue progenitor, or the artificial tissue is used to provide, secrete, or isolate biologically active molecules (such as hormones, growth factors, cytokines, ligands, etc.) to induce tissue regeneration in a subject receiving the bio-block, the multi-dimensional construct, the tissue progenitor, or the artificial tissue, or derived products thereof (such as biologically active molecules or cells). In some embodiments, the bio-block, the pharmaceutical composition, the multi-dimensional construct, the tissue progenitor, or the artificial tissue is used as a coating (such as an anticoagulant coating).

Kits and Articles of Manufacture

Further provided herein are kits, commercial batches, and articles of manufacture of any one of the bio-blocks (including MSC bio-blocks, such as Type I, II, III, or IV MSC bio-blocks), the compositions (such as the bio-ink compositions or the pharmaceutical compositions), the pluralities of isolated bio-blocks (including the containers comprising a plurality of isolated bio-blocks), the multi-dimensional constructs, the tissue progenitors, and the artificial tissues as described herein.

In some embodiments, there is provided a kit useful for bioprinting a multi-dimensional construct, an artificial tissue, or a tissue progenitor, comprising a plurality of any of the bio-blocks described herein. In some embodiments, the kit comprises at least about any of 1, 2, 3, 4, 5, 6, 7, 8, 9, 10 types of bio-blocks. Different types of bio-blocks may differ in the size and/or shape of the bio-blocks, number of cells and/or types of cells in the core of the bio-blocks, compositions of the biodegradable polymeric core material, compositions of the biodegradable polymeric shell material, agent(s) that facilitate activities (such as proliferation, differentiation, migration, metabolism and/or secretion) of the cells and incorporated in the core of the bio-blocks, nutrients and/or ECM molecules incorporated in the bio-blocks, and/or any of the other parameters described in the previous section. In some embodiments, the kit further comprises a carrier that can be mixed with the plurality of bio-blocks for bioprinting. In some embodiments, the kit further comprises a biocompatible (optionally bioadhesive) material for binding the bio-blocks in bioprinting. In some embodiments, the kit further comprises a model that defines a pre-determined pattern for the bioprinting. In some embodiments, the model is based on the natural structure and cell distribution of the multi-dimensional biological structure, tissue, or tissue progenitor to be bioprinted.

In some embodiments, there is provided a kit useful for bioprinting a multi-dimensional construct, an artificial tissue, or a tissue progenitor, comprising any of bio-ink compositions described herein. In some embodiments, the bio-ink composition comprises at least about any of 1, 2, 3, 4, 5, 6, 7, 8, 9, 10 types of bio-blocks. In some embodiments, the kit comprises at least about any of 1, 2, 3, 4, 5, 6, 7, 8, 9, 10 types of bio-ink compositions. In some embodiments, the kit further comprises a biocompatible (optionally bioadhesive) material for binding the bio-blocks in bioprinting. In some embodiments, the kit further comprises a model that defines a pre-determined pattern for the bioprinting. In some embodiments, the model is based on the natural structure and cell distribution of the multi-dimensional construct, artificial tissue, or tissue progenitor to be bioprinted.

In some embodiments, there is provided a kit for tissue engineering, in vitro research, or in vivo research, comprising any of the pluralities of isolated bio-blocks or the containers comprising a plurality of isolated bio-blocks described herein. In some embodiments, there is provided a kit for analyzing cellular functions in response to a stimulus or an agent, comprising any of the bio-blocks, the pluralities of isolated bio-blocks, or the containers comprising a plurality of isolated bio-blocks described herein. In some embodiments, there is provide a kit for drug screening or drug discovery, comprising a plurality of any of the bio-blocks, the bio-ink compositions, the pluralities of isolated bio-blocks, the tissue progenitors or the artificial tissues as describe herein. In some embodiments, there is provided a kit useful for treating a subject in need thereof, comprising any of the pharmaceutical compositions, the bio-ink compositions, the tissue progenitors, or the artificial tissues as described herein.

The kits may comprise additional components, such as containers, reagents, culturing media, buffers and the like that are necessary in the any one of the methods of bioprinting, treatment, or use described herein. In some embodiments, the kit further comprises a scaffold, or a material for preparing a scaffold. In some embodiments, the kit further comprises an instructional manual, such as a manual describing a protocol for preparing the multi-dimensional construct, the artificial tissue, or the tissue progenitor according to any of the methods described herein, including, for example, parameters for the bioprinting and culturing conditions. In some embodiments, the instructional manual describes a protocol, dosage, indications, administration schedule, etc. of the pharmaceutical composition.

The kits may comprise a unit package of bio-blocks, bio-ink compositions, pluralities of isolated bio-blocks, and pharmaceutical compositions, bulk packages (e.g. multi-unit packages) or sub-unit packages. In some embodiments, the kits comprise sufficient bio-blocks or bio-ink compositions to prepare at least about any of 1, 2, 3, 4, 5, 10, 20, 50, 100 or more artificial tissues, tissue progenitors or multi-dimensional constructs. In some embodiments, the kits comprise sufficient pluralities of isolated bio-blocks or containers comprising a plurality of isolated bio-blocks to carry out at least about any of 1, 2, 3, 4, 5, 10, 20, 50, 100 or more in vitro, in vivo, stem cell differentiation, tissue engineering, tissue regeneration, drug screening or drug discovery experiments. The kits may also include multiple units of bio-blocks, bio-ink compositions, pluralities of isolated bio-blocks, or pharmaceutical compositions, and instructions for use, and packaged in quantities sufficient for storage and use in a research laboratory or in pharmacies, such as hospital pharmacies.

In some embodiments, there is provided a kit comprising a multi-dimensional construct, a tissue progenitor, or an artificial tissue prepared by any of the methods of bioprinting using bio-blocks or bio-ink compositions as described herein. In some embodiments, the kit further comprises agents, culturing media, buffers, or other components useful for culturing the multi-dimensional construct, the tissue progenitor, or the artificial tissue to obtain a tissue or an organ. In some embodiments, the kit further comprises an instructional manual describing the culturing conditions. In some embodiments, the kit is useful for regenerative medicine, such as in vivo transplantation or cell therapy. In some embodiments, the kit is useful for in vitro assays. In some embodiments, the kit is useful for drug screening or drug discovery. In some embodiments, the multi-dimensional construct, the tissue progenitor, or the artificial tissue is placed in multi-well containers (such as a multi-well plate) for a drug screening assay or a drug discovery assay, for example a high throughput assay assisted by a computer or a robot. In some embodiments, the kit comprises reagents, or instructions that are useful for the assays or medical procedures (such as in vivo transplantation or cell therapy).

The kits of the invention are in suitable packaging. Suitable packaging include, but is not limited to, vials, bottles, jars, flexible packaging (e.g., Mylar or plastic bags), and the like. Kits may optionally provide additional components such as buffers and interpretative information. The present application thus also provides articles of manufacture, which include vials (such as sealed vials), bottles, jars, flexible packaging, and the like.

In some embodiments, there is provided a commercial batch of the bio-blocks, the bio-ink compositions, the pluralities of isolated bio-blocks, the pharmaceutical compositions, the artificial tissues, the tissue progenitors, or the kits as described herein. "Commercial batch" used herein refers to a batch size that is at least about 100 bio-blocks. In some embodiments, the batch size is at least about any of 100, 200, 500, 1000, 2000, 5000, 10000, 20000, or 50000 bio-blocks. In some embodiments, the commercial batch comprises a plurality of vials comprising any of the compositions (such as the bio-blocks, the bio-ink compositions, or the tissue progenitor). In some embodiments, the commercial batch comprises at least about any of 5, 10, 15, 20, 25, 50, 75, 100, 200, 300, 400, 500, 1000, 2000, 5000, or 10000 vials. For example, each vial comprises at least about any of 1, 2, 5, 10, or 100 bio-blocks.

EXEMPLARY EMBODIMENTS

Embodiment 1

In some embodiments, there is provided a bio-block comprising: a) a core comprising a biodegradable polymeric core material and a cell, and b) a shell comprising a biodegradable polymeric shell material.

Embodiment 2

In some embodiments, there is provided a bio-block comprising a core and a shell, wherein the core comprises a cell, and wherein the shell coats the core.

Embodiment 3

In some further embodiments of embodiment 2, the shell does not comprise a cell.

Embodiment 4

In some further embodiments of embodiment 2 or embodiment 3, the core comprises a biodegradable polymeric core material.

Embodiment 5

In some further embodiments of any one of embodiments 2-4, the shell comprises a biodegradable polymeric shell material.

Embodiment 6

In some further embodiments of any one of embodiments 1-5, the bio-block comprises at least two cores.

Embodiment 7

In some further embodiments of embodiment 6, each of the at least two cores independently enwraps a distinct type of cell.

Embodiment 8

In some further embodiments of any one of embodiments 1-7, the bio-block comprises at least two shells.

Embodiment 9

In some further embodiments of embodiment 8, each of the at least two shells comprises a distinct biodegradable polymeric shell material.

Embodiment 10

In some further embodiments of embodiment 8 or embodiment 9, each of the at least two shells serves distinct functions.

Embodiment 11

In some further embodiments of any one of embodiments 1-10, at least one shell is solidified.

Embodiment 12

In some further embodiments of embodiment 11, the outermost shell is solidified.

Embodiment 13

In some further embodiments of any one of embodiments 1-12, the core is in a gel state.

Embodiment 14

In some further embodiments of any one of embodiments 1-13, the shell provides mechanical support to the core.

Embodiment 15

In some further embodiments of any one of embodiments 1-14, the shell provides nutrients to the cell.

Embodiment 16

In some further embodiments of any one of embodiments 1-15, the core comprises the cell embedded in the biodegradable polymeric core material.

Embodiment 17

In some further embodiments of any one of embodiments 1-15, the core comprises the cell enwrapped by the biodegradable polymeric core material.

Embodiment 18

In some further embodiments of any one of embodiments 1-17, the core further comprises an agent selected from the group consisting of nutrients, extracellular matrix, cell factors, pharmaceutically active agents, and combinations thereof.

Embodiment 19

In some further embodiments of embodiment 18, the nutrients comprise nucleotides, amino acids, peptides, carbohydrates, lipids, or vitamins.

Embodiment 20

In some further embodiments of embodiment 18 or embodiment 19, the extracellular matrix comprises polysaccharide, glycosaminoglycan, glycoprotein, structural protein, or adhesion protein.

Embodiment 21

In some further embodiments of any one of embodiments 18-20, the pharmaceutically active agent is selected from the group consisting of rhIL-2, rhIL-11, rhEPO, IFN-α, IFN-β, IFN-γ, G-CSF, GM-CSF, rHuEPO, sTNF-R1, rhTNF-α, and combinations thereof.

Embodiment 22

In some further embodiments of any one of embodiments 1-21, the core further comprises an agent that facilitates cell proliferation, differentiation, migration, metabolism, or secretion.

Embodiment 23

In some further embodiments of embodiment 22, the core comprises an agent that facilitates cell proliferation and is selected from the group consisting of insulin, IGF-I, IGF-II, TGF, VEGF, PDGF, ODGF, SRIH, NGF, EGF, FGF, IL-1, IL-2, IL-3, IL-4, IL-5, IL6, IL-7, IL-8, IL-10, IL-12, CCL, CXC, XCL, MCP, TNF, EPO, CSF, cortisol, T3, T4, and combinations thereof.

Embodiment 24

In some further embodiments of embodiment 22 or embodiment 23, the core comprises an agent that facilitates cell differentiation and is selected from the group consisting of Oct3/4, Sox2, Klf4, c-Myc, GATA4, TSP1, β-glycerophosphate, dexamethasone, vitamin C, insulin, IBMX, indomethacin, PDGF-BB, 5-azacytidine, and combinations thereof.

Embodiment 25

In some further embodiments of any one of embodiments 22-24, the core comprises an agent that facilitates cell migration and is selected from the group consisting of cAMP, PIP3, SDF-1, N-cadherin, NF-κB, osteonectin, thromboxane A2, Ras, and combinations thereof.

Embodiment 26

In some further embodiments of any one of embodiments 22-25, the core comprises an agent that facilitates cell metabolism and is selected from the group consisting of IGF-I, TRIP-Br2, DKK-1, sRANKL, OPG, TRACP-5b, ALP, SIRT1, PGC-1α, PGC-1β, IL-3, IL-4, IL6, TGF-β, PGE2, G-CSF, TNFα, and combinations thereof.

Embodiment 27

In some further embodiments of any one of embodiments 22-26, the core comprises an agent that facilitates cell secretion and is selected from the group consisting of P600, P110, TCGFIII, BSF-2, glucagon, β-adrenergic agonist, arginine, $Ca^{2+}$, acetyl choline, somatostatin, and combinations thereof.

Embodiment 28

In some further embodiments of any one of embodiments 1-27, the bio-block is spherical, cubical, rectangular prism, cylindrical, or of irregular shape.

Embodiment 29

In some further embodiments of embodiment 28, the bio-block is spherical.

Embodiment 30

In some further embodiments of any one of embodiments 1-29, the length of the bio-block is about 20 μm to about 2 mm.

Embodiment 31

In some further embodiments of embodiment 30, the length of the bio-block is about 30 μm to about 800 μm.

Embodiment 32

In some further embodiments of any one of embodiments 1-31, the biodegradable polymeric core material comprises a naturally occurring polymer.

Embodiment 33

In some further embodiments of embodiment 32, the naturally occurring polymer is selected from the group consisting of collagen, fibrin, chitosan, alginate, starch, hyaluronic acid, laminin, agarose, gelatin, glucan, and combinations thereof.

Embodiment 34

In some further embodiments of embodiment 33, the alginate comprises unoxidized alginate, oxidized alginate, or a mixture thereof.

Embodiment 35

In some further embodiments of embodiment 33 or embodiment 34, the biodegradable polymeric core material comprises a mixture of type I collagen and alginate.

Embodiment 36

In some further embodiments of any one of embodiments 1-35, the biodegradable polymeric core material is a synthetic polymer.

Embodiment 37

In some further embodiments of embodiment 36, the synthetic polymer is selected from the group consisting of polyphosphazene, polyacrylic acid, polymethacrylic acid, polylactic acid (PLA), polyglycolic acid (PGA), poly-(lactide-coglycolide acid) (PLGA), polyorthoester (POE), polycaprolactone (PCL), polyhydroxyrate (PHB), polyamino acid (such as polylysine), degradable polyurethane, copolymers thereof, and combinations thereof.

Embodiment 38

In some further embodiments of any one of embodiments 1-37, the biodegradable polymeric core material is degradable by an enzyme.

Embodiment 39

In some further embodiments of embodiment 38, the enzyme is secreted from the cell.

Embodiment 40

In some further embodiments of embodiment 38 or embodiment 39, the degradation product of the biodegradable polymeric core material provides nutrients to the cell.

Embodiment 41

In some further embodiments of any one of embodiments 1-40, the core comprises a plurality of cells.

Embodiment 42

In some further embodiments of embodiment 41, the core comprises at least about 50 cells.

Embodiment 43

In some further embodiments of embodiment 42, the core comprises about 1 cell to about 5000 cells.

Embodiment 44

In some further embodiments of any one of embodiments 41-43, the plurality of cells is of the same type.

Embodiment 45

In some further embodiments of embodiment 44, the plurality of cells is of at least two different types.

Embodiment 46

In some further embodiments of any one of embodiments 1-45, the cell comprises a stem cell.

Embodiment 47

In some further embodiments of any one of embodiments 1-46, the cell comprises a bacterium, a yeast cell, a plant cell, or an animal cell.

Embodiment 48

In some further embodiments of embodiment 47, the cell comprises a mammalian cell.

Embodiment 49

In some further embodiments of embodiment 48, the cell comprises a human cell.

Embodiment 50

In some further embodiments of any one of embodiments 1-49, the cell comprises an adherent cell.

Embodiment 51

In some further embodiments of any one of embodiments 1-50, the cell is derived from a tissue selected from the group consisting of connective tissue, muscular tissue, urogenital tissue, gastrointestinal tissue, lung tissue, bone tissue, nerve tissue, epithelial tissue, endoderm-derived tissue, mesoderm-derived tissue, and ectoderm-derived tissue.

Embodiment 52

In some further embodiments of embodiment 51, the cell is selected from skeletal muscle cell, cardiomyocyte, smooth muscle cell, myoblast, bone cell, cartilage cell, fibroblast, lymphoid cell, bone marrow cell, endothelial cell, skin cell, epithelial cell, mammary cell, vascular cell, blood cell, lymphocyte, neuron, Schwann cell, gastrointestinal cell, liver cell, pancreatic cell, lung cell, tracheal cell, corneal cell, genitourinary cell, kidney cell, adipocyte, parenchymal cell, pericyte, mesothelial cell, stromal cell, stem cell, progenitor cell, endoderm-derived cell, mesoderm-derived cell, ectoderm-derived cell, tumor cell, cell lines, induced pluripotent stem cells (iPS), and combinations thereof.

Embodiment 53

In some further embodiments of any one of embodiments 1-52, the shell is permeable to nutrients.

Embodiment 54

In some further embodiments of embodiment 53, the nutrients are selected from the group consisting of water, oxygen, carbohydrates, lipids, proteins, amino acids, peptides, minerals, vitamins, cell factors, nucleic acids, and combinations thereof.

Embodiment 55

In some further embodiments of embodiment 53 or embodiment 54, the shell comprises one or more micropores.

Embodiment 56

In some further embodiments of embodiment 55, the diameter of the micropore is at least about 10 nm.

Embodiment 57

In some further embodiments of any one of embodiments 1-56, the shell has a thickness of about 0.1 μm to about 50 μm.

Embodiment 58

In some further embodiments of any one of embodiments 1-57, the shell has a modulus of elasticity of about 0.01 MPa to about 100 MPa.

Embodiment 59

In some further embodiments of any one of embodiments 1-58, the shell comprises a single layer.

Embodiment 60

In some further embodiments of any one of embodiments 1-59, the shell comprises two or more layers.

Embodiment 61

In some further embodiments of any one of embodiments 1-60, the biodegradable polymeric shell material comprises a naturally occurring polymer.

Embodiment 62

In some further embodiments of embodiment 61, the naturally occurring polymer is selected from the group consisting of collagen, fibrin, chitosan, alginate, starch, hyaluronic acid, laminin, agarose, gelatin, glucan, elastin, and combinations thereof.

Embodiment 63

In some further embodiments of embodiment 62, the alginate comprises unoxidized alginate, oxidized alginate, or a mixture thereof.

Embodiment 64

In some further embodiments of embodiment 62 or embodiment 63, the biodegradable polymeric shell material comprises alginate, and gelatin.

Embodiment 65

In some further embodiments of embodiment 64, the weight ratio of the alginate to the gelatin is about 10:1 to about 1:10.

Embodiment 66

In some further embodiments of embodiment 65, the biodegradable polymeric shell material further comprises elastin.

Embodiment 67

In some further embodiments of any one of embodiments 1-66, the biodegradable polymeric shell material comprises a synthetic polymer.

Embodiment 68

In some further embodiments of embodiment 67, the synthetic polymer is selected from the group consisting of polyphosphazene, polyacrylic acid, polymethacrylic acid, polylactic acid (PLA), polyglycolic acid (PGA), poly-(lactide-coglycolide acid) (PLGA), polyorthoester (POE), polycaprolactone (PCL), polyhydroxyrate (PHB), polyamino acid (such as polylysine), degradable polyurethane, copolymers thereof, and combinations thereof.

Embodiment 69

In some further embodiments of any one of embodiments 1-68, the biodegradable polymeric shell material is degradable by an enzyme.

Embodiment 70

In some further embodiments of embodiment 69, the enzyme is secreted from the cell.

Embodiment 71

In some further embodiments of embodiment 69 or embodiment 70, the degradation product of the biodegradable polymeric shell material provides nutrients to the cell.

Embodiment 72

In some further embodiments of any one of embodiments 1-71, the biodegradable polymeric shell material comprises calcium.

Embodiment 73

In some further embodiments of any one of embodiments 1-72, the bio-block has sufficient mechanical strength to endure elastic deformation during three-dimensional deposition.

Embodiment 74

In some further embodiments of any one of embodiments 1-73, the bio-block has a hardness of about 0.01 GPa to about 0.4 GPa.

Embodiment 75

In some further embodiments of any one of embodiments 1-74, the bio-block has a modulus of elasticity of about 0.01 MPa to about 100 MPa.

Embodiment 76

In some further embodiments of any one of embodiments 1-75, the bio-block is in a gel state.

Embodiment 77

In some further embodiments of any one of embodiments 1-76, the bio-block comprises a first shell, a second shell and a single core, wherein the first shell coats the single core, and the second shell coats the first shell.

Embodiment 78

In some further embodiments of any one of embodiments 1-76, the bio-block comprises a first core, a second core and a single shell, wherein the second core coats the first core, and the single shell coats the second core.

Embodiment 79

In some further embodiments of any one of embodiments 1-76, the bio-block comprises a first core, a second core, a first shell, and a second shell, wherein the second core coats the first core, the first shell coats the second core, and the second shell coats the first shell.

Embodiment 80

In some further embodiments of any one of embodiments 1-76, the bio-block comprises a first core, a second core, a first shell, and a second shell, wherein the first shell coats the first core, the second core coats the first shell, and the second shell coats the second core.

Embodiment 81

In some embodiments, there is provided a method of preparing a bio-block, comprising: (1) obtaining at least one core by each independently mixing a cell composition with a polymeric core material; and (2) coating the at least one core with at least one shell each independently comprising a polymeric shell material to obtain the bio-block.

Embodiment 82

In some further embodiments of embodiment 81, step (1) further comprises granulation of the innermost core.

Embodiment 83

In some further embodiments of embodiment 81 or embodiment 82, step (1) further comprises coating the innermost core with at least one different core, wherein each of the at least one different core independently comprises a polymeric core material and a cell composition.

Embodiment 84

In some further embodiments of any one of embodiments 81-83, the method further comprises: (3) coating the at least one shell with at least one additional core, wherein each of the at least one additional core independently comprises a polymeric core material and a cell composition; and (4) coating the at least one additional polymeric core material with at least one additional polymeric shell material.

Embodiment 85

In some further embodiments of embodiment 84, steps (3) and (4) are repeated for one or more times.

Embodiment 86

In some further embodiments of any one of embodiments 81-85, the polymeric core material and the polymeric shell material are biodegradable.

Embodiment 87

In some further embodiments of any one of embodiments 81-86, step (1) comprises obtaining at least one core by each independently and mixing the cell composition, the polymeric core material and an additional agent comprising nutrients, extracellular matrix, cell factors, or pharmaceutically active agents.

Embodiment 88

In some further embodiments of any one of embodiments 81-87, an encapsulator is used for granulation and coating.

Embodiment 89

In some further embodiments of any one of embodiments 81-88, each of steps (2) and (4) independently further comprises processing of the shell after said coating.

Embodiment 90

In some further embodiments of embodiment 89, the processing comprises solidifying the shell to improve mechanical properties of the shell.

Embodiment 91

In some further embodiments of embodiment 89 or embodiment 90, only the outermost shell is processed.

Embodiment 92

In some further embodiments of any one of embodiments 81-91, the method is carried out under sterile conditions.

Embodiment 93

In some further embodiments of embodiment 92, the method is carried out in a GMP workshop.

Embodiment 94

In some further embodiments of any one of embodiments 81-93, the bio-block can be stored under refrigerated conditions (such as about 4° C.) for about 3 hours to about 3 days.

Embodiment 95

In some embodiments, there is provided a bio-block prepared by the method according to any one of embodiments 81-94.

Embodiment 96

In some further embodiments of any one of embodiments 1-80 and 95, the bio-block is isolated.

Embodiment 97

In some further embodiments of any one of embodiments 1-80 and 95-96, the bio-block is provided in a container.

Embodiment 98

In some embodiments, there is provided a plurality of isolated bio-blocks of embodiment 96.

Embodiment 99

In some further embodiments of embodiment 98, the plurality of isolated bio-blocks is provided in a single container.

Embodiment 100

In some further embodiments of embodiment 98 or embodiment 99, at least two of the isolated bio-blocks are different.

Embodiment 101

In some further embodiments of embodiment 100, each of the at least two isolated bio-blocks comprises a different agent or combination of agents that facilitates cell proliferation, differentiation, migration, metabolism, secretion, or any combination thereof.

Embodiment 102

In some embodiments, there is provided a method of analyzing cellular functions in response to a stimulus or an agent, comprising exposing the cells in the bio-block of any one of embodiments 1-80 to the stimulus or the agent, and assessing a change in the cellular functions in the bio-block.

Embodiment 103

In some further embodiments of embodiment 102, the stimulus or the agent is provided in the core of the bio-block.

Embodiment 104

In some further embodiments of embodiment 102 or embodiment 103, the bio-block is an isolated bio-block.

Embodiment 105

In some further embodiments of embodiment 104, the isolated bio-block is provided in a container.

Embodiment 106

In some further embodiments of embodiment 102 or embodiment 103, the bio-block is positioned inside a subject.

Embodiment 107

In some further embodiments of any one of embodiments 102-106, the stimulus or the agent is a drug.

Embodiment 108

In some further embodiments of embodiment 107, the method is used for determining the efficacy of the drug.

Embodiment 109

In some further embodiments of embodiment 108, the method is used for screening the drug.

Embodiment 110

In some embodiments, there is provided a pharmaceutical composition comprising the bio-block of any one of embodiments 1-80 and 95-96 and a pharmaceutically acceptable carrier.

Embodiment 111

In some embodiments, there is provided a bio-ink composition comprising a plurality of bio-blocks of any one of embodiments 1-80 and 95-96.

Embodiment 112

In some further embodiments of embodiment 111, the plurality of bio-blocks is of the same type.

Embodiment 113

In some further embodiments of embodiment 111, the plurality of bio-blocks is of different types.

Embodiment 114

In some further embodiments of any one of embodiments 111-113, the bio-ink composition further comprises a carrier.

Embodiment 115

In some further embodiments of embodiment 114, the carrier is liquid or semi-solid.

Embodiment 116

In some further embodiments of embodiment 114 or embodiment 115, the carrier comprises a polymer selected from the group consisting of collagen, fibrin, chitosan, alginate, starch, hyaluronic acid, laminin, agarose, gelatin, glucan, elastin, methylcellulose, polyvinyl alcohol, polyamino acid (such as polylysine), acrylate copolymer, and combinations thereof.

Embodiment 117

In some further embodiments of any one of embodiments 114-116, the carrier has a viscosity of about 1 Pa·s to about 1000 Pa·s.

Embodiment 118

In some further embodiments of any one of embodiments 111-117, the bio-ink composition comprises at least about 50% bio-blocks (w/w).

Embodiment 119

In some further embodiments of any one of embodiments 111-118, the average size of the bio-blocks in the bio-ink composition is about 30 μm to about 800 μm.

Embodiment 120

In some embodiments, there is provided a method of preparing an artificial tissue or a tissue progenitor, comprising bioprinting the bio-ink composition of any one of embodiments 111-119 to obtain a multi-dimensional construct having a pre-determined pattern.

Embodiment 121

In some further embodiments of embodiment 120, the bio-ink composition is bioprinted onto a scaffold having a pre-determined pattern.

Embodiment 122

In some further embodiments of embodiment 120 or embodiment 121, the bioprinting is carried out by inkjet, microextrusion, or manual deposition.

Embodiment 123

In some further embodiments of any one of embodiments 120-122, the multi-dimensional construct has a shape selected from rectangular, square, circular, elliptical, hexagonal sheet, a sheet of irregular shape, a hollow tube, a hollow cube, a hollow sphere, a hollow rectangular prism, a hollow cylinder, a hollow multi-dimensional construct of irregular shape, a solid cube, a solid sphere, a solid rectangular prism, a solid cylinder, a solid multi-dimensional construct of irregular shape, and combinations thereof.

Embodiment 124

In some further embodiments of any one of embodiments 120-123, the multi-dimensional construct has a shape that mimics the natural shape of a tissue or an organ.

Embodiment 125

In some further embodiments of any one of embodiments 120-124, at least two bio-ink compositions are used to prepare the artificial tissue or the tissue progenitor.

Embodiment 126

In some further embodiments of any one of embodiments 120-125, the bioprinting is continuous or essentially continuous.

Embodiment 127

In some further embodiments of embodiment 126, the pre-determined pattern comprises a plurality of layers, the method comprises bioprinting sequentially a plurality of layers to obtain a multi-dimensional construct having a pre-determined pattern comprising the plurality of layers, wherein each layer is bioprinted with a bio-ink composition according to the pre-determined pattern of the layer.

Embodiment 128

In some further embodiments of any one of embodiments 120-127, the method further comprises preparing the bio-ink composition comprising mixing a plurality of bio-blocks with a carrier.

Embodiment 129

In some further embodiments of any one of embodiments 120-128, the pre-determined pattern is based on the shape and cell distribution pattern of a natural tissue or organ.

Embodiment 130

In some further embodiments of any one of embodiments 120-129, at least about 90% of the cells in the bio-blocks survive after the bioprinting.

Embodiment 131

In some further embodiments of any one of embodiments 120-130, at least about 90% of the cells in the bio-blocks can proliferate, differentiate, metabolize, migrate, secrete, or any combination thereof after the bioprinting.

Embodiment 132

In some further embodiments of any one of embodiments 120-131, the method further comprises culturing the multi-dimensional construct under a condition that allows the cells in the bio-blocks to proliferate, differentiate, metabolize, migrate, secrete, or any combination thereof.

Embodiment 133

In some further embodiments of embodiment 132, the multi-dimensional construct is cultured for about 1 hour to about 30 days.

Embodiment 134

In some further embodiments of embodiment 132 or embodiment 133, the multi-dimensional construct is cultured in a 3D-culturing incubator or a bioreactor.

Embodiment 135

In some further embodiments of any one of embodiments 132-134, the multi-dimensional construct is exposed to a physical stimulus selected from pressure, shearing, light and heat, and/or a chemical stimulus selected from hormones, cell factors and chemical agents during the culturing.

Embodiment 136

In some further embodiments of any one of embodiments 132-135, the polymeric core material, the polymeric shell material or the carrier are at least partially degraded.

Embodiment 137

In some further embodiments of any one of embodiments 132-136, the cells in the bio-blocks are connected to each other within the bio-blocks and/or across the bio-blocks during the culturing.

Embodiment 138

In some further embodiments of any one of embodiments 132-137, the bioprinting is carried out directly on a subject.

Embodiment 139

In some further embodiments of embodiment 138, the subject is a human subject.

Embodiment 140

In some further embodiments of embodiment 137 or embodiment 138, the bioprinting is carried out directly at a damaged site of a tissue of the subject.

Embodiment 141

In some further embodiments of embodiment 140, the tissue is a skin tissue.

Embodiment 142

In some further embodiments of any one of embodiments 120-141, the method further comprises obtaining cell distribution information of the damaged site of the tissue, wherein the bioprinting is carried out according to the cell distribution information.

Embodiment 143

In some further embodiments of any one of embodiments 138-142, the cells in the bio-ink composition are derived from the subject.

Embodiment 144

In some embodiments, there is provided an artificial tissue or a tissue progenitor produced by the method of any one of embodiments 120-144.

Embodiment 145

In some embodiments, there is provided a multi-dimensional construct comprising a plurality of bio-blocks of any one of embodiments 1-80 and 95-96.

Embodiment 146

In some further embodiments of embodiment 145, the bio-blocks are arranged in a predetermined pattern.

Embodiment 147

In some further embodiments of embodiment 145 or embodiment 146, the size of the multi-dimensional construct is about 30 µm to about 50 cm.

Embodiment 148

In some further embodiments of any one of embodiments 145-147, at least part of the multi-dimensional construct is bioprinted.

Embodiment 149

In some further embodiments of any one of embodiments 145-148, the multi-dimensional construct comprises at least one structural layer.

Embodiment 150

In some further embodiments of embodiment 149, each of the at least one structural layer comprises one or more layers of bio-blocks.

Embodiment 151

In some further embodiments of any one of embodiments 145-150, the multi-dimensional construct is further cultured for about 1 hour to about 30 days.

Embodiment 152

In some further embodiments of any one of embodiments 145-151, the multi-dimensional construct has a shape selected from rectangular, square, circular, elliptical, hexagonal sheet, a sheet of irregular shape, a hollow tube, a hollow cube, a hollow sphere, a hollow rectangular prism, a hollow cylinder, a hollow multi-dimensional construct of irregular shape, a solid cube, a solid sphere, a solid rectangular prism, a solid cylinder, a solid multi-dimensional construct of irregular shape, and combinations thereof.

Embodiment 153

In some further embodiments of any one of embodiments 145-152, the multi-dimensional construct has a shape that mimics the natural shape of a tissue or an organ.

Embodiment 154

In some further embodiments of any one of embodiments 145-153, the multi-dimensional construct comprises an endothelial layer, a smooth muscle layer and a fibroblast layer.

Embodiment 155

In some embodiments, there is provided a tissue progenitor derived from the multi-dimensional construct of any one of embodiments 145-154, wherein the cells in the different bio-blocks proliferate, differentiate, migrate, or any combination thereof, and optionally wherein the biodegradable polymeric core material is at least partially degraded.

Embodiment 156

In some embodiments, there is provided a tissue progenitor derived from the multi-dimensional construct of any one of embodiments 145-155, wherein the cells in different bio-blocks are connected to each other, and wherein the biodegradable polymeric core material and/or the biodegradable polymeric shell material are at least partially degraded.

Embodiment 157

In some embodiments, there is provided an artificial tissue derived from the multi-dimensional construct of embodiment 171 or embodiment 156.

Embodiment 158

In some further embodiments of embodiment 157, the size of the artificial tissue is about 100 μm to about 50 cm.

Embodiment 159

In some embodiments, there is provided a method of assessing the effect of a compound on a tissue, comprising exposing any one of the artificial tissue or the tissue progenitor of embodiments 144 and 155-158 to a compound, and evaluating activities of the cells in the artificial tissue or the tissue progenitor in response to the compound.

Embodiment 160

In some further embodiments of embodiment 159, the cells are derived from a subject in need of the compound.

Embodiment 161

In some embodiments, there is provided a kit comprising the bio-block of any one of embodiments 1-80 and 95-97.

Embodiment 162

In some embodiments, there is provided a kit comprising the bio-ink composition of any one of embodiments 111-119.

Embodiment 163

In some embodiments, there is provided a kit comprising the multi-dimensional construct of any one of embodiments 145-154.

Embodiment 164

In some embodiments, there is provided a kit comprising the tissue progenitor or the artificial tissue of any one of embodiments 144 and 155-158.

Examples

The examples, which are intended to be purely exemplary of the invention and should therefore not be considered to limit the invention in any way, also describe and detail aspects and embodiments of the invention discussed above.

Example 1: Preparation of Bio-Blocks

This example provides a method of preparing exemplary bio-blocks described in the present application. Bio-blocks were prepared under sterile conditions. If the bio-blocks are used in human, then such bio-blocks should be prepared in a workshop having a biosafety level of GMP.

An encapsulator (BUCHI™ Encapsulator B-395 Pro) was used to prepare a batch of bio-blocks. The concentric nozzles had the following diameters: inner nozzle: 200 μm; outer nozzle: 300 μm. A microinjection pump may be used in place of the Encapsulator. In one exemplary batch of the bio-blocks, each bio-block had 100 Human Umbilical Vein Endothelial cells (HUVECs) and a size of about 600 μm.

Materials used are as follows:
(1) Core:
(a) Type I collagen: 4 mg/mL, neutralized with a sterile 1M sodium hydroxide (NaOH) solution
(b) 2.5% (w/v) Sodium alginate: The sodium alginate was prepared by dissolving sodium alginate in sterile deionized water. In a second batch of bio-blocks, 2% sodium alginate solution was used.
(c) VEGF
A 1:1 (by weight) mixture of the type I collagen solution and the sodium alginate solution was prepared to prepare the core.
(2) Shell:
(a) 2.5% sodium alginate solution. In a second batch of bio-blocks, 4% sodium alginate solution was used.
(b) Elastin
(c) Solidifying (i.e., crosslinking) solution comprising an aqueous solution of 0.1 M calcium chloride ($CaCl_2$).
(3) Cell: Human Umbilical Vein Endothelial cells (HUVEC, purchased from ATCC).

The bio-blocks were prepared as described in the following steps, which were all carried out on ice.

(1) To a mixture of 120 μL NaOH solution and 750 μL type I collagen was added 130 μL of a suspension of vascular endothelial cells (density: $1 \times 10^5$ cells/mL) in phosphate buffered saline (PBS), to make 1 mL of cell enwrapping solution. The cell enwrapping solution was mixed with 1 mL of 2.5% (or 2%) sodium alginate, which comprised VEGF at a final concentration of about 20 ng/mL. The total mixture was thoroughly mixed to ensure even distribution of the cells in order to obtain a core mixture.

(2) To 2 mL of 2.5% (or 4%) sodium alginate solution was added 100 ng elastin to achieve a final concentration of 50 ng/mL, and the solution was thoroughly mixed to obtain a shell mixture. 300 mL 0.1 M $CaCl_2$ solution was placed in a beaker, which served as the solidifying (i.e., crosslinking) solution for the shell mixture.

(3) The core mixture and the shell mixture were each separately loaded into two 5 mL syringes. According to the manufacturer's instructions, pressure, centrifugal force, and pump speed of the encapsulator were set, and the core mixture and the shell mixture were used for granulation and coating. A concentric nozzle set with an inner nozzle having a size of 200 μm and an outer nozzle having a size of 300 μm was used. The prepared bio-block microdroplets were collected in the beaker containing 300 mL 0.1 M $CaCl_2$ solution and crosslinked for about 5 minutes to obtain the bio-blocks.

The bio-blocks can be stored at 4° C., or directly used in 3D bioprinting.

Example 2. Characterization of Bio-Blocks

This example analyzes characteristics of bio-blocks prepared using the method described in Example 1, including sizes of the bio-blocks, thickness of the shell, mechanical protection provided by the shell, and the number of cells in the bio-block.

Bio-blocks with different sizes were prepared using the method described in Example 1, wherein the sizes of the inner and outer nozzles of the concentric nozzle set were altered according to the final bio-block size in each preparation. The bio-blocks were examined under a microscopy, and the results are shown in FIGS. 3A-3C. In particular, the diameter of the bio-block in FIG. 3A is about 120 μm (scale is 100 μm); the diameter of the bio-block in FIG. 3B is about 200 μm (scale is 100 μm); the diameter of the bio-block in FIG. 3C is about 450 µm (scale is 200 µm). These results demonstrate that it is possible to control the size of the bio-blocks by adjusting parameters of the encapsulator, for example, the diameters of the inner nozzle and the outer nozzle of the concentric nozzle set. The size of the bio-blocks of the present application is controllable, and can be selected based on needs.

The thickness of the shell of the bio-blocks prepared in Example 1 was further examined under a microscope, and the results are shown in FIG. 4A, in which the highlighted part represented the shell of a bio-block. The thickness of the shell of the bio-block is about 2 µm (scale is 50 µm). The results demonstrate that the thickness of the shell can be controlled by adjusting the parameters of the encapsulator, such as the diameters of the inner nozzle and the outer nozzle of the concentric nozzle set, and the pumping speed of the shell material. The thickness of the shell of the bio-blocks of the present application is controllable, and can be selected based on needs.

Bio-blocks comprising different number of cells were also prepared using similar steps as in Example 1, wherein the cell density of the cell suspension used to make the core mixture was altered according to the target number of cells per bio-block in each preparation. The bio-blocks were examined under a microscope and the results are shown in FIG. 3D-3F. In particular, the bio-blocks in FIG. 3D each contained about 50 cells (scale is 100 µm); the bio-blocks in FIG. 3E each contained about 8 cells (scale is 100 µm); and the bio-blocks in FIG. 3F each contained about 2 cells (scale is 100 µm). These results demonstrate that the number of cells contained in the bio-blocks can be controlled by adjusting the cell density of the cell suspension. The number of cells contained in the bio-blocks is controllable, and can be selected based on needs.

Additionally, a nanoindenter (Hysitron TI 950, Minneapolis, Minn., USA) was used according to the manufacturer's instructions to measure the mechanical properties of the bio-blocks prepared using the method of Example 1 (size of the bio-blocks was about 400 µm). Three independent batches of bio-blocks were examined, and measurement was carried out at five different sampling locations within each batch. The bio-blocks had a hardness of about 0.141 GPa to about 0.218 GPa, with an average hardness of 0.186 GPa. The bio-blocks had a modulus of elasticity of about 2.942 MPa to about 3.562 MPa, with an average modulus of elasticity of about 3.278 MPa. In a second batch of bio-blocks, the average hardness of the bio-blocks was about 0.083 GPa, and the average modulus of elasticity was about 1.683 MPa.

These results demonstrate that the bio-blocks of the present application had excellent mechanical protection capabilities, which can effectively avoid physical injury or mechanical damage from external forces to the cells inside the bio-blocks. Additionally, it was discovered that the mechanical protection capabilities of the bio-blocks can be controlled by adjusting parameters, such as thickness of the shell and the polymeric shell material of the bio-blocks (data not shown). The mechanical protection capabilities of the bio-blocks of the present application are controllable, and can be selected based on needs.

Example 3. Preparation of Additional Bio-Blocks

Further exemplary bio-blocks (B1-B4 in Table 1 below) were prepared using an encapsulator with the method described in Example 1.

TABLE 1

Exemplary bio-blocks.

| Number | Cell | Biodegradable polymeric core material; concentration, w/v | Biodegradable polymeric shell material; concentration, w/v |
|---|---|---|---|
| Bio-block B1 | HUVEC | Starch 50% | Calcium alginate 4% |
| Bio-block B2 | HUVEC | Type I Collagen 0.4% | Polylysine 1% |
| Bio-block B3 | HUVEC | Type I Collagen 0.4% | Calcium alginate 4% |
| Bio-block B4 | HUVEC | Polyurethane 40% | Calcium alginate 4% |

FIGS. 5A-5D show images of bio-blocks B1-B4 under a microscope. FIG. 5A shows the bio-block B1, which has a diameter of 600 µm (scale=500 µm); FIG. 5B shows the bio-block B2, which has a diameter of 500 µm (scale=500 µm); FIG. 5C shows the bio-block B3, which has a diameter of 500 µm (scale=500 µm); FIG. 5D shows the bio-block B4, which has a diameter of 500 µm (scale=500 µm). These results suggest that a variety of suitable biodegradable materials can be used to prepare the bio-blocks of the present application.

Additionally, in order to clearly visualize the structure of the bio-blocks, the biodegradable polymeric core material of the bio-block B2 was stained using tracker CM-Dil (red fluorescence), and FITC (green fluorescence) conjugated polylysine was used as the biodegradable polymeric shell material. Confocal microscopy was used to examine the bio-blocks B2 prepared using the biodegradable polymeric core and shell materials each with fluorescent labels. As shown in FIG. 5E, green fluorescence represents the shell of B2, and red fluorescence represents the core of B2.

Example 4. Preparation of Bio-Blocks Comprising Shells Comprising Oxidized Alginate This example provides a method of preparing exemplary bio-blocks comprising a shell that contains oxidized alginate. Bio-blocks were prepared under sterile conditions. If the bio-blocks are used in human, then such bio-blocks should be prepared in a workshop having a biosafety level of GMP.

An encapsulator (BUCHI™ Encapsulator B-395 Pro) was used to prepare a batch of bio-blocks. The concentric nozzles had the following diameters: inner nozzle: 200 µm; outer nozzle: 300 µm. A microinjection pump may be used in place of the Encapsulator.

Materials used are as follows:

(1) Core: Type I collagen: 4 mg/mL, neutralized with a sterile 1M sodium hydroxide (NaOH) solution (2) Shell: oxidized sodium alginate solution at a predetermined concentration, or a mixture comprising oxidized sodium alginate and other polymeric shell molecules. The solidifying (i.e., crosslinking) solution comprises a solution of 0.1 M calcium chloride ($CaCl_2$).

(3) Cell: Human Umbilical Vein Endothelial cells (HUVEC, purchased from ATCC), hepatocellular carcinoma cells (HepG2, purchased from ATCC), human fibroblasts (purchased from ATCC), mouse mesenchymal stem cells (MSC, primary).

Exemplary bio-blocks were prepared as described in the following steps, which were all carried out on ice.

(1) To a mixture of 120 µL NaOH solution and 750 µL type I collagen was added 130 µL of a suspension of cells (density: $1 \times 10^5$ cells/mL) in phosphate buffered saline (PBS), to make 1 mL of core mixture.

(2) 50 mL of 5% (w/w) oxidized sodium alginate was prepared to serve as polymeric shell material.

(3) 300 mL 0.1 M CaCl$_2$ solution was placed in a beaker, which served as the solidifying (i.e., crosslinking) solution for the polymeric shell material.

(4) The core mixture was placed in a 2 mL syringe. 50 mL polymeric shell material was placed in the enwrapping solution bottle of the encapsulator. The core mix and the polymeric shell material were then used for granulation and coating.

(5) The product of step (4) was collected in a beaker containing 300 mL 0.1 M CaCl$_2$ solution, and crosslinked for 5 minutes to obtain the bio-blocks. The bio-blocks can be stored at 4° C., or directly used in 3D bioprinting.

Example 5. Characterization of Bio-Blocks Comprising Shells Comprising Oxidized Alginate This example analyzes characteristics of bio-blocks prepared using the method described in Example 4, including sizes of the bio-blocks, thickness of the shell, mechanical protection provided by the shell, and the number of cells in the bio-block.

Bio-blocks with different sizes were prepared the method described in Example 4, wherein the sizes of the inner and outer nozzles of the concentric nozzle set were altered according to the final bio-block size in each preparation. These results demonstrate that it is possible to control the size of the bio-blocks by adjusting parameters of the encapsulator, for example, the diameters of the inner nozzle and the outer nozzle of the concentric nozzle set. The size of the bio-blocks of the present application is controllable, and can be selected based on needs.

The thickness of the shell of the bio-blocks prepared in Example 4 was further examined under a microscope. The results demonstrate that the thickness of the shell can be controlled by adjusting the parameters of the encapsulator, such as the diameters of the inner nozzle and the outer nozzle of the concentric nozzle set, and the pumping speed of the shell material. The thickness of the shell of the bio-blocks of the present application is controllable, and can be selected based on needs.

Bio-blocks comprising different number of cells were also prepared using similar steps as in Example 4, wherein the cell density of the cell suspension used to make the core mixture was altered according to the target number of cells per bio-block in each preparation. The results demonstrate that the number of cells contained in the bio-blocks can be controlled by adjusting the cell density of the cell suspension. The number of cells contained in the bio-blocks is controllable, and can be selected based on needs.

Additionally, a nanoindenter (Hysitron TI 950, Minneapolis, Minn., USA) was used according to the manufacturer's instructions to measure the mechanical properties of the bio-blocks prepared using the method of Example 4. The results demonstrate that the bio-blocks of the present application had excellent mechanical protection capabilities, which can effectively avoid physical injury or mechanical damage from external forces to the cells inside the bio-blocks. Additionally, it was discovered that the mechanical protection capabilities of the bio-blocks can be controlled by adjusting parameters, such as thickness of the shell and the polymeric shell material of the bio-blocks (data not shown). The mechanical protection capabilities of the bio-blocks of the present application are controllable, and can be selected based on needs.

Example 6. Control of the Shell Degradation Rate of Bio-Blocks

The degradation rate of the shells of the bio-blocks (referred herein after as shell degradation rate) described in the present application was studied in this example. The bio-blocks were prepared using the method described in Example 4. The parameters of the encapsulator (e.g., the diameters of the inner nozzle and outer nozzle of the concentric nozzle set), cells (types and number), polymeric core material, and polymeric shell material) were adjusted according to the experimental design. The shell degradation rates of the prepared bio-blocks were measured as follows: the bio-blocks were cultured at 37° C. in an incubator. The weight of the bio-blocks was determined at specific time points to measure the rate of weight loss of the bio-blocks. Additionally, a degradation curve of the shell of the bio-block can be made by plotting the weight loss rate versus time.

We first examined the influence of the type and number of cells, as well as the oxidation level of the oxidized sodium alginate on the shell degradation rate of the bio-blocks.

Bio-blocks were prepared according to Example 4, wherein HUVEC, HepG2 and MSC cells were used, at a cell density of $4\times10^6$/mL, $6\times10^6$/mL, or $12\times10^6$/mL. The polymeric core material was type I collagen. The polymeric shell material was 5% (w/w) oxidized sodium alginate, with an oxidation level of 2.5%, 4.4%, 8.8%, 17.6%, or 22%. The degradation rates of the shells of the prepared bio-blocks were measured according to the method described above. The results are shown in Table 2 below.

TABLE 2

Degradation rates of the shells of various bio-blocks.

| Bio-block Number | Oxidation level (%) | Cell types and ratio | Cell density ($\times 10^6$/mL) | Shell thickness (μm) | Time for complete degradation of shell (days) |
|---|---|---|---|---|---|
| 1 | 2.5 | HUVEC/HepG2 (1:1) | 6 | About 200 | >14 |
| 2 | 2.5 | HUVEC/HepG2 (1:1) | 6 | About 200 | >14 |
| 3 | 4.4 | MSC | 4 | About 200 | >14 |
| 4 | 4.4 | HUVEC/HepG2 (1:1) | 12 | About 200 | 8 |
| 5 | 8.8 | HUVEC/HepG2 (1:1) | 12 | About 200 | 5 |
| 6 | 17.6 | HUVEC/HepG2 (1:1) | 12 | About 200 | 2 |
| 7 | 8.8 | HUVEC/HepG2 (1:1) | 6 | About 200 | 10 |
| 8 | 4.4 | HepG2 | 6 | About 200 | 14 |
| 9 | 4.4 | MSC | 12 | About 200 | 14 |
| 10 | 8.8 | MSC | 4 | About 200 | 14 |
| 11 | 22 | MSC | 12 | About 200 | 4 |

The above results demonstrated that cell type, cell number, and the oxidation level of oxidized sodium alginate all had impacts on the shell degradation rates of the bio-blocks. Specifically, (1) Bio-blocks having cells with faster growth and proliferation rates had faster shell degradation rates. For example, as HUVEC/HepG2 cells grew and proliferated at faster rates than MSC, under the same conditions, the shell degradation rate of bio-blocks comprising HUVEC/HepG2 cells was faster than that of bio-blocks comprising MSC (see bio-blocks 4 and 9). (2) Bio-blocks with larger number of cells had faster shell degradation rates. For example, see bio-blocks 5 and 7. (3) Bio-blocks having higher oxidation level of the oxidized sodium alginate had higher shell degradation rates. For example, see bio-blocks 4-6, or bio-blocks 9 and 11.

Next, we examined the impact of the relative amount of oxidized sodium alginate in the shells of the bio-blocks on the shell degradation rates. Bio-blocks were prepared according to Example 4, wherein the polymeric core material was type I collagen; and the polymeric shell material was oxidized sodium alginate at pre-determined concentrations (5%, 6%, 7%, 8%, 9%, or 10%), and the oxidation level of oxidized sodium alginate was 8.8%. The shell degradation rates of the prepared bio-blocks were measured according to the method described above. Results are shown in Table 3 below.

TABLE 3

Shell degradation rate vs. concentration of oxidized sodium alginate in shell.

| Oxidized alginate concentration in shell (wt %) | Oxidation level (%) | Cell types and ratio | Cell density ($\times 10^6$/mL) | Shell thickness (μm) | Time for complete degradation of shell (days) |
|---|---|---|---|---|---|
| 5 | 8.8 | HUVEC/HepG2 (1:1) | 12 | 200 | 5 |
| 6 | 8.8 | HUVEC/HepG2 (1:1) | 12 | 200 | 5 |
| 7 | 8.8 | HUVEC/HepG2 (1:1) | 12 | 200 | 6 |
| 8 | 8.8 | HUVEC/HepG2 (1:1) | 12 | 200 | 6 |
| 9 | 8.8 | HUVEC/HepG2 (1:1) | 12 | 200 | 8 |
| 10 | 8.8 | HUVEC/HepG2 (1:1) | 12 | 200 | 8 |

The results demonstrated that the concentration of oxidized sodium alginate in the shells of the bio-blocks could affect the shell degradation rates. Specifically, bio-blocks having higher concentrations of oxidized sodium alginate had slower shell degradation rates.

Additionally, we examined the impact of other biodegradable polymers (such as sodium alginate) in the shells of the bio-blocks on the shell degradation rates. Specifically, we prepared bio-blocks comprising shells having different ratios between sodium alginate (SA) and oxidized sodium alginate (OSA), while the total concentration of sodium alginate and oxidized sodium alginate in the shell was 5%, and investigated how the weight ratio between sodium alginate and oxidized sodium alginate affected the shell degradation rates of the bio-blocks.

Bio-blocks were prepared according to Example 4, wherein the polymeric core material was type I collagen; the polymeric shell material was oxidized sodium alginate at a pre-determined concentration and sodium alginate at a pre-determined concentration. The shell degradation rates of the prepared bio-blocks were measured according to the method described above. Results are shown in Table 4 below.

TABLE 4

Shell degradation rate vs. weight percentage of oxidized sodium alginate (OSA)

| OSA/(OSA + SA) (%) | Oxidation level (%) | Cell types and ratio | Cell density ($\times 10^6$/mL) | Shell thickness (μm) | Time for complete degradation of shell (days) |
|---|---|---|---|---|---|
| 0 | 8.8 | HUVEC/HepG2 (1:1) | 12 | 200 | >14 |
| 20 | 8.8 | HUVEC/HepG2 (1:1) | 12 | 200 | >14 |
| 40 | 8.8 | HUVEC/HepG2 (1:1) | 12 | 200 | >14 |
| 60 | 8.8 | HUVEC/HepG2 (1:1) | 12 | 200 | 14 |
| 80 | 8.8 | HUVEC/HepG2 (1:1) | 12 | 200 | 10 |
| 100 | 8.8 | HUVEC/HepG2 (1:1) | 12 | 200 | 5 |

The results demonstrated that decrease in the oxidized sodium alginate content of the shells of the bio-blocks led to decreased shell degradation rates. Specifically, bio-blocks having higher percentage of oxidized sodium alginate in the shells had faster shell degradation rates; conversely, bio-blocks having lower percentage of oxidized sodium alginate in the shells had slower shell degradation rates.

Additionally, we examined the impact of cell types on shell degradation rates of bio-blocks.

Bio-blocks were prepared according to Example 4, wherein cells used were MSC, HUVEC, HepG2 or fibroblasts. The same cell density (e.g., $6 \times 10^6$/mL), the same polymeric core material (e.g., type I collagen), the same polymeric shell material (e.g., 5% w/w oxidized sodium alginate with an oxidation level of 8.8%), and the same parameters of the encapsulator were used during the preparation of the bio-blocks. The shell degradation rates of the prepared bio-blocks were measured according to the method described above.

The results indicated that cell types used for bio-block preparation influenced the shell degradation rates. Specifically, bio-blocks having cells with faster growth and proliferation rates had faster shell degradation rates. For example, HUVEC/HepG2 cells grew and proliferated faster than MSC, so under the same conditions, bio-blocks comprising HUVEC/HepG2 cells had a faster shell degradation rate than that of bio-blocks comprising MSC.

Furthermore, we examined the impact of cell numbers on the shell degradation rates of bio-blocks.

Bio-blocks were prepared according to Example 4, wherein the cell density used was $4 \times 10^6$/mL, $6 \times 10^6$/mL, $8 \times 10^6$/mL, $12 \times 10^6$/mL, $16 \times 10^6$/mL, or $24 \times 10^6$/mL. The same cell type (e.g., HepG2 cells), the same polymeric core material (e.g., type I collagen), the same polymeric shell material (e.g., 5% w/w oxidized sodium alginate with an oxidation level of 8.8%), and the same parameters of the encapsulator were used during the preparation of the bio-blocks. The shell degradation rates of the prepared bio-blocks were measured according to the method described above.

The results indicated that the number of cells in each bio-block affected the shell degradation rate. Specifically, bio-blocks having higher cell numbers had faster shell degradation rates. Conversely, bio-blocks having lower cell numbers had slower shell degradation rates.

We further examined the impact of shell thickness of the bio-blocks on the shell degradation rate.

Bio-blocks were prepared according to Example 4, wherein the same cell type (e.g., HepG2 cells), the same cell density (e.g., 6×10⁶/mL), the same polymeric core material (e.g., type I collagen), and the same polymeric shell material (e.g., 5% w/w oxidized sodium alginate with an oxidation level of 8.8%) were used during the preparation of the bio-blocks, except that shells of different thickness were achieved by adjusting the parameters of encapsulator (e.g., the diameters of the inner nozzle and outer nozzle of the concentric nozzle set). The shell degradation rates of the prepared bio-blocks were measured according to the method described above.

The results indicated that the thickness of the shells in bio-blocks had an impact on the time of complete degradation of the shells. Specifically, it took a longer time to completely degrade thicker shells in the bio-blocks.

Example 7: Preparation and Characterization of Bio-Ink Compositions

Bio-blocks prepared using the method described in Example 1 was thoroughly mixed with a carrier comprising a bioadhesive material to prepare an exemplary bio-ink composition for bioprinting. The carrier comprises alginate and gelatin. The carrier comprises alginate and gelatin. The bio-blocks comprise a core comprising HUVEC, and a polymeric core material comprising sodium alginate and type I collagen; and a shell comprising calcium alginate. As the bio-block and the carrier share certain common materials, in order to facilitate visualization, methyl violet was further added to the core of some bio-blocks during the preparation step.

The bio-ink composition was visualized using phase contrast microscopy immediately after the bio-ink composition was prepared. Bio-blocks with methyl violet in the cores were stained purple (shown as dark grey in the figure) as shown in FIG. 6A. FIG. 6A further shows that the purple color was present inside the bio-blocks, but not in the carrier (i.e., bio-adhesive material) of the bio-ink, which indicates that the shells preserved the integrity of the contents of the bio-blocks within the bio-ink composition.

The bio-ink composition was further bioprinted into a single cell layer with a width of about 250 μm, and visualized under a phase contrast microscope (FIG. 6B). The bio-block shown in FIG. 6B was stained purple (shown as dark grey in the figure). FIG. 6B further shows that the purple color was present inside the bio-block, but not in the carrier (i.e., bio-adhesive material), which indicates that the shell preserved the integrity of the contents of the bio-block during the bioprinting process.

To further characterize the bio-ink composition, viscosity of the bio-ink composition was measured as a function of ambient temperature from 25° C. to 40° C. As shown in FIG. 7, the viscosity (TO) of the carrier (alginate and gelatin) had a viscosity of 30-160 Pa·s under a temperature of 25° C.-40° C. As the temperature increased, the viscosity of the carrier decreased steadily. Additionally, it was discovered that mixing of the bio-blocks and the carrier (i.e. to produce the bio-ink composition) did not significantly change the viscosity of the composition (data not shown). Thus, the viscosity of the bio-ink composition is mainly determined by the viscosity of the carrier (such as bio-adhesive material).

It is possible to control the viscosity of the carrier (such as bio-adhesive material) or the bio-ink composition by adjusting the composition, including content and weight percentage of each component, of the carrier (such as bio-adhesive material). Typically, a bio-ink composition with a viscosity in the range of 1-1000 Pa·s is compatible with bioprinters. Therefore, the exemplary bio-ink composition described herein can be readily used for bioprinting with known systems in the art at a temperature range of about 4° C. to 40° C.

Example 8. Characterization of Bio-Blocks and Bio-Ink Compositions

Cell Viability

The viability of cells inside the bio-blocks was examined by staining. Reagents used are as follows:

CaAM (purchased from Invitrogen) was used to stain live cells by staining the cytoplasm, which was visualized as green fluorescence. Specifically, 50 μg CaAM was dissolved in 10 μL DMSO, which was then mixed with 10 mL PBS. The final concentration of CaAM in the solution was 5 mmol/L.

Propidium iodide (purchased from Invitrogen) was used to stain dead cells by staining the nuclei, which was visualized as red fluorescence. Specifically, propidium iodide nucleic acid stain was diluted in deionized water to 1 mg/mL to be used as a stock solution, which was further diluted at a1:3000 ratio to a final concentration of 500 nM to be used as a working solution.

The staining method was as follows:

Bio-blocks prepared using the method of Example 1 were incubated in 1 mL Calcein AM solution at about 37° C. for about 1 hours, then transferred to 1 mL Propidium iodide Nucleic Acid Stain for about 15 minutes, and imaged using laser scanning confocal microscopy. The bio-blocks each contained about 100 human umbilical vein endothelial cells (HUVEC). The polymeric shell material mainly contained calcium alginate, and the polymeric core material mainly contained sodium alginate and type I collagen. Results are shown in FIG. 8A-8D.

Figure 8A:
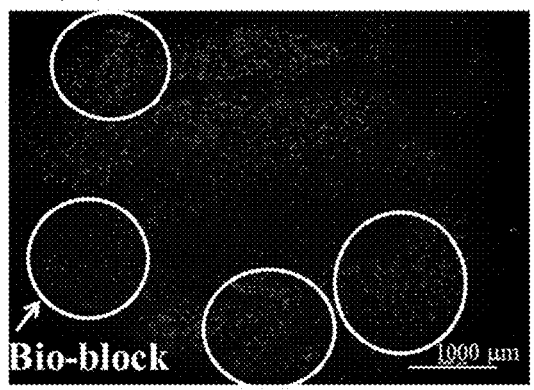
FIGS. 8A-8D depict survival of Human Umbilical Vein Endothelial Cells (HUVECs) in bio-blocks.
Figure 8B:
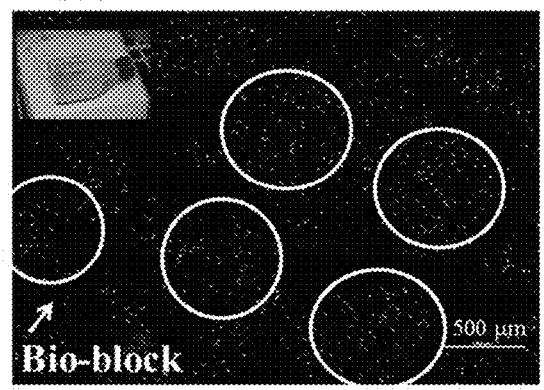

Images of the Calcein AM and propidium iodide stained bio-blocks under various conditions, such as immediately after preparation (FIG. 8A), after storage at 4° C. for about 3 hours (FIG. 8B), after bioprinting (FIG. 8C), and after incubation at about 37° C. for about 72 hours (FIG. 8D) were collected and analyzed using Image-Pro Plus software (Media Cybernetics). In FIGS. 8A and 8B, each white circle represented a bio-block. In FIGS. 8A-8D, white spots with high saturation levels (such as the spots pointed by the white arrows) represented red fluorescence (i.e. dead cells), and white spots with low saturation levels represented green fluorescence (i.e. live cells). Red and green pixels in the images were clustered, and various parameters, such as number of red or green spots, area, average optical density, diameter, and accumulated optical density, were statistically analyzed to obtain the number of red and green pixels. Cell survival rate was calculated based on the number of red and green pixels, as follows: cell survival rate=live cell number/ (live cell number+dead cell number).

Figure 8C:
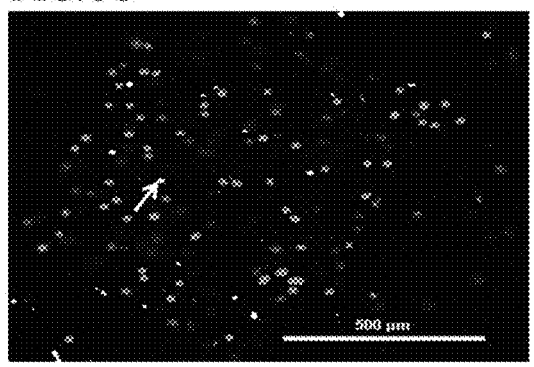
Figure 8D:
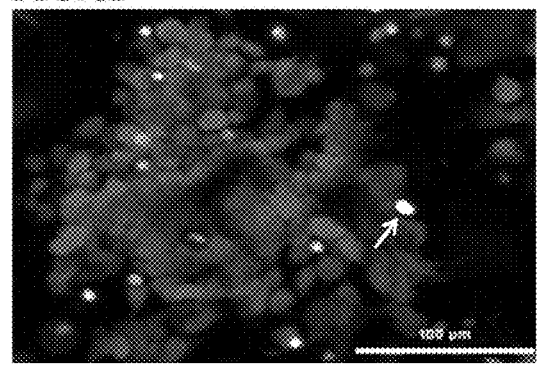

As shown in FIG. 8A, more than about 98% of cells in the bio-blocks were alive in the bio-blocks immediately after preparation. FIG. 8B shows that after storage at 4° C. for 3 hours, cells in the bio-blocks still maintained a high viability (survival rate was 98%). FIG. 8C shows that after bioprinting of the bio-ink composition comprising the bio-blocks, cells in the bio-blocks still maintained a high viability (survival rate was 97%). FIG. 8D shows that after incubation in H-DMEM media at 37° C. for about 72 hours, cells in the bio-blocks still maintained high viability (survival rate was 95%).

Adhesion and Spreading

Bio-blocks with human HepG2 cells prepared using the method of Example 1 were cultured at about 37° C. with about 5% $CO_2$ in H-DMEM media containing about 10% FBS (fetal bovine serum) to allow cells to spread, proliferate, and establish connection (i.e. adhere) to each other inside the bio-blocks. The bio-blocks were stained with Calcein AM and propidium iodide as described in the viability section, and imaged by laser scanning confocal microscopy. The bio-blocks were prepared using the method of Example 1. The polymeric shell material mainly contained calcium alginate. The polymeric core material mainly contained sodium alginate and type I collagen. Results are shown in FIGS. 9A-9B.

Figure 9A:
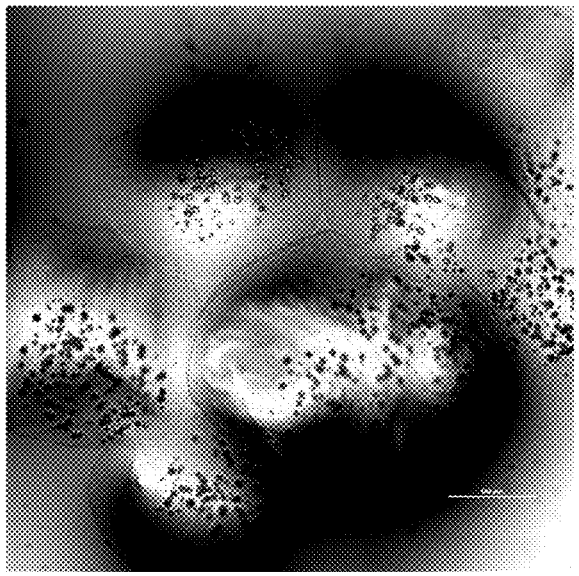
FIGS. 9A-9B depict adhesion and spreading of HepG2 cells inside bio-blocks.
Figure 9B:
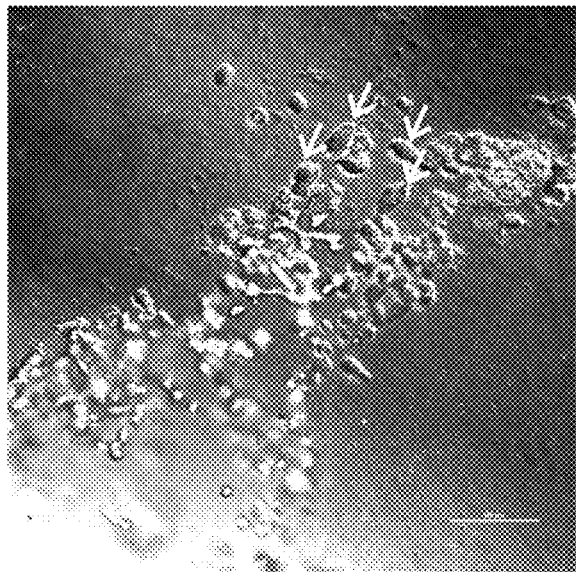

FIG. 9A (40× magnification) shows that after 1 day of incubation, the cells in the bio-blocks were round, and yet to spread. FIG. 9B (200× magnification) shows that after 5 days of incubation, the cells in the bio-blocks adhered and spread. FIGS. 9A-9B demonstrate that cells in the bio-blocks spread and established intercellular connections after incubation for 5 days.

Proliferation

Bio-blocks each with about 100 human HepG2 cells were cultured at about 37° C. with about 5% $CO_2$ in H-DMEM media containing about 10% FBS (fetal bovine serum) for about 5 days after preparation to allow proliferation of cells inside the bio-blocks. The cultured bio-blocks were stained with DAPI (blue fluorescence) and 5-Ethynyl-2'deoxyuridine (EdU, red fluorescence), and imaged using a laser scanning confocal microscopy. The bio-blocks comprise HepG2 cells. The polymeric shell material mainly contained Calcium alginate, and the polymeric core material mainly contained sodium alginate and type I collagen.

Figure 10:
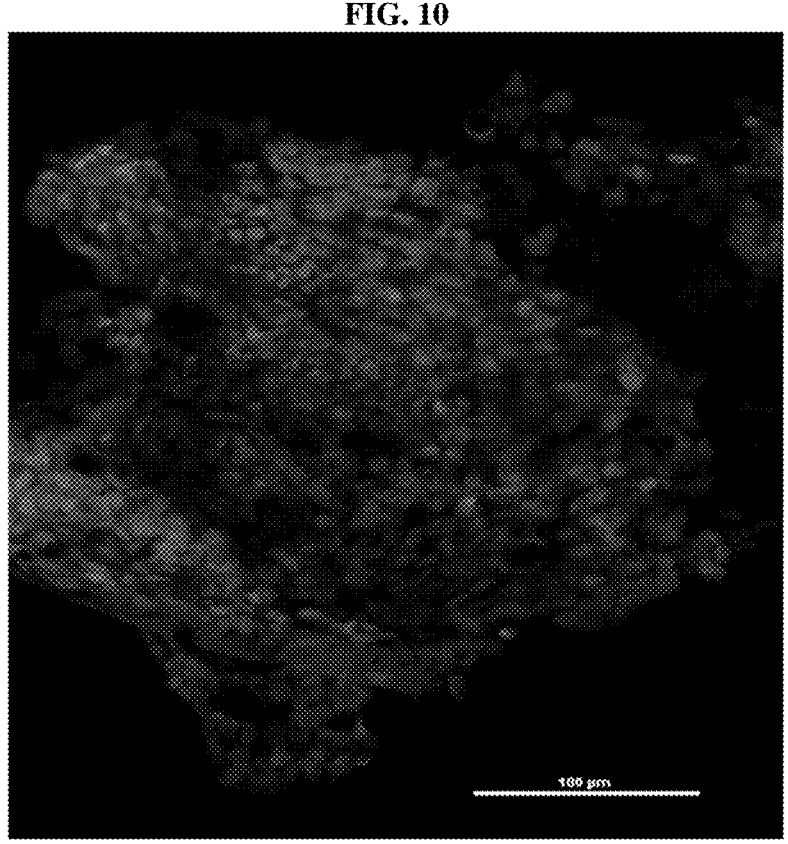
FIG. 10 depicts proliferation of HepG2 cells inside bio-blocks that had been cultured at about 37° C. for about 5 days after preparation of the bio-blocks. Cell nuclei were stained by DAPI (blue channel), and proliferating cells were stained using EdU (red channel). Cells in gray are proliferating HepG2 cells stained by EdU. The image was collected under 200 times magnification using confocal scanning microscopy.

As shown in FIG. 10 (200× magnification), cells in bio-blocks had undergone proliferation during the 5-day incubation. The cells were actively proliferating as evident in the staining of the same cells that co-localized with the DAPI-stained cell nuclei (FIG. 10).

Comparison Between Bio-Blocks and Cell Capsules

In this experiment, bio-blocks and traditional cell capsules were compared in terms of proliferation and connection among cells.

Traditional cell capsules were prepared using a mixture of a sodium alginate solution (such as 2.5% (weight/volume) sodium alginate solution) and cells. The mixture was loaded onto an Encapsulator or a microinjection pump to form microdroplets, which was then exposed to a $CaCl_2$ solution (such as 0.1 M $CaCl_2$ solution) to allow crosslinking of the sodium alginate by forming calcium alginate to obtain the traditional cell capsules. The traditional cell capsules lack a core-shell structure in comparison to the bio-blocks.

Bio-blocks comprising HepG2 cells were prepared using the method described in Example. The polymeric shell material mainly contained calcium alginate, and the polymeric core material mainly contained sodium alginate and type I collagen.

The cell capsules and bio-blocks were cultured at about 37° C. with about 5% $CO_2$ for about 7 days to allow proliferation of cells inside the bio-blocks or the traditional cell capsules. Before and after culturing for 7 days, the bio-blocks and cell capsules were stained using Calcein and imaged using a laser scanning confocal microscope.

Figure 11A:
FIGS. 11A-11D show proliferation of cells inside traditional cell capsules or bio-blocks.
Figure 11B:
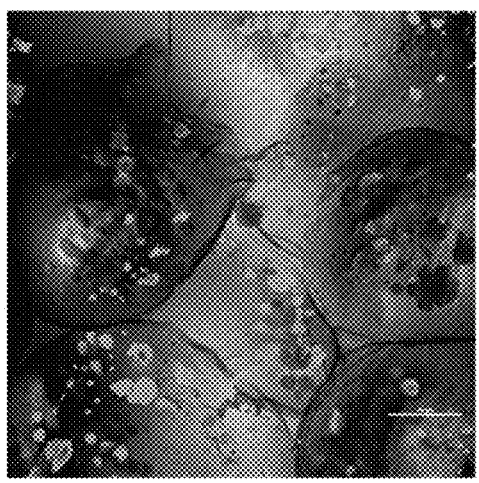

FIG. 11A shows cell capsules immediately after preparation. FIG. 11B shows cell capsules after 7 days of culturing. Comparison of FIG. 11A and FIG. 11B reveals that there was no significant proliferation of cells inside the spheroids over the course of culturing. The cells were present as flat and round clusters, which were sparsely distributed in the spheroids after culturing.

Figure 11C:
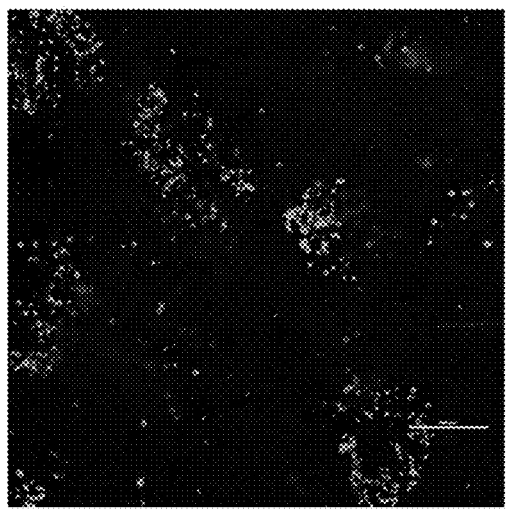
Figure 11D:
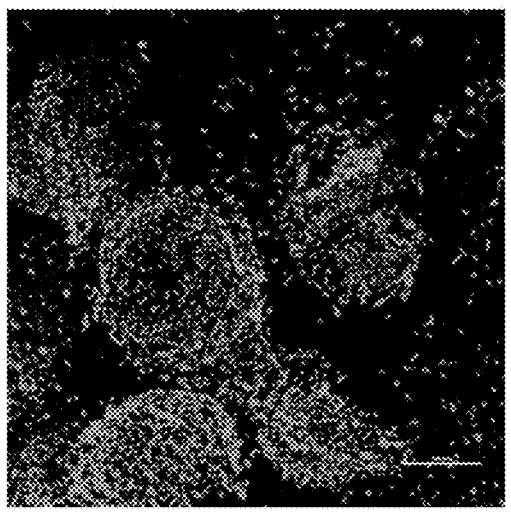

By contrast, FIG. 11C shows bio-blocks immediately after preparation, and FIG. 11D shows bio-blocks after 7 days of culturing. Comparison of FIG. 11C and FIG. 11D reveals significant proliferation of cells inside the bio-blocks over the course of culturing. Additionally, there was clear evidence of cell spreading, adhesion and connection to each other by day 7 of culturing in FIG. 11D.

Results in FIGS. 11A-11D demonstrate that compared to traditional cell capsules, the bio-blocks of the present application are superior in promoting cell proliferation and establishment of connections among cells. Such properties are significant for subsequent tissue development and formation.

Connections Among Cells in Neighboring Bio-Blocks

Figure 12A:
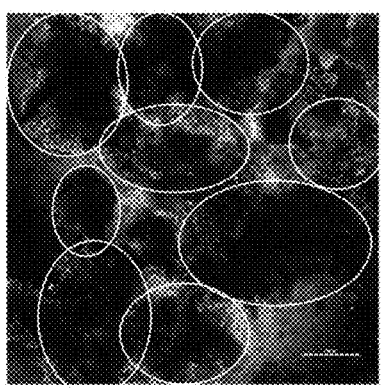
FIGS. 12A-12C depict connections among cells across the boundaries of different bio-blocks. All bio-blocks contain HepG2 cells and HUVEC cells.
Figure 12B:
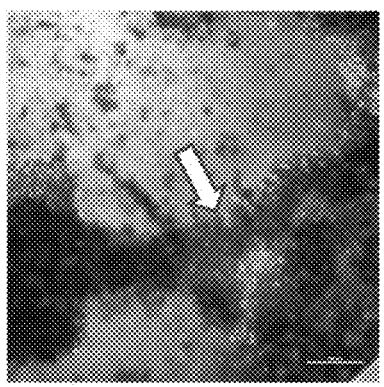
Figure 12C:
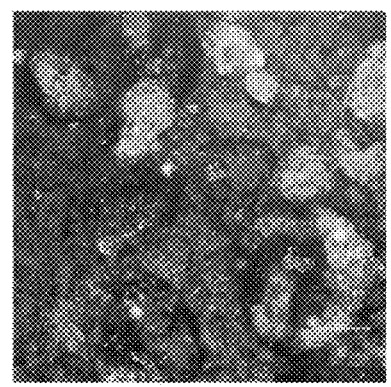

In this experiment, connections Bio-blocks comprising HepG2 cells and bio-blocks comprising HUVECs were prepared using the method of Example 1, and were co-cultured at about 37° C. with about 5% $CO_2$ in H-DMEM media containing about 10% FBS (fetal bovine serum) to allow degradation of shells of the bio-blocks and establishment of connections among cells in neighboring bio-blocks. FIG. 12A shows connections among HepG2 and HUVEC cells across the borders of multiple bio-blocks forming an integrated structure. White circles mark the approximate boundaries of the original bio-blocks. FIG. 12B provides a close-up view of the connections among HepG2 and HUVEC cells across a border (dark feature pointed out by an arrow) between two bio-blocks. In FIGS. 12A-12B, HepG2 and HUVEC were both labeled with cell tracker Green CMFDA (green signal). FIG. 12C shows connections between HepG2 cells (overlap of green signals), between HUVEC cells (overlap of red signals), and between HepG2 cells and HUVEC cells (overlap of green and red signals resulting in yellow signals) across different bio-blocks. In FIG. 12C, HepG2 cells were labeled with cell tracker Green CMFDA, and HUVEC cells were labeled with tracker CM-Dil.

This Example has demonstrated that cells in the bio-blocks of the present application has high viability (survival rate was 98% or more), and can grow, proliferate, spread, differentiate, and establish connections inside the bio-blocks as under normal cell culturing conditions. The results show that the bio-blocks and methods of preparation described herein can effectively maintain the viability of cells, which is beneficial for downstream applications, such as bioprinting.

Example 9. Examples of Bio-Blocks, Bio-Ink Compositions, and Bioprinted Constructs Bio-Block is an Independent Structural and Functional Unit Comprising a Shell and a Core.

Batches of bio-blocks comprising different core and/or shell compositions as listed in Table 5 were prepared, and examined under microscopy. Examples of the bio-blocks are shown in FIG. 3A, and FIGS. 5A-5F. The bio-blocks with shells containing oxidized sodium alginate can be used to stimulate cell proliferation. The bio-blocks with shells containing polylysine can be used to form elaborate structures.

TABLE 5

Bio-blocks comprising various core and shell compositions

| Bio-block | Polymeric core material, concentration (w/v) | Polymeric shell material, concentration |
|---|---|---|
| 1 | Sodium alginate + type I collagen | Calcium alginate + elastin |
| 2 | Type I Collagen | Calcium alginate |
| 3 | type I collagen | oxidized calcium alginate |
| 4 | type I collagen | 90% calcium alginate + 10% oxidized calcium alginate |
| 5 | type I collagen | 70% calcium alginate + 30% oxidized calcium alginate |
| 6 | Laminin | 80% calcium alginate + 20% agarose |
| 7 | Starch | oxidized calcium alginate |
| 8 | Starch | 70% calcium alginate + 30% oxidized calcium alginate |
| 9 | biodegradable polyurethane | oxidized calcium alginate |
| 10 | biodegradable polyurethane | 90% calcium alginate + 10% oxidized calcium alginate |
| 11 | biodegradable polyurethane | 85% calcium alginate + 15% gelatin |
| 12 | Sodium alginate | calcium alginate |
| 13 | Sodium alginate | Polylysine |
| 14 | Type I Collagen | Polylysine |

* percentages are based on weight.

Bio-Blocks have Excellent Mechanical Properties.

Bio-blocks prepared using different biodegradable polymeric materials have different mechanical properties. In this example, three commonly used cell culturing materials were used to prepare the bio-blocks: (1) alginate as the polymeric shell material, and type I collagen as the polymeric core material; (2) polylysine as the polymeric shell material, and type I collagen as the polymeric core material; and (30 polylysine as the polymeric shell material, and alginate as the polymeric core material. The prepared bio-blocks were each mixed sodium alginate to form the bio-ink compositions respectively. B series 3D bioprinter invented by Sichuan Revotek co., Ltd (FIGS. 13A, 13B) was used to bioprint various bio-ink compositions. A methyl violet dye was further included in the core mixture in order to test the mechanical durability of the bio-blocks in the bio-ink composition. All bio-blocks maintained integrity during the printing process.

Figure 13A:
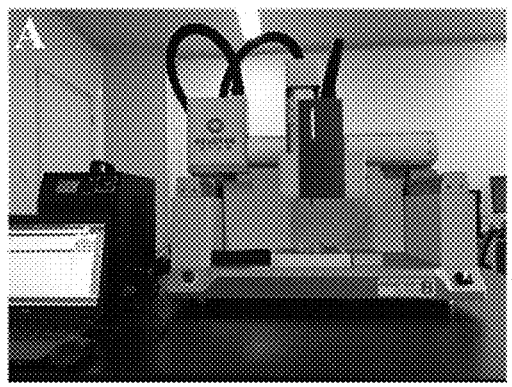
FIG. 13A and FIG. 13B are pictures of Revotek B series 3D bioprinters.
Figure 13B:
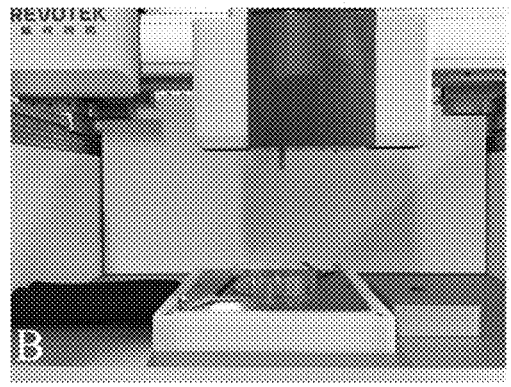
Figure 13C:
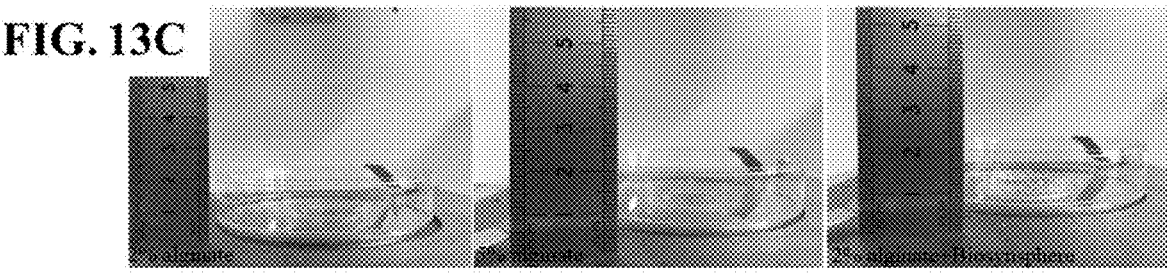
FIGS. 13C (side view) and 13D (top view) are ring-shaped three-dimensional structures printed using a bio-ink comprising 2% sodium alginate (left panels), using a bio-ink comprising 5% sodium alginate (middle panels), or using a bio-ink comprising 2% sodium alginate and bio-blocks. The bio-ink containing bio-blocks had better mechanical support capacity to form tissues compared to other kinds of hydrogel.
Figure 13D:
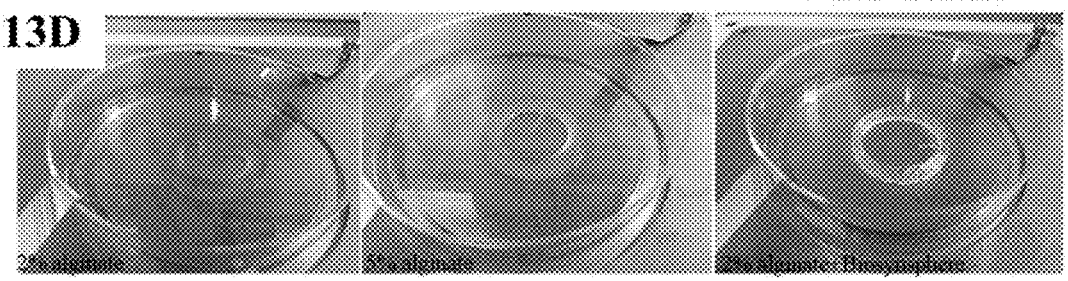

This represents a significant progress in the field, because without bio-blocks, printing with 2% alginate, which is suitable for cell living, could not form the ring-shaped structure (FIGS. 13C, 13D, left panel). However, 5% alginate, which provides enough mechanical strength for printing structures with defined shapes (FIGS. 13C, 13D, middle panel), was seldom used for bioprinting, because it would cause massive cell death in the process of embedding the cells. However, 2% alginate mixed with bio-block had better compression resistance than 5% alginate without bio-blocks (FIGS. 13C, 13D, right panel). The mechanical strength of the bio-ink comprising 2% alginate and bio-blocks enabled the cells in the bio-blocks to avoid being crushed by the printer jet nozzle.

Bio-Blocks have Excellent Biological Properties.

Bio-blocks protect cells from damage. Bio-blocks comprising human umbilical vein endothelial cells (HUVEC), polylysine (Sigma, USA) as the polymeric shell material, and type I collagen (Adranced Biomatrix, US) as the polymeric core material were prepared, and the cells viability was tested under different conditions by staining with Calcein AM (Invitrogen, US) and propidium iodide (Invitrogen, US), followed by imaging with laser scanning confocal microscopy. The results showed that, cell viability was more than 90% throughout the 3D bioprinting process, including immediately after bio-block preparation (FIG. 14A), after bioprinting (FIG. 14B), and after incubation at about 37° C. with about 5% $CO_2$ in H-DMEM media containing 10% fetal bovine serum (FBS) (Gibco, US) for 72 hours (FIG. 14C). In addition, after storage at 4° C., cell viability in the bio-blocks was more than 90% after 3 h, more than 80% after 24 h, and more than 50% after 48 h (FIG. 14D).

Bio-blocks provide a suitable microenvironment for the embedded cells to support normal growth and functions of cells (FIGS. 14E-14I). Using polylysine as the polymeric shell material, type I collagen as the polymeric core material, bio-blocks were prepared and cultured at 37° C. with 5% $CO_2$ in H-DMEM media containing about 10% FBS, and imaged by laser scanning confocal microscopy. Different types of cells were used as the seed cells to test the biological property of bio-blocks, including adhesion, spreading, proliferation, migration, secretion, differentiation, and establishing connections with each other.

Bio-blocks comprising HUVECs labeled with cell tracker Green CMFDA (Life Technologies, US) were prepared and cultured for about 24 h. Results show that more than 70% of cells exhibited evidence of adhesion and spreading (FIG. 14E).

Bio-blocks comprising HepG2 cells were prepared and cultured for about 48 h. The cells were actively proliferating as evident in positive 5-Ethynyl-2'deoxyuridine (EdU) (Life Technologies, US) staining co-localized with the DAPI-stained cell nuclei (FIG. 14F).

Bio-blocks comprising primary cultured rat hepatocytes were prepared and used to test albumin secretion by staining with an albumin antibody (Life technologies, US). Results show that hepatocytes in the bio-blocks secreted albumin (FIG. 14G).

Bio-blocks comprising HUVECs labeled with cell tracker Green CMFDA and bio-blocks comprising HepG2 cells labeled with cell tracker CM-Dil (Life Technologies, US) were mixed at 1:1 ratio. Bio-blocks comprising the cell mixture were prepared and cultured for about 72 h. Connections among HUVECs and HepG2 cells in the bio-blocks were observed (FIG. 14H).

Bio-blocks comprising primary cultured rat BMSCs labeled with cell tracker CM-Dil were prepared and cultured for about 4 hours. Free migration of BMSCs in the bio-blocks was observed (FIG. 14I).

Bio-Block-Based Bio-Ink is Suitable for 3D Bioprinting

Bio-blocks comprising primary cultured BMSCs and HUVECs mixed at 1:1 ratio, polylysine labeled with FITC (Sigma, US) as the polymeric shell material, and type I collagen as the polymeric core material were prepared and imaged by laser scanning confocal microscopy (FIG. 15A). Depending on the structure and cell types of the printed tissue, the degradation rate of the shell can be controlled accurately. The shell was degraded completely in 0.25% trypsin (TN, GIBCO, USA) for 10 minutes (min) without interfering with cell viability (FIG. 15B). The shell was also degraded by cells embedded in the bio-blocks after being cultured at 37° C. with 5% $CO_2$ in H-DMEM media containing about 10% FBS for 9 d (FIG. 15C). In addition, several bio-blocks integrated together by cells that connected with each other after degradation of the shells (FIG. 15D).

Figure 16A:
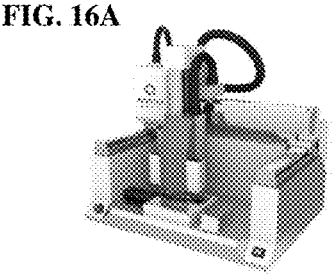
FIGS. 16A-16I show cartoon schematic of 3D bioprinting by a REVOTEK B series 3D bioprinter.
Figure 16B:
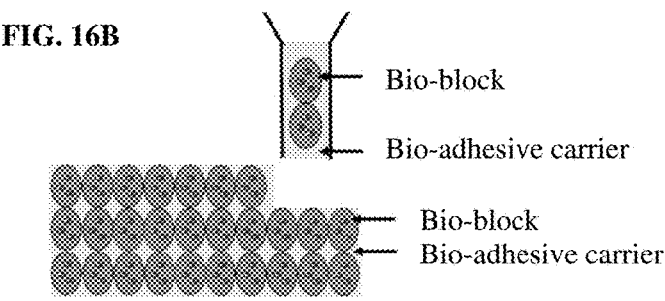
Figure 16C:
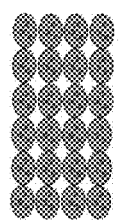
Figure 16D:
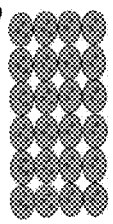
Figure 16E:
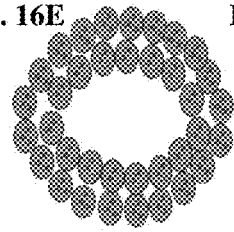
Figure 16F:
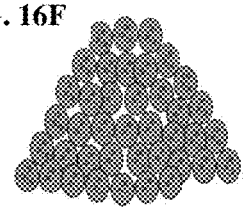
Figure 16G:
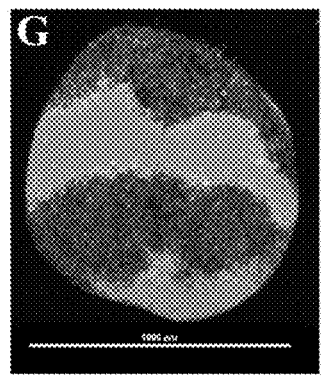
Figure 16H:
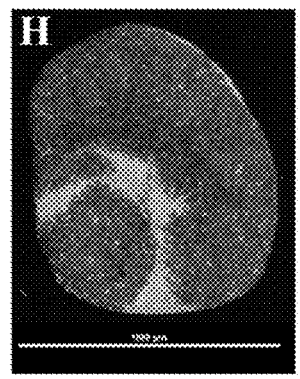
Figure 16I:
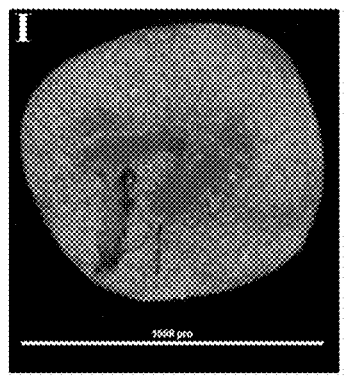

Using a bio-ink comprising the bio-blocks and sodium alginate, artificial tissues was bioprinted by a B series 3D bioprinter invented by Sichuan Revotek co., Ltd. According to the structural information of the artificial tissue, the bio-ink was extruded by the jet of the 3D bioprinter to build the artificial tissue (FIGS. 16A, 16B). The bioprinted structures included a sheet formed by one type of bio-blocks (FIG. 16C), as well as block-shaped (FIG. 16D), ring-shaped (FIG. 16E), and irregular-shaped (FIG. 16F) formed by two or more types of bio-blocks. Accurate cell distribution could be achieved by bioprinting the bio-blocks (FIGS. 16G-I).

Figure 17H:
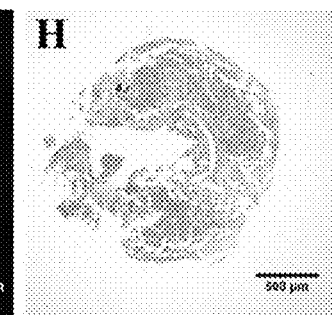
Figure 17J:
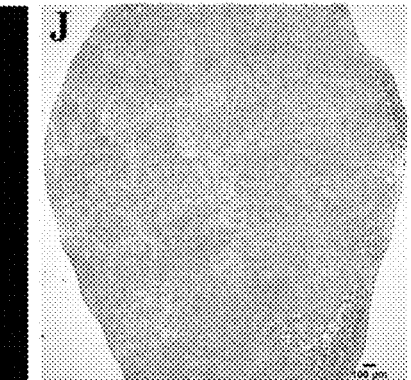

A first type of bio-blocks (FIG. 17A) comprising HepG2 cells, type I collagen as the biodegradable polymeric core material, and polylysine as the biodegradable polymeric shell material were prepared. A second type of bio-blocks (FIG. 17B) comprising BMSCs, type I collagen as the biodegradable polymeric core material, and polylysine as the biodegradable polymeric shell material were prepared. Bio-ink compositions comprising each type of bio-blocks were prepared and used to bioprint various artificial tissues according to the structural models in the left panels of FIGS. 17C, 17E, 17G, 17I. The artificial tissues were cultured at 37° C. and with about 5% $CO_2$. The HepG2 cells were stained with cell tracker Green CMFDA (green fluorescence), and the BMSCs were stained with cell tracker CM Dil (red fluorescence). The artificial tissues were imaged using a laser scanning confocal microscopy in FIG. 17D, and the right panels of FIGS. 17C, 17E, 17G, and 17I. Histological staining results of the artificial tissues are shown in FIGS. 17F, 17H, and 17J. The imaging results revealed that cells across different bio-blocks fused together (FIGS. 17E-17J). In particular, FIG. 17B shows a single bio-block comprising BMSCs on Day 2 of the culturing (scale=100 μm). FIG. 17C right panel shows the bio-blocks in the bioprinted artificial tissue on Day 7 of the culturing (scale=500 μm), which demonstrated clear evidence of fusion of neighboring bio-blocks. By Day 9 of the culturing, as shown in FIG. 17D (scale=500 μm), the bio-blocks were fully integrated into a single entity, as the borders of the bio-blocks were no longer visible at this stage, and the surface of the construct became very smooth.

Discussion

In this example, we demonstrated that bio-blocks-based bio-ink provides a unique and efficient medium for engineering biological tissues by bioprinting. With the specific feature that the shell of the bio-block provides mechanical support, and the core permits growth, proliferation and differentiation of cells, bio-blocks are suitable for building complex artificial tissues.

We have shown that cell line (HUVECs), primary culture of adult cells (rat liver cells) and primary culture of mesenchymal stem cells (MSCs) were all compatible with the bio-block system. All three types of cells presented high levels of cell viability and proper biological activities (FIGS. 14A-14I), suggesting that bio-blocks could be applied to cells from different sources.

The core is where the cells live. Thus, to manipulate the core is to regulate the microenvironment of the encapsulated cells. We used biodegradable materials as the major component of the core. With relevant factors, multiple aspects of microenvironment (e.g., biological factors for growth or differentiation for specific types of cells, spatial structure, mechanical stimulation, PH, temperature and chemical factors) could be supplied so that proliferation, differentiation and even interaction among cells are regulated (FIG. 14A-14I).

The shells separate the bio-blocks so that every bio-block has a unique microenvironment if necessary, suggesting that delicate regulation could be achieved by manipulation of individual bio-block. In that sense, pluripotent stem cells that require sequential manipulation, or multiple cell types that require different microenvironments could be arranged and induced simultaneously in one piece of bioprinted product.

As basic building units, bio-blocks could be arranged precisely. Mechanical support provided by the shell not only protects the cells during the process of bioprinting, but also allows complex structure building (FIGS. 13C-13D). Different mechanical strength could be achieved by manipulating the polymeric shell material, without requiring additional scaffold in 3D bioprinting products. Besides, there are fewer restrictions on the bioprinters. Shear force caused by interaction between the bio-ink and printer jet nozzle during bioprinting, which represents a major bottleneck in bioprinting (see, for example, Khalil, S., Sun, W. Biopolymer deposition for freeform fabrication of hydrogel tissue constructs. Mater. Sci. Eng. C. 27(3), 469-478 (2007)), is no longer a threat to the cells. This means more printing trials could be attempted without updating the equipment, and various bioprinting protocols could be explored without worrying about cell damage.

The foundation of functional tissues is a well-arranged structure. Proper cell types and precise layout is indispensable for functional tissues. However, such precise cell distribution used to be unachievable due to insufficient accuracy and impossibility of implanting cells inside an artificial construct at specific sites. However, 3D bioprinting with bio-blocks promise to solve many of the existing challenges in tissue bioprinting owing to the shell-core structure of bio-blocks. For example, the volume and cell number of each bio-block is controllable. We were even able to print a bio-block with one cell in certain location of the artificial tissue. The controllable degradation of the bio-block shells ensure cell living in certain space and connecting with each other. The protection and mechanical support provided by the shells enable accurate control of the position of each bio-ink microdroplet by the 3D bioprinter jet during the bioprinting process. All these features make bio-blocks an ideal tool that can be designed and arranged as needed (FIGS. 16G-16I).

In addition to serving as building blocks in a bio-ink, bio-blocks can be used as a potent research tool. As a 3D culture system, bio-blocks could be manipulated so that the contents of the core and the shell could provide certain microenvironments for the cells. In that case, various types of (physical, chemical and biological) influences on cells could be studied. Besides, multiple bio-blocks could be assembled to establish a more complex microenvironment, imitating a natural environment (maybe even as complex as a pregnancy uterus). With (almost) every element being controllable, the proliferation and differentiation of stem cells could be further studied. In tissue engineering, bio-blocks enable seed cells to grow inside a scaffold, which cannot be achieved by known methods in the art that seed cells onto the scaffold. Additionally, targeted therapeutic protein could be incorporated in the shell of bio-blocks, so that the bio-blocks may serve as a delivery vehicle for the targeted therapy.

Methods

Cell Culture.

HFF-1 and HepG2 were purchased from Chinese Academy of Sciences cell bank, HUVECs were purchased from China Center for Type Culture Collection (CCTCC). BMSC: Primary cultures of rat bone marrow derived stroma cells (BMSCs) were conducted according to a procedure published previously. Briefly, 7 day-old Sprague-Dawley rats were narcotized by ether and then sacrificed and soaked in 75% ethanol to allow degradation for 10 min. The femurs were removed and the soft tissues were cleanly shaved. Both sides of the bones were opened with a rongeur, and the two femurs were placed in 10 ml L-DMEM medium containing 10% FBS. The bone marrow cavity was repeatedly flushed until the bones turned white using medium in a 5-ml sterile syringe. The obtained cell suspension was repeatedly pipetted and mixed, then the cell suspension was seeded in T-75 culture flask, and cultured at 37° C. with 5% $CO_2$ in L-DMEM (GIBCO, US) medium containing 10% FBS. The medium was replaced every 3-4 days. When the cells covered 90% of the flask, the cells were subsequently digested with 0.25% trypsin containing 0.1% EDTA and subcultured in L-DMEM. Third-generation cells were used in the experiment. Hepatocytes: Primary cultures of rat hepatocytes were conducted according to a procedure published previously. Briefly, the livers excised from 1-3 day-old Sprague-Dawley rats were cut into 1.0 mm and digested with 0.125% Trypsin for 15 h at 4° C., then the mixture was shaken for 15 min, and repeated for 4 times. The animal procedure was approved by the Institutional Animal Care and Use Committee of Sichuan University. The liver tissue digests were suspended in H-DMEM (GIBCO, US) supplemented with antibiotics (GIBCO, US) and 10% FBS (Hyclone, US).

Oxidized Sodium Alginate Preparation.

The alginate oxidation reaction was carried out in aqueous solution at room temperature for 24 hours. In a dark bottle, 10.00 g of sodium alginate was dissolved in 750 mL of distilled water. To the mixture was added an aqueous solution of 10 mL 0.25 M sodium periodate, reaching a final volume of 1 L with distilled water. The reaction was thoroughly mixed by stirring. After 24 hours, the reaction was quenched by addition of 40 mL ethylene glycol and stirred for 0.5 hour. The oxidized alginate was purified from the quenched reaction mixture by precipitation with the addition of 25 g NaCl and 2 L ethanol. The isolated polymer was then dissolved in 1 L water and re-precipitated by the addition of 2 L ethanol in the presence of NaCl (10 g). Finally, the precipitate was dried at room temperature under vacuum to obtain oxidized sodium alginate.

Bio-Block Preparation.

(1) Bio-blocks with simple materials of core and shell were prepared with a culture dish and a micropipette. For example, for the bio-blocks with type I collagen as the core material and 0.05% polylysine solution as the shell material, type I collagen was prepared as described above. 0.05% polylysine solution was prepared by dissolving polylysine (Sigma, Mn150,000-300,000) in H-DMEM at pH 7.2, and microdroplets of the bio-block core were prepared by using a micropipette to extrude type I collagen onto the culture dish (e.g., 8 µl per microdroplet) and solidified at 37° C. for 30 min. Then, the solidified core was placed in 0.05% polylysine solution and shaken for 10 min, until polylysine was absorbed onto the core, and the shell formed by self-assembly. More layers of shells were prepared by adding materials with negative charges, such as 0.03% sodium alginate, with repeated shaking in 0.05% polylysine solution for 10 min.

(1) Bio-blocks with complex materials of core and shell were prepared with a BUCHI™ Encapsulator B-395 Pro. Take the bio-blocks with type I collagen as the core material and 2.5% oxidative sodium alginate as the shell material as an example. The pH 7.2 type I collagen solution with concentration of about 4 mg/ml was prepared by adding 1 M sodium hydroxide (NaOH) solution on the ice. The 2.5% oxidative sodium alginate was prepared by dissolving oxidative sodium alginate in sterile deionized water. The core material was loaded into a 5 ml injector after mixed with seed cells and the shell material was loaded into a 100 ml culture bottle. A concentric nozzle set with an inner 150 µm nozzle and an outer 200 µm nozzle was installed on the Encapsulator. Microdroplets were prepared by using Encapsulator with 400 µm diameter and solidified in 0.1 M calcium chloride ($CaCl_2$) solution at 37° C. for 10 min.

Bio-Ink Preparation and Bioprinting.

Three bio-ink compositions were prepared for bioprinting, including (1) 5 ml 2% alginate (Sigma, USA) containing $1 \times 10^6$ HUVECs; (2) 5 ml 5% alginate; and (3) 5 ml 2% alginate mixed with HUVECs bio-blocks. B series 3D bioprinter invented by Sichuan Revotek co., Ltd (FIGS. 13A,13B) was used to jet the bio-inks. The pressure of 3D bioprinter jet was 120 KPa for 5% alginate, 5 KPa for 2% alginate and 40 KPa for 2% alginate mixed with bio-blocks. The temperature of printing inkjet nozzle for all kinds of bio-ink was 37° C. and the rate of printing was 300 mm/min. All of the processes were operated on a clean bench at room temperature.

Cell Viability Assays.

Living cells were labelled by Calcein AM at 37° C. for 1 h, and the dead cells were labelled by propidium iodide at 37° C. for 15 min. The results were imaged by laser scanning confocal microscopy.

Assays for Biological Properties.

(1) Adhesion and spreading: Cells were labeled with cell tracker Green CMFDA showing green fluorescence, cell morphology was imaged by laser scanning confocal microscopy. (2) Proliferation: Proliferating cells were stained using EdU (red channel) and cell nuclei were stained by DAPI (blue channel), the images were collected under 200 times magnification using laser scanning confocal microscopy. (3) Migration: Cells were stained by CD31 and imaged by laser scanning confocal microscopy for 24 h. (4) Secretion: Albumin secreted by hepatocytes in bio-block was tested by albumin test kit. The printed artificial tissue formed by bio-block was fixed in 4% paraformaldehyde. After incubation in 1% BSA for 30 min at 37° C., rabbit anti-rat polyclonal antibody of albumin (1:100) was used for incubation at 37° C. for 2 h and 4° C. for 12 h, followed by incubation of the secondary antibody, goat anti-rabbit IgG (1:200). The images were got by laser scanning confocal microscopy. (5) Cell connection: Two types of cells were labeled by cell tracker Green CMFDA and cell tracker CM-Dil, respectively. Overlapped fluorescence, the yellow fluorescence, indicates cells connecting with each other. The images were captured by laser scanning confocal microscopy.

Histological and Histochemical Staining.

Bioprinted artificial tissue formed by bio-block was cultured at 37° C. with 5% $CO_2$ in H-DMEM containing 10% FBS for 9 d and then was washed with PBS, fixed in 4% paraformaldehyde and embedded in paraffin according to the conventional methods. It was cut into 4-µm slices and H&E staining were performed according to conventional methods, the results were examined under an inverted optical microscope.

Immunohistochemistry.

HUVECs and hepatocytes in bioprinted artificial tissue using bio-blocks were determined by immunohistochemistry. The bioprinted artificial tissue was cultured at 37° C. with 5% $CO_2$ in H-DMEM containing 10% FBS for 9 d and then was washed with PBS, fixed in 4% paraformaldehyde and embedded in paraffin according to the conventional methods. It was cut into 4-µm slices. CD31 immunostain (RD, US) was used to detect HUVECs and HNF4α immunostain (Santa Cruz, US) was used to detect hepatocytes. The primary antibody of CD31 was goat anti-rat CD31 polyclonal antibody (1:50), and the secondary antibody was rabbit anti-goat IgG (1:500) (Sigma, US). The primary antibody of HNF4α was rabbit anti-rat CD31 polyclonal antibody (1:200), and the secondary antibody was goat anti-rabbit IgG (CST, US). The protocol was based on the manufacturer's instructions, and the results were observed and tested under an inverted optical microscope and photographed.

Example 10. Preparation of Msc Bio-Blocks with Osteoblast or Chondrocyte Differentiation Factors This example provides a method of preparing two exemplary types of MSC bio-blocks having microenvironments for osteoblast or chondrocyte differentiation, namely Type I MSC bio-blocks which comprise osteoblast differentiation agents, and Type II MSC bio-blocks which comprise chondrocyte differentiation agents. Bio-blocks were prepared under sterile conditions. If the bio-blocks are used in human, then such bio-blocks should be prepared in a workshop having a biosafety level of GMP.

An encapsulator (BUCHI™ Encapsulator B-395 Pro) was used to prepare the Type I and Type II MSC bio-blocks. The concentric nozzles had the following diameters: inner nozzle: 200 μm; outer nozzle: 300 μm.

Materials used are as follows:

(1) Core:

(a) Sodium alginate: The sodium alginate was prepared by dissolving sodium alginate in sterile deionized water.

(b) Type I collagen: 4 mg/mL, neutralized with a sterile 1M sodium hydroxide (NaOH) solution. To the type I collagen was added each of the following groups of cell factors:

(i) Cell factors that induce differentiation of the MSCs to osteoblasts (i.e., osteoblast differentiation agents): 0.1 μM dexamethasone, 0.05 mM ascorbic acid, and 10 mM glycerophosphate, for preparation of the Type I MSC bio-blocks.

(ii) Cell factors that induce differentiation of the MSCs to chondrocytes (i.e., chondrocyte differentiation agents): 10 ng/ml TGF-β3, 100 nM dexamethasone, 50 μg/ml ascorbic acid 2-phosphate, 100 μg/ml sodium pyruvate, 40 μg/ml proline and insulin-transferrin-selenous acid solution (ITS+, Collaborative Biomedical, Bedford, Mass., USA), for preparation of the Type II MSC bio-blocks.

A 1:1 (by weight) mixture of the type I collagen solution and the 2% (weight/volume) sodium alginate solution was prepared to prepare the core.

(2) Shell:

(a) 4% sodium alginate solution (b) Elastin (c) Solidifying (i.e., crosslinking) solution comprising an aqueous solution of 0.1 M calcium chloride ($CaCl_2$).

(3) Cell: rat bone marrow derived stroma cells (BMSCs), prepared as described in Example 9.

The bio-blocks were prepared as described in the following steps, which were all carried out on ice.

(1) To a mixture of 120 μL NaOH solution and 750 μL type I collagen was added 130 μL of a suspension of BMSCs (cell density: $1\times10^5$ cells/mL) in phosphate buffered saline (PBS), to make 1 mL of cell enwrapping solution. The cell enwrapping solution was mixed with 1 mL of 2% sodium alginate solution thoroughly to ensure even distribution of the cells in order to obtain a core mixture.

(2) To 2 mL of 4% sodium alginate solution was added 100 ng elastin to achieve a final concentration of 50 ng/mL, and the solution was thoroughly mixed to obtain a shell mixture. 300 mL 0.1 M $CaCl_2$ solution was placed in a beaker, which served as the solidifying (i.e., crosslinking) solution for the shell mixture.

(3) The core mixture and the shell mixture were each separately loaded into two 5 mL syringes. According to the manufacturer's instructions, pressure, centrifugal force, and pump speed of the encapsulator were set, and the core mixture and the shell mixture were used for granulation and coating. A concentric nozzle set with an inner nozzle having a size of 200 μm and an outer nozzle having a size of 300 μm was used. The prepared bio-block microdroplets were collected in the beaker containing 300 mL 0.1 M $CaCl_2$ solution and crosslinked for about 5 minutes to obtain the Type I MSC bio-blocks and Type II MSC bio-blocks. The bio-blocks can be stored at 4° C., or directly used for 3D bio-printing.

Figure 18A:
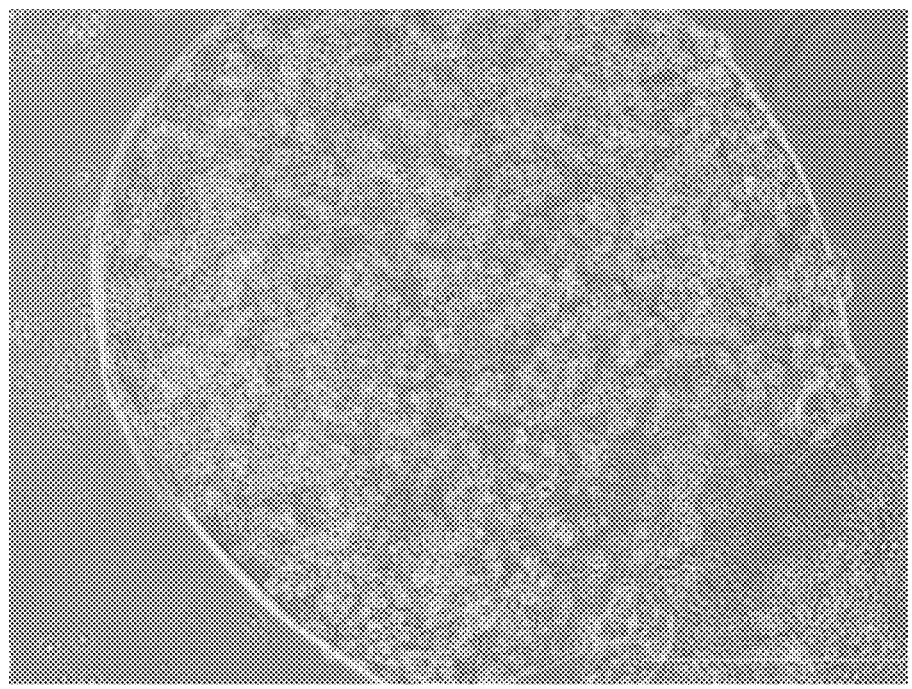
FIG. 18A shows an exemplary Type I MSC bio-block after one day of culturing at 37° C. and 5% $CO_2$.
Figure 18B:
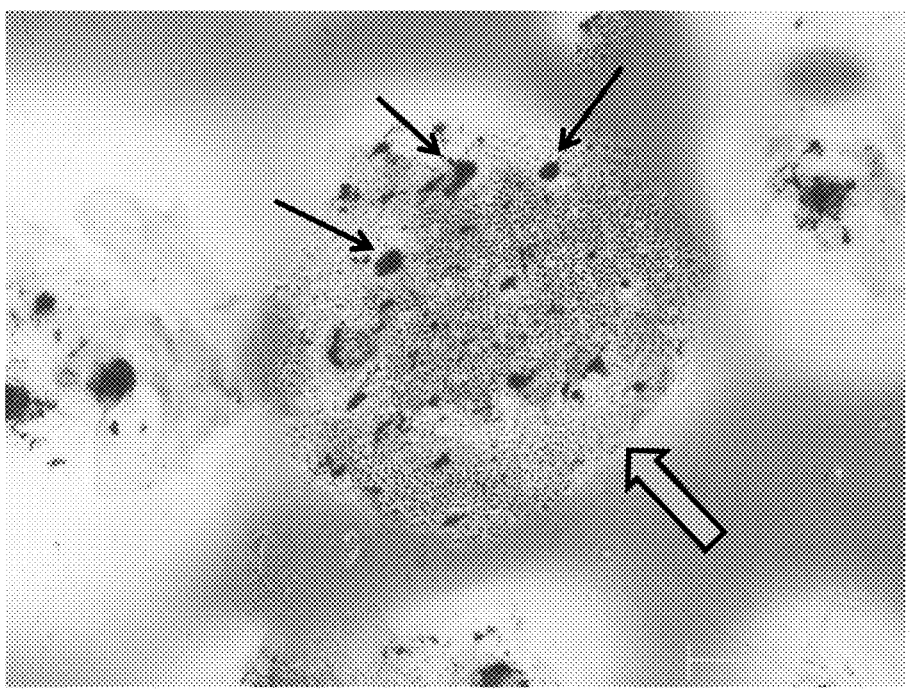
FIG. 18B shows BMSCs differentiating into osteocyte in the Type I MSC bio-blocks after 10 days of culturing at 37° C. and 5% $CO_2$. Thin arrows designate locations of calcium nodes stained by alizarin red.

Example 11. Characterization of Msc Bio-Blocks with Osteoblast or Chondrocyte Differentiation Factors The Type I MSC bio-blocks prepared using the method described in Example 10 were examined under a microscope, and the results are shown in FIGS. 18A and 18B. FIG. 18A shows the image of a Type I MSC bio-block after incubation at 37° C., 5% $CO_2$ for about 1 day. The results suggest that cells grew normally, and no differentiation was observed. FIG. 18B shows the Type I MSC bio-blocks stained with alizarin red after incubation at 37° C., 5% $CO_2$ for about 10 days. Specifically, the thick arrow points to an intact bio-block. Thin arrow point to calcium nodes. The results showed a large number of calcium nodes in the bio-blocks, which suggest differentiation of the MSC cells towards osteoblasts inside the bio-blocks. This example demonstrates that differentiation of cells could be regulated by manipulating the core contents. Osteogenesis differentiation was successfully induced in MSCs of this example. Importantly, we observed calcium nodules in 10 days after stimulation, which is only half of the typical 20 days of stimulation in ordinary 2D culture.

Additionally, the size of the MSC bio-blocks, number of cell in the MSC bio-blocks thickness of the shell, and mechanical properties can all be controlled in the same ways as described in Example 2. The mechanical properties (such as hardness and modulus of elasticity) of the MSC bio-blocks prepared in this Example could offer excellent mechanical protection for the cells inside.

The MSC bio-blocks can be mixed with a carrier (such as bioadhesive material) to prepare bio-ink compositions. The shell of the MSC bio-blocks could maintain its integrity over the course of bio-printing. Viscosity of the MSC bio-ink compositions could be controlled by adjusting the composition of the carrier.

MSCs in the bio-blocks and the bio-ink compositions had high viability before and after bio-printing, and after 5 days of incubation post bio-printing. The MSCs inside the bio-blocks were able to proliferate, spread and adhere after 5 days of incubation. These properties are beneficial for downstream applications, such as bio-printing.

Example 12. Preparation of a Composite Construct

This example describes exemplary methods of preparing three-dimensional constructs, such as a composite construct comprising artificial bone and cartilage, using the bio-blocks prepared in Example 11. Briefly, the method comprise the following steps:

(1) Collect bioinformatics information about a joint (such as knee) of a rat, and build a digital model of the structure of the joint.

(2) Prepare the Type I MSC bio-blocks and Type II MSC bio-blocks as described in Example 11.

(3) For each type of bio-block, mix the bio-blocks with a bioadhesive material to obtain a bio-ink composition. The bioadhesive material is sodium alginate and gelatin. The weight ratio between the bioadhesive material and the bio-blocks is 1:4.

It is to be noted that step (1) can be carried out between step (2) or step (3), simultaneously or after steps (2) and (3).

Figure 22B:
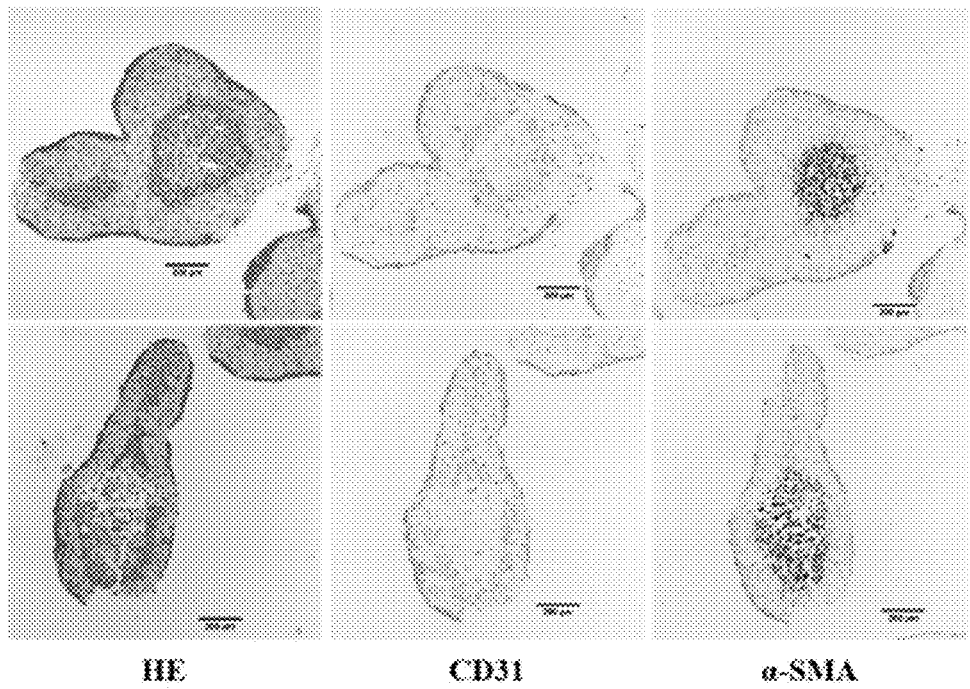

(4) A bioprinter is used to bioprint the blood vessel progenitor using a rotational printing mode. In the bioprinting process, corresponding bio-ink compositions are used to bioprint each layer according to the digital model of the joint. For example, FIGS. 22A and 22B show the side view and cross-section view of an exemplary model of the composite construct having a first layer for differentiation into osteoblasts (i.e., osteoblast progenitor layer) and a second layer for differentiation into chondrocytes (i.e., chondrocyte progenitor layer). The model has a tube-like structure, with the osteoblast progenitor layer on the exterior side of the tube, and the chondrocyte progenitor layer on the interior side of the tube. The bio-ink composition comprising Type I MSC bio-blocks is used to bioprint the osteoblast progenitor layer, and the bio-ink composition comprising Type II MSC bio-blocks is used to bioprint the chondrocyte progenitor layer. The bioadhesive material in the carrier of the bio-ink compositions helps to secure the positions of the bio-blocks in the bioprinted composite construct to yield a joint progenitor.

(5) The joint progenitor is placed in a 3D-culture incubator, and incubated using typical culturing conditions for joint progenitors on normal cell culture media (e.g., H-DMEM media containing 10% fetal bovine serum) at 37° C. and 5% $CO_2$. During the incubation process, mechanical stimulations, such as shearing and stretching, are applied to the joint progenitor. The progenitor is cultured for about 7-10 consecutive days to yield a joint tissue.

Discussion

Viability of the articular cartilage is the key to maintaining the normal structure and functions of joints. Loss of articular cartilage leads to arthritis and severely limits the functions of joints. Due to absence of vasculature in the articular cartilage, inability of the chondrocytes to migrate autonomously, and inability of mature chondrocytes to proliferate, etc., it is difficult for articular cartilage to heal even after minor injuries.

Clinically, cartilage defects are often accompanied by defects in the subchondral bone tissue. In recent years, researchers have attempted to repair or replace damaged cartilage with artificial cartilage. However, long-term studies have found that after simple implantation of artificial cartilage into the body, owing to the difficulty of rapid fusion at the cartilage-bone interface, the implanted artificial cartilage is usually unable to fully integrate with the surrounding bone tissue, and even suffers from shifts or dislocations, leading to failure of the repair. Studies have shown that bone-bone fusion is more rapid and firm than the cartilage-bone fusion; thus, when repairing cartilage defects, it is advisable to consider repair of the subchondral bone tissue, i.e., to build an artificial implant comprising both cartilage tissue and bone tissue.

Mesenchymal stem cells (MSC) are commonly used seed cells in tissue engineering of bone tissues or cartilage tissues. Researchers can induce differentiation of MSCs to osteoblasts by adding 0.1 µM dexamethasone, 0.05 mM ascorbic acid (AA), and 10 mM glycerophosphate to the culturing media; MSCs can be induced to differentiate into chondrocytes by adding 10 ng/ml TGF-β3, 100 nM dexamethasone, 50 µg/ml ascorbic acid 2-phosphate, 100 µg/ml sodium pyruvate, 40 µg/ml proline and insulin-transferrin-selenous acid solution (ITS+, Collaborative Biomedical, Bedford, Mass., USA) to the culturing media. Typical options for inducing MSC differentiation on scaffold include: 1. build a bone tissue using seed cells on a scaffold, and simultaneously grow seed cells for cartilage tissues directly on top of the bone tissue scaffold to form a cartilage tissue; 2. separately use a scaffold and seed cells to form a bone tissue and a cartilage tissue, and integrate the two types of tissues to form a composite implant; 3. simultaneously grow seed cells for bone tissue and cartilage tissue on a single or composite scaffold, and culture the scaffold-seed cell composition in vitro to form the composite implant comprising bone tissue and cartilage tissue; 4. Deposit the common progenitor cells on a dual-layered scaffold having different differentiation induction factors, and co-culture the scaffold-progenitor cell composition in a single or dual-chamber bioreactor.

Despite many years of development in the field, current methods of preparing artificial cartilage still suffers from many deficiencies, including, but not limited to: 1. Incubation of the MSCs for induced differentiation is very complicated. Thus, different incubation systems are needed to induce differentiation of MSCs into different types of cells. 2. It is necessary to proliferate the MSCs, induce their differentiation, prepare a composition comprising differentiated cells on a scaffold material, and culture the composition in vivo or in vitro to obtain the artificial implant. Consequently, the entire process expands a long period of time, which greatly increases the risk of contamination. 3. Using an artificial implant constructed by depositing seed cells on top of a scaffold, it is difficult to precisely distribute the cells that are grown on top of the scaffold material, thereby resulting in artificial implants having disordered structures and impaired functions. There is a clear need for improved method of preparing artificial cartilage tissues.

To overcome the above technical issues, inventors of the present application developed the methods described herein for constructing a composite artificial tissue comprising bone and cartilage, which uses two types of MSC bio-blocks. Compared to the currently known technologies, methods of the present application do not require growth of seed cells on a scaffold. Rather, bio-blocks comprising MSCs are directly used to build the artificial tissue. Additionally, the methods of the present application do not need significant in vitro proliferation of the cells prior to building the artificial tissue. On the contrary, in the present methods, MSCs proliferate significantly inside the bio-blocks after the construction of the artificial tissue using the MSC bio-blocks, which eventually forms a complete and integrated artificial tissue after the proliferation. Furthermore, the present methods do not need multiple culturing systems. On the contrary, the present methods can simultaneously induce MSCs to differentiate into osteoblasts and chondrocytes respective under the same culturing system. Lastly, through precise distribution of the MSC bio-blocks, the present methods can achieve precise distribution of osteoblasts and chondrocytes, thereby providing an artificial implant (i.e., composite construct comprising artificial bone and cartilage) with complete structures and functions. The composite construct described herein can be useful for repairing joint damage.

Example 13: Bioprinting of Three-Dimensional Constructs

This example describes exemplary methods of bioprinting three-dimensional constructs (such as blood vessel and cardiac muscle tissue) using the bio-blocks and bio-ink compositions described herein.

Figure 20:
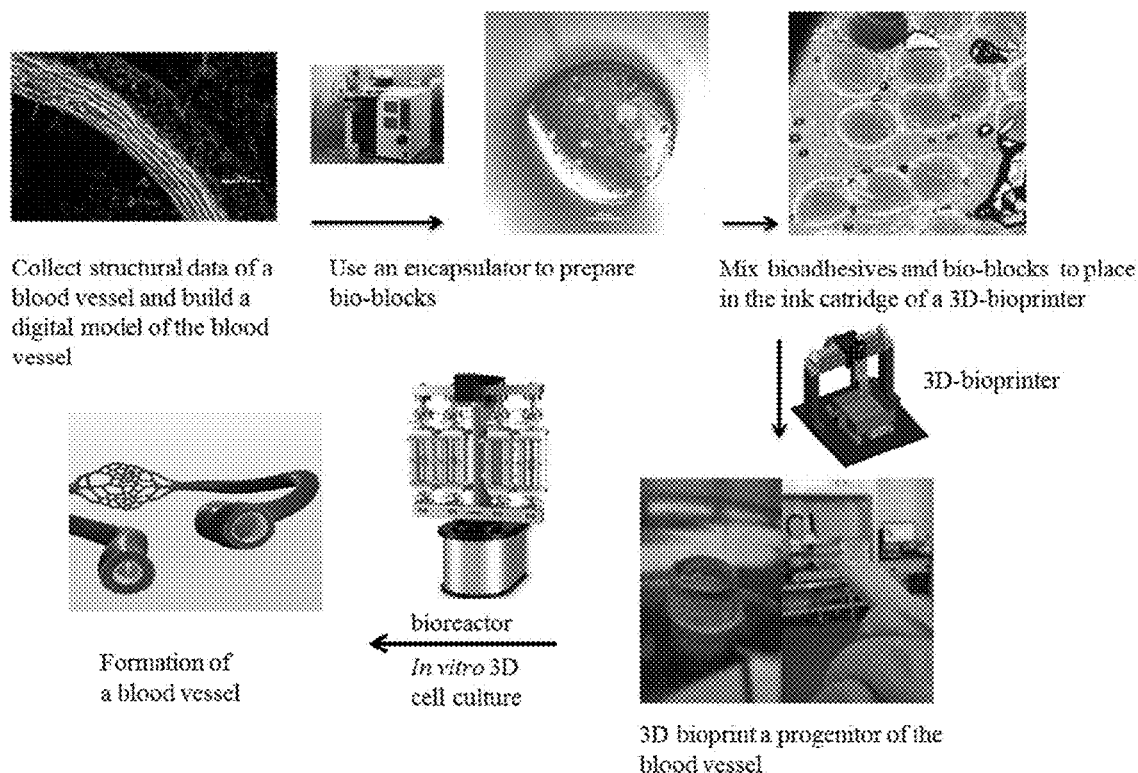
FIG. 20 depicts a schematic diagram of an exemplary process for using bio-blocks to bioprint a blood vessel.

FIG. 20 illustrates an exemplary workflow of bioprinting a blood vessel using the bio-blocks and bio-ink compositions of the present application. The detailed steps are as follows:

(1) Biological information of blood vessels, such as their structure and cell type distribution, is collected to build a digital model of the structure of a blood vessel based on bio-blocks. Specifically, the endothelial cells, smooth muscle cells, and fibroblast cells in a rat blood vessel are stained with DIO (green), Mitotracker (red) and Hoechst (Blue), and bioinformatics information of the blood vessel is collected to build a digital model of the blood vessel. According to the model, a blood vessel has a three-layered structure, including a layer of vascular endothelial cells in the interior, a layer of vascular smooth muscle cells in the middle, and a layer of fibroblast cells in the exterior.

(2) Using the method of Example 1, three types of bio-blocks are prepared, including bio-blocks comprising vascular endothelial cells, bio-blocks comprising vascular smooth muscle cells, and bio-blocks comprising fibroblast cells. The vascular endothelial cells, vascular smooth muscle cells, and fibroblasts are obtained from primary cell culture of the rat. The polymeric core material and polymeric shell material are the same as in Example 1. Additionally, to promote cell proliferation and differentiation, VEGF is added to the cores of the bio-blocks comprising the vascular endothelial cells; and PDGF is added to the cores of the bio-blocks comprising the vascular smooth muscle cells; and FGF is added to the cores of the bio-blocks comprising the fibroblasts.

The size of the bio-blocks comprising the vascular endothelial cells is about 30 μm, and each bio-block contains 2-3 vascular endothelial cells. The size of the bio-blocks comprising the vascular smooth muscle cells is about 200 μm, and each bio-block contains about 50 vascular smooth muscle cells. The size of the bio-blocks comprising fibroblasts is about 100 μm, and each bio-block contains about 10 fibroblasts.

(2) A carrier comprising a bioadhesive material is mixed with each of the three types of bio-blocks respectively to prepare three types of bio-ink compositions. The bioadhesive material is sodium alginate and gelatin. The weight ratio of the bioadhesive material and bio-blocks is 1:4.

It is to be noted that step (1) could be performed between step (2) and step (3), or concurrently or after steps (2) and (3).

(4) A bioprinter is used to bioprint the blood vessel progenitor using a rotational printing mode. In the bioprinting process, corresponding bio-ink compositions are used to bioprint each layer according to the digital model of the blood vessel. In particular, as shown in FIG. 2, the bio-ink composition comprising the bio-blocks containing vascular endothelial cells is used to bioprint the innermost layer of the blood vessel; the bio-ink composition comprising the bio-blocks containing vascular smooth muscle cells is used to bioprint the middle layer of the blood vessel; and the bio-ink composition comprising the bio-blocks containing fibroblasts is used to bioprint the outermost layer of the blood vessel. The bioadhesive material in the carrier of the bio-ink compositions helps to secure the positions of the bio-blocks in the bioprinted construct to yield a blood vessel progenitor.

(5) The blood vessel progenitor is placed in a 3D-culture incubator, and incubated using typical culturing conditions for blood vessel progenitors on normal cell culture media (e.g., H-DMEM media containing 10% fetal bovine serum) at 37° C. and 5% $CO_2$. During the incubation process, mechanical stimulations, such as shearing and stretching, are applied to the blood vessel progenitor. The progenitor is cultured for about 7-10 consecutive days to yield a blood vessel.

Additionally, bio-blocks comprising stem cells are used to bioprint a multi-layered construct (such as cardiac muscle tissue). Briefly, the steps of the method include the following:

Bio-blocks for bioprinting cardiac heart tissue: Bio-blocks are prepared using the method of Example 1. Each bio-block comprises a small number of cardiomyocytes and a large number of stem cells. The polymeric core material and the polymeric shell material are the same as in example 1. Additionally, cardiomyocyte differentiation factors, such as 5-azacytidine, are added to the core of the bio-blocks to induce differentiation and proliferation of the stem cells into cardiomyocytes.

Bio-ink preparation: The bio-blocks are mixed with a carrier comprising a bioadhesive material to prepare a bio-ink composition. The bio-adhesive material is sodium alginate and gelatin, and extracellular matrix molecules related to the cardiac muscle tissue is added to the carrier, including, for example, type I collagen. Additionally, cell factors that promote migration, metabolism and secretion of the cardiomyocytes are added to the carrier.

Figure 21:
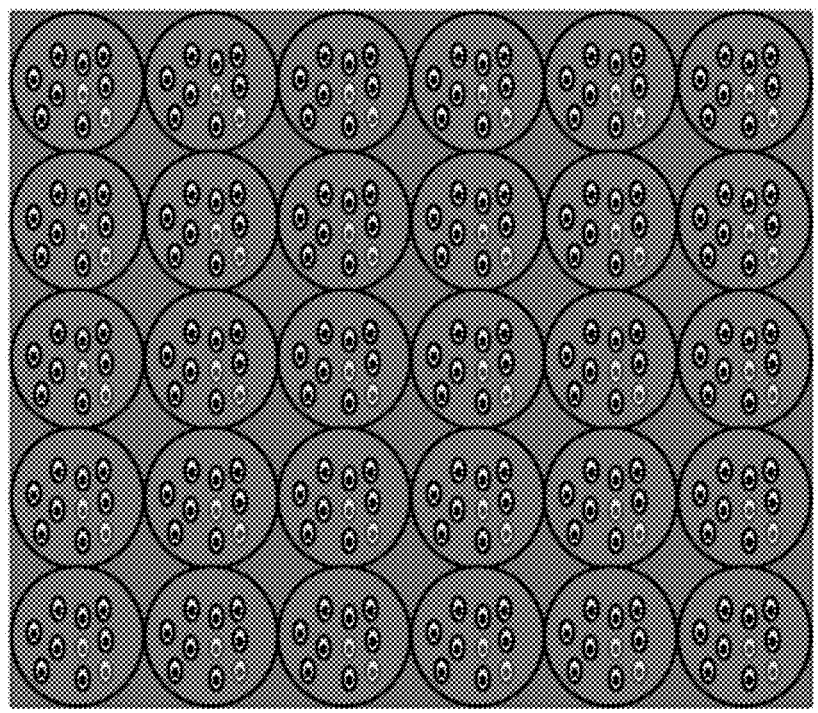
FIG. 21 depicts a schematic cross-section layout of an exemplary cardiac muscle tissue progenitor prepared by bioprinting using bio-blocks.

Bioprinting: Using a bioprinter, the bio-ink composition is bioprinted to form a multi-layered cardiac muscle tissue progenitor according to a pre-determined pattern, such as the schematic layout shown in FIG. 21. The biocompatible material (such as in the carrier) binds the bio-blocks in the cardiac muscle tissue progenitor.

In vitro culture: The cardiac muscle tissue progenitor is placed in a 3D incubator, and cultured under normal conditions for cardiac muscle tissues at 37° C. and 5% $CO_2$. The culturing of the bioprinted cardiac muscle tissue progenitor promotes proliferation, differentiation, and migration of the cells inside and beyond the shells of the bio-blocks. Cells penetrate the shells, and eventually form connections with cells in neighboring bio-blocks to form an integrated artificial cardiac muscle tissue.

Example 14. Preparation of Msc Bio-Blocks Comprising Endothelial Cells or Smooth Muscle Cells This example describes exemplary methods of preparing a composite construct using Type III MSC bio-blocks and Type IV MSC bio-blocks.

Preparation of Bio-Blocks

1. Preparation of MSC bio-blocks comprising endothelial cells (i.e. a Type III MSC bio-block).

MSCs and endothelial cells were mixed at a 10:1 ratio to provide a cell suspension with a cell concentration of $4 \times 10^6$/ml for use as seed cells in the bio-blocks. Polylysine was used as the polymeric shell material. Type I collagen was used as the polymeric core material. Bio-blocks were prepared using the cell suspension, polymeric core material, and polymeric shell material.

2. Preparation of MSC bio-blocks comprising smooth muscle cells (i.e., a Type IV MSC bio-block).

MSCs and smooth muscle cells were mixed at a 3:1 ratio to provide a cell suspension with a cell concentration of $4 \times 10^6$/ml for use as seed cells in the bio-blocks. Polylysine was used as the polymeric shell material. Type I collagen was used as the polymeric core material. Bio-blocks were prepared using the cell suspension, polymeric core material, and polymeric shell material.

Bioprinting Method

According to FIG. 22A, MSC bio-blocks comprising smooth muscle cells were bioprinted to form the exterior layers of the tissue-progenitor, and MSC bio-blocks comprising endothelial cells were bioprinted to form the interior layers of the tissue progenitor. The MSC bio-blocks comprising smooth muscle cells provided microenvironments for differentiation of the MSCs to smooth muscle cells. The MSC bio-blocks comprising endothelial cells provided microenvironments for differentiation of the MSCs to endothelial cells.

The bioprinted tissue progenitor was cultured in H-DMEM media containing 10% fetal bovine albumin, at 37° C., and 5% $CO_2$ for 7 days to obtain a tissue having a diameter of about 3 mm. As shown in FIG. 22B, HE staining of the tissue demonstrated that the two types of bio-blocks fused to form an integrated tissue. Immunohistochemical staining results showed that cells were arranged in an orderly fashion according to the pre-determined pattern in the tissue.

Example 15. Preparation of Msc Bio-Blocks Comprising Endothelial Cells

This example describes an exemplary method of preparing MSC bio-blocks using a super-hydrophobic U-bottom plate. Materials and cells used were as follows:

Polymeric core material: 4 mg/mL type I collagen, neutralized with a sterile 1M NaOH solution.

Polymeric shell material: 1% (w/w) polylysine.

Cells: HUVEC and MSC mixed at a 1:10 ratio, with a total cell concentration of $3.7 \times 10^6$ cells/mL.

The bio-blocks were prepared using the following steps:

(1) Preparation of a super-hydrophobic U-bottom plate: In a clean room, a U-bottom plate was washed with alcohol, and placed in a hydrogen/peroxide/concentrated sulfuric acid solution (30% v/v, $H_2O_2$:$H_2SO_4$=1:3) for hydroxylation treatment at 80° C. for 1 hour. The hydroxylated U-bottom plate was placed in 1% 1H, 1H, 2H, 2H-perfluorodecyl triethoxysilane (Sigma) solution for 12 hours, and then heated in a 100° C. oven for 4 hours for silanization treatment. Finally, the U-bottom late was washed and air-dried.

(2) Preparation of a core mix: To a mixture of 120 µL NaOH solution and 750 µL type I collagen (4 mg/mL) was added 130 µL of a suspension of a mixture of HUVEC and rat MSC stained with Tracker CM-Dil (total cell density: $3.7 \times 10^5$ cells/mL) in phosphate buffered saline (PBS), to make 1 mL of the core mixture.

An alternative cell mixture (such as mixture of MSCs and hepatocytes, mixture of human MSCs and HUVEC, mixture of MSCs, endothelial cells, and smooth muscle cells, mixture of MSCs, endothelial cells, and hepatocytes, etc.) could be used in place of the mixture of HUVEC and rat MSC in this step to prepare a core mix, which could be used in the following steps to prepare bio-blocks comprising corresponding cell types in the alternative cell mixture.

(3) Preparation of a polylysine-FITC solution: FITC (green fluorescence) labeled polylysine (Sigma, average molecular weight was 150,000-300,000) was dissolved in DMEM high glucose medium to obtain a 1% (w/w) polylysine solution.

(4) Preparation of the core: A digital pipetting apparatus that can draw and dispense nanoliter amount of liquid was used to draw 0.1 µL of the core mix prepared in step (2), and dispense as microdroplets into a well of the super-hydrophobic U-bottom plate. The microdroplets formed after incubation in the plate at 37° C. for 30 minutes. For example, Eppendorf Xplorer 0.5-10 µL or Transferpette Electronic 0.5-10 µL system could be used to dispense microdroplets as with a volume as low as 0.1 µL. Alternatively, an SGE autosampler could be used with a 1 µL or 0.5 µL setting to prepare 10 or 5 microdroplets at a time, with each microdroplet having a volume of 0.1 µL. Conical needles could be used for dispensing to improved accuracy.

(5) Preparation of the shell: After changing the pipette tip of the digital pipetting apparatus, 0.5 µL of the polylysine-FITC solution prepared in step (3) was precisely drawn and dispensed to the middle of the well in the super-hydrophobic plate containing the core microdroplets, and incubated for 10 minutes, to obtain bio-blocks comprising HUVEC and MSC.

Example 16. Bioprinting of an Artificial Liver Tissue

Bio-blocks prepared using the method described in Example 15 were used to bio-print an artificial liver tissue. Each bio-block comprise a mixture of a MSC derived from an adipose tissue and primary hepatocytes as seed cells, type I collagen as the polymeric core material, and polylysine as the polymeric shell material.

A bioprinter was used to bioprint the bio-blocks to obtain a tissue progenitor. The tissue progenitor was cultured at 37° C. and 5% $CO_2$, in H-DMEM medium supplemented with 10% fetal bovine serum for 7 days to obtain the artificial liver tissue.

Figure 23:
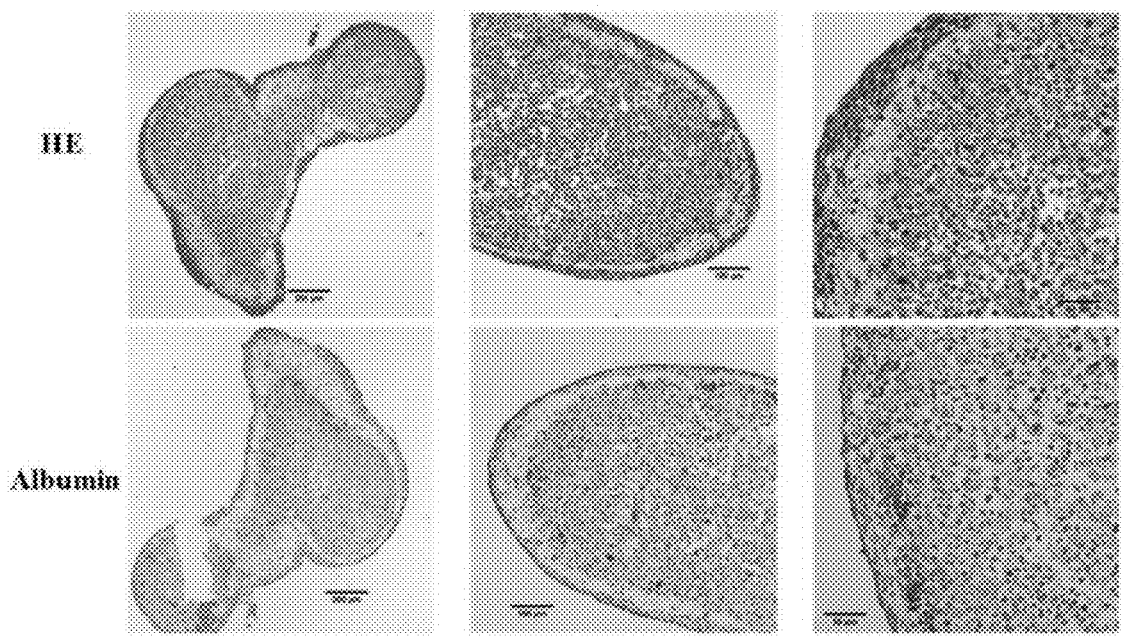
FIG. 23 shows HE staining results (top panel) and immunohistochemical staining results against albumin (bottom panel) of an exemplary artificial liver tissue bioprinted using bio-blocks comprising adipose-derived MSC.

The artificial liver tissue was HE stained and immunohistochemically stained against albumin. As shown in FIG. 23, the HE staining results (top panel) demonstrate that cells are arranged as cords in the artificial liver tissue, and the artificial tissue prepared a lobular structure which is similar to those found in normal liver tissues. Additionally, the immunohistochemical staining results revealed that hepatocytes in the interior of the artificial liver tissue could secrete albumin, a liver-specific protein, as in normal liver. Also, non-hepatocytes on the border of the artificial liver tissue did not express albumin. These results demonstrate that the bio-blocks of the present application can be used to bioprint artificial liver tissues.

Example 17. Bioprinting of Constructing Comprising Blood Capillaries

Figure 24:
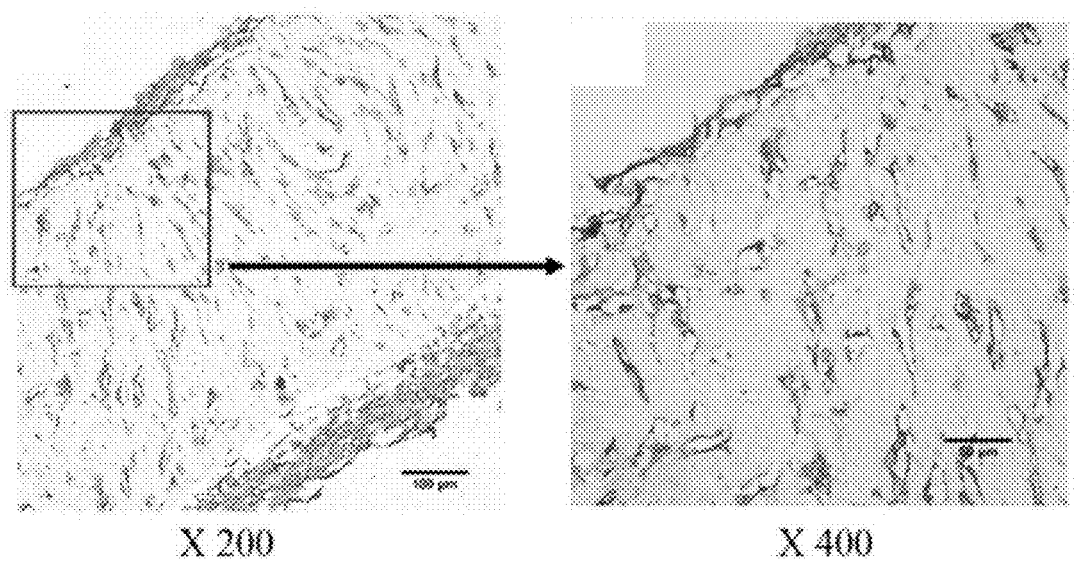
FIG. 24 shows anti-CD31 immunostaining results of a slice of an exemplary artificial tissue having a large number of blood capillaries.

Bio-blocks prepared using the method described in Example 15 were bioprinted using a bioprinter to obtain a construct, which was cultured at 37° C. with 5% $CO_2$ in H-DMEM media containing about 10% FBS for 9 days to obtain an artificial tissue. The bio-printed artificial tissue was sliced and stained with anti-CD31 immunostain. As shown in FIG. 24, a large number of blood capillaries were observed in the bioprinted artificial tissue.

These results demonstrate that the bio-blocks of the present application can be used to bioprint constructs having blood capillaries. Importantly, the blood capillaries are the only routes for cells in deep tissues to get nutrition and discharge metabolites. It is thus critical for the bioprinted artificial tissues to have blood capillaries in order to connect to the main blood vessels to ensure cell survival.

Example 18. Effect of Cell Types and Ratios on Blood Capillary Formation

Bio-blocks comprising various cell compositions as shown in Table 6 were prepared using the method described in Example 15. The bio-blocks were then bioprinted and cultured using the method described in Example 17 to obtain artificial tissues, which were sliced and stained to observe formation of blood capillaries. The results are shown in FIGS. 25A-25G.

TABLE 6

Bio-blocks comprising different cell types and ratios.

| Number | Cell types and ratio | Results |
|---|---|---|
| 1 | HUVEC:BMSC = 1:20 | Blood capillaries formed |
| 2 | HUVEC:BMSC = 1:10 | Large number of blood capillaries formed |
| 3 | HUVEC:BMSC = 1:3 | Blood capillaries formed |
| 4 | HUVEC:BMSC = 1:1.5 | Blood capillaries formed |
| 5 | HUVEC:rat hepatocyte:BMSC = 1:1:10 | Large number of blood capillaries formed |
| 6 | HUVEC:SMC:BMSC = 1:3:16 | Blood capillaries formed |
| 7 | HUVEC:HUMSC = 1:3 | Blood capillaries formed |

BMSC = rat bone marrow-derived mesenchymal stem cell;
SMC = smooth muscle cells;
HUMSC = human MSC.

Figure 25A:
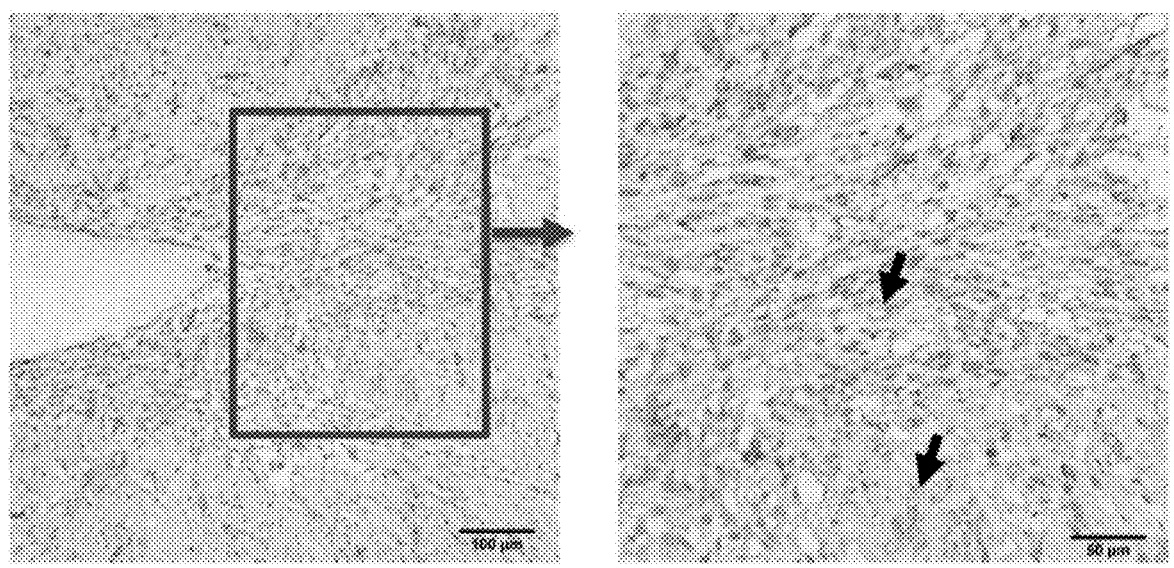
FIGS. 25A-25F show formation of blood capillaries in artificial tissues bioprinted using bio-blocks comprising various types and ratios of cells. Black arrows point to examples of blood capillaries in the artificial tissues.
Figure 25B:
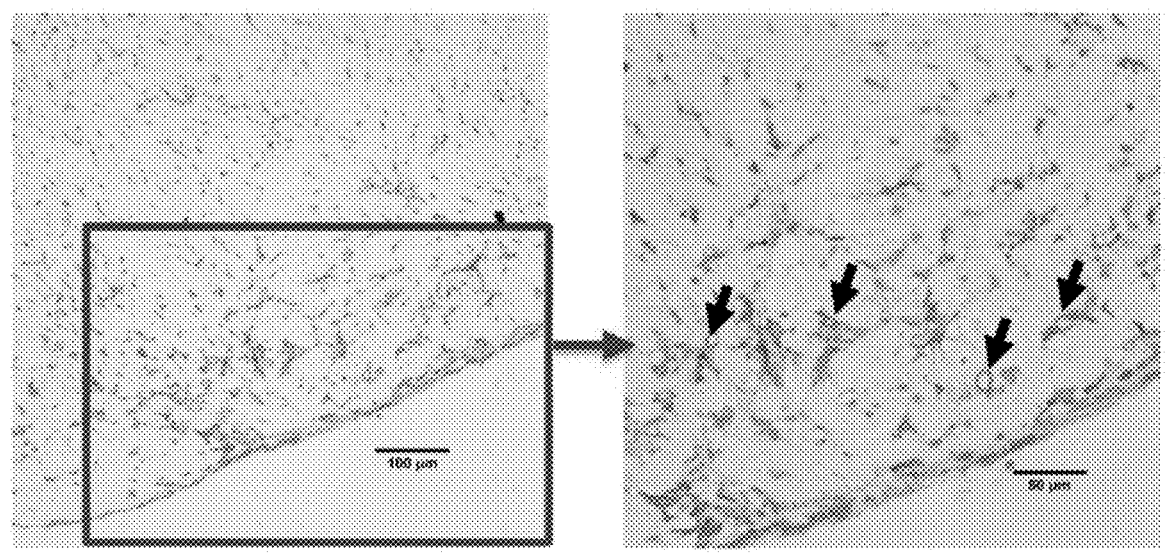
Figure 25C:
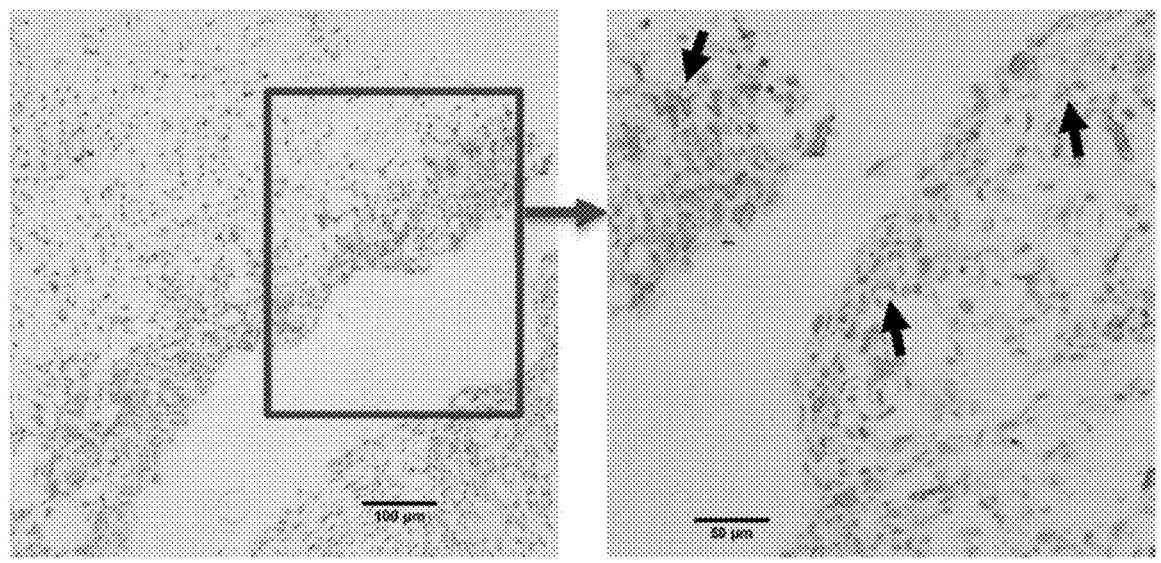
Figure 25D:
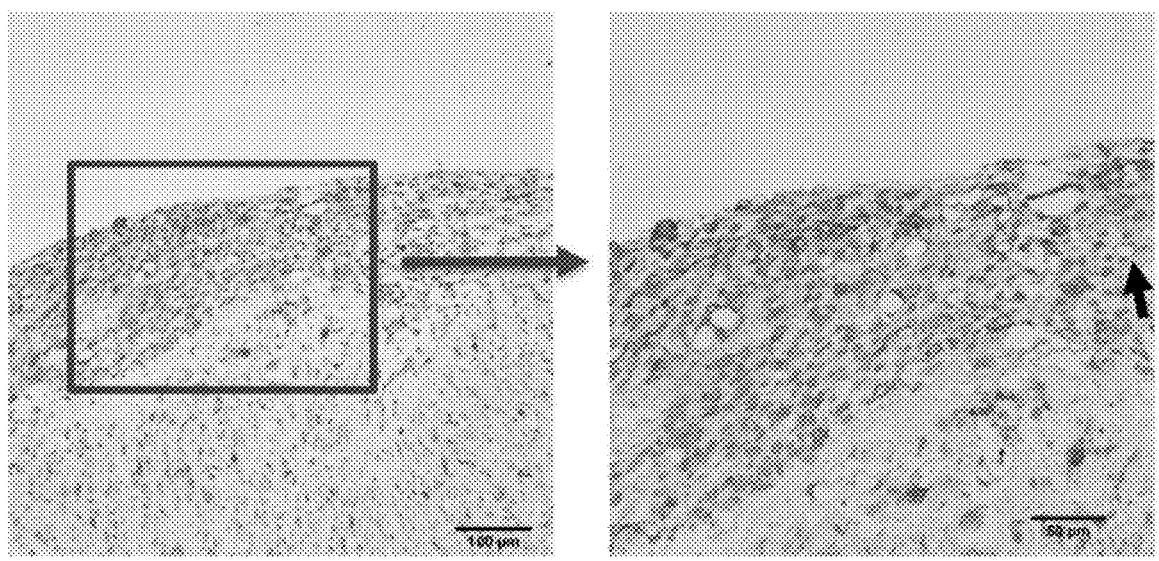
Figure 25E:
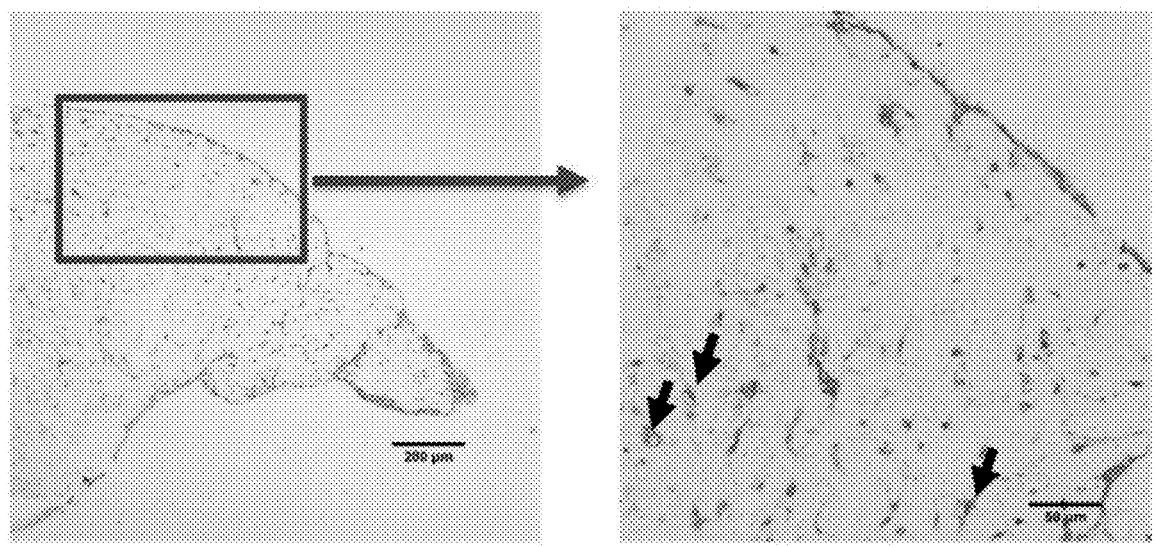
Figure 25F:
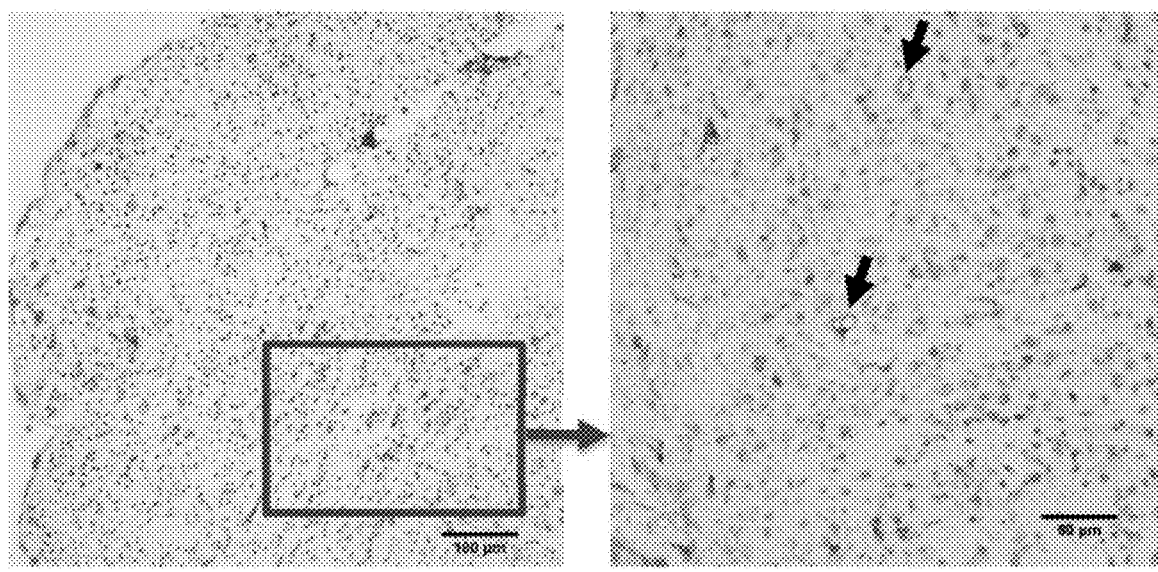
Figure 25G:
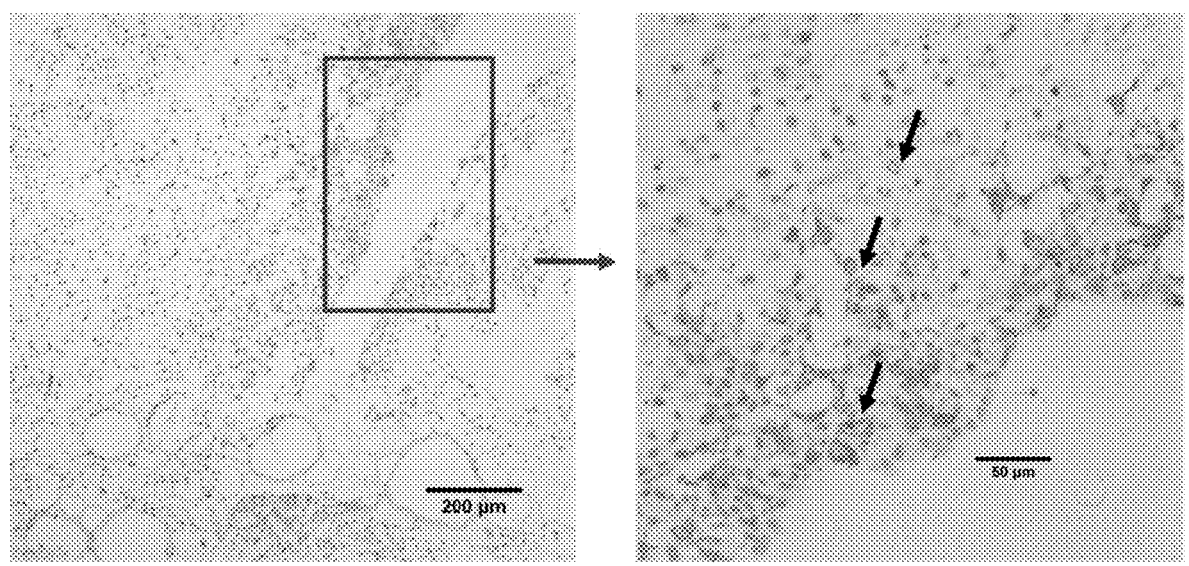
FIG. 25G shows formation of a small number of blood capillaries in an artificial tissue bioprinted using bio-blocks comprising a mixture of human MSC and HUVEC at a ratio of 3:1.

These results show that when HUVEC and BMSC were used as seed cells at various ratios between 1:1.5 to 1:20 to prepare bio-blocks (FIG. 25A-25D), blood capillaries were observed in all artificial tissues prepared using such bio-blocks. In particular, at a ratio of 1:10 (HUVEC:BMSC), the artificial tissue prepared using such bio-blocks had a large number of blood capillaries (FIG. 25B). When rat hepatocytes were included in the bio-blocks in addition to HUVEC and BMSC, blood capillaries were also observed in the artificial tissues bioprinted using such bio-blocks. In particular, at a ratio of 1:1:10 (HUVEC: rat hepatocyte: BMSC), the artificial tissue prepared using such bio-blocks had a large number of blood capillaries (FIG. 25E). Additionally, when smooth muscle cells were included in the bio-blocks in addition to HUVEC and BMSC, blood capillaries were observed in the artificial tissues bioprinted using such bio-blocks (FIG. 25F). When HUVEC and human MSC were used as seed cells at a ratio of 3:1 to prepare bio-blocks (FIG. 25G), blood capillaries were also observed in the artificial tissue bioprinted using such bio-blocks.

Example 19. Various Applications of the Bio-Blocks

Stem Cell Differentiation Research

A plurality of isolated bio-blocks, each comprising a mesenchymal stem cell derived from the bone marrow, is prepared. To each of the isolated bio-blocks is added one agent or agent combination that induces differentiation of the stem cell towards or into one of the following four types of cells: osteoblasts, adipocytes, chondrocytes, and myocytes. The plurality of isolated bio-blocks is cultured in the same culturing system, such as in the same container (e.g. culture dish or culture flask). The cells in each isolated bio-block are observed to evaluate the effects of different microenvironments on stem cell differentiation.

Tissue Regeneration

The exemplary tissue regeneration method described in this example is particularly useful for repairing a large wound in the skin, as the natural healing process of a large wound in the skin may result in a large scar.

First, a medical imaging method is used to scan the wound to determine the structural information, such as the layers of the skin tissue that is damaged by the wound, including the epithelium, endothelium, and the muscle layer.

Next, based on the medical imaging data, a digital repair model is constructed based on the structural information of the wound and cell distribution information of the skin tissue. Based on the digital repair model, appropriate types of bio-blocks (such as fibroblast-containing bio-blocks for the epithelium, and endothelial cell-containing bio-blocks for the endothelium) are chosen and obtained for repairing the wound. The appropriate bio-blocks are bioprinted directly onto the wound according to the digital repair model.

In some scenarios, the cells in the bio-blocks are derived from autologous stem cells from the subject having the wound.

Cells in the bioprinted bio-blocks proliferate and differentiate within different layers and microenvironments of the wound, forming the corresponding tissue layers and substructures, and repairing the wound in the skin.

Example 20: Various Applications of the Constructs

In Vitro Research on Tissue Development

Different batches of bio-blocks, each comprising a different type of stem cell, are prepared. Based on the cell distribution patterns of the tissues in the study, corresponding tissue progenitors are bioprinted using the appropriate batches of bio-blocks. The bioprinted tissue progenitors are cultured in vitro under appropriate conditions to develop into the desired tissues. The cells in the bio-blocks are exposed to a selected agent or agent combination to influence the development of the cells. Cells in the bio-blocks and the tissues are observed throughout the developmental process.

In Vivo Research on Transplant Immunology

Bio-blocks comprising cells derived from a subject that receives the tissue transplant (such as a research animal) are prepared. The tissue progenitor or artificial tissue bioprinted using the bio-blocks is implanted in the subject to observe immune responses to the tissue progenitor or artificial tissue, such as biocompatibility, and immune rejection.

Drug Screening

Suitable bio-blocks are prepared and used to bioprint an artificial tissue relevant for drug screening. The cells of the bio-blocks used in the preparation process may be derived from the subject (such as a human subject) that receives a drug (including different dosages, formulations etc.). The artificial tissue is exposed to a panel of drugs at a predetermined dosage to evaluate the efficacy of each drug. The artificial tissue is exposed to the drug at different dosages to determine the efficacy of the drug dosage. The drug and the dosage with the highest efficacy and/or lowest side effects are recommended to the subject for treating a disease or condition that affects the tissue.

Drug Discovery

An artificial tissue relevant to the function of the drug is bioprinted using appropriate bio-blocks. The artificial tissue may be a healthy tissue, or a diseased tissue, depending on manipulations during the preparation process, for example, the source of cells in the bio-blocks, the agent(s) or the stimulus included in the bio-blocks, or the culturing conditions. The artificial tissue is exposed to a panel of compounds, and effects of each compound on a diseased artificial tissue are optionally compared to the effects of the same compound on a corresponding healthy artificial tissue, in order to determine the efficacy of each compound on treating a particular disease or condition related to the tissue. Toxicity of each compound is also evaluated based on the effects of the compound on the artificial tissue (such as a healthy artificial tissue). The compound with the highest efficacy and/or the lowest toxicity, or the best tradeoff between efficacy and toxicity, is chosen as a lead compound for further drug discovery and development processes.

What is claimed is:

1. A method of preparing an artificial tissue or a tissue progenitor, comprising subjecting a bio-ink composition to bio-printing through an inkjet or microextrusion nozzle of a three-dimensional (3D) bio-printer to obtain a multi-dimensional construct having a pre-determined pattern, wherein the bio-ink composition comprises a plurality of bio-blocks, wherein each bio-block comprises: a) a core comprising a biodegradable core material and 25-5000 cells, and b) a shell comprising a biodegradable shell material, wherein the shell provides mechanical support to the core, wherein the bio-block has a modulus of elasticity of about 0.01 MPa to about 100 MPa, and wherein the bio-block has a hardness of about 0.01 GPa to about 0.4 GPa.

2. The method of claim 1, wherein the bio-ink composition further comprises a carrier.

3. The method of claim 2, wherein the carrier has a viscosity of about 1 Pa·s to about 1000 Pa·s.

4. The method of claim 1, wherein the bio-ink composition comprises at least about 50% bio-blocks (w/w).

5. The method of claim 1, wherein the shell has a thickness of about 0.1 μm to about 50 μm.

6. The method of claim 1, wherein the shell degrades completely within no more than about 28 days.

7. The method of claim 1, wherein the shell is permeable to a macromolecule having a molecular weight of at least about 110 kDa.

8. The method of claim 1, wherein the ratio between the length and the thickness of each bio-block is no more than about 50:1.

9. The method of claim 1, wherein the plurality of bio-blocks is of the same type.

10. The method of claim 1, wherein the plurality of bio-blocks is of different types.

11. The method of claim 1, wherein the core comprises an agent selected from a nutrient, an extracellular matrix factor, a cell factor, and a pharmaceutically active agent.

12. The method of claim 11, wherein the core comprises at least 3 different agents.

13. The method of claim 1, wherein the biodegradable core material comprises type I collagen.

14. The method of claim 1, wherein the biodegradable shell material comprises oxidized alginate.

15. The method of claim 14, wherein the oxidation level of the oxidized alginate is about 1% to about 40%.

16. The method of claim 1, wherein the biodegradable shell material comprises polylysine.

17. The method of claim 1, wherein the cell is a mesenchymal stem cell (MSC).

18. The method of claim 1, wherein the plurality of bio-blocks comprises a bio-block comprising at least two shells.

19. The method of claim 1, wherein the bio-ink composition is not bio-printed onto a scaffold.

20. The method of claim 1, further comprising culturing the multi-dimensional construct in vitro under a condition that allows the cells in the plurality of bio-blocks to proliferate, differentiate, metabolize, migrate, secrete, or any combination thereof.

21. The method of claim 20, wherein the shell is at least partially degraded during the culturing.

22. The method of claim 21, wherein the cells in different bio-blocks are connected to each other upon the culturing.

23. The method of claim 1, wherein the bio-ink composition is pre-formed prior to the bio-printing.

24. The method of claim 1, wherein the shell does not comprise a cell.

25. The method of claim 1, wherein the method comprises subjecting the bio-ink composition to bio-printing through an inkjet nozzle of a three-dimensional bio-printer.

* * * * *